United States Patent
De La Rosa et al.

(10) Patent No.: US 9,163,023 B2
(45) Date of Patent: Oct. 20, 2015

(54) COMPOUNDS AND METHODS FOR TREATING HIV

(71) Applicant: VIIV HEALTHCARE UK LIMITED, Brentford, Middlesex (GB)

(72) Inventors: Martha Alicia De La Rosa, Research Triangle Park, NC (US); Brian Alvin Johns, Research Triangle Park, NC (US); Wieslaw Mieczyslaw Kazmierski, Research Triangle Park, NC (US); Vicente Samano, Research Triangle Park, NC (US); Lita Suwandi, Research Triangle Park, NC (US); David Temelkoff, Research Triangle Park, NC (US); Emile Velthuisen, Research Triangle Park, NC (US); Jason Gordon Weatherhead, Research Triangle Park, NC (US)

(73) Assignee: ViiV Healthcare UK Limited, Brentford, Middlesex (GB)

( * ) Notice: Subject to any disclaimer, the term of this patent is extended or adjusted under 35 U.S.C. 154(b) by 0 days.

(21) Appl. No.: 14/413,425

(22) PCT Filed: Jul. 10, 2013

(86) PCT No.: PCT/IB2013/001501
§ 371 (c)(1),
(2) Date: Jan. 8, 2015

(87) PCT Pub. No.: WO2014/009794
PCT Pub. Date: Jan. 16, 2014

(65) Prior Publication Data
US 2015/0191469 A1    Jul. 9, 2015

Related U.S. Application Data

(60) Provisional application No. 61/670,800, filed on Jul. 12, 2012, provisional application No. 61/671,787, filed on Jul. 15, 2012, provisional application No. 61/755,047, filed on Jan. 22, 2013, provisional application No. 61/764,716, filed on Feb. 14, 2013.

(51) Int. Cl.
*A61K 31/437*    (2006.01)
*C07D 471/04*    (2006.01)
*C07D 471/14*    (2006.01)

(52) U.S. Cl.
CPC ............ *C07D 471/14* (2013.01); *C07D 471/04* (2013.01)

(58) Field of Classification Search
CPC ............................. A61K 31/437; C07D 471/04
USPC ........................................ 514/230.5; 546/113
See application file for complete search history.

(56) References Cited

FOREIGN PATENT DOCUMENTS

| WO | WO 2012/019003 | 2/2012 |
|---|---|---|
| WO | WO 2013/012649 | 1/2013 |
| WO | WO 2013/073875 | 5/2013 |

*Primary Examiner* — John Mabry
(74) *Attorney, Agent, or Firm* — Robert H. Brink

(57) ABSTRACT

Provided are compounds and pharmaceutically acceptable salts thereof, their pharmaceutical compositions, their methods of preparation, and their use for treating viral infections mediated by a member of the retrovirus family of viruses such as the Human Immunodeficiency Virus (HIV).

17 Claims, No Drawings

COMPOUNDS AND METHODS FOR TREATING HIV

CROSS-REFERENCE TO RELATED APPLICATIONS

This application is filed pursuant to 35 USC 371 as a United States National Phase Application of International Patent Application Serial No. PCT/IB2013/001501 filed on Jul. 10, 2013, which claims priority from 61/670,800 filed on Jul. 12, 2012, 61/671,787 filed on Jul. 15, 2012, 61/755,047 filed on Jan. 22, 2013 and 61/764,716 filed on Feb. 14, 2013 in the United States.

FIELD OF THE INVENTION

The present invention relates to substituted azaindole compounds, pharmaceutical compositions, and methods of use thereof for (i) inhibiting HIV replication in a subject infected with HIV, or (ii) treating a subject infected with HIV, by administering such compounds.

BACKGROUND OF THE INVENTION

Human immunodeficiency virus type 1 (HIV-1) leads to the contraction of acquired immune deficiency disease (AIDS). The number of cases of HIV continues to rise, and currently over twenty-five million individuals worldwide suffer from the virus. Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still required because of undesirable drug-drug interactions; drug-food interactions; non-adherence to therapy; and drug resistance due to mutation of the enzyme target.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur. The emergence of multidrug-resistant HIV-1 isolates has serious clinical consequences and must be suppressed with a new drug regimen, known as salvage therapy.

Current guidelines recommend that salvage therapy includes at least two, and preferably three, fully active drugs. Typically, first-line therapies combine three to four drugs targeting the viral enzymes reverse transcriptase and protease. One option for salvage therapy is to administer different combinations of drugs from the same mechanistic class that remain active against the resistant isolates. However, the options for this approach are often limited, as resistant mutations frequently confer broad cross-resistance to different drugs in the same class. Alternative therapeutic strategies have recently become available with the development of fusion, entry, and integrase inhibitors. However, resistance to all three new drug classes has already been reported both in the lab and in patients. Sustained successful treatment of HIV-1-infected patients with antiretroviral drugs will therefore require the continued development of new and improved drugs with new targets and mechanisms of action.

For example, over the last decade HIV inhibitors have been reported to target the protein-protein interaction between HIV-1 integrase and Lens Epithelium Derived Growth Factor/p75 ("LEDGF"). LEDGF is a cellular transcriptional cofactor of HIV-1 integrase that promotes viral integration of reverse transcribed viral cDNA into the host cell's genome by tethering the preintegration complex to the chromatin. Because of its crucial role in the early steps of HIV replication, the interaction between LEDGF and integrase represents another attractive target for HIV drug therapy.

SUMMARY OF THE INVENTION

In accordance with one embodiment of the present invention, there is provided a compound of Formula I:

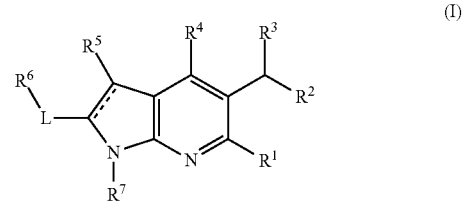

or a pharmaceutically acceptable salt thereof, wherein:

L is selected from the group consisting of a bond, a branched or straight chain $(C_1-C_6)$alkylene, $(C_1-C_6)$alkene, $(C_1-C_6)$alkyne, $-N_3-$, $-NO_2-$, $-NR^9S(O)_2-$, $-S(O)-$, $-SO_2-$, $-S(O)_2R^8-$, $-NR^9-$, $-C(O)NR^9-$, $-NR^9C(O)NR^9-$, $-OR^8-$, $-C(O)-$, $-C(O)R^{15}-$, $-NR^9C(O)OR^8-$, $-C(O)R^8-$, $-C(O)OR^8-$, $-OC(O)OR^8-$, $-OC(O)R^8-$, $-OC(O)NR^9-$, $-C(S)-$, $-C(S)OR^8-$, $-C(S)OR^8-$, $-C(S)NR^9-$, $-NR^9C(S)R^8-$, $-NR^8C(S)NR^9-$, $-OC(S)R^8-$, $-OC(S)OR^8-$, $-OC(S)NR^8-$, $C(NR^8)OR^9-$, $-C(NR^8)R^9-$, $-OC(O)Y-$, $-OC(S)Y-$, $-NR^9C(S)Y-$, $-NR^9C(O)Y-$, $-C(S)Y-$, $-C(O)Y-$, monocyclic or bicyclic $(C_5-C_{14})$aryl, monocyclic or bicyclic $(C_2-C_9)$heterocycle, monocyclic or bicyclic $(C_2-C_9)$heteroaryl, monocyclic or bicyclic $(C_3-C_{14})$cycloalkyl, and

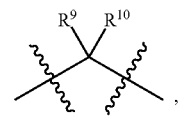

wherein the $R^9$ and $R^{10}$ groups together with the carbon atom to which they are bonded may optionally join together to form a $(C_3-C_7)$cycloalkyl;

$R^1$ is selected from $(C_1-C_6)$alkyl or $(C_3-C_7)$cycloalkyl;

$R^2$ is selected from the group consisting of

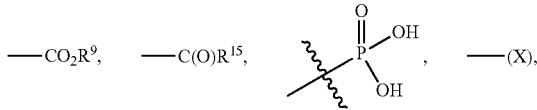

-continued

—(Y), and —(Z),

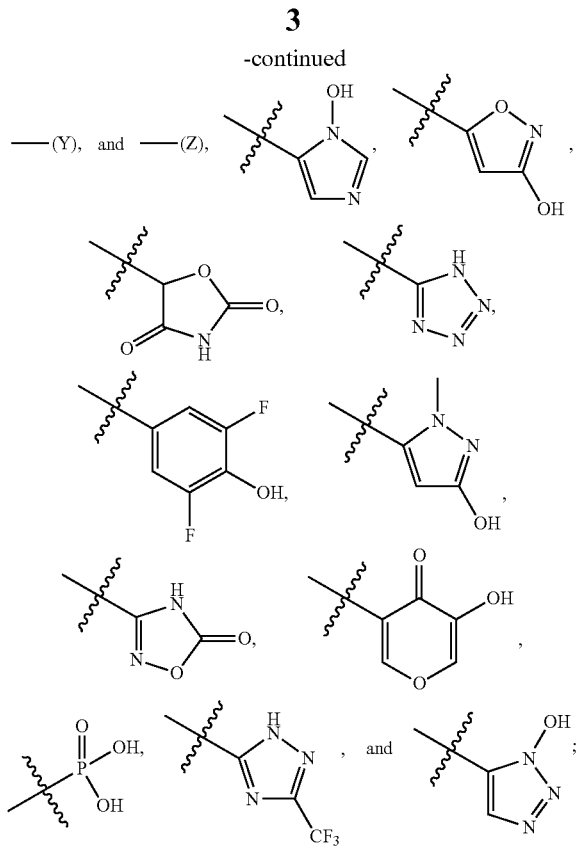

R³ is selected from the group consisting of (C₁-C₆)alkyl, —OR¹⁰, —R¹⁰(R¹⁴)_q, tetrahydrofuranyl, oxetanyl, furanyl, dioxolanyl, pyranyl, dioxanyl, dioxinyl, —O—(C₃-C₇)cycloalkyl, and —(C₃-C₇)cycloalkyl(R¹⁰);

R⁴ is selected from the group consisting of (C₅-C₁₄)aryl, (C₃-C₇)cycloalkyl, (C₂-C₉)heterocycle, and (C₂-C₉)heteroaryl, wherein the heterocycle and heteroaryl each comprise one to three heteroatoms selected from S, N or O, and wherein each R⁴ group is optionally substituted by one to four substituents selected from R¹¹;

R⁵ is selected from —H, (C₁-C₆)alkyl, and halogen;

R⁶ is selected from —H, (C₁-C₆)alkyl, (C₁-C₆)alkoxy, halo, nitrile, —OR¹⁰(C₅-C₁₄)aryl, —OR¹⁰(C₅-C₁₄)aryl(R¹¹)_m, —R¹⁰(Y)(R¹²)_n, —OR¹⁰R¹⁷, —R¹⁰R¹⁷, —R¹⁷R¹⁵, —R¹⁰(R¹⁴)_q, —OR¹⁰(R¹⁴)_q, —OR¹⁰(Y), —OR¹⁰R¹⁸, —OSO₂R¹⁵, —R¹⁵, —(C₅-C₁₄)aryl, —C(O)(Y), —C(O)R¹⁵, —R¹⁰(C₅-C₁₄)aryl, —R¹⁰R¹⁵, —(C₅-C₁₄)arylR¹⁵—(X), —(Y), —(Z), —(X)—(X), —(X)—(Y), —(X)—(Z), —(Y)—(X), —(Y)—(Y), —(Y)—(Z), —(Z)—(X), —(Z)—(Y), and —(Z)—(Z), and wherein each R⁶ group is optionally substituted by one to four substituents selected from R¹³, and wherein when L is a bond, then R⁵ and R⁶ together with the carbon atoms to which they are bonded may optionally join together to form a (C₅-C₁₄) aryl, or alternatively, when L is a bond, then R⁶ and R⁷ together with the carbon atoms to which they are bonded may optionally join together to form a (C₃-C₇)heterocycle;

R⁷ is selected from the group consisting of —H, (C₁-C₆) alkyl, (C₁-C₆)alkoxy, halo, (C₃-C₇)cycloalkyl, —R¹⁰(R¹⁴)_q, and oxetanyl;

R⁸ is selected from the group consisting of —H, (C₁-C₆) alkyl, —NH—, and —C(O)NH—;

R⁹ is independently selected from —H and (C₁-C₆)alkyl;

R¹⁰ is (C₁-C₆)alkyl;

R¹¹, R¹², and, R¹³ are independently selected from the group consisting of (C₁-C₆)alkyl, (C₁-C₆)alkoxy, butoxycarbonyl, oxo, R¹⁰OR¹⁰, halo, —R¹⁵, —R¹⁰(R¹⁴)_q, —OR¹⁰(R¹⁴)_q, —SO₂R¹⁰; —C(O)R¹⁰, —C(O)R¹⁵, and —R¹⁰R¹⁷;

R¹⁴ is halo;

R¹⁵ is —N(R¹⁶)₂;

R¹⁶ is independently selected from the group consisting of —H, (C₁-C₆)alkyl, hydroxyl, —SO₂R¹⁰, —SO₂N(R¹⁰)₂, —C(O)NHR¹⁰, —C(O)NHR¹⁸, and —(C₅-C₁₄)aryl(R¹¹);

R¹⁷ is —OR⁹;

R¹⁸ is —CO₂R⁹;

X is a monocyclic or bicyclic (C₅-C₁₄)aryl or —C(O)(C₅-C₁₄)aryl, wherein each aryl of X is optionally substituted by one to four substituents independently selected from R¹¹;

Y is independently selected from a monocyclic or bicyclic (C₂-C₉)heterocycle or —C(O) (C₂-C₉)heterocycle; or monocyclic or bicyclic (C₂-C₉)heteroaryl or —C(O) (C₂-C₉)heteroaryl, each heterocycle or heteroaryl having one to four heteroatoms selected from S, N or O, and wherein each heterocycle or heteroaryl of Y is optionally substituted by one to four substituents independently selected from R¹²;

Z is a monocyclic or bicyclic (C₃-C₁₄)cycloalkyl or —C(O)(C₃-C₁₄)cycloalkyl, wherein each cycloalkyl of Z is optionally substituted by one to four substituents independently selected from R¹³;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

Also provided is a pharmaceutical composition comprising a pharmaceutically acceptable carrier or excipient and a therapeutically effective amount of a compound of Formula I, or a pharmaceutically acceptable salt thereof.

Also provided are synthetic intermediates, methods for preparing the compounds of Formula I, or a pharmaceutically acceptable salt or solvate thereof, and compositions thereof and for their therapeutic uses.

In some embodiments, provided is a method for treating a viral infection in a patient mediated at least in part by a virus in the retrovirus family of viruses, comprising administering to said patient a composition comprising a compound of Formula I, or a pharmaceutically acceptable salt thereof. In some embodiments, the viral infection is mediated by the HIV virus.

In another aspect, a particular embodiment of the present invention provides a method of treating a subject infected with HIV comprising administering to the subject a therapeutically effective amount of a compound of Formula I, or a pharmaceutically acceptable salt thereof.

In yet another aspect, a particular embodiment of the present invention provides a method of inhibiting progression of HIV infection in a subject at risk for infection with HIV comprising administering to the subject a therapeutically effective amount of a compound of Formula I, or a pharmaceutically acceptable salt thereof. Those and other embodiments are further described in the text that follows.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to a monovalent saturated aliphatic hydrocarbyl group having from 1 to 14 carbon atoms and, in some embodiments, from 1 to 6 carbon atoms. "$(C_x\text{-}C_y)$alkyl" refers to alkyl groups having from x to y carbon atoms. The term "alkyl" includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylidene" or "alkylene" refers to divalent saturated aliphatic hydrocarbyl groups having from 1 to 10 carbon atoms and, in some embodiments, from 1 to 6 carbon atoms. "$(C_{u\text{-}v})$alkylene" refers to alkylene groups having from u to v carbon atoms. The alkylidene and alkylene groups include branched and straight chain hydrocarbyl groups. For example, the term "branched or straight chain ($C_{1\text{-}6}$)alkylene" is meant to include methylene, ethylene, propylene, 2-methypropylene, methylmethylene, pentylene, and so forth.

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, ($C_x\text{-}C_y$)alkenyl refers to alkenyl groups having from x to y carbon atoms and is meant to include for example, ethenyl, propenyl, isopropylene, 1,3-butadienyl, and the like.

"Alkynyl" refers to a linear monovalent hydrocarbon radical or a branched monovalent hydrocarbon radical containing at least one triple bond. The term "alkynyl" is also meant to include those hydrocarbyl groups having one triple bond and one double bond. For example, ($C_2\text{-}C_6$)alkynyl is meant to include ethynyl, propynyl, and the like.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Acyl" refers to the groups H—C(O)—, alkyl-C(O)—, alkenyl-C(O)—, alkynyl-C(O)—, cycloalkyl-C(O)—, aryl-C(O)—, heteroaryl-C(O)—, and heterocyclic-C(O)—. Acyl includes the "acetyl" group $CH_3C(O)$—.

"Acylamino" refers to the groups —$NR^{20}C(O)$alkyl, —$NR^{20}C(O)$cycloalkyl, —$NR^{20}C(O)$alkenyl, —$NR^{20}C(O)$alkynyl, —$NR^{20}C(O)$aryl, —$NR^{20}C(O)$heteroaryl, and —$NR^{20}C(O)$heterocyclic, wherein $R^{20}$ is hydrogen or alkyl.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O—, and heterocyclic-C(O)O—.

"Amino" refers to the group —$NR^{21}R^{22}$ where $R^{21}$ and $R^{22}$ are independently selected from hydrogen, alkyl, alkenyl, alkynyl, aryl, cycloalkyl, heteroaryl, heterocyclic, —$SO_2$-alkyl, —$SO_2$-alkenyl, —$SO_2$-cycloalkyl, —$SO_2$-aryl, —$SO_2$-heteroaryl, and —$SO_2$-heterocyclic, and wherein $R^{21}$ and $R^{22}$ are optionally joined together with the nitrogen bound thereto to form a heterocyclic group. When $R^{21}$ is hydrogen and $R^{22}$ is alkyl, the amino group is sometimes referred to herein as alkylamino. When $R^{21}$ and $R^{22}$ are alkyl, the amino group is sometimes referred to herein as dialkylamino. When referring to a monosubstituted amino, it is meant that either $R^{21}$ or $R^{22}$ is hydrogen but not both. When referring to a disubstituted amino, it is meant that neither $R^{21}$ nor $R^{22}$ are hydrogen.

"Hydroxyamino" refers to the group —NHOH.

"Alkoxyamino" refers to the group —NHO-alkyl wherein alkyl is defined herein.

"Aminocarbonyl" refers to the group —$C(O)NR^{26}R^{27}$ where $R^{26}$ and $R^{27}$ are independently selected from hydrogen, alkyl, alkenyl, alkynyl, aryl, cycloalkyl, heteroaryl, heterocyclic, hydroxy, alkoxy, amino, and acylamino, and where $R^{26}$ and $R^{27}$ are optionally joined together with the nitrogen bound thereto to form a heterocyclic group.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Cyano" or "nitrile" refers to the group —CN.

"Cycloalkyl" refers to a saturated or partially saturated cyclic group of from 3 to 14 carbon atoms and no ring heteroatoms and having a single ring or multiple rings including fused, bridged, and Spiro ring systems. For multiple ring systems having aromatic and non-aromatic rings that have no ring heteroatoms, the term "cycloalkyl" applies when the point of attachment is at a non-aromatic carbon atom (e.g. 5,6,7,8,-tetrahydronaphthalene-5-yl). The term "Cycloalkyl" includes cycloalkenyl groups, such as cyclohexenyl. Examples of cycloalkyl groups include, for instance, adamantyl, cyclopropyl, cyclobutyl, cyclohexyl, cyclopentyl, cyclooctyl, cyclopentenyl, and cyclohexenyl. Examples of cycloalkyl groups that include multiple bicycloalkyl ring systems are bicyclohexyl, bicyclopentyl, bicyclooctyl, and the like. Two such bicycloalkyl multiple ring structures are illustrated below:

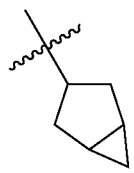 [SMILES: *C1CC2CC2C1]

bicyclohexyl, and

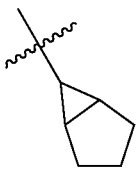 [SMILES: *C1C2CCCC12]

bicyclohexyl.

"$(C_u\text{-}C_v)$cycloalkyl" refers to cycloalkyl groups having u to v carbon atoms.

"Spiro cycloalkyl" refers to a 3 to 10 member cyclic substituent formed by replacement of two hydrogen atoms at a common carbon atom in a cyclic ring structure or in an alkylene group having 2 to 9 carbon atoms, as exemplified by the following structure wherein the group shown here attached to bonds marked with wavy lines is substituted with a spiro cycloalkyl group:

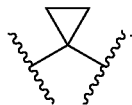 [SMILES: *C1(*)CC1]

"Fused cycloalkyl" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused cycloalkyl group:

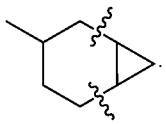

"Halo" or "halogen" refers to fluoro, chloro, bromo, and iodo.

"Haloalkoxy" refers to substitution of alkoxy groups with 1 to 5 (e.g. when the alkoxy group has at least 2 carbon atoms) or in some embodiments 1 to 3 halo groups (e.g. trifluoromethoxy).

"Hydroxy" or "hydroxyl" refers to the group —OH.

"Heteroaryl" refers to an aromatic group of from 1 to 14 carbon atoms and 1 to 6 heteroatoms selected from oxygen, nitrogen, and sulfur and includes single ring (e.g. imidazolyl) and multiple ring systems (e.g. benzimidazol-2-yl and benzimidazol-6-yl). For multiple ring systems, including fused, bridged, and Spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl: benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from nitrogen, sulfur, phosphorus or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom and the point of attachment is at an atom of a non-aromatic ring (e.g. 1,2,3,4-tetrahydroquinoline-3-yl, 5,6,7,8-tetrahydroquinoline-6-yl, and decahydroquinolin-6-yl). In one embodiment, the nitrogen, phosphorus and/or sulfur atom(s) of the heterocyclic group are optionally oxidized to provide for the N-oxide, phosphinane oxide, sulfinyl, sulfonyl moieties. More specifically the heterocyclyl includes, but is not limited to, tetrahydropyranyl, piperidinyl, piperazinyl, 3-pyrrolidinyl, 2-pyrrolidon-1-yl, morpholinyl, and pyrrolidinyl. A prefix indicating the number of carbon atoms (e.g., $C_3$-$C_{10}$) refers to the total number of carbon atoms in the portion of the heterocyclyl group exclusive of the number of heteroatoms.

Examples of heterocycle and heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Fused heterocyclic" refers to a 3 to 10 member cyclic substituent formed by the replacement of two hydrogen atoms at different carbon atoms in a cycloalkyl ring structure, as exemplified by the following structure wherein the cycloalkyl group shown here contains bonds marked with wavy lines which are bonded to carbon atoms that are substituted with a fused heterocyclic group:

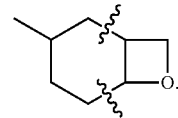

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {$N^+$—$O^-$} and sulfur such as S(O) and S(O)$_2$, and the quaternized form of any basic nitrogen.

"Oxazolidinone" refers to a 5-membered heterocyclic ring containing one nitrogen and one oxygen as heteroatoms and also contains two carbons and is substituted at one of the two carbons by a carbonyl group as exemplified by any of the following structures, wherein the oxazolidinone groups shown here are bonded to a parent molecule, which is indicated by a wavy line in the bond to the parent molecule:

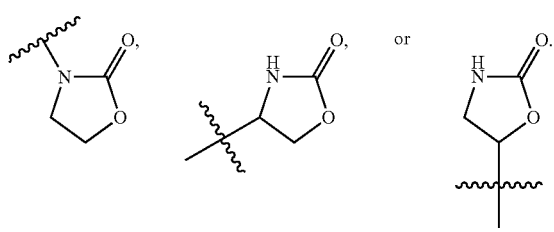 [SMILES: *N1CCOC1=O ; *C1COC(=O)N1 ; "or" ; *C1CNC(=O)O1]

"Racemates" refers to a mixture of enantiomers. In an embodiment of the invention, some of the compounds of Formulas I, II, or III, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt. Where a compound of Formula I, II, or III or Tables 1-2 is drawn to indicate its stereoisomer bonds or a specific enantiomer, it will be understood by one of skill in the art that such drawing also implicitly teaches the racemic form and structure of the compound where there are no stereoisomer bonds indicated in a drawing of the structure of such compound.

"Stereoisomer" or "stereoisomers" refer to compounds that differ in the chirality of one or more stereocenters. Stereoisomers include enantiomers and diastereomers.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" or "subject" refers to mammals and includes humans and non-human mammals.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Wherever dashed lines occur adjacent to single bonds denoted by solid lines, then the dashed line represents an optional double bond at that position. Likewise, wherever dashed circles appear within ring structures denoted by solid lines or solid circles, then the dashed circles represent one to three optional double bonds arranged according to their proper valence taking into account whether the ring has any optional substitutions around the ring as will be known by one of skill in the art. For example, the dashed line in the structure below could either indicate a double bond at that position or a single bond at that position:

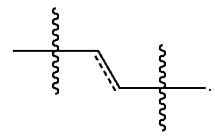

Similarly, ring A below could be a cyclohexyl ring without any double bonds or it could also be a phenyl ring having three double bonds arranged in any position that still depicts the proper valence for a phenyl ring. Likewise, in ring B below, any of $X^1$-$X^5$ could be selected from: C, CH, or $CH_2$, N, or NH, and the dashed circle means that ring B could be a cyclohexyl or phenyl ring or a N-containing heterocycle with no double bonds or a N-containing heteroaryl ring with one to three double bonds arranged in any position that still depicts the proper valence:

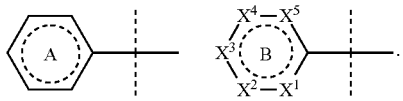

Where specific compounds or generic formulas are drawn that have aromatic rings, such as aryl or heteroaryl rings, then it will understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

A

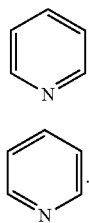

B

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C(Rx)$_2$", it should be understood that the two Rx groups can be the same, or they can be different if Rx is defined as having more than one possible identity. In addition, certain substituents are drawn as —R$^x$R$^y$, where the "-" indicates a bond adjacent to the parent molecule and R$^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In accordance with one embodiment of the present invention, there is provided a compound of Formula I:

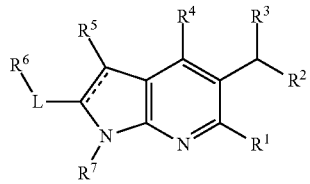

(I)

or a pharmaceutically acceptable salt thereof, wherein:

L is selected from the group consisting of a bond, a branched or straight chain (C$_1$-C$_6$)alkylene, (C$_1$-C$_6$)alkene, (C$_1$-C$_6$)alkyne, —N$_3$—, —NO$_2$—, —NR$^9$S(O)$_2$—, —S(O)—, —SO$_2$—, —S(O)$_2$R$^8$—, —NR$^9$—, —C(O)NR$^9$—, —NR$^9$C(O)NR$^9$—, —C(O)—, —C(O)R$^{15}$—, —NR$^9$C(O)OR$^9$—, —C(O)R$^9$—, —C(O)OR$^9$—, —OC(O)OR$^9$—, —OC(O)R$^9$—, —OC(O)NR$^9$—, —C(S)—, —C(S)OR$^9$—, —C(S)OR$^9$—, —C(S)NR$^9$—, —NR$^9$C(S)R$^8$—, —NR$^9$C(S)NR$^9$—, —OC(S)R$^8$—, —OC(S)OR$^9$—, —OC(S)NR$^8$—, —C(NR$^9$)OR$^9$—, —C(NR$^8$)R$^9$—, —OC(O)Y—, —OC(S)Y—, —NR$^9$C(S)Y—, —NR$^9$C(O)Y—, —C(S)Y—, —C(O)Y—, monocyclic or bicyclic (C$_6$-C$_{14}$)aryl, monocyclic or bicyclic (C$_2$-C$_9$)heterocycle, monocyclic or bicyclic (C$_2$-C$_9$)heteroaryl, monocyclic or bicyclic (C$_3$-C$_{14}$)cycloalkyl, and

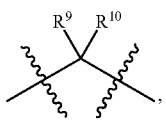

wherein the R$^9$ and R$^{19}$ groups together with the carbon atom to which they are bonded may optionally join together to form a (C$_3$-C$_7$)cycloalkyl;

R$^1$ is selected from (C$_1$-C$_6$)alkyl or (C$_3$-C$_7$)cycloalkyl;

R$^2$ is selected from the group consisting of

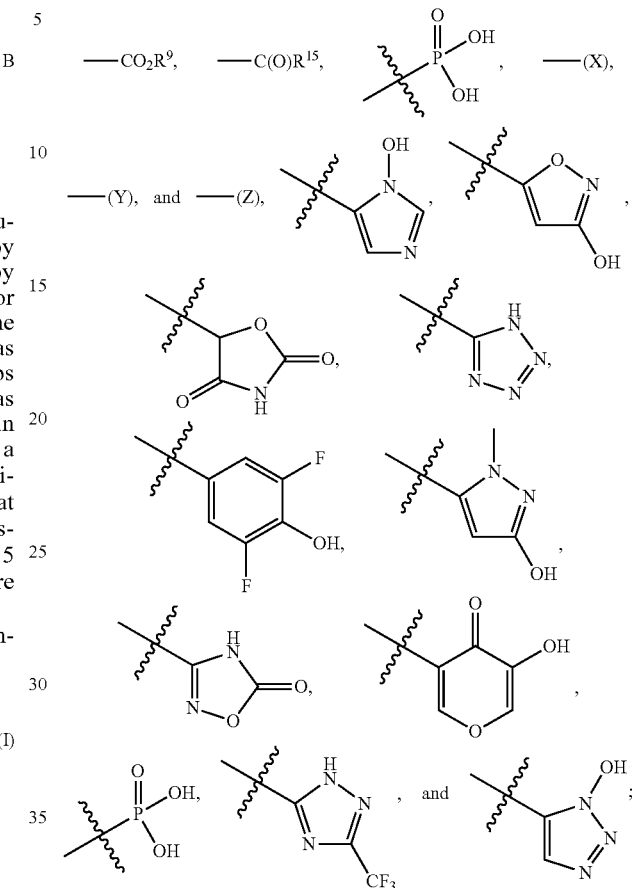

R$^3$ is selected from the group consisting of (C$_1$-C$_6$)alkyl, —OR$^{10}$, —R$^{10}$(R$^{14}$)$_q$, tetrahydrofuranyl, oxetanyl, furanyl, dioxolanyl, pyranyl, dioxanyl, dioxinyl, —O—(C$_3$-C$_7$)cycloalkyl, and —(C$_3$-C$_7$)cycloalkyl(R$^{10}$);

R$^4$ is selected from the group consisting of (C$_5$-C$_{14}$)aryl, (C$_3$-C$_7$)cycloalkyl, (C$_2$-C$_9$)heterocycle, and (C$_2$-C$_9$)heteroaryl, wherein the heterocycle and heteroaryl each comprise one to three heteroatoms selected from S, N or O, and wherein each R$^4$ group is optionally substituted by one to four substituents selected from R$^{11}$;

R$^5$ is selected from —H, (C$_1$-C$_6$)alkyl, and halogen;

R$^6$ is selected from —H, (C$_1$-C$_6$)alkyl, (C$_1$-C$_6$)alkoxy, halo, nitrile, —OR$^{10}$(C$_5$-C$_{14}$)aryl, —OR$^{10}$(C$_5$-C$_{14}$)aryl(R$^{11}$)$_m$, —(Y)(R$^{12}$)$_n$, —OR$^{10}$R$^{17}$, —R$^{10}$R$^{17}$, —R$^{17}$R$^{15}$, —R$^{10}$(R$^{14}$)$_q$, —OR$^{10}$(R$^{14}$)$_q$, —OR$^{10}$(Y), —OR$^{10}$R$^{18}$, —OSO$_2$R$^{15}$, —R$^{15}$, —(C$_5$-C$_{14}$)aryl, —C(O)(Y), —C(O)R$^{15}$, —R$^{10}$(C$_5$-C$_{14}$)aryl, —R$^{10}$R$^{15}$, —(C$_5$-C$_{14}$)arylR$^{15}$—(X), —(Y), —(Z), —(X)—(X), —(X)—(Y), —(X)—(Z), —(Y)—(X), —(Y)—(Y), —(Y)—(Z), —(Z)—(X), —(Z)—(Y), and —(Z)—(Z), and wherein each R$^6$ group is optionally substituted by one to four substituents selected from R$^{13}$, and wherein when L is a bond, then R$^5$ and R$^6$ together with the carbon atoms to which they are bonded may optionally join together to form a (C$_5$-C$_{14}$)aryl, or alternatively, when L is a bond, then R$^6$ and R$^7$ together with the carbon atoms to which they are bonded may optionally join together to form a (C$_3$-C$_7$)heterocycle;

R⁷ is selected from the group consisting of —H, $(C_1-C_6)$ alkyl, $(C_1-C_6)$alkoxy, halo, $(C_3-C_7)$cycloalkyl, —$R^{10}(R^{14})_q$, and oxetanyl;

R⁸ is selected from the group consisting of —H, $(C_1-C_6)$ alkyl, —NH—, and —C(O)NH—;

R⁹ is independently selected from —H and $(C_1-C_6)$alkyl;

R¹⁰ is $(C_1-C_6)$alkyl;

R¹¹, R¹², and R¹³ are independently selected from the group consisting of $(C_1-C_6)$alkyl, $(C_1-C_6)$alkoxy, butoxycarbonyl, oxo, —$R^{10}OR^{10}$, halo, —$R^{15}$, —$R^{10}(R^{14})_q$, —$OR^{10}(R^{14})_q$, —$SO_2R^{10}$; —$C(O)R^{10}$, —$C(O)R^{15}$, and —$R^{10}R^{17}$;

R¹⁴ is halo;

R¹⁵ is —$N(R^{16})_2$;

R¹⁶ is independently selected from the group consisting of —H, $(C_1-C_6)$alkyl, hydroxyl, —$SO_2R^{10}$, —$SO_2N(R^{10})_2$, —$C(O)NHR^{10}$, —$C(O)R^{18}$, and —$(C_5-C_{14})$aryl$(R^{11})$;

R¹⁷ is —$OR^9$;

R¹⁸ is —$CO_2R^9$;

X is a monocyclic or bicyclic $(C_5-C_{14})$aryl or —$C(O)(C_5-C_{14})$aryl, wherein each aryl of X is optionally substituted by one to four substituents independently selected from R¹¹;

Y is independently selected from a monocyclic or bicyclic $(C_2-C_9)$heterocycle or —O(O) $(C_2-C_9)$heterocycle; or monocyclic or bicyclic $(C_2-C_9)$heteroaryl or —C(O) $(C_2-C_9)$heteroaryl, each heterocycle or heteroaryl having one to four heteroatoms selected from S, N or O, and wherein each heterocycle or heteroaryl of Y is optionally substituted by one to four substituents independently selected from R¹²;

Z is a monocyclic or bicyclic $(C_3-C_{14})$cycloalkyl or —$C(O)(C_3-C_{14})$cycloalkyl, wherein each cycloalkyl of Z is optionally substituted by one to four substituents independently selected from R¹³;

m is zero or an integer selected from 1, 2, 3, or 4;

n is zero or an integer selected from 1, 2, or 3;

p is zero or an integer selected from 1, 2, or 3; and q is an integer selected from 1, 2, or 3.

In accordance with another embodiment of the present invention, there is provided a compound of Formula I, wherein L is selected from the group consisting of a bond, methylene, ethylene, ethane, ethyne, —$NHS(O)_2$—, —S(O)—, —$SO_2$—, —NH—, —C(O)NH—, —NHC(O) NH—, —C(O)—, —C(S)—, —C(S)NH—, monocyclic or bicyclic $(C_6-C_{14})$aryl, monocyclic or bicyclic $(C_2-C_9)$heterocycle, monocyclic or bicyclic $(C_2-C_9)$heteroaryl, and

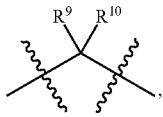

wherein the R⁹ and R¹⁰ groups together with the carbon atom to which they are bonded may optionally join together to form a cyclopropyl ring.

In accordance with another embodiment of the present invention, there is provided a compound of Formula I, wherein L is selected from the group consisting of a bond, —$NHS(O)_2$—, —S(O)—, —$SO_2$—, —NH—, —C(O) NH—, —NHC(O)NH—, —C(O)—, —C(S)—, —C(S) NH—, methylene, ethylene, ethyne, ethane, pyridinyl, pyrimidinyl, phenyl, dihydrobenzopyranyl, naphthalenyl, acetidinyl, pyrrolyl, pyrrolidinyl, pyrrolinyl, piperidinyl, morpholinyl, oxetanyl, pyranyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, tetrahydropyridoquinolinyl, pyrazolopyridine, benzoimidazole, pyridinone, benzotriazole, imidazopyridine, thienyl, isothiazolyl, triazolyl, imidazolyl, imidazolinyl, isoxazolyl, pyrrolyl, pyrazolyl, pyridazinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

In accordance with another embodiment of the present invention, there is provided a compound of Formula I, wherein L is a bond.

In accordance with another embodiment of the present invention, there is provided a compound of Formula I, In accordance with another embodiment of the present invention, there is provided a compound of Formula I, wherein L is methylene.

In accordance with another embodiment of the present invention, there is provided a compound of Formula I, wherein R¹ is selected from the group consisting of methyl, ethyl, and cyclopropyl.

In accordance with another embodiment of the present invention, there is provided a compound of Formula I, wherein R¹ is methyl.

In accordance with another embodiment of the present invention, there is provided a compound of Formula I, wherein R² is selected from the group consisting of carboxyl, hydroxyamide, hydroxymethylamide, methylsulfonylamide,

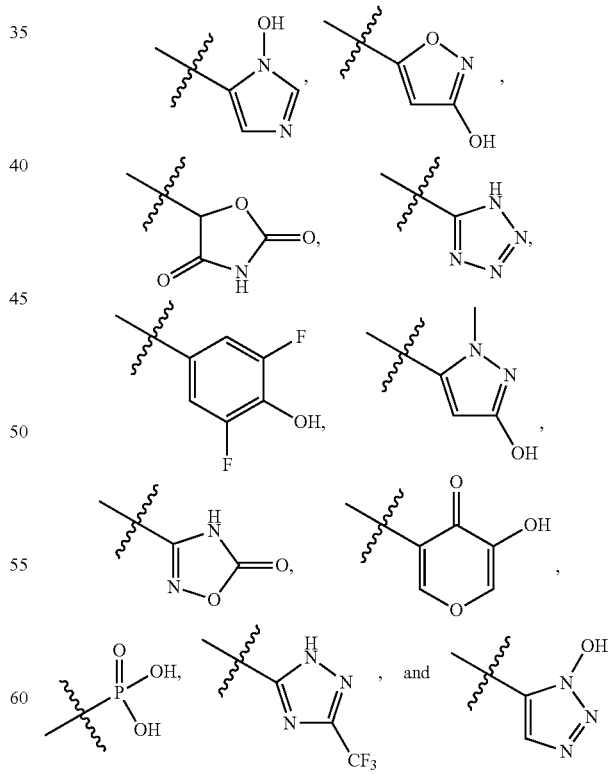

In accordance with another embodiment of the present invention, there is provided a compound of Formula I, wherein R² is carboxyl.

In accordance with another embodiment of the present invention, there is provided a compound of Formula I, wherein $R^3$ is selected from the group consisting of methyl, ethyl, propyl, butyl, methoxy, ethoxy, propoxy, butoxy, pentoxy, tetrahydrofuranyl, oxetanyl, furanyl, dioxolanyl, pyranyl, dioxanyl, dioxinyl, fluoromethyl, difluoromethyl, trifluoromethyl, cyclopropoxy, cyclobutoxy, cyclopentoxy, and methylcyclobutoxy.

In accordance with another embodiment of the present invention, there is provided a compound of Formula I, wherein $R^3$ is butoxy.

In accordance with another embodiment of the present invention, there is provided a compound of Formula I, wherein $R^3$ is tert-butoxy.

In accordance with another embodiment of the present invention, there is provided a compound of Formula I, wherein $R^4$ is selected from the group consisting of ($C_5$-$C_{14}$) aryl, ($C_3$-$C_7$)cycloalkyl, ($C_2$-$C_9$)heterocycle, and ($C_2$-$C_9$)heteroaryl, wherein the heterocycle and heteroaryl each comprise one to three heteroatoms selected from S, N or O, and wherein each $R^4$ group is optionally substituted by one to four substituents selected from $R^{11}$.

In accordance with another embodiment of the present invention, there is provided a compound of Formula I, wherein $R^4$ is selected from the group consisting of phenyl, dihydrobenzopyranyl, dihydrooxazine, naphthalenyl, pyridinyl, pyrrolyl, pyrrolidinyl, pyrrolinyl, piperidinyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, cyclohexenyl, furanyl, pyrazolyl, and tetrahydropyridoquinolinyl, and wherein each $R^4$ group is optionally substituted by one to four substituents selected from $R^{11}$.

In accordance with another embodiment of the present invention, there is provided a compound of Formula I, wherein $R^4$ is selected from phenyl or dihydrooxazine, and wherein each $R^4$ group is optionally substituted by one to four substituents selected from $R^{11}$.

In accordance with another embodiment of the present invention, there is provided a compound of Formula I, wherein $R^4$ is dihydrooxazine, and wherein each $R^4$ group is optionally substituted by one to four substituents selected from $R^{11}$.

In accordance with another embodiment of the present invention, there is provided a compound of Formula I, wherein $R^4$ is phenyl, and wherein each $R^4$ group is optionally substituted by one to four substituents selected from $R^{11}$.

In accordance with another embodiment of the present invention, there is provided a compound of Formula I, wherein $R^4$ is optionally substituted by one to three groups selected from methyl, ethyl, oxo, methoxy, ethoxy, propoxy, methoxymethyl, flouro, chloro, bromo, trifluoromethoxy, trifluoromethyl, methylsulfonyl, dimethylamide, cyclohexyloxy, acetyl, and fluoromethyl.

In accordance with another embodiment of the present invention, there is provided a compound of Formula I, wherein $R^4$ is optionally substituted by one to three groups selected from methyl, methoxy, flouro, chloro, trifluoromethoxy, trifluoromethyl, and acetyl.

In accordance with another embodiment of the present invention, there is provided a compound of Formula I, wherein $R^4$ is substituted by one to two groups selected from methyl, flouro, chloro.

In accordance with another embodiment of the present invention, there is provided a compound of Formula I, wherein $R^4$ is substituted by one to two groups selected from methyl and fluoro.

In accordance with another embodiment of the present invention, there is provided a compound of Formula I, wherein $R^4$ is substituted by one to two methyl groups.

In accordance with another embodiment of the present invention, there is provided a compound of Formula I, wherein $R^4$ is substituted by one methyl group.

In accordance with another embodiment of the present invention, there is provided a compound of Formula I, wherein $R^4$ is substituted by one or two fluoro groups.

In accordance with another embodiment of the present invention, there is provided a compound of Formula I, wherein $R^4$ is substituted by one to two chloro groups.

In accordance with another embodiment of the present invention, there is provided a compound of Formula I, wherein $R^4$ is substituted by one to two methoxy groups.

In accordance with another embodiment of the present invention, there is provided a compound of Formula I, wherein $R^5$ is hydrogen.

In accordance with another embodiment of the present invention, there is provided a compound of Formula I, wherein $R^6$ is independently selected from the group consisting of —H, methyl, ethyl, propyl, butyl, hydroxyl, fluoro, chloro, bromo, methoxy, ethoxy, propoxy, methoxyethoxy, cyclopropyl, cyclohexyl, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, dimethylpyrazolyl, pyrazolyl, methoxypyridinyl, dimethylisoxazotyl, pyridinyl, pyrimidinyl, phenyl, dihydrobenzopyranyl, naphthalenyl, acetidinyl, pyrrolyl, pyrrolidinyl, pyrrolinyl, piperidinyl, morpholinyl, oxetanyl, pyranyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazotyl, furanyl, pyrazolyl, tetrahydropyridoquinolinyl, pyrazolopyridine, benzoimidazole, pyridinone, benzotriazole, imidazopyridine, thienyl, isothiazolyl, triazolyl, imidazolyl, imidazolinyl, isoxazolyl, pyrrolyl, pyrazolyl, pyridazinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indotizinyl, dihydroindolyl, indazolyl, indolinyl, benzoxazolyl, quinolyl, isoquinolyl, quinolizyl, quianazolyl, quinoxatyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

In accordance with another embodiment of the present invention, there is provided a compound of Formula I, wherein $R^6$ is substituted by zero to four substituents selected from the group consisting of halo, $(C_1-C_6)$alkyl, $(C_1-C_6)$alkoxy, trifluoroalkyl, trifluoroalkoxy, triazolyl, and butoxycarbonyl.

In accordance with another embodiment of the present invention, there is provided a compound of Formula I, wherein $R^6$ is substituted by zero to four substituents selected from the group consisting of chloro, fluoro, methyl, methoxy, trifluoromethyl, and trifluoromethoxy.

In accordance with another embodiment of the present invention, there is provided a compound of Formula I, wherein $R^6$ is pyridine.

In accordance with another embodiment of the present invention, there is provided a compound of Formula I, wherein $R^6$ is substituted by one to three fluoro groups.

In accordance with another embodiment of the present invention, there is provided a compound of Formula I, wherein $R^6$ is substituted by two fluoro groups.

In accordance with another embodiment of the present invention, there is provided a compound of Formula I, wherein $R^5$ and $R^6$ together with the carbon atoms to which they are bonded join together to form a $(C_4-C_7)$cycloalkyl, $(C_2-C_9)$heterocycle, or $(C_5-C_{14})$aryl ring.

In accordance with another embodiment of the present invention, there is provided a compound of Formula I, wherein $R^5$ and $R^6$ together with the carbon atoms to which they are bonded join together to form a $(C_5-C_{14})$aryl ring.

In accordance with another embodiment of the present invention, there is provided a compound of Formula I, In accordance with another embodiment of the present invention, there is provided a compound of Formula I, The compound according to claim 1, wherein $R^5$ and $R^6$ together with the carbon atoms to which they are bonded join together to form a phenyl ring.

In accordance with another embodiment of the present invention, there is provided a compound of Formula I, wherein $R^5$ and $R^6$ together with the carbon atoms to which they are bonded join together to form a $(C_4-C_7)$cycloalkyl ring.

In accordance with another embodiment of the present invention, there is provided a compound of Formula I, wherein $R^5$ and $R^6$ together with the carbon atoms to which they are bonded join together to form a cyclohexyl ring.

In accordance with another embodiment of the present invention, there is provided a compound of Formula I, wherein $R^5$ and $R^6$ together with the carbon atoms to which they are bonded join together to form a $(C_2-C_9)$heterocycle ring.

In accordance with another embodiment of the present invention, there is provided a compound of Formula I, wherein $R^5$ and $R^6$ together with the carbon atoms to which they are bonded join together to form a $(C_2-C_9)$heterocycle ring, wherein the heterocycle ring comprises one to three heteroatoms selected from S, N or O.

In accordance with another embodiment of the present invention, there is provided a compound of Formula I, wherein $R^7$ is hydrogen or methyl.

In accordance with another embodiment of the present invention, there is provided a compound of Formula I, wherein $R^7$ is methyl.

In accordance with another embodiment of the present invention, there is provided a compound of Formula I, wherein, when L is a bond, $R^6$ and $R^7$ together with the carbon atoms to which they are bonded may optionally join together to form a $(C_3-C_7)$heterocycle ring.

In accordance with another embodiment of the present invention, there is provided a compound of Formula I, wherein, when L is a bond, $R^6$ and $R^7$ together with the carbon atoms to which they are bonded may optionally join together to form a $(C_3-C_7)$heterocycle ring, wherein the heterocycle ring comprises one nitrogen heteroatom.

In accordance with another embodiment of the present invention, there is provided a compound of Formula I, wherein, when L is a bond, $R^6$ and $R^7$ together with the carbon atoms to which they are bonded may optionally join together to form a pyrrolidinyl ring.

In accordance with another embodiment of the present invention, there is provided a compound of Formula I, wherein $R^9$ is independently selected from the group consisting of —H, methyl, ethyl, propyl, isopropyl, butyl, isobutyl, tert-butyl, pentyl, and septyl.

In accordance with another embodiment of the present invention, there is provided a compound of Formula I, wherein $R^9$ is independently selected from the group consisting of methyl, ethyl, propyl, isopropyl, butyl, isobutyl, tert-butyl, pentyl, and septyl.

In accordance with another embodiment of the present invention, there is provided a compound of Formula I, wherein $R^9$ is methyl.

In accordance with another embodiment of the present invention, there is provided a compound of Formula I, wherein $R^9$ is —H.

In accordance with another embodiment of the present invention, there is provided a compound of Formula I, wherein $R^{10}$ is independently selected from the group consisting of methyl, ethyl, propyl, isopropyl, butyl, isobutyl, tert-butyl, penty and septyl.

In accordance with another embodiment of the present invention, there is provided a compound of Formula I, wherein $R^{10}$ is independently selected from the group consisting of methyl.

In accordance with another embodiment of the present invention, there is provided a compound of Formula I, wherein $R^{11}$, $R^{12}$, and $R^{13}$ are independently selected from the group consisting of —H, methyl, ethyl, methoxy, ethoxy, oxo, chloro, fluoro, bromo, trifluoromethyl, trifluoromethoxy, methylsulfonyl, —C(O)methyl, —C(O)$R^{15}$, and methylmethoxy.

In accordance with another embodiment of the present invention, there is provided a compound of Formula I, wherein $R^{11}$, $R^{12}$, and $R^{13}$ are independently selected from the group consisting of —H, methyl, methoxy, chloro, and fluoro.

In accordance with another embodiment of the present invention, there is provided a compound of Formula I, wherein $R^{11}$, $R^{12}$, and $R^{13}$ are independently —H or methyl.

In accordance with another embodiment of the present invention, there is provided a compound of Formula I, wherein $R^{16}$ is independently selected from the group consisting of —H, methyl, ethyl, hydroxyl, methylsulfonyl, —SO$_2$N(methyl)$_2$, —C(O)NHmethyl, and —C(O)$R^{18}$.

In accordance with another embodiment of the present invention, there is provided a compound of Formula I, wherein X is phenyl, wherein phenyl is optionally substituted by one to four substituents independently selected from $R^{11}$.

In accordance with another embodiment of the present invention, there is provided a compound of Formula I, wherein Y is benzoxazinyl, pyridinyl, pyrimidinyl, oxanyl, indolyl, indazolyl, piperazinyl, dihydroindolyl, tetrahydropyridinyl, thiazolyl, tetrahydroquinolinyl, dihydrobenzopyranyl, naphthalenyl, acetidinyl, pyrrolyl, pyrrolidinyl, pyrrolinyl, piperidinyl, morpholinyl, oxetanyl, pyranyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, pyridinyl, pyrimidinyl, dihydrobenzopyranyl, naphthalenyl, acetidinyl, pyrrolyl, pyrrolidinyl, pyrrolinyl, piperidinyl, morpholinyl, oxetanyl, pyranyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, tetrahydropyridoquinolinyl, pyrazolopyridine, benzoimidazole, pyridinone, benzotriazole, imidazopyridine, thienyl, isothiazolyl, triazolyl, imidazolyl, imidazolinyl, isoxazolyl, pyrrolyl, pyrazolyl, pyridazinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl, tetrahydropyridoquinolinyl, wherein Y is optionally substituted by one to four substituents independently selected from $R^{12}$.

In accordance with another embodiment of the present invention, there is provided a compound of Formula I, wherein Z is selected from the group consisting of cyclopropyl, cyclobutyl, cyclohexyl, and cycloheptyl, wherein Z is optionally substituted by one to four substituents independently selected from $R^{13}$.

In accordance with another embodiment of the present invention, there is provided a compound that is selected from the group consisting of:

2S)(M)-2-(tert-butoxy)-2-(1,6-dimethyl-2-(2-(1-methyl-1H-indazol-5-yl)pyridin-4-yl)-4-(5-methylchroman-6-yl)-1H-pyrrolo[2,3-b]pyridin-5-yl)acetic acid, (2S)-2-(tert-butoxy)-2-[4-(8-fluoro-5-methyl-3,4-dihydro-2H-1-benzopyran-6-yl)-1,6-dimethyl-2-{2-[3-(morpholin-4-yl)azetidin-1-yl]pyridin-4-yl}-1H-pyrrolo[2,3-b]pyridin-5-yl]acetic acid, (2S)-2-(tert-butoxy)-2-[4-(8-fluoro-5-methyl-3,4-dihydro-2H-1,4-benzoxazin-6-yl)-1,6-dimethyl-2-[2-(1-methyl-1H-indazol-5-yl)pyridin-4-yl]-1H-pyrrolo[2,3-b]pyridin-5-yl]acetic acid, (2S)-2-(tert-butoxy)-2-[1,6-dimethyl-2-(2-{1-methyl-1H-pyrazolo[3,4-b]pyridin-5-yl}pyridin-4-yl)-4-(5-methyl-3,4-dihydro-2H-1-benzopyran-6-yl)-1H-pyrrolo[2,3-b]pyridin-5-yl]acetic acid, (2S)-2-(tert-butoxy)-2-(2-{2-[2-(dimethylamino)pyrimidin-5-yl]pyridin-4-yl}-4-(8-fluoro-5-methyl-3,4-dihydro-2H-1-benzopyran-6-yl)-1,6-dimethyl-1H-pyrrolo[2,3-b]pyridin-5-yl)acetic acid, (2S)-2-(tert-butoxy)-2-[4-(8-fluoro-5-methyl-3,4-dihydro-2H-1-benzopyran-6-yl)-1,6-dimethyl-2-[2-(pyridin-3-yl)pyridin-4-yl]-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-6-methyl-2-[2-(1-methyl-1H-indazol-5-yl)pyridin-4-yl]-1-(2,2,2-trifluoroethyl)-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-[2-(1-methyl-2,3-dihydro-1H-indol-5-yl)pyridin-4-yl]-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-{2-[1-(oxan-4-yl)-1H-pyrazol-4-yl]pyridin-4-yl}-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-[2-(4-methylpiperazin-1-yl)pyridin-4-yl]-1H-pyrrolo[2,3-b]pyridin-5-yl] acetic acid, (2S)-2-(tert-butoxy)-2-[4-(8-fluoro-5-methyl-3,4-dihydro-2H-1-benzopyran-6-yl)-1,6-dimethyl-2-{[4-(1-methyl-1H-indazol-5-yl)piperazin-1-yl]carbonyl}-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-{[(4-methylpiperazin-1-yl)carbonyl]amino}-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-(pyridine-3-sulfonamido)-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-(pyridine-3-amido)-1H-pyrrolo[2,3-b]pyridin-5-yl]acetic acid, (2S)-2-(tert-butoxy)-2-[4-(4-chlorophenyl)-1,6-dimethyl-2-[2-(1-methyl-1H-indazol-5-yl)pyridin-4-yl]-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-{2-[(4-methylpiperazin-1-yl)carbonyl]pyridin-4-yl}-1H-pyrrolo[2,3-b]pyridin-5-yl]acetic acid, (2S)-2-[2-(3-amino-3-methylbut-1-yn-1-yl)-4-(8-fluoro-5-methyl-3,4-dihydro-2H-1-benzopyran-6-yl)-1,6-dimethyl-1H-pyrrolo[2,3-b]pyridin-5-yl]-2-(tert-butoxy)acetic acid, (2S)-2-(tert-butoxy)-2-[4-(8-fluoro-5-methyl-3,4-dihydro-2H-1-benzopyran-6-yl)-1,6-dimethyl-2-[6-(1-methyl-1H-indazol-5-yl)pyridin-3-yl]-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-{1-[(pyridin-3-yl)carbonyl]-1,2,3,6-tetrahydropyridin-4-yl}-1H-pyrrolo[2,3-b]pyridin-5-yl]acetic acid, (2S)-2-(tert-butoxy)-2-[4-(8-fluoro-5-methyl-3,4-dihydro-2H-1-benzopyran-6-yl)-1,6-dimethyl-2-{4-[(pyridin-3-yl)carbonyl]piperazin-1-yl}-1H-pyrrolo[2,3-b]pyridin-5-yl]acetic acid, (2S)-2-(tert-butoxy)-2-[4-(4-chlorophenyl)-1,6-dimethyl-2-[2-(pyridin-3-yl)-1,3-thiazol-4-yl]-1H-pyrrolo[2,3-b]pyridin-5-yl]acetic acid, (2S)-2-[2-(1-acetyl-1,2,3,4-tetrahydroquinolin-7-yl)-4-(4-chlorophenyl)-1,6-dimethyl-1H-pyrrolo[2,3-b]pyridin-5-yl]-2-(tert-butoxy)acetic acid, (2S)-2-{2-[(4-acetylpiperazin-1-yl)methyl]-4-(4-chlorophenyl)-1,6-dimethyl-1H-pyrrolo[2,3-b]pyridin-5-yl}-2-(tert-butoxy)acetic acid, (2S)-2-(tert-butoxy)-2-{1,6-dimethyl-2-[2-(1-methyl-1H-indazol-5-yl)pyridin-4-yl]-4-(piperidin-1-yl)-1H-pyrrolo[2,3-b]pyridin-5-yl}acetic acid, and (2S)-2-(tert-butoxy)-2-[4-(8-fluoro-5-methyl-3,4-dihydro-2H-1-benzopyran-6-yl)-1,6-dimethyl-2-{2-[4-(oxetan-3-yl)piperazin-1-yl]pyridin-4-yl}-1H-pyrrolo[2,3-b]pyridin-5-yl]acetic acid, and pharmaceutically acceptable salts thereof.

In accordance with another embodiment of the present invention, there is provided a compound as defined in Table 1 or Table 2, wherein the compound is in its racemic form and not as an individual isomer.

In accordance with another embodiment of the present invention, there is provided a compound as defined in Formula I, or any of Tables 1 or 2, wherein the compound is in the form of a salt.

In accordance with another embodiment of the present invention, there is provided a compound as defined in Formula I, or any of Tables 1 or 2, wherein the compound is in the form of a trifluoroacetic acid salt.

In accordance with another embodiment of the present invention, there is provided a compound as defined in Formula I, or any of Tables 1 or 2, wherein there is use of a compound or salt thereof in the manufacture of a medicament for use in the treatment of a viral infection in a human.

In accordance with another embodiment of the present invention, there is provided a therapeutically effective amount of a compound as defined in Formula I or any of Tables 1 or 2, wherein the compound is in the form of a pharmaceutical composition comprising a pharmaceutically acceptable diluent.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I or any of Tables 1 or 2.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, or any of Tables 1 or 2, wherein said virus is an HIV virus.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, or any of Tables 1 or 2, wherein said virus is an HIV virus and further comprising administration of a therapeutically effective amount of one or more agents active against an HIV virus.

In accordance with another embodiment of the present invention, there is provided a method for preventing or treating a viral infection in a mammal mediated at least in part by a virus in the retrovirus family of viruses which method comprises administering to a mammal, that has been diagnosed with said viral infection or is at risk of developing said viral infection, a compound as defined in Formula I, or any of Tables 1 or 2, wherein said virus is an HIV virus and further comprising administration of a therapeutically effective amount of one or more agents active against an HIV virus, wherein said agent active against the HIV virus is selected from the group consisting of Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

Such compounds of the invention can exist in particular geometric or stereoisomeric forms. The invention contemplates all such compounds, including cis- and trans-isomers, (−)- and (+)-enantiomers, (R)- and (S)-enantiomers, (P)- and (M)-atropisomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, and their racemic forms are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formulas I, II, or III, wherein the compound or salt of the compound is used in the manufacture of a medicament for use in the treatment of a viral infection in a human.

In another embodiment of the invention, there is provided a pharmaceutical composition comprising a pharmaceutically acceptable diluent and a therapeutically effective amount of a compound as defined in Formulas I, II, or III.

In one embodiment, the pharmaceutical formulation containing a compound of Formulas I, II, or III or a salt thereof is a formulation adapted for parenteral administration. In another embodiment, the formulation is a long-acting parenteral formulation. In a further embodiment, the formulation is a nano-particle formulation.

The compounds of the present invention and their salts, solvates, or other pharmaceutically acceptable derivatives thereof, may be employed alone or in combination with other therapeutic agents. The compounds of the present invention and any other pharmaceutically active agent(s) may be administered together or separately and, when administered separately, administration may occur simultaneously or sequentially, in any order. The amounts of the compounds of the present invention and the other pharmaceutically active agent(s) and the relative timings of administration will be selected in order to achieve the desired combined therapeutic effect. The administration in combination of a compound of the present invention and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formulas I, II, or III or salts thereof and the other pharmaceutically active agent(s) and the relative timings of administration will be selected in order to achieve the desired combined therapeutic effect.

As such, the compounds of the present invention may be used in combination with one or more agents useful in the prevention or treatment of HIV.

Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Inteqrase inhibitors such as raltegravir, elvitegravir, GSK1349572, GSK1265744 and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

The scope of combinations of compounds of this invention with HIV agents is not limited to those mentioned above, but includes in principle any combination with any pharmaceutical composition useful for the treatment of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452.

Ritonavir is 10-hydroxy-2-methyl-5-(1-methyethyl)-1-1 [2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer.

SPI-452 is a compound being developed by *Sequoia* Pharmaceuticals of Gaithersburg, Md., as a pharmacological enhancer.

In one embodiment of the present invention, a compound of Formulas I, II, or III is used in combination with ritonavir. In one embodiment, the combination is an oral fixed dose combination. In another embodiment, the compound of Formulas I, II, or III is formulated as a long acting parenteral injection and ritonavir is formulated as an oral composition. In one embodiment, is a kit containing the compound of Formulas I, II, or III formulated as a long acting parenteral injection and ritonavir formulated as an oral composition. In another embodiment, the compound of Formulas I, II, or III is formulated as a long acting parenteral injection and ritonavir is formulated as an injectable composition. In one embodiment, is a kit containing the compound of Formulas I, II, or III formulated as a long acting parenteral injection and ritonavir formulated as an injectable composition.

In another embodiment of the present invention, a compound of Formulas I, II, or III is used in combination with GS-9350. In one embodiment, the combination is an oral fixed dose combination. In another embodiment, the compound of Formulas I, II, or III is formulated as a long acting parenteral injection and GS-9350 is formulated as an oral composition. In one embodiment, is a kit containing the compound of Formulas I, II, or III formulated as a long acting parenteral injection and GS-9350 formulated as an oral composition. In another embodiment, the compound of Formulas I, II, or III is formulated as a long acting parenteral injection and GS-9350 is formulated as an injectable composition. In one embodiment, is a kit containing the compound of Formulas I, II, or III formulated as a long acting parenteral injection and GS-9350 formulated as an injectable composition.

In one embodiment of the present invention, a compound of Formulas I, II, or III is used in combination with SPI-452. In one embodiment, the combination is an oral fixed dose combination. In another embodiment, the compound of Formulas I, II, or III is formulated as a long acting parenteral injection and SPI-452 is formulated as an oral composition. In one embodiment, is a kit containing the compound of Formulas I, II, or III formulated as a long acting parenteral injection and SPI-452 formulated as an oral composition. In another embodiment, the compound of Formulas I, II, or III is formulated as a long acting parenteral injection and SPI-452 is formulated as an injectable composition. In one embodiment, is a kit containing the compound of Formulas I, II, or III formulated as a long acting parenteral injection and SPI-452 formulated as an injectable composition.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III, wherein said virus is an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III, further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formulas I, II, or III, further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In further embodiments, the compound of the present invention, or a pharmaceutically acceptable salt thereof, is chosen from the compounds set forth in Table 1 and/or Table 2 below.

TABLE 1

| Compound No. Example No. | Structure | Name |
|---|---|---|
| 1 | 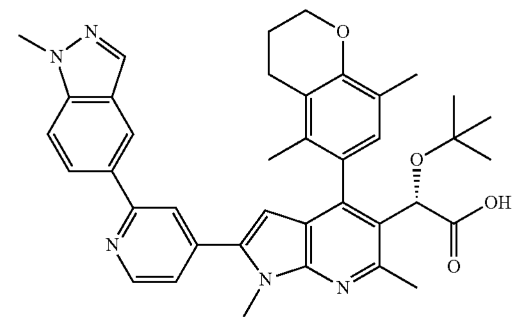 [SMILES: Cc1cc(-c2c([C@H](OC(C)(C)C)C(=O)O)c(C)nc3c2cc(-c2ccnc(-c4ccc5c(cnn5C)c4)c2)n3C)c(C)c2c1OCCC2] | (2S)(M)-2-(tert-butoxy)-2-(1,6-dimethyl-2-(2-(1-methyl-1H-indazol-5-yl)pyridin-4-yl)-4-(5-methylchroman-6-yl)-1H-pyrrolo[2,3-b]pyridin-5-yl)acetic acid |

TABLE 2

| Compound No. Example No. | Structure | Name |
|---|---|---|
| 2 | 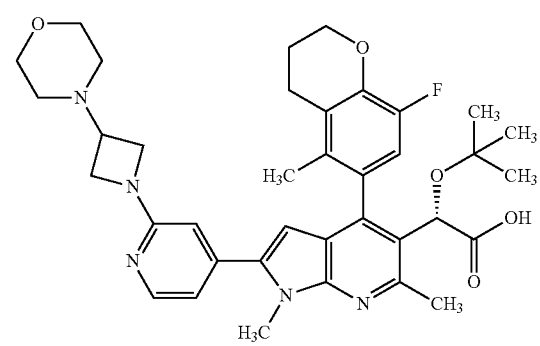 [SMILES: Cc1nc2c(cc(-c3ccnc(N4CC(N5CCOCC5)C4)c3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-{2-[3-(morpholin-4-yl)azetidin-1-yl]pyridin-4-yl}-1H-pyrrolo[2,3-b]pyridin-5-yl]acetic acid |
| 3 | 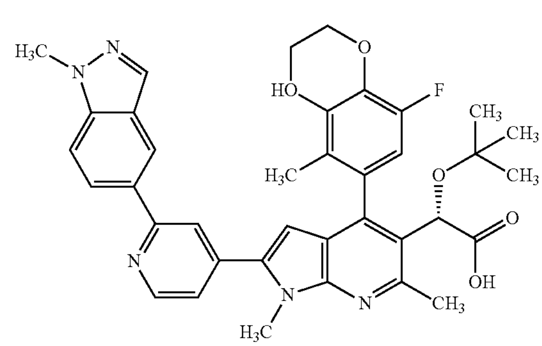 [SMILES: Cc1nc2c(cc(-c3ccnc(-c4ccc5c(cnn5C)c4)c3)n2C)c(-c2cc(F)c3c(c2C)OCCO3)c1[C@H](OC(C)(C)C)C(=O)O] | (2S)-2-(tert-butoxy)-2-[4-(8-fluoro-5-methyl-3,4-dihydro-2H-1,4-benzoxazin-6-yl)-1,6-dimethyl-2-[2-(1-methyl-1H-indazol-5-yl)pyridin-4-yl]-1H-pyrrolo[2,3-b]pyridin-5-yl]acetic acid |

TABLE 2-continued

| Compound No. Example No. | Structure | Name |
|---|---|---|
| 4 | 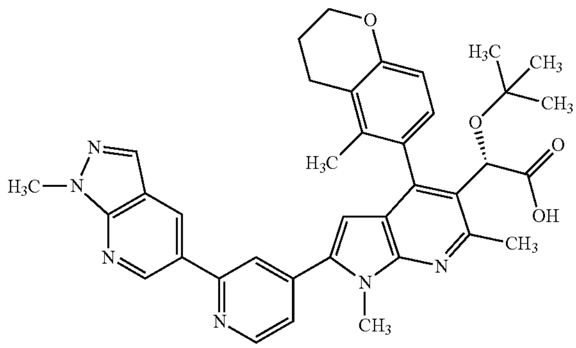 [SMILES: Cc1nc2c(cc(-c3ccnc(-c4cnc5c(cnn5C)c4)c3)n2C)c(-c2ccc3c(c2C)CCCO3)c1[C@H](OC(C)(C)C)C(=O)O] | (2S)-2-(tert-butoxy)-2-[1,6-dimethyl-2-(2-{1-methyl-1H-pyrazolo[3,4-b]pyridin-5-yl}pyridin-4-yl)-4-(5-methyl-3,4-dihydro-2H-1-benzopyran-6-yl)-1H-pyrrolo[2,3-b]pyridin-5-yl]acetic acid |
| 5 | 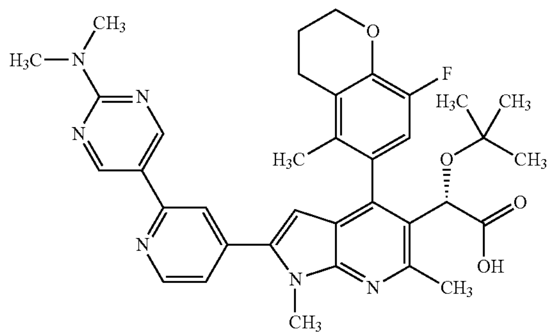 [SMILES: Cc1nc2c(cc(-c3ccnc(-c4cnc(N(C)C)nc4)c3)n2C)c(-c2cc(F)c3c(c2C)CCCO3)c1[C@H](OC(C)(C)C)C(=O)O] | (2S)-2-(tert-butoxy)-2-(2-{2-[2-(dimethylamino)pyrimidin-5-yl]pyridin-4-yl}-4-(8-fluoro-5-methyl-3,4-dihydro-2H-1-benzopyran-6-yl)-1,6-dimethyl-1H-pyrrolo[2,3-b]pyridin-5-yl)acetic acid |
| 6 | 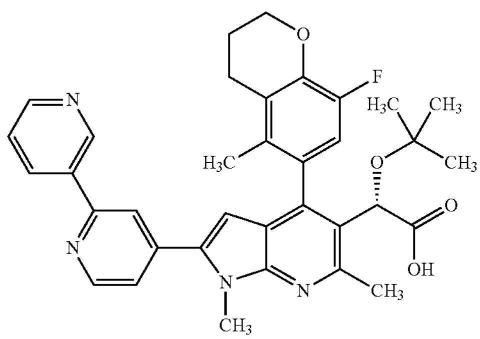 [SMILES: Cc1nc2c(cc(-c3ccnc(-c4cccnc4)c3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-[2-(pyridin-3-yl)pyridin-4-yl]-1H-pyrrolo[2,3-b]pyridin-5-yl]acetic acid |
| 7 | 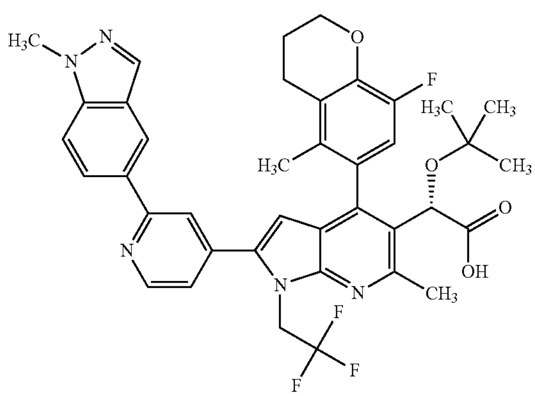 [SMILES: Cc1nc2c(cc(-c3ccnc(-c4ccc5c(cnn5C)c4)c3)n2CC(F)(F)F)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-6-methyl-2-[2-(1-methyl-1H-indazol-5-yl)pyridin-4-yl]-1-(2,2,2-trifluoroethyl)-1H-pyrrolo[2,3-b]pyridin-5-yl]acetic acid |

TABLE 2-continued

| Compound No. Example No. | Structure | Name |
|---|---|---|
| 8 | 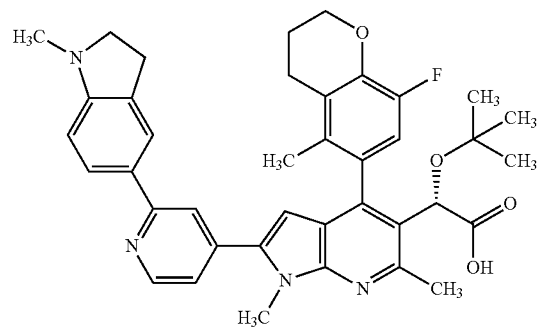 [SMILES: Cc1nc2c(cc(-c3ccnc(-c4ccc5c(c4)CCN5C)c3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-[2-(1-methyl-2,3-dihydro-1H-indol-5-yl)pyridin-4-yl]-1H-pyrrolo[2,3-b]pyridin-5-yl]acetic acid |
| 9 | 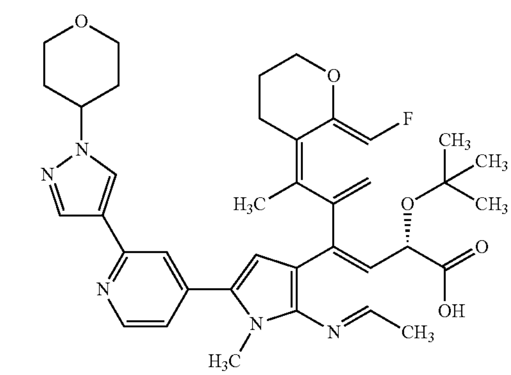 [SMILES: C=C(/C(C)=C1/CCCO/C1=C\F)/C(=C\[C@H](OC(C)(C)C)C(=O)O)c1cc(-c2ccnc(-c3cnn(C4CCOCC4)c3)c2)n(C)c1/N=C/C] | (2S)-2-(tert-butoxy)-2-[4-(8-fluoro-5-methyl-3,4-dihydro-2H-1-benzopyran-6-yl)-1,6-dimethyl-2-{2-[1-(oxan-4-yl)-1H-pyrazol-4-yl]pyridin-4-yl}-1H-pyrrolo[2,3-b]pyridin-5-yl]acetic acid |
| 10 | 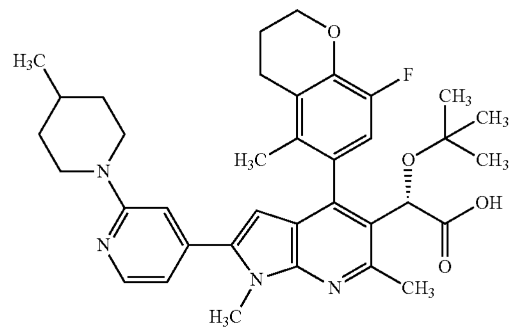 [SMILES: Cc1nc2c(cc(-c3ccnc(N4CCC(C)CC4)c3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-[2-(4-methylpiperazin-1-yl)pyridin-4-yl]-1H-pyrrolo[2,3-b]pyridin-5-yl]acetic acid |
| 11 | 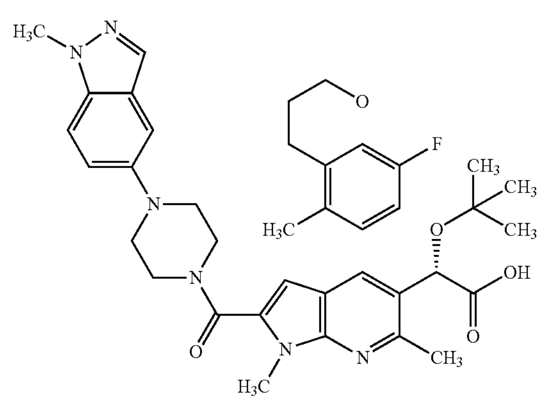 | (2S)-2-(tert-butoxy)-2-[4-(8-fluoro-5-methyl-3,4-dihydro-2H-1-benzopyran-6-yl)-1,6-dimethyl-2-{[4-(1-methyl-1H-indazol-5-yl)piperazin-1-yl]carbonyl}-1H-pyrrolo[2,3-b]pyridin-5-yl]acetic acid |

TABLE 2-continued

| Compound No. Example No. | Structure | Name |
|---|---|---|
| 12 | 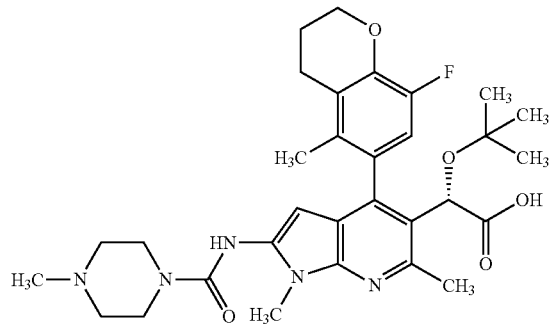 [SMILES: Cc1nc2c(cc(NC(=O)N3CCN(C)CC3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-{[(4-methylpiperazin-1-yl)carbonyl]amino}-1H-pyrrolo[2,3-b]pyridin-5-yl]acetic acid |
| 13 | 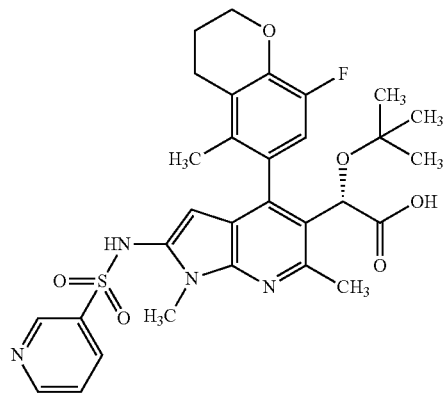 [SMILES: Cc1nc2c(cc(NS(=O)(=O)c3cccnc3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-(pyridine-3-sulfonamido)-1H-pyrrolo[2,3-b]pyridin-5-yl]acetic acid |
| 14 | 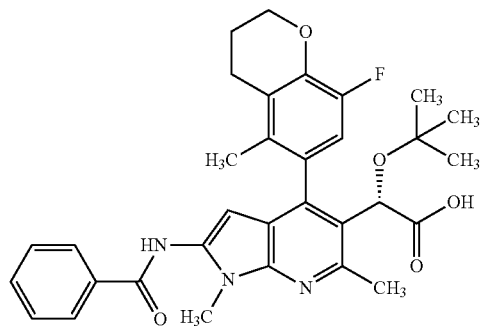 [SMILES: Cc1nc2c(cc(NC(=O)c3ccccc3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-(pyridine-3-amido)-1H-pyrrolo[2,3-b]pyridin-5-yl]acetic acid |
| 15 | 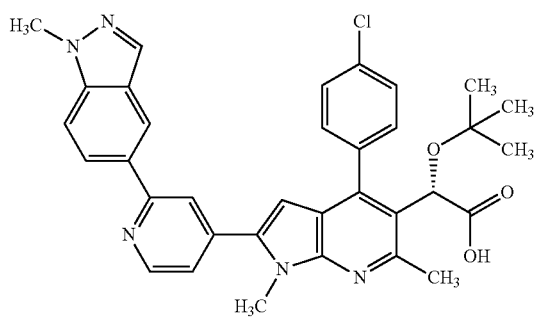 [SMILES: Cc1nc2c(cc(-c3ccnc(-c4ccc5c(cnn5C)c4)c3)n2C)c(-c2ccc(Cl)cc2)c1[C@H](OC(C)(C)C)C(=O)O] | (2S)-2-(tert-butoxy)-2-[4-(4-chlorophenyl)-1,6-dimethyl-2-[2-(1-methyl-1H-indazol-5-yl)pyridin-4-yl]-1H-pyrrolo[2,3-b]pyridin-5-yl]acetic acid |

TABLE 2-continued

| Compound No. Example No. | Structure | Name |
|---|---|---|
| 16 | 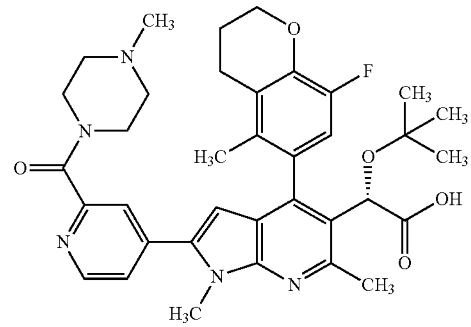 [SMILES: Cc1nc2c(cc(-c3ccnc(C(=O)N4CCN(C)CC4)c3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-{2-[(4-methylpiperazin-1-yl)carbonyl]pyridin-4-yl}-1H-pyrrolo[2,3-b]pyridin-5-yl]acetic acid |
| 17 | 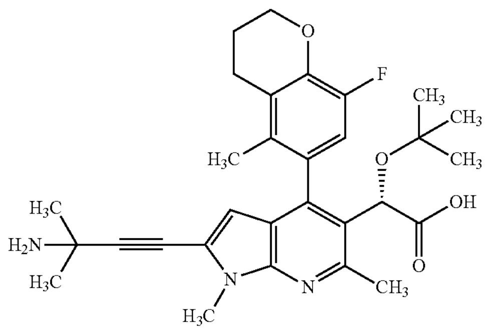 [SMILES: Cc1nc2c(cc(C#CC(C)(C)N)n2C)c(-c2cc(F)c3c(c2C)CCCO3)c1[C@H](OC(C)(C)C)C(=O)O] | (2S)-2-[2-(3-amino-3-methylbut-1-yn-1-yl)-4-(8-fluoro-5-methyl-3,4-dihydro-2H-1-benzopyran-6-yl)-1,6-dimethyl-1H-pyrrolo[2,3-b]pyridin-5-yl]-2-(tert-butoxy)acetic acid |
| 18 | 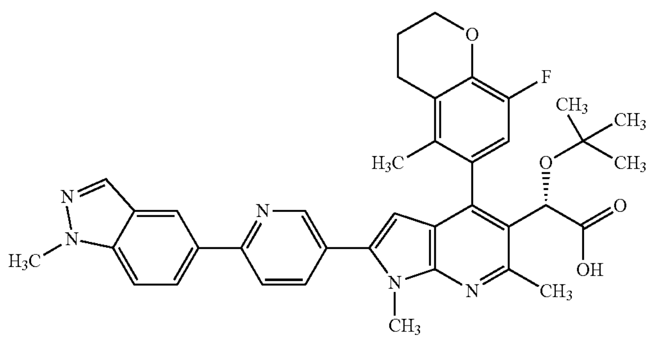 [SMILES: Cc1nc2c(cc(-c3ccc(-c4ccc5c(cnn5C)c4)nc3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-[6-(1-methyl-1H-indazol-5-yl)pyridin-3-yl]-1H-pyrrolo[2,3-b]pyridin-5-yl]acetic acid |
| 19 | 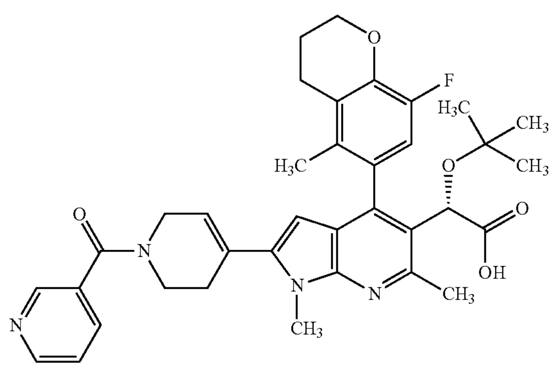 [SMILES: Cc1nc2c(cc(C3=CCN(C(=O)c4cccnc4)CC3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-{1-[(pyridin-3-yl)carbonyl]-1,2,3,6-tetrahydropyridin-4-yl}-1H-pyrrolo[2,3-b]pyridin-5-yl]acetic acid |

TABLE 2-continued

| Compound No. Example No. | Structure | Name |
|---|---|---|
| 20 | 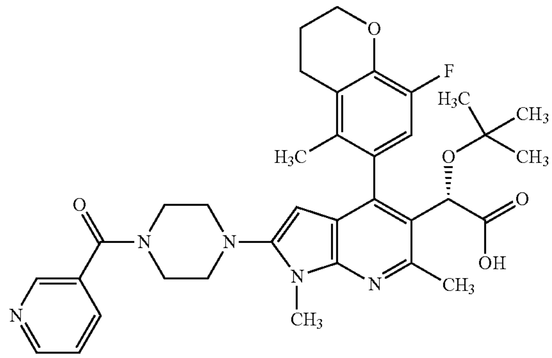 [SMILES: Cc1nc2c(cc(N3CCN(C(=O)c4cccnc4)CC3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-{4-[(pyridin-3-yl)carbonyl]piperazin-1-yl}-1H-pyrrolo[2,3-b]pyridin-5-yl]acetic acid |
| 21 | 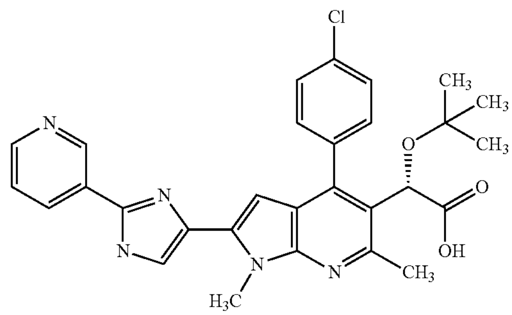 [SMILES: Cc1nc2c(cc(-c3c[nH]c(-c4cccnc4)n3)n2C)c(-c2ccc(Cl)cc2)c1[C@H](OC(C)(C)C)C(=O)O] | (2S)-2-(tert-butoxy)-2-[4-(4-chlorophenyl)-1,6-dimethyl-2-[2-(pyridin-3-yl)-1,3-thiazol-4-yl]-1H-pyrrolo[2,3-b]pyridin-5-yl]acetic acid |
| 22 | 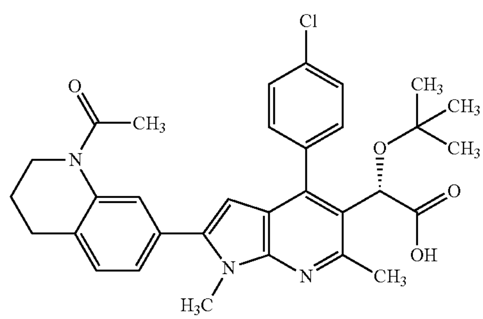 [SMILES: CC(=O)N1CCCc2ccc(-c3cc4c(-c5ccc(Cl)cc5)c([C@H](OC(C)(C)C)C(=O)O)c(C)nc4n3C)cc21] | (2S)-2-[2-(1-acetyl-1,2,3,4-tetrahydroquinolin-7-yl)-4-(4-chlorophenyl)-1,6-dimethyl-1H-pyrrolo[2,3-b]pyridin-5-yl]-2-(tert-butoxy)acetic acid |
| 23 | 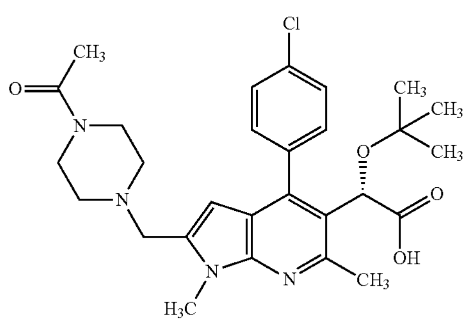 [SMILES: CC(=O)N1CCN(Cc2cc3c(-c4ccc(Cl)cc4)c([C@H](OC(C)(C)C)C(=O)O)c(C)nc3n2C)CC1] | (2S)-2-{2-[(4-acetylpiperazin-1-yl)methyl]-4-(4-chlorophenyl)-1,6-dimethyl-1H-pyrrolo[2,3-b]pyridin-5-yl}-2-(tert-butoxy)acetic acid |

TABLE 2-continued

| Compound No. Example No. | Structure | Name |
|---|---|---|
| 24 | 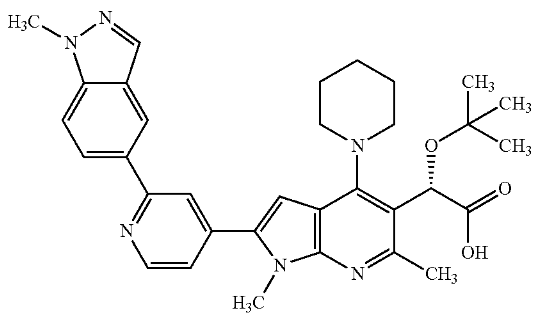 [SMILES: Cc1nc2c(cc(-c3ccnc(-c4ccc5c(cnn5C)c4)c3)n2C)c(N2CCCCC2)c1[C@H](OC(C)(C)C)C(=O)O] | (2S)-2-(tert-butoxy)-2-{1,6-dimethyl-2-[2-(1-methyl-1H-indazol-5-yl)pyridin-4-yl]-4-(piperidin-1-yl)-1H-pyrrolo[2,3-b]pyridin-5-yl}acetic acid |
| 25 | 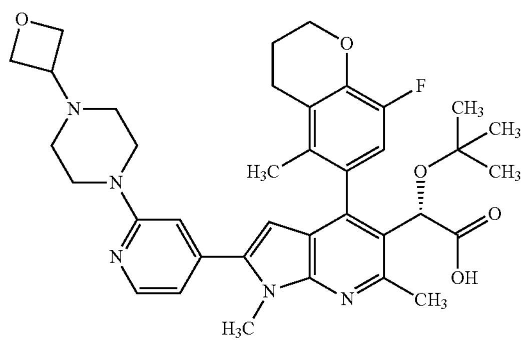 [SMILES: Cc1nc2c(cc(-c3ccnc(N4CCN(C5COC5)CC4)c3)n2C)c(-c2cc(F)c3c(c2C)CCCO3)c1[C@H](OC(C)(C)C)C(=O)O] | (2S)-2-(tert-butoxy)-2-[4-(8-fluoro-5-methyl-3,4-dihydro-2H-1-benzopyran-6-yl)-1,6-dimethyl-2-{2-[4-(oxetan-3-yl)piperazin-1-yl]pyridin-4-yl}-1H-pyrrolo[2,3-b]pyridin-5-yl]acetic acid |
| 26 | 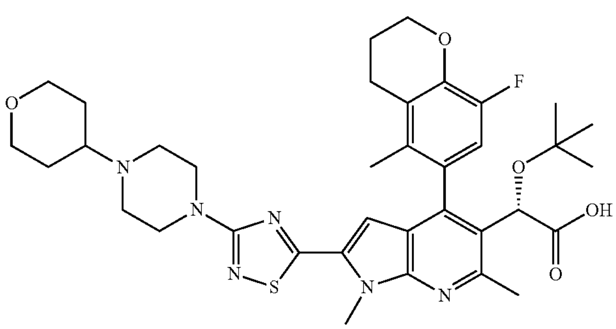 [SMILES: Cc1nc2c(cc(-c3nc(N4CCN(C5CCOCC5)CC4)ns3)n2C)c(-c2cc(F)c3c(c2C)CCCO3)c1[C@H](OC(C)(C)C)C(=O)O] | (2S)(M)-2-(tert-butoxy)-2-(4-(8-fluoro-5-methylchroman-6-yl)-1,6-dimethyl-2-(3-(4-(tetrahydro-2H-pyran-4-yl)piperazin-1-yl)-1,2,4-thiadiazol-5-yl)-1H-pyrrolo[2,3-b]pyridin-5-yl)acetic acid |
| 27 | 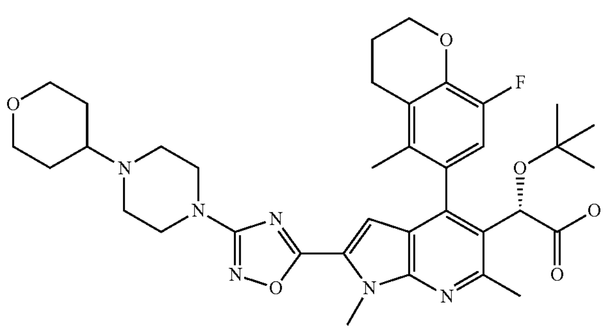 [SMILES: Cc1nc2c(cc(-c3nc(N4CCN(C5CCOCC5)CC4)no3)n2C)c(-c2cc(F)c3c(c2C)CCCO3)c1[C@H](OC(C)(C)C)C(=O)O] | (2S)(M)-2-(tert-butoxy)-2-(4-(8-fluoro-5-methylchroman-6-yl)-1,6-dimethyl-2-(3-(4-(tetrahydro-2H-pyran-4-yl)piperazin-1-yl)-1,2,4-oxadiazol-5-yl)-1H-pyrrolo[2,3-b]pyridin-5-yl)acetic acid |

TABLE 2-continued

| Compound No. Example No. | Structure | Name |
|---|---|---|
| 28 | 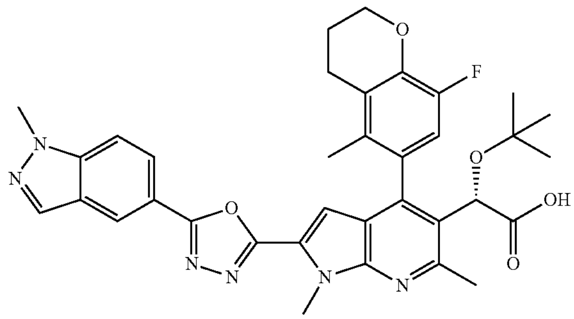 [SMILES: Cc1nc2c(cc(-c3nnc(-c4ccc5c(cnn5C)c4)o3)n2C)c(-c2cc(F)c3c(c2C)CCCO3)c1[C@H](OC(C)(C)C)C(=O)O] | (2S)(M)-2-(tert-butoxy)-2-(4-(8-fluoro-5-methylchroman-6-yl)-1,6-dimethyl-2-(5-(1-methyl-1H-indazol-5-yl)-1,3,4-oxadiazol-2-yl)-1H-pyrrolo[2,3-b]pyridin-5-yl)acetic acid |
| 29 | 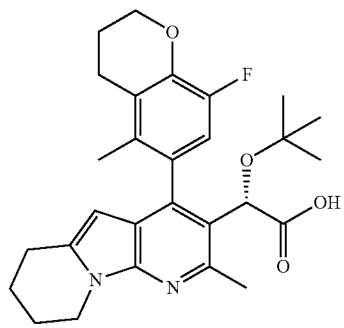 [SMILES: Cc1nc2c(cc3n2CCCC3)c(-c2cc(F)c3c(c2C)CCCO3)c1[C@H](OC(C)(C)C)C(=O)O] | (2S)(M)-2-(tert-butoxy)-2-(4-(8-fluoro-5-methylchroman-6-yl)-2-methyl-6,7,8,9-tetrahydropyrido[3,2-b]indolizin-3-yl)acetic acid |

The compounds of Table 1 were synthesized according to the synthetic methods, general schemes, and the examples described below. The compounds of Table 2 may be synthesized according to the synthetic methods, general schemes, and the examples described below.

In certain embodiments, the compound(s) of the present invention, or a pharmaceutically acceptable salt thereof, is chosen from the compounds set forth in Table 1 and/or Table 2.

Synthetic Methods

The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Ernka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=aqueous
μL=microliters
μM=micromolar
NMR=nuclear magnetic resonance
boc=tert-butoxycarbonyl
br=broad
Cbz=benzyloxycarbonyl
d=doublet
δ=chemical shift
° C.=degrees celcius
DCM=dichloromethane
dd=doublet of doublets
DMEM=Dulbeco's Modified Eagle's Medium
DMF=N,N-dimethylformamide
DMSO=dimethylsulfoxide
EtOAc=ethyl acetate
g=gram
h or hr=hours
HCV=hepatitus C virus
HPLC=high performance liquid chromatography
Hz=hertz
IU=International Units
$IC_{50}$=inhibitory concentration at 50% inhibition J=coupling constant (given in Hz unless otherwise indicated)
m=multiplet
M=molar
$M+H^+$=parent mass spectrum peak plus $H^+$
mg=milligram
min=minutes
mL=milliliter
mM=millimolar
mmol=millimole
MS=mass spectrum
nm=nanomolar
ppm=parts per million
q.s.=sufficient amount
s=singlet
RT=room temperature
sat.=saturated
t=triplet
TFA=trifluoroacetic acid Examples

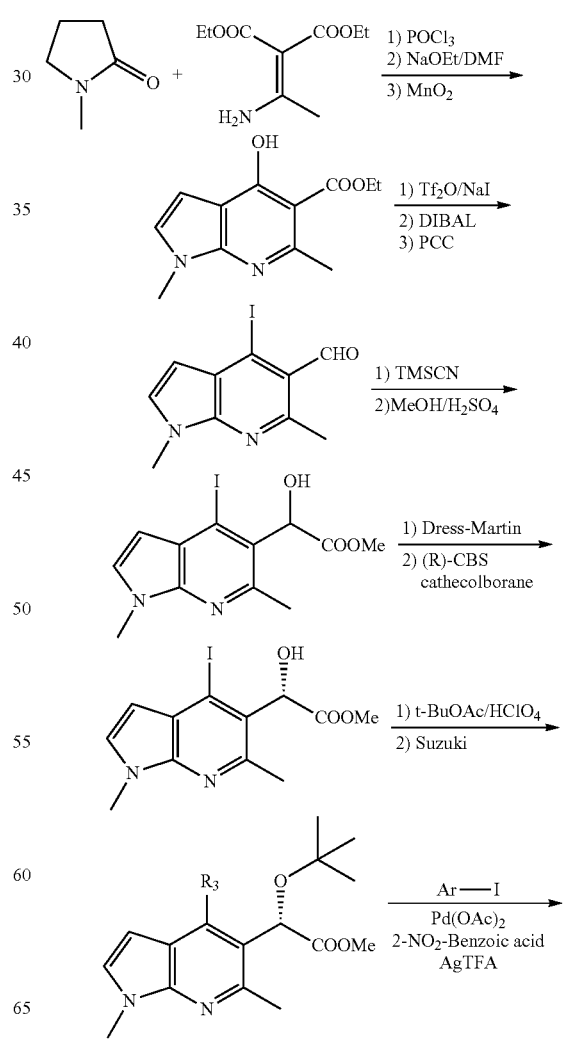

General Scheme 1

43
-continued
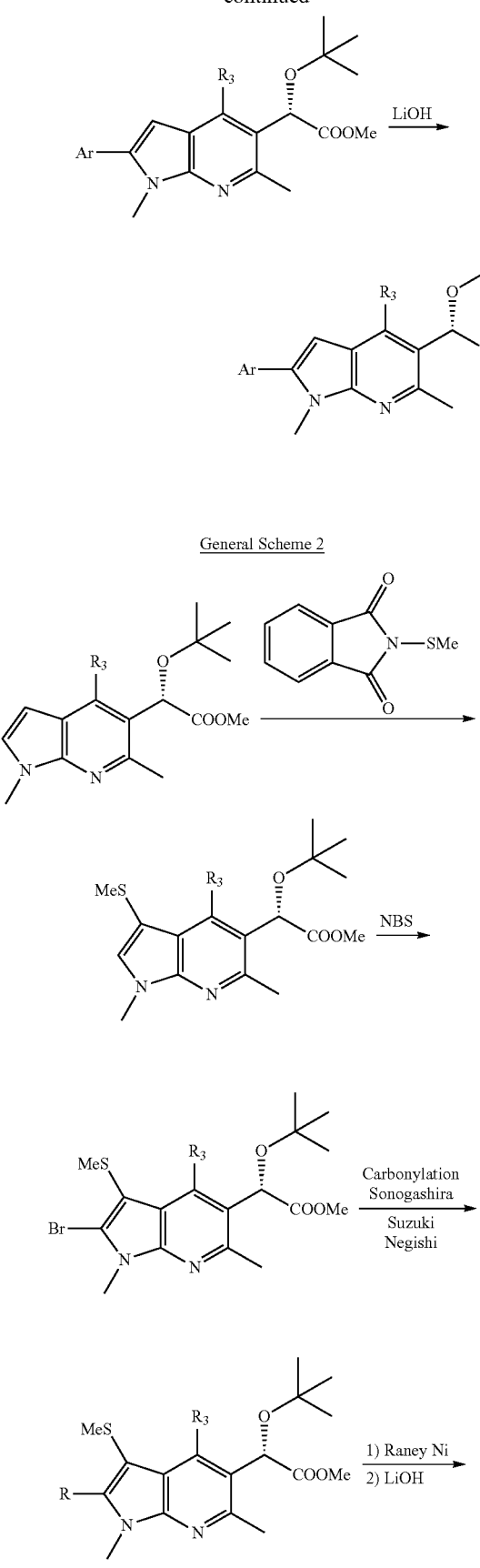
General Scheme 2
44
-continued
General Scheme 3
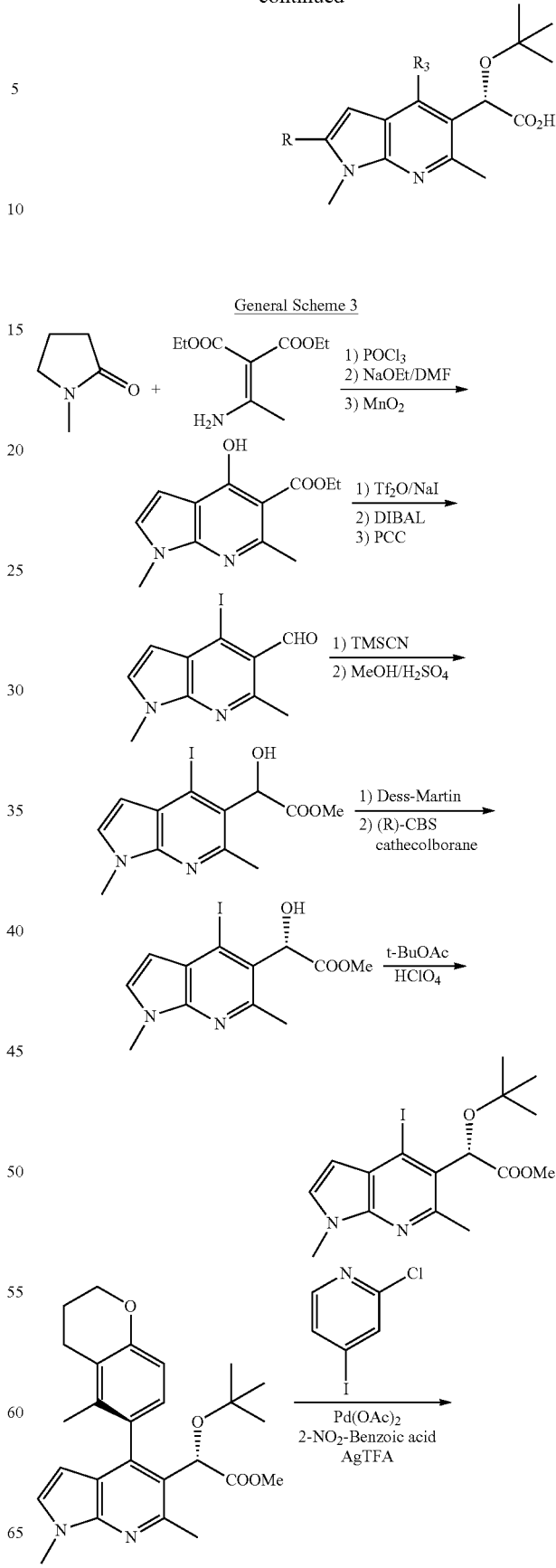

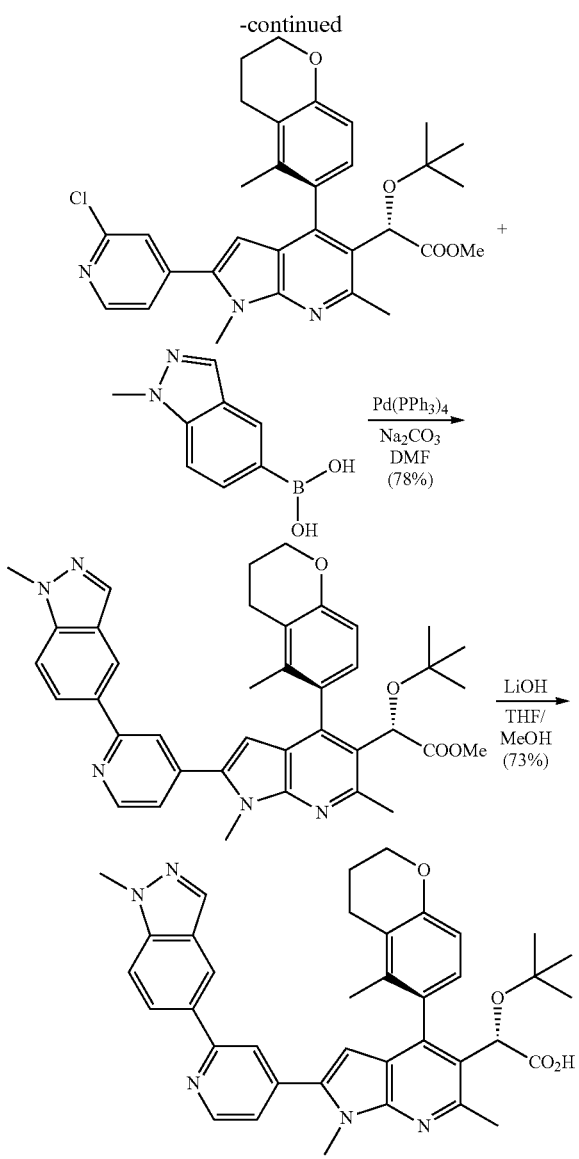

Example 1

(2S)(M)-2-(tert-butoxy)-2-(1,6-dimethyl-2-(2-(1-methyl-1H-indazol-5-yl)pyridin-4-yl)-4-(5-methyl-chroman-6-yl)-1H-pyrrolo[2,3-b]pyridin-5-yl)acetic acid, Trifluoroacetic acid salt

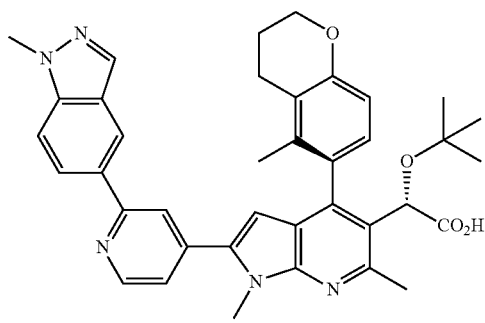

Step A

Ethyl 4-hydroxy-1,6-dimethyl-2,3-dihydro-1H-pyrrolo[2,3-b]pyridine-5-carboxylate

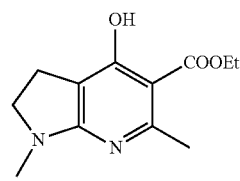 [SMILES: CCOC(=O)c1c(C)nc2c(c1O)CCN2C]

A solution of 1-methylpyrrolidin-2-one (14.81 ml, 154 mmol) in anhydrous 1,2-dichloroethane (DCE) (250 ml) under a nitrogen atmosphere was added drop wise $POCl_3$ (28.5 ml, 307 mmol) over a 10 min period and the mixture was stirred at ambient temperature. After 1 h, a solution of diethyl 2-(1-aminoethylidene)malonate (30.9 g, 154 mmol) in DCE (10 mL) was added and the mixture was heated to 40° C. After 18 h, the reaction mixture was partitioned between sat. aq. $NaHCO_3$ and DCM. The organic later was washed with brine, dried ($Na_2SO_4$), filtered and concentrated in vacuo, The residue was dissolved in N,N-dimethylformamide (DMF) (150 ml) and treated dropwise with sodium ethoxide (172 ml, 461 mmol) and heated to 100° C. After 3 h, the reaction mixture was cooled to ambient temperature and the pH was adjusted to pH 7 with 1M HCl. The mixture was partitioned between water and EtOAc and the organics washed with brine, dried ($Na_2SO_4$), filtered and concentrated in vacuo. The residue was purified on silica gel (EtOAc-hexanes, 0-25%) to afford ethyl 4-hydroxy-1,6-dimethyl-2,3-dihydro-1H-pyrrolo[2,3-b]pyridine-5-carboxylate (11.0 g, 30.3% yield) as a white solid. $^1$H NMR (CHLOROFORM-d) δ: 11.89 (s, 1H), 4.37 (q, J=7.0 Hz, 2H), 3.54 (t, J=8.7 Hz, 2H), 2.87-3.05 (m, 5H), 2.64 (s, 3H), 1.41 (t, J=7.1 Hz, 3H); LC/MS (m/z) $ES^+$=237.1 $(M+1)^+$

Step B

Ethyl 4-hydroxy-1,6-dimethyl-1H-pyrrolo[2,3-b]pyridine-5-carboxylate

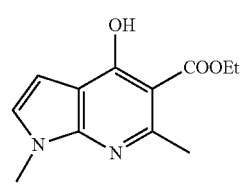 [SMILES: CCOC(=O)c1c(C)nc2c(ccn2C)c1O]

A solution of ethyl ethyl 4-hydroxy-1,6-dimethyl-2,3-dihydro-1H-pyrrolo[2,3-b]pyridine-5-carboxylate (11.0 g, 46.6 mmol) in benzene (150 mL) was added manganese(IV) oxide (20.24 g, 233 mmol) in one portion, and the mixture was heated to reflux. After 18 h, the reaction mixture was filtered through a pad of Celite™ and the filtrate concentrated in vacuo to afford the title compound (10.0 g, 42.7 mmol, 92% yield) as a light yellow solid: $^1$H NMR (CHLOROFORM-d) δ: 6.94 (d, J=3.5 Hz, 1H), 6.59 (d, J=3.5 Hz, 1H), 4.46 (q, J=7.0 Hz, 2H), 3.82 (s, 3H), 2.84 (s, 3H), 1.46 (t, J=7.1 Hz, 3H). LC/MS (m/z) ES$^+$=235.1 (M+1)$^+$ Steps C, D, & E 4-iodo-1,6-dimethyl-1H-pyrrolo[2,3-b]pyridine-5-carbaldehyde

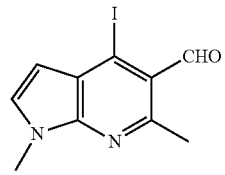

A 0° C. solution of ethyl 4-hydroxy-1,6-dimethyl-1H-pyrrolo[2,3-b]pyridine-5-carboxylate (10.0 g, 42.7 mmol) in acetonitrile (200 mL) and pyridine (4.13 mL, 51.2 mmol) was treated dropwise with Tf$_2$O (8.65 mL, 51.2 mmol). After 1 h, the reaction mixture was treated with NaI (19.20 g, 128 mmol) followed by dropwise addition of 3M HCl (17.08 mL, 51.2 mmol) and warmed to 70° C. After 3 h, the reaction mixture was cooled to ambient temperature and added to a sat. aq. solution of Na$_2$S$_2$O$_3$. After stirring for 15 min, ethyl acetate was added and the layers partitioned. The organic layer was washed with brine, dried (Na$_2$SO$_4$), filtered and concentrated in vacuo to afford ethyl 4-iodo-1,6-dimethyl-1H-pyrrolo[2,3-b]pyridine-5-carboxylate (14.7 g).

A −78° C. solution of ethyl 4-iodo-1,6-dimethyl-1H-pyrrolo[2,3-b]pyridine-5-carboxylate in dichloromethane (DCM) (150 mL) was treated dropwise with DIBAL-H (128 mL, 128 mmol) and warmed to ambient temperature. After 30 min, the reaction mixture was cooled to 0° C. and treated sequentially with water (5.1 mL), 15% NaOH (5.1 mL) and finally water (12.8 mL) with a 10 minute delay in between each addition. The fine suspension was then filtered through a pad of celite and washed with ethyl acetate 3×. The filtrate was concentrated in vacuo to afford (4-iodo-1,6-dimethyl-1H-pyrrolo[2,3-b]pyridin-5-yl)methanol (12.4 g, 41.0 mmol, 96% yield) as a yellow solid.

A solution of (4-iodo-1,6-dimethyl-1H-pyrrolo[2,3-b]pyridin-5-yl)methanol in dichloromethane (DCM) (300 mL) was treated with PCC (11.96 g, 55.5 mmol) and Celite™ (17 g) in one portion. After 3 h, the mixture was diluted with DCM (100 mL) and filtered through a pad of celite and washed with DCM/ethyl acetate (10:1). The filtrate was concentrated in vacuo to afford the title compound (10.8 g, 36.0 mmol, 84% yield) as a yellow solid: $^1$H NMR (400 MHz, CHLOROFORM-d) δ ppm 2.88 (s, 3H) 3.88 (s, 3H) 6.48 (d, J=3.52 Hz, 1H) 7.22 (d, J=3.52 Hz, 1H) 10.36 (s, 1H). LC/MS (m/z) ES$^+$=301 (M+1)$^+$ Steps F, G, & H Methyl 2-(4-iodo-1,6-dimethyl-1H-pyrrolo[2,3-b]pyridin-5-yl)-2-oxoacetate

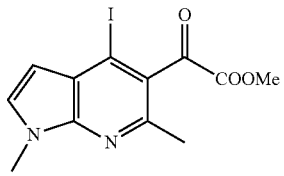 [SMILES: COC(=O)C(=O)c1c(C)nc2c(ccn2C)c1I]

An ice-cooled solution of 4-iodo-1,6-dimethyl-1H-pyrrolo[2,3-b]pyridine-5-carbaldehyde (10.8 g, 36.0 mmol) in dichloromethane (DCM) (200 mL) was treated with TMSCN (14.47 ml, 108 mmol) and ZnI$_2$ (22.97 g, 72.0 mmol). After 30 min, the reaction mixture was poured into water and extracted with DCM. The organic layer was washed with water, brine, dried (Na$_2$SO$_4$), filtered and concentrated in vacuo to afford 2-(4-iodo-1,6-dimethyl-1H-pyrrolo[2,3-b]pyridin-5-yl)-2-((trimethylsilyl)oxy)acetonitrile (14.2 g, 35.6 mmol, 99% yield) as a light yellow solid.

A 0° C. solution of 2-(4-iodo-1,6-dimethyl-1H-pyrrolo[2,3-b]pyridin-5-yl)-2-((trimethylsilyl)oxy)acetonitrile in methanol (200 mL), was treated with concentrated sulfuric acid (54.2 ml, 1094 mmol) and warmed to 80° C. After 18 h, the reaction mixture was concentrated in vacuo and poured into water (1 L). The pH was adjusted to 7 with solid Na$_2$CO$_3$ and extracted with EtOAc. The organics were washed with brine, dried (Na$_2$SO$_4$), filtered and concentrated in vacuo to afford methyl 2-hydroxy-2-(4-iodo-1,6-dimethyl-1H-pyrrolo[2,3-b]pyridin-5-yl)acetate (12.0 g, 33.3 mmol, 93% yield) as a yellow foam.

An 0° C. solution of methyl 2-hydroxy-2-(4-iodo-1,6-dimethyl-1H-pyrrolo[2,3-b]pyridin-5-yl)acetate (12.0 g, 33.3 mmol) in dichloromethane (DCM) (120 mL) was treated with Dess-Martin periodinane (19.84 g, 46.8 mmol) in one portion and warmed to ambient temperature. After 18 h, sat. aq. Na$_2$S$_2$O$_3$ was added and the reaction mixture was stirred for 20 min. Ethyl acetate was added and the layers partitioned. The organic phase was washed with sat. aq. NaHCO$_3$, brine, dried (Na2SO4), filtered and concentrated in vacuo. The residue was purified by ISCO (0-30% EtOAc-hexanes) to afford methyl 2-(4-iodo-1,6-dimethyl-1H-pyrrolo[2,3-b]pyridin-5-yl)-2-oxoacetate (9.6 g, 26.8 mmol, 74.5% yield) as light yellow solid: $^1$H NMR (400 MHz, CHLOROFORM-d) δ ppm 2.58 (s, 3H) 3.86 (s, 3H) 3.93 (s, 3H) 6.35 (d, J=3.52 Hz, 1H) 7.22 (d, 1H). LC/MS (m/z) ES$^+$=359.9 (M+1)$^+$ Steps I & J (2S)-methyl 2-(tert-butoxy)-2-(4-iodo-1,6-dimethyl-1H-pyrrolo[2,3-b]pyridin-5-yl)acetate

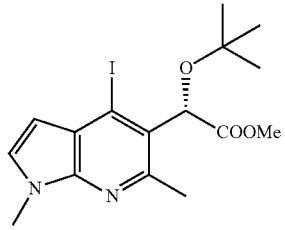 [SMILES: COC(=O)[C@@H](OC(C)(C)C)c1c(C)nc2c(ccn2C)c1I]

A solution of methyl 2-(4-iodo-1,6-dimethyl-1H-pyrrolo[2,3-b]pyridin-5-yl)-2-oxoacetate (9.6 g, 26.8 mmol, 74.5% yield) in toluene (120 mL) was cooled to −50° C. and then treated with (R)-2-methyl-CBS-oxazaborolidine (1.857 g, 6.7 mmol). Catecholborane (8.57 ml, 80.4 mmol) was slowly added over 30 min while maintaining a −50° C. cooling bath temperature. After 1 h, the bath was allowed to expire and stirring continued for 4 h. The reaction mixture was treated with 2M Na$_2$CO$_3$ and after 10 min was extracted with EtOAc. The organic layer was washed with 1M NaOH, brine, dried (Na$_2$SO$_4$), filtered and concentrated in vacuo to afford (S)-methyl 2-hydroxy-2-(4-iodo-1,6-dimethyl-1H-pyrrolo[2,3-b]pyridin-5-yl)acetate (9.6 g, 26.7 mmol, 74.1% yield).

A solution of (S)-methyl 2-hydroxy-2-(4-iodo-1,6-dimethyl-1H-pyrrolo[2,3-b]pyridin-5-yl)acetate (9.6 g, 26.7 mmol) in tert-butyl acetate (349 ml, 2583 mmol) was treated dropwise with HClO$_4$ (12.37 ml, 144 mmol). After 1 h, the reaction mixture was poured into 2M Na$_2$CO$_3$ and the layers partitioned. The organic phase was washed with brine, dried (Na$_2$SO$_4$), filtered and concentrated. The residue was purified by ISCO (0-60% EtOAc-hexanes) to afford the title compound as a white foam (8.0 g, 71%). $^1$H NMR (CHLOROFORM-d) δ 7.13 (d, J=3.3 Hz, 1H), 6.30 (d, J=3.3 Hz, 1H), 5.75 (s, 1H), 3.84 (s, 3H), 3.67 (s, 3H), 2.73 (s, 3H), 1.25 (s, 9H). LC/MS (m/z) ES$^+$=416.9 (M+1)$^+$ Step K (2S)(M)-methyl 2-(tert-butoxy)-2-(-1,6-dimethyl-4-(5-methylchroman-6-yl)-1H-pyrrolo[2,3-b]pyridin-5-yl)acetate

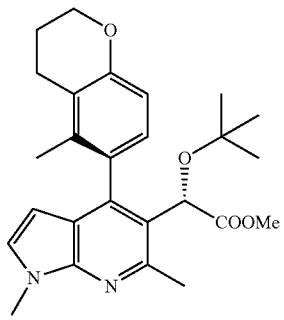

A solution of (S)-methyl 2-(tert-butoxy)-2-(4-iodo-1,6-dimethyl-1H-pyrrolo[2,3-b]pyridin-5-yl)acetate (905 mg, 2.174 mmol), 4,4,5,5-tetramethyl-2-(5-methylchroman-6-yl)-1,3,2-dioxaborolane (715 mg, 2.61 mmol) and potassium carbonate (901 mg, 6.52 mmol) in DMF (10 mL) (21.6 mL) and water (2.16 mL) was degassed with a stream of nitrogen for 5 min then Pd(PPh$_3$)$_4$ (176 mg, 0.152 mmol) was added and the mixture was heated to 70° C. under nitrogen. After 18 h, the reaction mixture was cooled to ambient temperature and diluted with EtOAc. The phases were partitioned and the organic layer was washed with brine, dried (Na$_2$SO4), filtered and concentrated in vacuo. The residue was purified by ISCO (0-30% EtOAc-hexanes) to afford the title compound (865 mg, 1.981 mmol, 91% yield) as a white foam. $^1$H NMR (400 MHz, CHLOROFORM-d) δ=6.97 (d, J=3.5 Hz, 1H), 6.89 (d, J=8.4 Hz, 1H), 6.71 (d, J=8.2 Hz, 1H), 5.85 (d, J=3.5 Hz, 1H), 5.16 (s, 1H), 4.21 (t, J=5.2 Hz, 2H), 3.85 (s, 3H), 3.56 (s, 3H), 2.80 (s, 3H), 2.73-2.68 (m, 2H), 2.14-2.08 (m, 2H), 1.82 (s, 3H), 1.08 (s, 9H). LC/MS (m/z) ES+=437.46 (M+1).

Step L (2S) (M)-methyl 2-(tert-butoxy)-2-(2-(2-chloropyridin-4-yl)-1,6-dimethyl-4-(-5-methylchroman-6-yl)-1H-pyrrolo[2,3-b]pyridin-5-yl)acetate

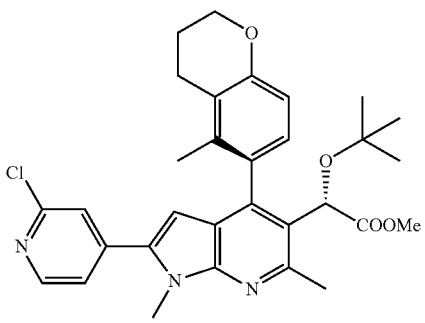

A solution of (2S)(M)-methyl 2-(tert-butoxy)-2-(1,6-dimethyl-4-(-5-methylchroman-6-yl)-1H-pyrrolo[2,3-b]pyridin-5-yl)acetate (863 mg, 1.977 mmol), 2-chloro-4-iodopyridine (947 mg, 3.95 mmol), (2,2,2-trifluoroacetoxy)silver (327 mg, 1.483 mmol), 2-nitrobenzoic acid (496 mg, 2.97 mmol) in DMF (10 mL/mmol) (20 mL) was degassed with N$_2$ for 10 mins, diacetoxypalladium (444 mg, 1.977 mmol) was added, and the mixture was heated to 60° C. After 18 h, the reaction mixture was cooled to ambient temperature, diluted with EtOAc and filtered through a pad of celite. The filtrate was washed with water, sat. aq. NaHCO$_3$, dried (Na$_2$SO$_4$), filtered and concentrated in vacuo. The residue was purified by ISCO (0-100% EtOAc-hexanes) to afford the title compound (243 mg, 0.399 mmol, 20% yield) as a yellow foam. $^1$H NMR (400 MHz, CHLOROFORM-d) δ=8.39 (d, J=5.3 Hz, 1H), 7.43 (s, 1H), 7.32 (dd, J=1.4, 5.3 Hz, 1H), 6.89 (d, J=8.4 Hz, 1H), 6.73 (d, J=8.4 Hz, 1H), 6.15 (s, 1H), 5.17 (s, 1H), 4.22 (t, J=5.2 Hz, 2H), 3.94 (s, 3H), 3.59 (s, 3H), 2.82 (s, 3H), 2.73-2.69 (m, 2H), 2.12 (m, 2H), 1.84 (s, 3H), 1.09 (s, 9H). LC/MS (m/z) ES$^+$=548.28 (M+1)$^+$.

Step M (S)-methyl 2-(tert-butoxy)-2-((R)-1,6-dimethyl-2-(2-(1-methyl-1H-indazol-5-yl)pyridin-4-yl)-4-(5-methylchroman-6-yl)-1H-pyrrolo[2,3-b]pyridin-5-yl)acetate

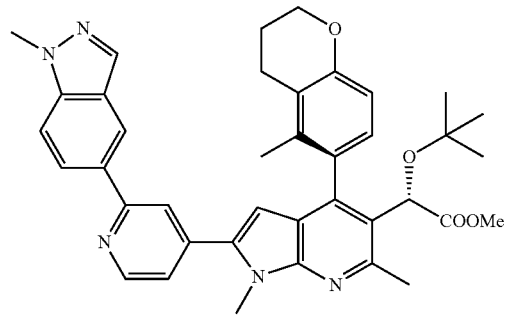

A solution of (2S)(M)-methyl 2-(tert-butoxy)-2-(2-(2-chloropyridin-4-yl)-1,6-dimethyl-4-((R)-5-methylchroman-6-yl)-1H-pyrrolo[2,3-b]pyridin-5-yl)acetate (243 mg, 0.399 mmol), (1-methyl-1H-indazol-5-yl)boronic acid (105 mg, 0.599 mmol) and 2M sodium carbonate (0.599 mL, 1.197 mmol) in DMF (18.5 mL/mmol) (8.2 mL) was degassed with N$_2$ for 5 min. Pd(PPh$_3$)$_4$ (46.1 mg, 0.040 mmol) was added and the reaction mixture was irradiated in the microwave at 120° C. for 20 minutes. The mixture was diluted with EtOAc, washed with water, brine, dried (Na$_2$SO$_4$), filtered and concentrated. The residue was purified on silica gel (0-100% EtOAc-hexanes) to afford the title compound (199.9 mg, 0.311 mmol, 78% yield) as a foam. $^1$H NMR (400 MHz, CHLOROFORM-d) δ=8.71 (d, J=5.1 Hz, 1H), 8.36 (s, 1H), 8.10 (dd, J=1.4, 8.8 Hz, 1H), 8.06 (s, 1H), 7.84 (s, 1H), 7.48 (d, J=8.8 Hz, 1H), 7.32 (dd, J=1.4, 5.1 Hz, 1H), 6.94 (d, J=8.2 Hz, 1H), 6.75 (d, J=8.2 Hz, 1H), 6.18 (s, 1H), 5.19 (s, 1H), 4.22 (t, J=5.2 Hz, 2H), 4.11 (s, 3H), 3.99 (s, 3H), 3.60 (s, 3H), 2.84 (s, 3H), 2.75-2.68 (m, 2H), 2.12 (m, 2H), 1.87 (s, 3H), 1.11 (s, 9H); LC/MS (m/z) ES$^+$=644.62 (M+1).

Step N (2S)(M)-2-(tert-butoxy)-2-(1,6-dimethyl-2-(2-(1-methyl-1H-indazol-5-yl)pyridin-4-yl)-4-(5-methyl-chroman-6-yl)-1H-pyrrolo[2,3-b]pyridin-5-yl)acetic acid, Trifluoroacetic acid salt

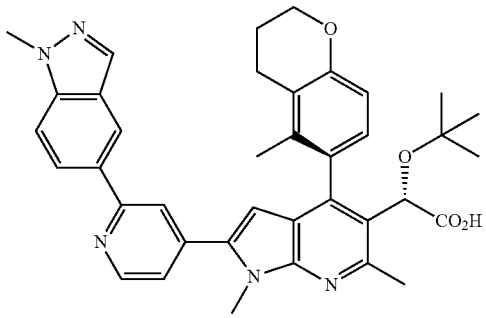

A solution of (2S)(M)-methyl 2-(tert-butoxy)-2-(1,6-dimethyl-2-(2-(1-methyl-1H-indazol-5ll)pyridin-4-yl)-4-(-5-methylchroman-6-yl)-1H-pyrrolo[2,3-b]pyridin-5-yl)acetate (289.4 mg, 0.450 mmol) in THF/MeOH/H₂O=2/2/1 (9 mL) was treated with LiOH (200 mg, 8.35 mmol) and heated to 70° C. After 18 h, the reaction mixture was concentrated, water was added and then pH adjusted to 2 with 1N HCl. Ethyl acetate was added and the layers partitioned. The organic layer was washed with brine, dried (Na₂SO₄), filtered and concentrated in vacuo. The residue was purified by reverse HPLC to afford the title compound (245.5 mg, 0.330 mmol, 73.4% yield) as a yellow solid. ¹H NMR (400 MHz, CHLOROFORM-d) δ=8.94 (d, J=6.1 Hz, 1H), 8.34 (s, 1H), 8.15 (s, 1H), 8.00 (s, 1H), 7.96 (d, J=8.8 Hz, 1H), 7.67 (d, J=7.0 Hz, 1H), 7.59 (d, 1H), 6.93 (d, J=8.4 Hz, 1H), 6.78 (d, J=8.4 Hz, 1H), 6.49 (s, 1H), 5.28 (s, 1H), 4.21 (t, J=5.1 Hz, 2H), 4.14 (s, 3H), 4.10 (s, 3H), 2.84 (s, 3H), 2.75-2.63 (m, 2H), 2.16-2.04 (m, 2H), 1.96 (s, 3H), 1.11 (s, 9H). LC/MS (m/z) ES⁺=630.55 (M+1).

Example 2

(2S)(M)-2-(tert-butoxy)-2-[4-(8-fluoro-5-methyl-3,4-dihydro-2H-1-benzopyran-6-yl)-1,6-dimethyl-2-{2-[3-(morpholin-4-yl)azetidin-1-yl]pyridin-4-yl}-1H-pyrrolo[2,3-b]pyridin-5-yl]acetic acid

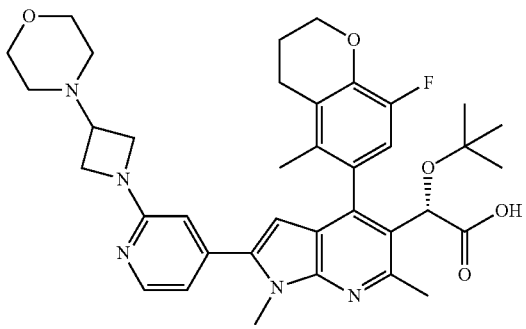 [SMILES: Cc1nc2c(cc(-c3ccnc(N4CC(N5CCOCC5)C4)c3)n2C)c(-c2cc(F)c3c(c2C)CCCO3)c1[C@H](OC(C)(C)C)C(=O)O]

Example 2 was synthesized using the procedure described in General Scheme 7 except using 4-(azetidin-3-yl)morpholine, 2 Hydrochloride as the amine.

¹H NMR (400 MHz, CHLOROFORM-d) δ ppm 8.06 (br. s., 1H), 7.00 (br. s., 1H), 6.78 (s, 1H), 6.64 (s, 1H), 6.37 (s, 1H), 5.21 (s, 1H), 5.03 (br. s., 2H), 4.82 (br. s., 3H), 4.32 (br. s., 2H), 4.09 (br. s., 6H), 3.88 (s, 1H), 2.92 (br. s., 3H), 2.69-2.83 (m, 2H), 2.16 (br. s., 2H), 1.90 (s, 3H), 1.23-1.33 (m, 2H), 1.11-1.21 (m, 9H), 0.77-0.92 (m, 2H). LC/MS (m/z) ES⁺=658 (M+1).

Example 3

(2S)(M)-2-(tert-butoxy)-2-(-4-(8-fluoro-5-methyl-3,4-dihydro-2H-benzo[b][1,4]oxazin-6-yl)-1,6-dimethyl-2-(2-(1-methyl-1H-indazol-5-yl)pyridin-4-yl)-1H-pyrrolo[2,3-b]pyridin-5-yl)acetic acid

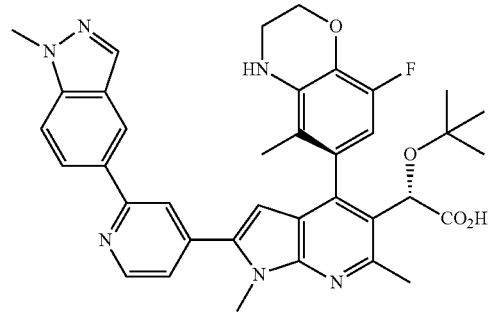

Example 2 was synthesized using the procedure described in General Scheme 1 except using 8-fluoro-5-methyl-6-(4,4,5,5-tetramethyl-1,3,2-dioxaborolan-2-yl)-3,4-dihydro-2H-benzo[b][1,4]oxazine as the boronic ester coupling partner.

1H NMR (400 MHz, Chloroform-d) δppm=8.96 (6, J=5.7 Hz, 1H), 8.37 (s, 1H), 8.16 (s, 1H), 8.04 (s, 1H), 7.98 (d, J=8.6 Hz, 1H), 7.71 (d, J=5.3 Hz, 1H), 7.61 (d, J=8.8 Hz, 1H), 6.55 (s, 1H), 6.40 (d, J=10.7 Hz, 1H), 5.27 (s, 1H), 4.35-4.44 (m, 2H), 4.14 (s, 3H), 4.11 (s, 3H), 3.53-3.67 (m, 2H), 2.84 (s, 3H), 1.80 (s, 3H), 1.15 (s, 9H); LC/MS (m/z) ES+=649.2 (M+1).

Example 4

(2S)(M)-2-(tert-butoxy)-2-(-1,6-dimethyl-2-(2-(1-methyl-1H-pyrazolo[3,4-b]pyridin-5-yl)pyridin-4-yl)-4-(5-methylchroman-6-yl)-1H-pyrrolo[2,3-b]pyridin-5-yl)acetic acid

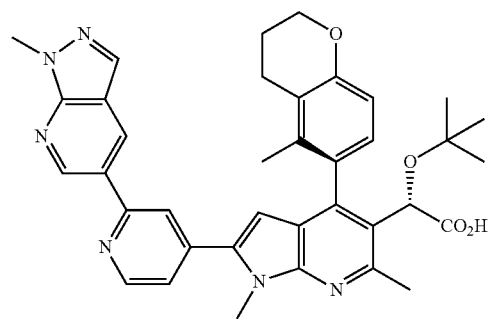

Example 4 was synthesized using the procedure described in General Scheme 1 except using (1-methyl-1H-pyrazolo[3,4-b]pyridin-5-yl)boronic acid as the coupling partner.

¹H NMR (400 MHz, CHLOROFORM-d) δ ppm 1.09-1.23 (m, 9H) 1.90-2.02 (m, 3H) 2.11 (m, 2H) 2.59-2.82 (m, 2H) 2.94-3.07 (m, 3H) 4.12-4.39 (m, 8H) 5.27-5.35 (m, 1H) 6.43-6.50 (m, 1H) 6.73-6.98 (m, 2H) 7.55-7.67 (m, 1H) 7.94 (s, 1H) 8.19 (s, 1H) 8.74-8.98 (m, 2H) 9.12 (d, 1H); LCMS (m/z) ES⁺=631 (M+1).

Example 5

(2S)(M)-2-(tert-butoxy)-2((R)-2-(2-(2-(dimethylamino)pyrimidin-5-yl)pyridin-4-yl)-4-(8-fluoro-5-methylchroman-6-yl)-1,6-dimethyl-M-pyrrolo[2,3-b]pyridin-5-yl)acetic acid

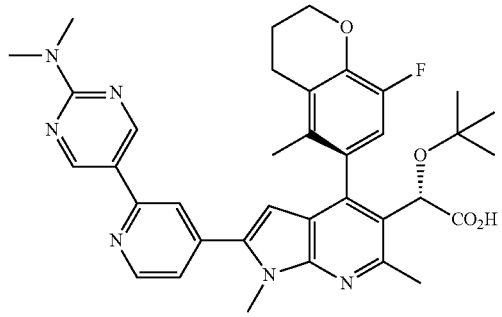

Example 5 was synthesized using the procedure described in General Scheme 2 except using (2-(dimethylamino)pyrimidin-5-yl)boronic acid as the coupling partner.

¹H NMR (400 MHz, CHLOROFORM-d) δ ppm 8.98 (s, 2H), 8.85 (d, J=5.5 Hz, 1H), 7.76 (s, 1H), 7.50 (dd, J=1.4, 5.6 Hz, 1H), 6.80 (d, J=11.0 Hz, 1H), 6.34 (s, 1H), 5.25 (s, 1H), 4.31 (t, J=5.1 Hz, 2H), 4.05 (s, 3H), 3.32 (s, 6H), 2.85 (s, 3H), 2.80-2.67 (m, 2H), 2.24-2.06 (m, 2H), 1.92 (s, 3H), 1.22-1.03 (m, 9H); LCMS (m/z) ES⁺=639 (M+1).

Example 6

(2S)(M)-2-(-2-([2,3':6,3"-terpyridin]-4-yl)-4-(8-fluoro-5-methylchroman-6-yl)-1,6-dimethyl-1H-pyrrolo[2,3-b]pyridin-5-yl)-2-(tert-butoxy)acetic acid

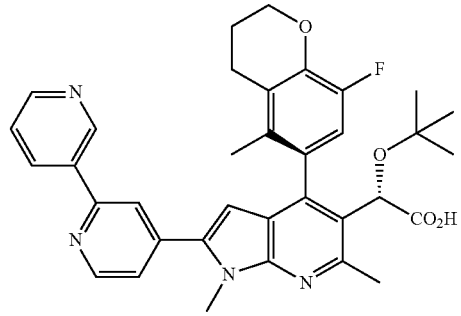

Example 6 was synthesized using the procedure described in General Scheme 2 except using pyridin-3-ylboronic acid as the coupling partner.

¹H NMR (400 MHz, CHLOROFORM-d) δ=9.52 (br. s., 1H), 8.97 (d, J=8.2 Hz, 1H), 8.90-8.83 (m, 2H), 7.99 (s, 1H), 7.91 (dd, J=5.9, 7.6 Hz, 1H), 7.51 (d, J=5.3 Hz, 1H), 6.77 (d, J=10.9 Hz, 1H), 6.31 (s, 1H), 5.23 (s, 1H), 4.28 (t, J=5.1 Hz, 2H), 4.06 (s, 3H), 2.91 (s, 3H), 2.73 (m, 2H), 2.11 (m, 2H), 1.88 (s, 3H), 1.13 (s, 9H); LCMS (m/z) ES⁺=595 (M+1).

Example 8

(2S)(M)-2-(tert-butoxy)-2-(-4-(8-fluoro-5-methylchroman-6-yl)-1,6-dimethyl-2-(2-(1-methylindolin-5-yl)pyridin-4-yl)-1H-pyrrolo[2,3-b]pyridin-5-yl)acetic acid

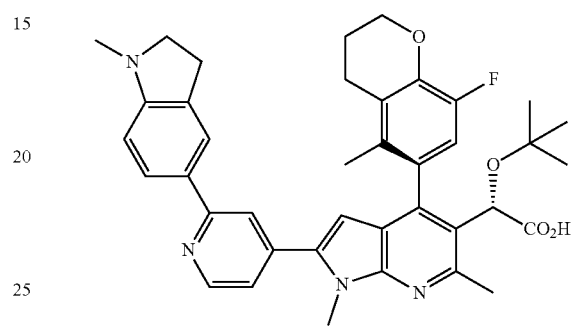

Example 8 was synthesized using the procedure described in General Scheme 2 except using 1-methyl-5-(4,4,5,5-tetramethyl-1,3,2-dioxaborolan-2-yl)indoline as the coupling partner.

¹H NMR (400 MHz, CHLOROFORM-d) δ=8.70 (d, J=6.1 Hz, 1H), 7.86 (s, 1H), 7.70 (d, J=8.2 Hz, 1H), 7.63 (s, 1H), 7.49 (d, J=5.9 Hz, 1H), 6.80 (d, J=10.9 Hz, 1H), 6.48 (d, J=8.0 Hz, 1H), 6.42 (s, 1H), 5.24 (s, 1H), 4.30 (t, J=4.9 Hz, 2H), 4.05 (s, 3H), 3.60-3.56 (m, 2H), 3.10 (t, J=8.4 Hz, 2H), 2.89 (s, 3H), 2.81 (s, 3H), 2.72 (m, 2H), 2.14 (m, 2H), 1.91 (s, 3H), 1.13 (s, 9H); LCMS (m/z) ES⁺=649 (M+1).

Example 9

(2S)(M)-2-(tert-butoxy)-2-((R)-4-(8-fluoro-5-methylchroman-6-yl)-1,6-dimethyl-2-(2-(1-(tetrahydro-2H-pyran-4-yl)-1H-pyrazol-4-yl)pyridin-4-yl)-1H-pyrrolo[2,3-b]pyridin-5-yl)acetic acid

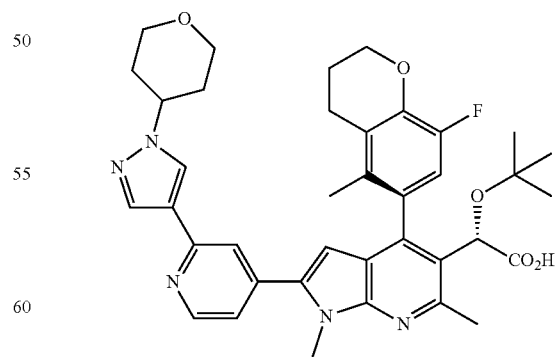

Example 9 was synthesized using the procedure described in. General Scheme 2 except using 1-(tetrahydro-2H-pyran-4-yl)-4-(4,4,5,5-tetra methyl-1,3,2-dioxaborolan-2-yl)-1H-pyrazole as the coupling partner.

¹H NMR (400 MHz, METHANOL-d₄) δ=8.61 (s, 1H), 8.54 (d, J=6.3 Hz, 1H), 8.29-8.20 (m, 2H), 7.84 (dd, J=1.8, 6.3 Hz, 1H), 6.75 (d, J=11.1 Hz, 1H), 6.62 (s, 1H), 5.17 (s, 1H), 4.58-4.46 (m, 1H), 4.25 (t, J=5.1 Hz, 2H), 4.13-4.00 (m, 5H), 3.66-3.51 (m, 2H), 2.84 (s, 3H), 2.80-2.68 (m, 2H), 2.20-2.04 (m, 6H), 1.86 (s, 3H), 1.11 (s, 9H); LC/MS (m/z) ES⁺=668 (M+1).

Example 10

(2S)(M)-2-(tert-butoxy)-2-(-4-(8-fluoro-5-methyl-chroman-6-yl)-1,6-dimethyl-2-(2-(4-methylpiper-azin-1-yl)pyridin-4-yl)-1H-pyrrolo[2,3-b]pyridin-5-yl)acetic acid

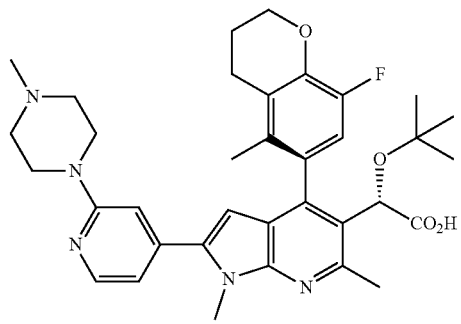

Step A (2S) (M)-methyl 2-(tert-butoxy)-2-(-4-(8-fluoro-5-methylchroman-6-yl)-1,6-dimethyl-2-(2-(4-methylpiperazin-1-yl)pyridin-4-yl)-1H-pyrrolo[2,3-b]pyridin-5-yl)acetate

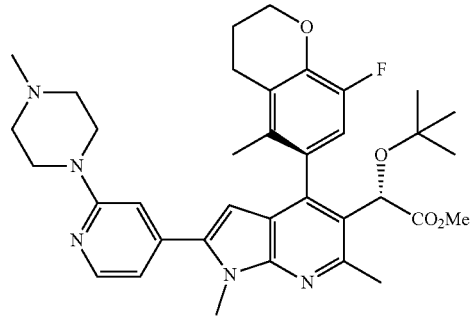

A solution of (2S)(M)-methyl 2-(tert-butoxy)-2-(-2-(2-chloropyridin-4-yl)-4-(8-fluoro-5-methylchroman-6-yl)-1,6-dimethyl-1H-pyrrolo[2,3-b]pyridin-5-yl)acetate (45 mg, 0.079 mmol) and 1-methylpiperazine (0.035 mL, 0.318 mmol) in tetrahydrofuran (2.5 mL) was purged with N₂, treated with Ruphos precatalyst (12.99 mg, 0.016 mmol), purged with N₂ again, and treated dropwise with LiHMDS (1M in THF) (0.238 mL, 0.238 mmol). The reaction was stirred at ambient temperature for 40 min, cooled to 0° C., quenched with sat. NH₄Cl, extracted with EtOAc, washed with Brine, dried over Na₂SO₄, filtered, and concentrated. The residue was purified by silica gel chromatography (0-20% MeOH/DCM) to afford the title compound (35.7 mg, 0.057 mmol, 71.3% yield) as yellow oil: ¹H NMR (400 MHz, CHLOROFORM-d) S=8.22 (d, J=5.0 Hz, 1H), 6.78 (d, J=11.2 Hz, 1H), 6.75-6.66 (m, 2H), 6.02 (s, 1H), 5.16 (s, 1H), 4.31 (t, J=5.0 Hz, 2H), 3.90 (s, 3H), 3.65 (s, 2H), 3.63-3.49 (m, 7H), 2.84 (s, 3H), 2.80-2.67 (m, 2H), 2.54 (t, J=4.3 Hz, 4H), 2.36 (s, 3H), 2.24-2.06 (m, J=5.2 Hz, 2H), 1.83 (s, 3H), 1.13 (s, 9H); LCMS (m/z) ES+=630 (M+1).

Step B (2S)(M)-2-(tert-butoxy)-2-(-4-(8-fluoro-5-methyl-chroman-6-yl)-1,6-dimethyl-2-(2-(4-methylpiper-azin-1-yl)pyridin-4-yl)-1H-pyrrolo[2,3-b]pyridin-5-yl)acetic acid

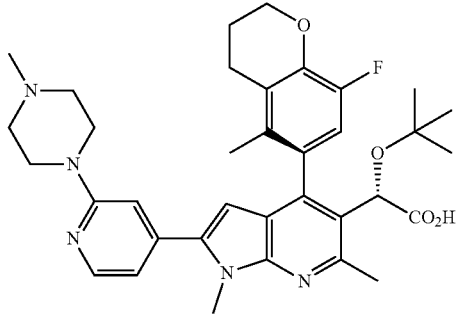

A suspension of (2S)(M)-methyl 2-(tert-butoxy)-2-(-4-(8-fluoro-5-methylchroman-6-yl)-1,6-dimethyl-2-(2-(4-methylpiperazin-1-yl)pyridin-4-yl)-1H-pyrrolo[2,3-b]pyridin-5-yl)acetate (35.7 mg, 0.057 mmol) in Methanol (0.5 mL) and tetrahydrofuran (0.5 mL) was treated with 4 M LiOH (0.1 mL, 0.400 mmol) and irradiated in microwave at 120° C. for 20 min. The mixture was treated with additional 4 M LiOH (0.2 mL, 0.800 mmol) and irradiated in microwave at 120° C. for 20 min. The mixture was diluted with 1N HCl and concentrated in vacuo. The residue was purified by reverse phase HPLC to afford the title compound (25 mg, 0.028 mmol, 49.7% yield) as yellow solid: ¹H NMR (400 MHz, CHLOROFORM-d) δ ppm 8.26 (d, J=5.7 Hz, 1H), 6.95 (dd, J=0.8, 5.6 Hz, 1H), 6.86 (s, 1H), 6.75 (d, J=10.9 Hz, 1H), 6.27 (s, 1H), 5.24 (s, 1H), 4.54-3.90 (m, 9H), 3.88-3.44 (m, 2H), 3.26-2.83 (m, 8H), 2.81-2.63 (m, 2H), 2.23-2.08 (m, 2H), 1.88 (s, 3H), 1.14 (s, 9H); LCMS (m/z) ES⁺=616 (M+1).

Example 11

(2S)(M)-2-(tert-butoxy)-2-(-4-(8-fluoro-5-methyl-chroman-6-yl)-1,6-dimethyl-2-(4-(1-methyl-1H-indazol-5-yl)piperazine-1-carbonyl)-1H-pyrrolo[2,3-b]pyridin-5-yl)acetic acid

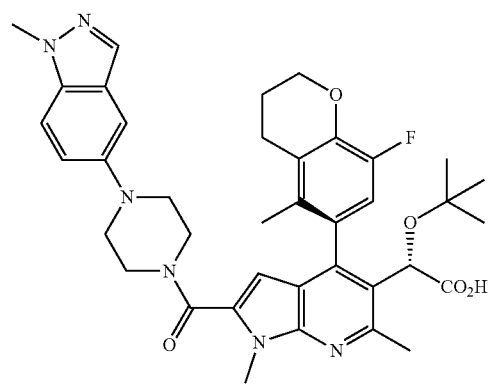

Example 11 was synthesized using the procedure described in General Scheme 11 except using 1-methyl-5-(piperazin-1-yl)-1H-indazole as the coupling partner.

$^1$H NMR (400 MHz, CHLOROFORM-d) δ ppm 7.86 (1H, s), 7.40 (1H, d), 7.20 (2H, m), 6.75 (1H, d), 6.05 (s, 1H), 5.20 (s, 1H), 4.38 (m, 2H), 4.03 (s, 3H), 3.85 (s, 3H), 3.80 (m, 2H), 3.20 (2H, m), 2.76 (s, 3H), 2.67 (m, 2H), 2.15 (m, 2H), 1.78 (s, 3H), 1.20 (4H, m), 1.10 (s, 9H) LCMS (m/z) ES$^+$=683 (M+1).

Example 15

(2S)(M)-2-(tert-butoxy)-2-(4-(4-chlorophenyl)-1,6-dimethyl-2-(2-(1-methyl-1H-indazol-5-yl)pyridin-4-yl)-1H-pyrrolo[2,3-b]pyridin-5-yl)acetic acid

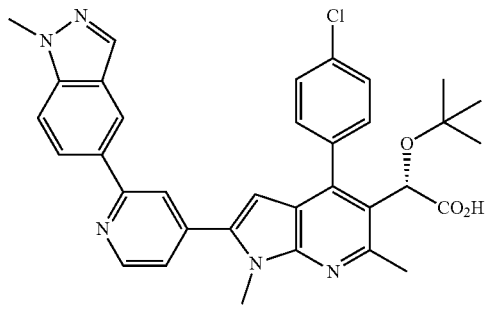 [SMILES: Cc1nc2c(cc(-c3ccnc(-c4ccc5c(cnn5C)c4)c3)n2C)c(-c2ccc(Cl)cc2)c1[C@H](OC(C)(C)C)C(=O)O]

Example 15 was synthesized using the procedure described in General Scheme 1 except using 4-chlorophenyl boronic acid as the coupling partner.

$^1$H NMR (400 MHz, Chloroform-d) δ ppm=8.98 (d, J=6.0 Hz, 1H), 8.36 (s, 1H), 8.18 (s, 1H), 8.06 (d, J=1.2 Hz, 1H), 7.96 (dd, J=8.8, 1.4 Hz, 1H), 7.52-7.71 (m, 6H), 6.72 (s, 1H), 5.42 (s, 1H), 4.16 (s, 3H), 4.11 (s, 3H), 2.82 (s, 3H), 1.00 (s, 9H); LC/MS (m/z) ES+=594.3 (M+1).

Example 18

(2S)(M)-2-(tert-butoxy)-2-(-4-(8-fluoro-5-methyl-chroman-6-yl)-1,6-dimethyl-2-(6-(1-methyl-1H-indazol-5-yl)pyridin-3-yl)-1H-pyrrolo[2,3-b]pyridin-5-yl)acetic acid

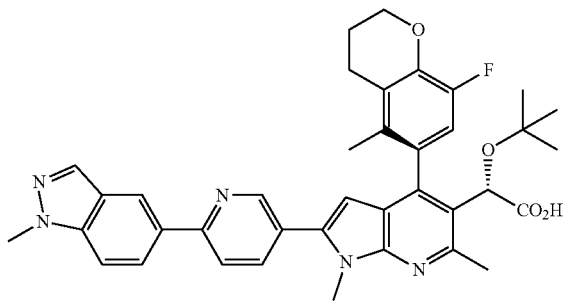

Example 18 was synthesized using the procedure described in General Scheme 1 except using 2-chloro-5-iodopyridine and (1-methyl-1H-indazol-5-yl)boronic acid.

$^1$H NMR (400 MHz, CHLOROFORM-d) δ=8.96 (s, 1H), 8.39 (s, 1H), 8.14 (s, 1H), 8.06 (d, J=8.8 Hz, 2H), 8.00-7.95 (m, 1H), 7.57 (d, J=8.8 Hz, 1H), 6.81 (d, J=10.9 Hz, 1H), 6.27 (s, 1H), 5.27 (s, 1H), 4.33-4.30 (m, 2H), 4.15 (s, 3H), 4.05 (s, 3H), 2.90 (s, 3H), 2.74 (br. s., 2H), 2.17 (d, J=5.1 Hz, 2H), 1.92 (s, 3H), 1.16 (s, 9H); LC/MS (m/z) ES+=648 (M+1).

Example 25

(2S)(M)-2-(tert-butoxy)-2-(-4-(8-fluoro-5-methyl-chroman-6-yl)-1,6-dimethyl-2-(2-(4-(oxetan-3-yl)piperazin-1-yl)pyridin-4-yl)-1H-pyrrolo[2,3-b]pyridin-5-yl)acetic acid

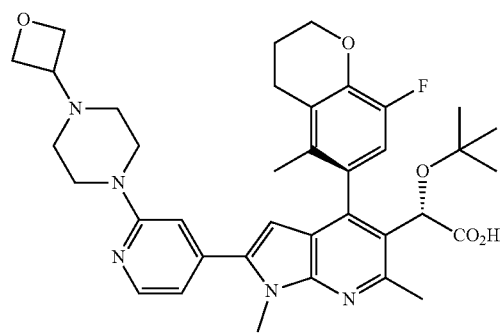

Example 25 was synthesized using the procedure described in General Scheme 7 except using 1-(oxetan-3-yl)piperazine as the coupling partner.

$^1$H NMR (400 MHz, METHANOL-d$_4$) δ ppm 8.16 (d, J=5.7 Hz, 1H), 7.15 (s, 1H), 7.05 (dd, J=5.7, 1.2 Hz, 1H), 6.71 (d, J=11.1 Hz, 1H), 6.24 (s, 1H), 5.15 (s, 1H), 4.83-4.87 (m, 2H), 4.73-4.80 (m, 2H), 4.19-4.28 (m, 4H), 3.93 (s, 3H), 3.88 (br. s., 3H), 3.09-3.20 (m, 4H), 2.84 (s, 3H), 2.66-2.79 (m, 2H), 2.05-2.16 (m, 2H), 1.83 (s, 3H), 1.09 (s, 9H). LC/MS (m/z) ES+=658 (M+1).

General Scheme 4

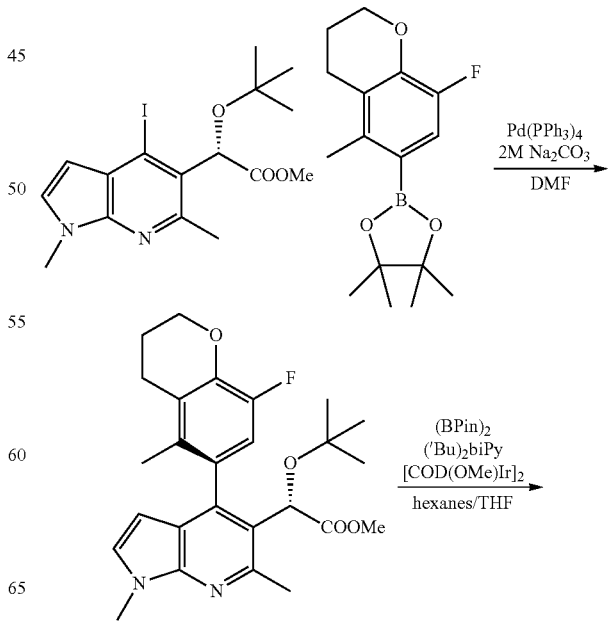

59

-continued

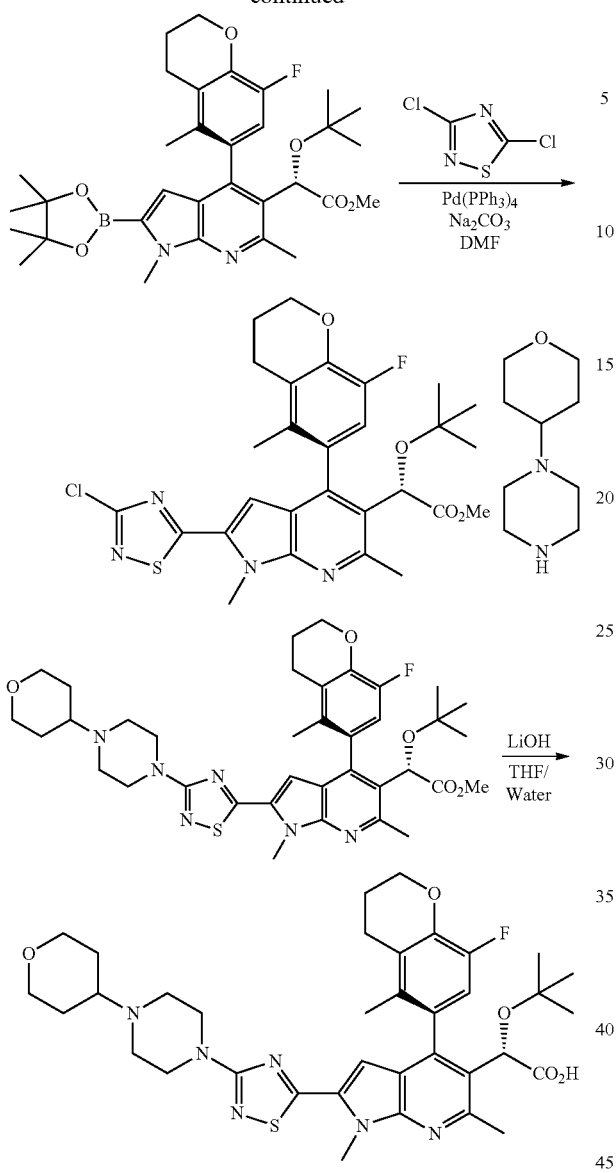

Example 26

(2S)(M)-2-(tert-butoxy)-2-(-4-(8-fluoro-5-methyl-chroman-6-yl)-1,6-dimethyl-2-(3-(4-(tetrahydro-2H-pyran-4-yl)piperazin-1-yl)-1,2,4-thiadiazol-5-yl)-1H-pyrrolo[2,3-b]pyridin-5-yl)acetic acid

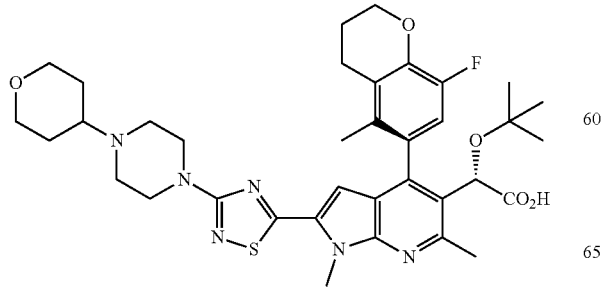

60

Step A (2S)(M)-methyl 2-(tert-butoxy)-2-(-4-(8-fluoro-5-methylchroman-6-yl)-1,6-dimethyl-1H-pyrrolo[2,3-b]pyridin-5-yl)acetate

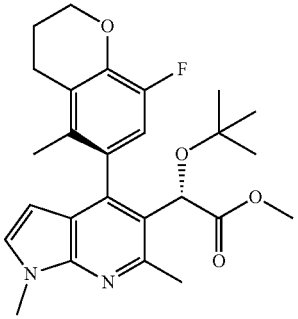

A mixture of (S)-methyl 2-(tert-butoxy)-2-(4-iodo-1,6-dimethyl-1H-pyrrolo[2,3-b]pyridin-5-yl)acetate (51.4 g, 123 mmol), 2-(8-fluoro-5-methylchroman-6-yl)-4,4,5,5-tetramethyl-1,3,2-dioxaborolane (37.9 g, 130 mmol), $K_2CO_3$ (51.2 g, 370 mmol) in N,N-Dimethylformamide (DMF) (500 mL) and Water (100 mL) was degassed with $N_2$ for 10 min. $Pd(PPh_3)_4$ (7.13 g, 6.17 mmol) was added and the mixture heated to 70° C. After 7 h, water was added and the mixture was extracted with ethyl acetate. The organic phase was washed with brine, dried ($Na_2SO_4$), filtered and concentrated. The residue was purified by silica gel chromatography (Ethyl acetate/hexanes 0-40%) to afford the title compound (55 g). 1H NMR (400 MHz, Chloroform-d) δ ppm=6.98 (d, J=3.3 Hz, 1H), 6.74 (d, J=11.3 Hz, 1H), 5.84 (d, J=3.5 Hz, 1H), 5.13 (s, 1H), 4.29 (t, J=5.3 Hz, 2H), 3.85 (s, 3H), 3.57 (s, 3H), 2.80 (s, 3H), 2.78-2.66 (m, 2H), 2.14 (d, J=3.3 Hz, 2H), 1.79 (s, 3H), 1.10 (s, 9H). LC/MS (m/z) ES⁺=455.3 (M+1).

Step B (2S)(M)-methyl-2-(tert-butoxy)-2-(4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate

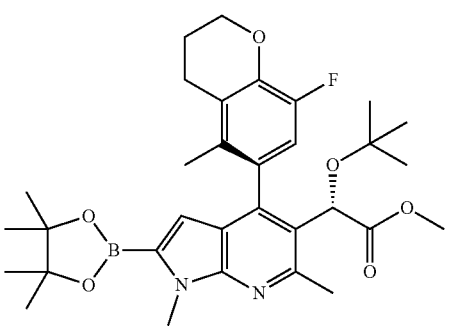

To a degassed mixture of 4,4,4',4',5,5,5',5'-octamethyl-2,2'-bi(1,3,2-dioxaborolane) (3.35 g, 13.20 mmol), 4,4'-di-tert-butyl-2,2'-bipyridine (0.189 g, 0.704 mmol) and [(COD)(OMe)Ir]$_2$ (0.233 g, 0.352 mmol) was added n-hexanes (100 mL) under nitrogen. The reaction was heated at 50° C. for 10 mins. Then, a solution of (2S)(M)-methyl-2-(tert-butoxy)-2-(4-(8-fluoro-5-methylchroman-6-yl)-1,6-dimethyl-1H-pyrrolo[2,3-b]pyridin-5-yl)acetate (4 g, 8.80 mmol) in degassed tetrahydrofuran (20.00 mL) was added. The reaction was then heated to 90° C. for 30 min. The solvent was concentrated and purified on silica gel (0-40% ethyl acetate/n-hexanes) to give the title compound (4.6 g, 7.92 mmol, 90% yield) as a yellow solid. $^1$H NMR (400 MHz, CHLOROFORM-d) 5=6.71 (d, J=11.33 Hz, 1H), 6.49 (s, 1H), 5.13 (s, 1H), 4.28 (m, 2H), 4.02 (s, 3H), 3.57 (s, 3H), 2.80 (s, 3H), 2.70 (d, J=3.62 Hz, 2H), 2.14 (d, J=2.64 Hz, 2H), 1.77 (s, 3H), 1.32 (s, 12H), 1.09 (s, 9H); LC/MS (m/z) ES$^+$=581 (M+1); 499 (M+1) appeared as a mixture of boronic ester and boronic acid.

Step C (2S)(M)-methyl 2-(tert-butoxy)-2-(-2-(3-chloro-1,2,4-thiadiazol-5-yl)-4-(8-fluoro-5-methylchroman-6-yl)-1,6-dimethyl-1H-pyrrolo[2,3-b]pyridin-5-yl)acetate

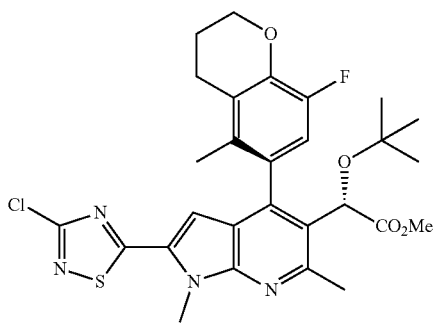

A solution of (2S)(M)-methyl 2-(tert-butoxy)-2-(-4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate (3.38 g, 5.82 mmol) in N,N-Dimethylformamide (DMF) (51 ml) was treated with 3,5-dichloro-1,2,4-thiadiazole (0.992 g, 6.402 mmol) and 2M Na$_2$CO$_3$ (8.73 ml, 17.46 mmol). The mixture was degassed with N2 for 5 min, treated with Pd(Ph$_3$P)$_4$ (1.345 g, 1.164 mmol), and stirred at 75° C. for 1 hour. The reaction mixture was cooled to ambient temperature diluted with sat. NaHCO$_3$, extracted with EtOAc, washed with brine, dried over Na$_2$SO$_4$, filtered, and concentrated. The residue was purified by silica gel chromatography to afford the title compound (1.39 g, 43%) as a yellow solid. $^1$H NMR (400 MHz, CHLOROFORM-d) δ ppm 6.75 (d, J=11.0 Hz, 1H), 6.64 (s, 1H), 5.16 (s, 1H), 4.33 (t, J=5.0 Hz, 2H), 4.24 (s, 3H), 3.62 (s, 3H), 2.85 (s, 3H), 2.76 (t, J=6.5 Hz, 2H), 2.25-2.14 (m, 2H), 1.81 (s, 3H), 1.13 (s, 9H); LCMS (m/z) ES$^+$=573 (M+1).

Step D (2S)(M)-methyl 2-(tert-butoxy)-2-(-4-(8-fluoro-5-methylchroman-6-yl)-1,6-dimethyl-2-(3-(4-(tetrahydro-2H-pyran-4-yl)piperazin-1-yl)-1,2,4-thiadiazol-5-yl)-1H-pyrrolo[2,3-b]pyridin-5-yl)acetate

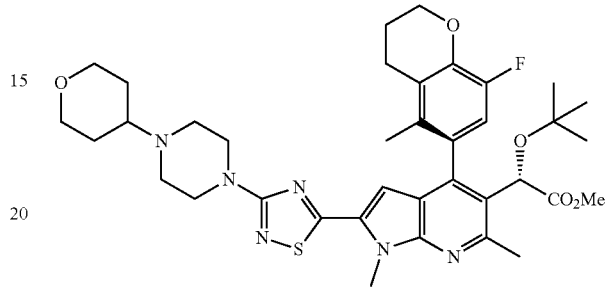

A mixture of (2S)(M)-methyl 2-(tert-butoxy)-2-(2-(3-chloro-1,2,4-thiadiazol-5-yl)-4-(8-fluoro-5-methylchroman-6-yl)-1,6-dimethyl-1H-pyrrolo[2,3-b]pyridin-5-yl)acetate (1.6 g, 2.79 mmol) and 1-(tetrahydro-2H-pyran-4-yl)piperazine, 2 Hydrochloride (1.215 mL, 4.19 mmol) in DMSO (24 mL) was treated with sodium carbonate (1.775 g, 16.75 mmol) and the mixture was stirred at 90° C. After 18 h, the mixture was cooled to ambient temperature and poured into water. The resulting precipitate was collected and purified by silica gel chromatography (MeOH/DCM 0-10%) to afford the title compound (1.79 g, 91%) as a yellow solid. $^1$H NMR (400 MHz, CHLOROFORM-d) δ ppm 1.11 (s, 9H) 1.62 (br. s., 4H) 1.80 (s, 4H) 2.13-2.22 (m, 2H) 2.65-2.72 (m, 2H) 2.75 (t, J=6.90 Hz, 3H) 2.83 (s, 3H) 3.40 (t, J=11.04 Hz, 2H) 3.60 (s, 3H) 3.79 (d, J=3.76 Hz, 3H) 4.05 (dd, J=11.54, 3.51 Hz, 2H) 4.21 (s, 3H) 4.32 (t, J=5.02 Hz, 2H) 5.13 (s, 1H) 6.48 (s, 1H) 6.74 (d, J=11.29 Hz, 1H). LCMS (m/z) ES$^+$=707 (M+1).

Step E (2S)(M)-2-(tert-butoxy)-2-((R)-4-(8-fluoro-5-methylchroman-6-yl)-1,6-dimethyl-2-(3-(4-(tetrahydro-2H-pyran-4-yl)piperazin-1-yl)-1,2,4-thiadiazol-5-yl)-1H-pyrrolo[2,3-b]pyridin-5-yl)acetic acid

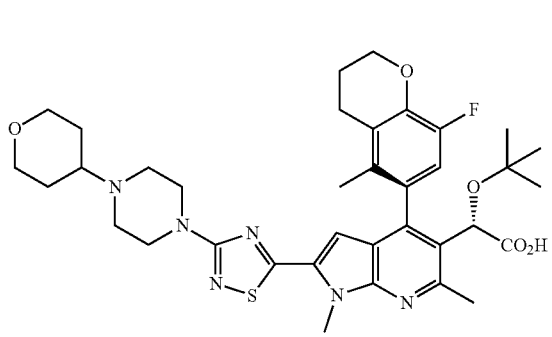

A solution of (2S)(M)-methyl 2-(tert-butoxy)-2-(4-(8-fluoro-5-methylchroman-6-yl)-1,6-dimethyl-2-(3-(4-(tetrahydro-2H-pyran-4-yl)piperazin-1-yl)-1,2,4-thiadiazol-5-yl)-1H-pyrrolo[2,3-b]pyridin-5-yl)acetate (1.8 g, 2.55 mmol)

in THF (45 mL) and Water (6.43 mL) was treated with LiOH (0.610 g, 25.5 mmol) and the mixture was stirred at 60° C. After 18 h, the reaction mixture was concentrated in vacuo and diluted with water and then acidified to pH 4 with 1N HCl. The aqueous layer was exhaustively extracted with DCM and the combined organics were washed with brine, dried (Na$_2$SO$_4$), filtered and concentrated in vacuo to afford the title compound (1.53 g, 87% yield) as a yellow solid. $^1$H NMR (400 MHz, DMSO-d$_6$) δ ppm 1.03 (s, 9H) 1.45 (br. s., 2H) 1.65-1.77 (m, 2H) 1.78 (s, 3H) 2.06 (d, J=4.52 Hz, 2H) 2.58 (br. s., 3H) 2.66-2.73 (m, 3H) 2.74 (s, 3H) 3.28 (t, J=11.29 Hz, 3H) 3.63 (br. s., 3H) 3.89 (br. s., 2H) 4.12 (s, 3H) 4.23 (t, J=4.89 Hz, 2H) 4.98 (s, 1H) 6.55 (s, 1H) 6.77 (d, J=11.29 Hz, 1H) 12.62 (br. s., 1H). LCMS (m/z) ES$^+$=693 (M+1).

Example 27

(2S)(M)-2-(tert-butoxy)-2-((R)-4-(8-fluoro-5-methylchroman-6-yl)-1,6-dimethyl-2-(3-(4-(tetrahydro-2H-pyran-4-yl)piperazin-1-yl)-1,2,4-oxadiazol-5-yl)-1H-pyrrolo[2,3-b]pyridin-5-yl)acetic acid

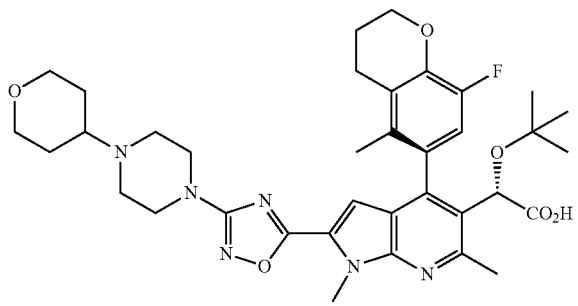

Step A 4-(tetrahydro-2H-pyran-4-yl)piperazine-1-carbonitrile

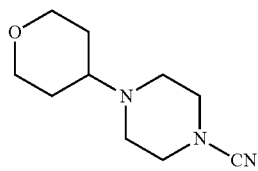 [SMILES: N#CN1CCN(C2CCOCC2)CC1]

A suspension of 1-(tetrahydro-2H-pyran-4-yl)piperazine dihydrochloride (600 mg, 2.467 mmol) in anhydrous Ethanol (10 mL) was added solid NaHCO$_3$ (1555 mg, 18.51 mmol) followed by cyanic bromide (523 mg, 4.93 mmol) and the mixture was stirred at ambient temperature. The mixture was diluted by 50 mL of CH$_2$Cl$_2$ and the solids were filtered off. The filtrated was concentrated in vacuo to afford to give the title compound (632 mg, 3.24 mmol, >100% yield). $^1$H NMR (400 MHz, Chloroform-d) δ ppm=4.02 (dd, J=3.8, 11.2 Hz, 2H), 3.42-3.31 (m, 2H), 3.31-3.22 (m, 4H), 2.74-2.61 (m, 4H), 2.59-2.47 (m, 1H), 1.73 (d, J=11.5 Hz, 2H), 1.67-1.49 (m, 2H); LC/MS (m/z) ES$^+$ (ELSD)=196.1 (M+1).

Step B (Z)-N'-hydroxy-4-(tetrahydro-2H-pyran-4-yl)piperazine-1-carboximidamide 2 Hydrochloride

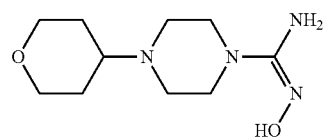 [SMILES: N/C(=N/O)N1CCN(C2CCOCC2)CC1]

A mixture of 4-(tetrahydro-2H-pyran-4-yl)piperazine-1-carbonitrile (632 mg, 3.24 mmol), Ethanol (10 mL), hydroxylamine hydrochloric acid (257 mg, 3.70 mmol) and Na$_2$CO$_3$ (785 mg, 7.40 mmol) was heated to 80° C. After 1.5 h, the solids were filtered off and the filtrate concentrated in vacuo. The residue was dissolved into a minimum amount of methanol and treated with 5 mL of 1 M of HCl/Ether and diluted by acetone. Resulting solids were collected and dried in vacuo to afford the title compound (566 mg, 1.879 mmol, 76% yield) as white solid. $^1$H NMR (400 MHz, DMSO-d6) δ ppm=11.88 (br. s., 4H), 11.20 (br. s., 1H), 10.17 (br. s., 1H), 8.26 (br. s., 2H), 4.09-3.87 (m, 5H), 3.69-3.49 (m, 4H), 3.42 (br. s., 1H), 3.26 (t, J=11.5 Hz, 2H), 3.17-2.98 (m, 2H), 2.00 (d, J=11.1 Hz, 2H), 1.83-1.64 (m, 2H); LC/MS (m/z) ES$^+$ (ELSD)=229.2 (M+1).

Step C (M)(2S)-methyl 2-(tert-butoxy)-2-(4-(8-fluoro-5-methylchroman-6-yl)-1,6-dimethyl-2-vinyl-1H-pyrrolo[2,3-b]pyridin-5-yl)acetate

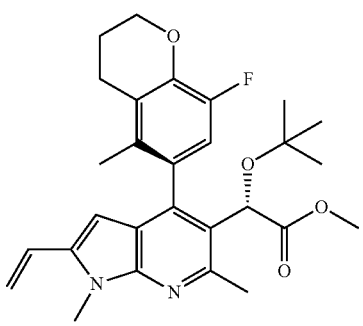

To a degassed mixture of (M)(2S)-methyl-2-(tert-butoxy)-2-(4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate (4.6 g, 7.92 mmol), bromoethene (9.51 mL, 9.51 mmol)(1M solution in THF), and xphos precatalyst (0.480 g, 0.610 mmol) in tetrahydrofuran (50 mL) under nitrogen was added K$_3$PO$_4$ (31.7 mL, 15.85 mmol). Stirred at room temperature for 2 hours, evaporated solvent and diluted with ethyl acetate. Organic phase was separated, dried over Na$_2$SO$_4$, filtered, concentrated and purified on silica gel (0-50% ethyl acetate/n-hexanes) to give the title compound (3.1 g, 6.45 mmol, 81% yield) as a yellow solid. $^1$H NMR (400 MHz, CHLOROFORM-d) δ=6.67-6.77 (m, 2H), 6.02

(s, 1H), 5.73 (m, 1H), 5.30 (m, 1H), 5.11 (s, 1H), 4.30 (t, J=5.23 Hz, 2H), 3.85 (s, 3H), 3.57 (s, 3H), 2.78 (s, 3H), 2.70-2.76 (m, 2H), 2.10-2.19 (m, 2H), 1.80 (s, 3H), 1.10 (s, 9H); LC/MS (m/z) ES$^+$=481 (M+1).

Step D (M)(2S)-methyl 2-(tert-butoxy)-2-(4-(8-fluoro-5-methylchroman-6-yl)-2-formyl-1,6-dimethyl-1H-pyrrolo[2,3-b]pyridin-5-yl)acetate

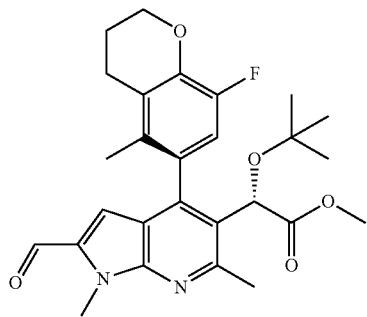

To a solution of (M)(2S)-methyl 2-(tert-butoxy)-2-(4-(8-fluoro-5-methylchroman-6-yl)-1,6-dimethyl-2-vinyl-1H-pyrrolo[2,3-b]pyridin-5-yl)acetate (1.5 g, 3.12 mmol) in tetrahydrofuran (150 mL) and Water (50.0 mL) was added potassium osmate dihydrate (0.161 g, 0.437 mmol) followed by addition of sodium periodate (4.01 g, 18.73 mmol) portionwise over a period of 20 min. Stirred at RT for 1.5 h. Added sodium thiosulfate (10% solution, 370 mL), stirred for 5 min and extracted with dichloromethane. Organic phase was washed with water and brine, dried over Na$_2$SO$_4$, filtered and concentrated to give the title compound (1.47 g, 98% yield) as a yellow solid. $^1$H NMR (400 MHz, CHLOROFORM-δ=9.76 (s, 1H), 6.75 (d, J=11.1 Hz, 1H), 6.65 (s, 1H), 5.14 (s, 1H), 4.32 (t, J=5.2 Hz, 2H), 4.16 (s, 3H), 3.61 (s, 3H), 2.84 (s, 3H), 2.65-2.80 (m, 2H), 2.10-2.25 (m, 2H), 1.81 (s, 3H), 1.12 (s, 9H); LC/MS (m/z) ES$^+$=483 (M+1).

Step E (2S)(M) 5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid

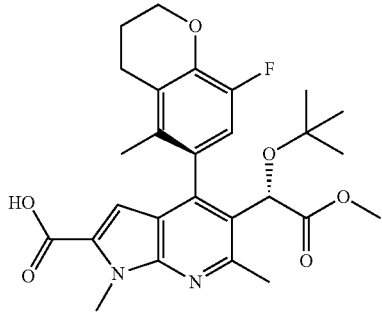

To a solution of (2S)(M)-methyl 2-(tert-butoxy)-2-(4-(8-fluoro-5-methylchroman-6-yl)-2-formyl-1,6-dimethyl-1H-pyrrolo[2,3-b]pyridin-5-yl)acetate (1.0 g, 2.072 mmol) in acetone (170 mL) and water (56.7 mL) cooled to 0° C. was added sulfamic acid (11.87 g, 122 mmol) followed by addition of a solution of sodium chlorite (0.131 g, 1.451 mmol) (0.7 eq. from a solution of 8.73 mg/mL, 131 mg added 15 mL). Stirred at 0° C. for 15 min, added sodium chlorite (0.3 eq., 56 mg, 6.4 mL) and stirred at 0° C. for 15 min. Diluted with EtOAc and added water, aqueous layer was extracted with ethyl acetate. Organic phase was washed with water and brine, dried over Na$_2$SO$_4$, filtered and concentrated to give the title compound (0.988 g, 96% yield) as a yellow solid. $^1$H NMR (400 MHz, CHLOROFORM-d) δ=6.81 (s, 1H), 6.73 (d, J=11.1 Hz, 1H), 5.15 (s, 1H), 4.26-4.37 (m, 2H), 4.12-4.22 (m, 3H), 3.61 (s, 3H), 2.86 (s, 3H), 2.67-2.77 (m, 2H), 2.11-2.24 (m, 2H), 1.79 (s, 3H), 1.12 (s, 9H); LC/MS (m/z) ES$^+$=499 (M+1).

Step F (2S)(M)-Methyl-2-(tert-butoxy)-2-((R)-4-(8-fluoro-5-methylchroman-6-yl)-1,6-dimethyl-2-(3-(4-(tetrahydro-2H-pyran-4-yl)piperazin-1-yl)-1,2,4-oxadiazol-5-yl)-1H-pyrrolo[2,3-b]pyridin-5-yl)acetic acid

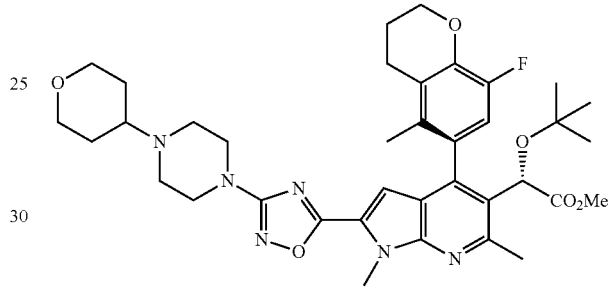

A solution of (2S)(M) 5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid (150 mg, 0.301 mmol) in N,N-Dimethylformamide (DMF) (2 mL) was added HOBT (52.9 mg, 0.391 mmol) followed by addition of EDC (75.0 mg, 0.391 mmol) and the mixture was stirred at ambient temperature for 35 min. then TEA (0.168 mL, 1.204 mmol) and (Z)—N'-hydroxy-4-(tetrahydro-2H-pyran-4-yl)piperazine-1-carboximidamide, 2 Hydrochloride (118 mg, 0.391 mmol) was added and the mixture was heated at 80° C. for 2 h. Added a small amount of MeOH and purified by reverse phase HPLC to afford the title compound (84 mg, 30.4%). LC/MS (m/z) ES$^+$=691(M+1).

Step G (2S)(M)-2-(tert-butoxy)-2-(-4-(8-fluoro-5-methylchroman-6-yl)-1,6-dimethyl-2-(3-(4-(tetrahydro-2H-pyran-4-yl)piperazin-1-yl)-1,2,4-oxadiazol-5-yl)-1H-pyrrolo[2,3-b]pyridin-5-yl)acetic acid

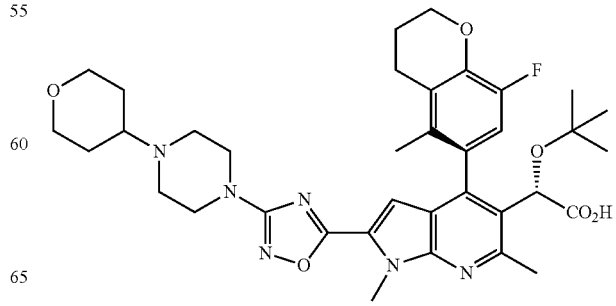

To a solution of (2S)(M)-Methyl-2-(tert-butoxy)-2-(-4-(8-fluoro-5-methylchroman-6-yl)-1,6-dimethyl-2-(3-(4-(tetrahydro-2H-pyran-4-yl)piperazin-1-yl)-1,2,4-oxadiazol-5-yl)-1H-pyrrolo[2,3-b]pyridin-5-yl)acetic acid (84 mg, 0.091 mmol) in 1,4-Dioxane (5 mL) and Water (0.667 mL) was added LiOH monohydrate (46.0 mg, 1.097 mmol) and heated to 85° C. After 18 h, the reaction mixture was cooled to ambient temperature and concentrated in vacuo. The residue was purified by reverse phase HPLC to afford the title compound (56 mg, 68%) as a pale yellow solid. $^1$H NMR (400 MHz, CHLOROFORM-d) δ ppm 12.33 (br. s., 1H), 6.86 (s, 1H), 6.77 (d, J=10.9 Hz, 1H), 5.26 (s, 1H), 4.30-4.36 (m, 2H), 4.27 (s, 3H), 4.02-4.25 (m, 5H), 3.57-3.81 (m, 4H), 3.44 (t, J=11.2 Hz, 3H), 3.03 (br. s., 2H), 2.85 (s, 3H), 2.73 (br. s., 2H), 2.11-2.23 (m, 2H), 1.95-2.09 (m, 2H), 1.82-1.92 (m, 4H), 1.14 (s, 9H). LC/MS (m/z) ES$^+$=677 (M+1).

General Scheme 5

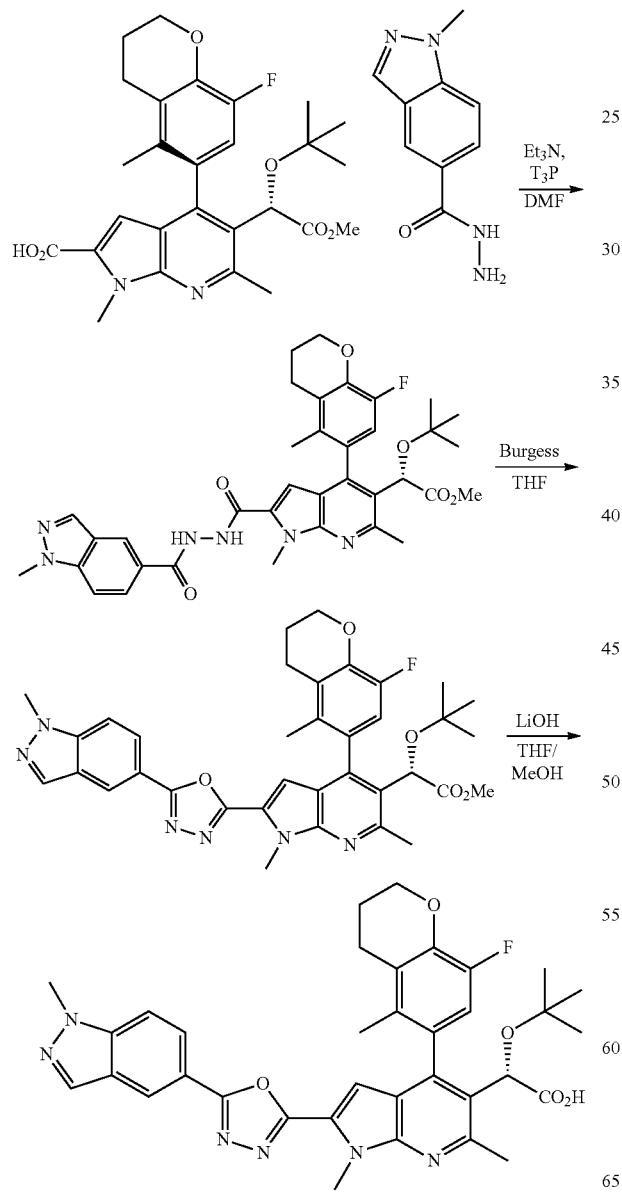

Example 28

(2S)(M)-2-(tert-butoxy)-2-(4-(8-fluoro-5-methyl-chroman-6-yl)-1,6-dimethyl-2-(5-(1-methyl-H-indazol-5-yl)-1,3,4-oxadiazol-2-yl)-1H-pyrrolo[2,3-b]pyridin-5-yl)acetic acid

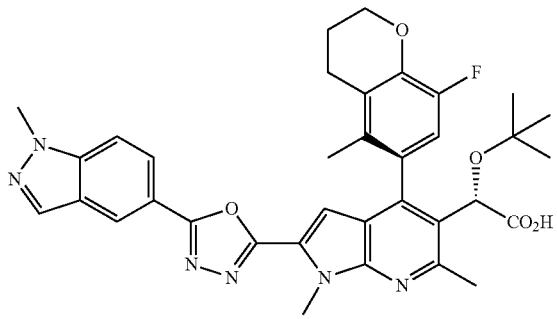

Step A (2S) (M)-methyl 2-(tert-butoxy)-2-(4-(8-fluoro-5-methylchroman-6-yl)-1,6-dimethyl-2-vinyl-1H-pyrrolo[2,3-b]pyridin-5-yl)acetate

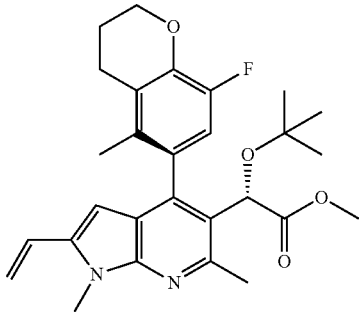

To a degassed mixture of (2S)(M)-methyl-2-(tert-butoxy)-2-(4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate (4.6 g, 7.92 mmol), bromoethene (9.51 mL, 9.51 mmol)(1M solution in THF), and xphos precatalyst (0.480 g, 0.610 mmol) in tetrahydrofuran (50 mL) under nitrogen was added K$_3$PO$_4$ (31.7 mL, 15.85 mmol). Stirred at room temperature for 2 hours, evaporated solvent and diluted with ethyl acetate. Organic phase was separated, dried over Na$_2$SO$_4$, filtered, concentrated and purified on silica gel (0-50% ethyl acetate/n-hexanes) to give the title compound (3.1 g, 6.45 mmol, 81% yield) as a yellow solid. $^1$H NMR (400 MHz, CHLOROFORM-d) δ=6.67-6.77 (m, 2H), 6.02 (s, 1H), 5.73 (m, 1H), 5.30 (m, 1H), 5.11 (s, 1H), 4.30 (t, J=5.23 Hz, 2H), 3.85 (s, 3H), 3.57 (s, 3H), 2.78 (s, 3H), 2.70-2.76 (m, 2H), 2.10-2.19 (m, 2H), 1.80 (s, 3H), 1.10 (s, 9H); LC/MS (m/z) ES+=481 (M+1).

Step C (2S)(M)-methyl 2-(tert-butoxy)-2-(4-(8-fluoro-5-methylchroman-6-yl)-2-formyl-1,6-dimethyl-1H-pyrrolo[2,3-b]pyridin-5-yl)acetate

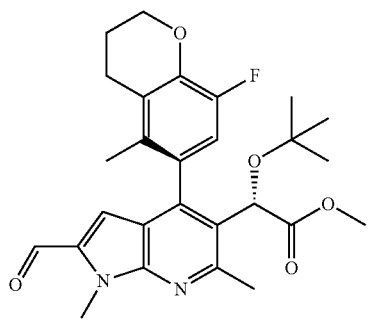

To a solution of (2S)(M)-methyl 2-(tert-butoxy)-2-(4-(8-fluoro-5-methylchroman-6-yl)-1,6-dimethyl-2-vinyl-1H-pyrrolo[2,3-b]pyridin-5-yl)acetate (1.5 g, 3.12 mmol) in tetrahydrofuran (150 mL) and Water (50.0 mL) was added potassium osmate dihydrate (0.161 g, 0.437 mmol) followed by addition of sodium periodate (4.01 g, 18.73 mmol) portionwise over a period of 20 min. Stirred at RT for 1.5 h. Added sodium thiosulfate (10% solution, 370 mL), stirred for 5 min and extracted with dichloromethane. The organic phase was washed with water and brine, dried over Na$_2$SO$_4$, filtered and concentrated in vacuo to give the title compound (1.47 g, 98% yield) as a yellow solid. $^1$H NMR (400 MHz, CHLOROFORM-d) δ=9.76 (s, 1H), 6.75 (d, J=11.1 Hz, 1H), 6.65 (s, 1H), 5.14 (s, 1H), 4.32 (t, J=5.2 Hz, 2H), 4.16 (s, 3H), 3.61 (s, 3H), 2.84 (s, 3H), 2.65-2.80 (m, 2H), 2.10-2.25 (m, 2H), 1.81 (s, 3H), 1.12 (s, 9H); LC/MS (m/z) ES+=483 (M+1).

Step D (2S)(M) 5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid

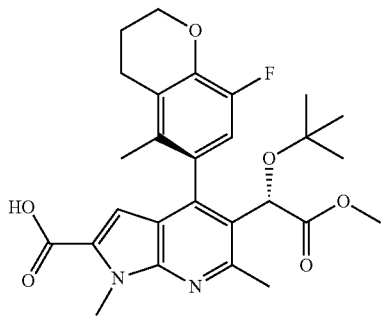

To a solution of (2S)(M)-methyl 2-(tert-butoxy)-2-(4-(8-fluoro-5-methylchroman-6-yl)-2-formyl-1,6-dimethyl-1H-pyrrolo[2,3-b]pyridin-5-yl)acetate (1.0 g, 2.072 mmol) in acetone (170 mL) and water (56.7 mL) cooled to 0° C. was added sulfamic acid (11.87 g, 122 mmol) followed by addition of a solution of sodium chlorite (0.131 g, 1.451 mmol) (0.7 eq. from a solution of 8.73 mg/mL, 131 mg added 15 mL). Stirred at 0° C. for 15 min, added sodium chlorite (0.3 eq., 56 mg, 6.4 mL) and stirred at 0° C. for 15 min. Diluted with EtOAc and added water, aqueous layer was extracted with ethyl acetate. Organic phase was washed with water and brine, dried over Na$_2$SO$_4$, filtered and concentrated to give the title compound (0.988 g, 96% yield) as a yellow solid. $^1$H NMR (400 MHz, CHLOROFORM-d) δ=6.81 (s, 1H), 6.73 (d, J=11.1 Hz, 1H), 5.15 (s, 1H), 4.26-4.37 (m, 2H), 4.12-4.22 (m, 3H), 3.61 (s, 3H), 2.86 (s, 3H), 2.67-2.77 (m, 2H), 2.11-2.24 (m, 2H), 1.79 (s, 3H), 1.12 (s, 9H), COOH proton not found; LC/MS (m/z) ES+=499 (M+1).

Step E (2S) (M)-methyl 2-(tert-butoxy)-2-(-4-(8-fluoro-5-methylchroman-6-yl)-1,6-dimethyl-2-(2-(1-methyl-1H-indazole-5-carbonyl)hydrazinecarbonyl)-1H-pyrrolo[2,3-b]pyridin-5-yl)acetate

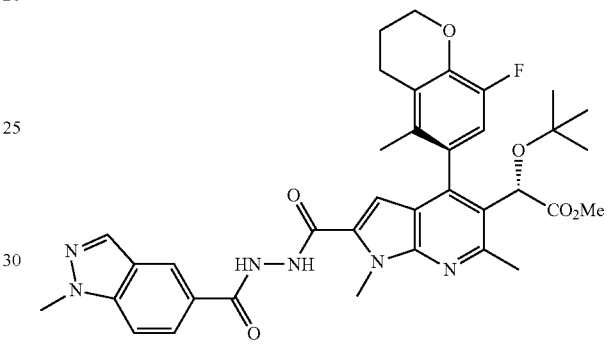

A solution of (2S)(M)-5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid (99 mg, 0.199 mmol), 1-methyl-1H-indazole-5-carbohydrazide (40.2 mg, 0.211 mmol) and triethylamine (0.083 mL, 0.596 mmol) in N,N-Dimethylformamide (DMF) (1.5 mL) was treated with T3P (0.282 mL, 0.397 mmol). After 15 min, the reaction mixture was diluted with EtOAc, washed with water, then brine, dried over Na$_2$SO$_4$, filtered and concentrated afford the title compound as an off-white solid. LC/MS (m/z) ES+=671 (M+1).

Step F (2S)(M)-methyl 2-(tert-butoxy)-2-(4-(8-fluoro-5-methylchroman-6-yl)-1,6-dimethyl-2-(5-(1-methyl-1H-indazol-5-yl)-1,3,4-oxadiazol-2-yl)-1H-pyrrolo[2,3-b]pyridin-5-yl)acetate

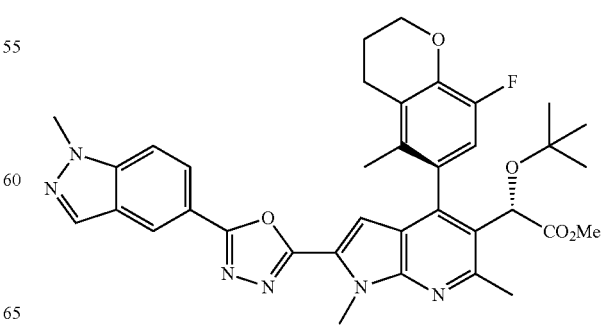

A solution of (2S)(M)-methyl 2-(tert-butoxy)-2-(-4-(8-fluoro-5-methylchroman-6-yl)-1,6-dimethyl-2-(2-(1-methyl-1H-indazole-5-carbonyl)hydrazinecarbonyl)-1H-pyrrolo[2,3-b]pyridin-5-yl)acetate (135 mg, 0.20 mmol) in Tetrahydrofuran (3.0 mL) was treated with Burgess reagent (237 mg, 0.993 mmol) and then heated to 60° C. After 10 min, the reaction mixture was concentrated in vacuo and the residue partitioned between EtOAc and water. The organics were washed with brine, dried (Na₂SO₄), filtered and concentrated in vacuo. The residue was purified by silica gel chromatography to afford the title compound as an opaque solid. LC/MS (m/z) ES⁺=653 (M+1).

Step G (2S)(M)-2-(tert-butoxy)-2-(4-(8-fluoro-5-methyl-chroman-6-yl)-1,6-dimethyl-2-(5-(1-methyl-1H-indazol-5-yl)-1,3,4-oxadiazol-2-yl)-1H-pyrrolo[2,3-b]pyridin-5-yl)acetic acid

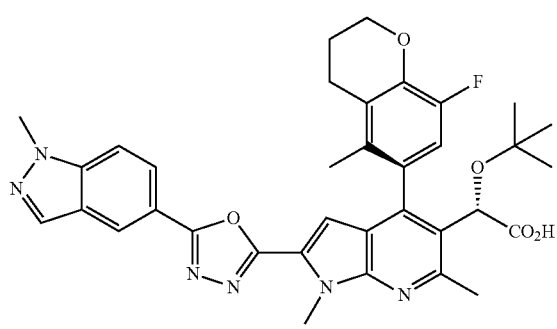

A solution of (2S)(M)-methyl 2-(tert-butoxy)-2-(4-(8-fluoro-5-methylchroman-6-yl)-1,6-dimethyl-2-(5-(1-methyl-1H-indazol-5-yl)-1,3,4-oxadiazol-2-yl)-1H-pyrrolo[2,3-b]pyridin-5-yl)acetate (119 mg, 0.182 mmol) in THF (0.6 mL)/MeOH (0.6 mL) and water (0.3 mL) was treated with lithium hydroxide monohydrate (50.0 mg, 1.192 mmol) and then irradiated in the microwave at 120° C. for 10 minutes. The mixture was purified directly by reverse phase HPLC to afford the title compound (40 mg, 0.063 mmol, 35%) as a pale yellow solid. ¹H NMR (400 MHz, CHLOROFORM-d) δ=8.53 (s, 1H), 8.21 (dd, J=1.5, 8.8 Hz, 1H), 8.15 (s, 1H), 7.54 (d, J=9.0 Hz, 1H), 6.86 (d, J=11.0 Hz, 1H), 6.75 (s, 1H), 5.27 (s, 1H), 4.39 (s, 3H), 4.35 (t, J=4.5 Hz, 2H), 4.15 (s, 3H), 2.84 (s, 3H), 2.81-2.71 (m, 2H), 2.25-2.12 (m, 2H), 1.95 (s, 3H), 1.16 (s, 9H); LC/MS (m/z) ES⁺=639 (M+1).

Scheme 6

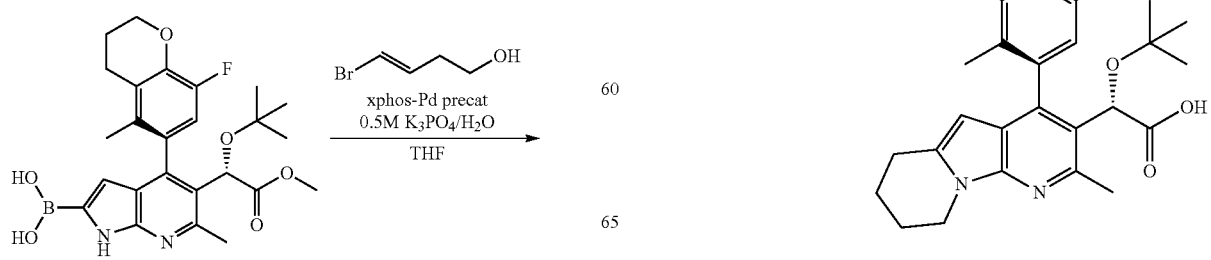

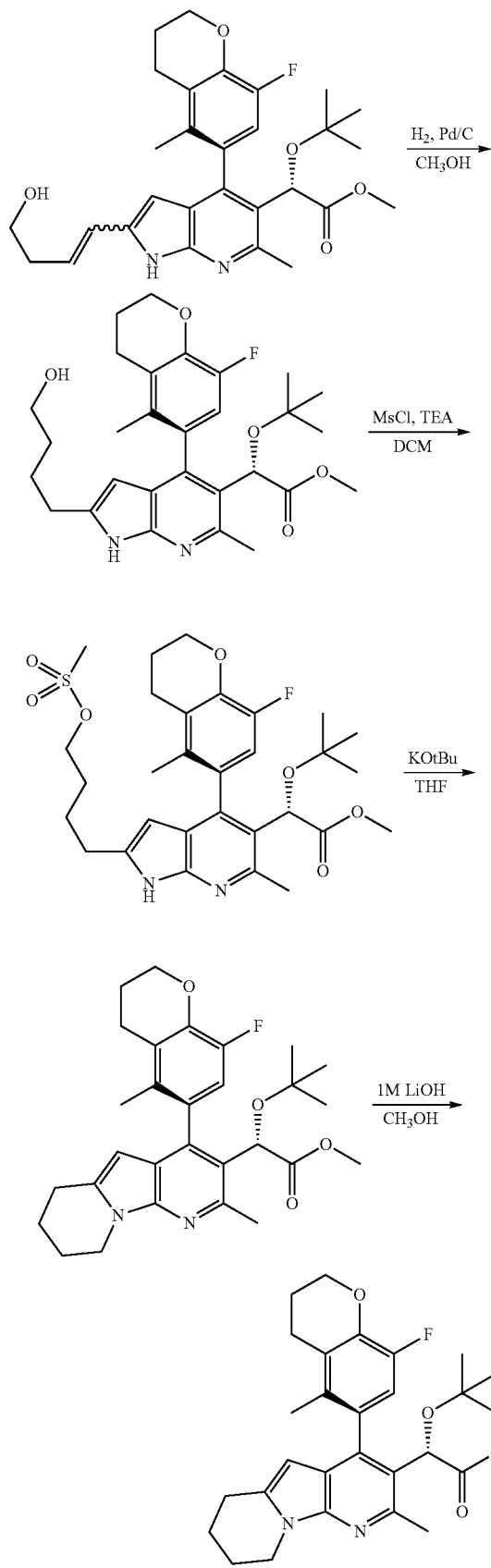

Example 29

(2S)(M)-2-(tert-butoxy)-2-(-4-(8-fluoro-5-methyl-chroman-6-yl)-2-methyl-6,7,8,9-tetrahydropyrido[3,2-b]indolizin-3-yl)acetic acid

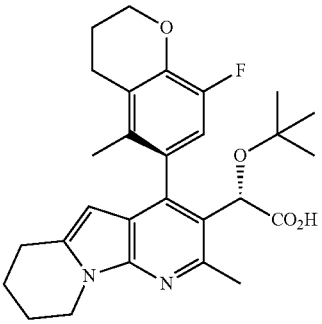

Step A
(2S)(M)-Methyl 2-(tert-butoxy)-2-(-4-(8-fluoro-5-methylchroman-6-yl)-2-(4-hydroxybut-1-en-1-yl)-6-methyl-1H-pyrrolo[2,3-b]pyridin-5-yl)acetate

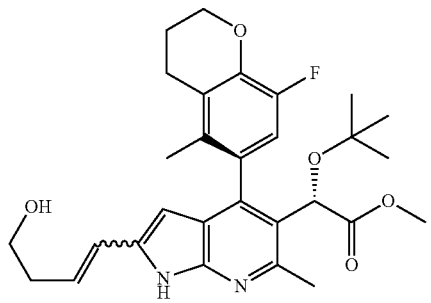

A solution of (2S)(M)-5-(-1-(tert-butoxy)-2-methoxy-2-oxoethyl)-4-(8-fluoro-5-methylchroman-6-yl)-6-methyl-1H-pyrrolo[2,3-b]pyridin-2-yl)boronic acid (26.7 mg, 0.055 mmol), 4-bromobut-3-en-1-ol (10.9 mg, 0.072 mmol) and 0.5 M tripotassium phosphate/water (0.19 mL, 0.095 mmol) was degassed with $N_2$ for 5 min and treated with chloro(2-dicyclohexylphosphino-2',4',6'-triisopropyl-1,1'-biphenyl)[2-(2-aminoethyl)phenyl)]palladium(II) (6.2 mg, 7.88 μmol) and stirred at ambient temperature under an atmosphere of $N_2$. After 3 h, the reaction mixture was partitioned between EtOAc and water and the organic layer washed with brine, dried (MgSO$_4$), filtered and concentrated in vacuo to afford the title compound (37.2 mg, 0.073 mmol, >100% yield) that was used without further purification. LC/MS (m/z) ES$^+$=511 (M+1).

Step B
(2S)(M)-methyl 2-(tert-butoxy)-2-(-4-(8-fluoro-5-methylchroman-6-yl)-2-(4-hydroxybutyl)-6-methyl-1H-pyrrolo[2,3-b]pyridin-5-yl)acetate

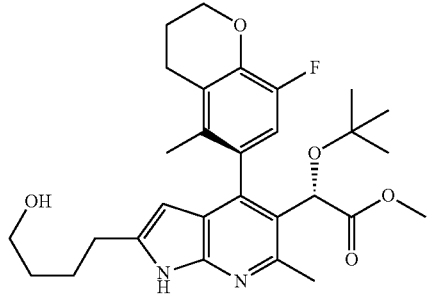

A solution of (2S)(M)-Methyl 2-(tert-butoxy)-2-(-4-(8-fluoro-5-methylchroman-6-yl)-2-(4-hydroxybut-1-en-1-yl)-6-methyl-1H-pyrrolo[2,3-b]pyridin-5-yl)acetate (37.2 mg, 0.073 mmol) in MeOH was degassed with $N_2$ for 5 min and treated with Pd/C (30 mg) and placed under an atmosphere of $H_2$ (1 atm). After 15 min, the reaction mixture was purged with $N_2$ and filtered through a pad of Celite. The filtrate was concentrated in vacuo and the residue purified by silica gel chromatography (0-20% methanol/dichloromethane) to afford the title compound (27 mg, 0.053 mmol, 73%). LC/MS (m/z) ES$^+$=513 (M+1).

Step C
(2S)(M)-Methyl 2-(tert-butoxy)-2-(-4-(8-fluoro-5-methylchroman-6-yl)-2-methyl-6,7,8,9-tetrahydropyrido[3,2-b]indolizin-3-yl)acetate

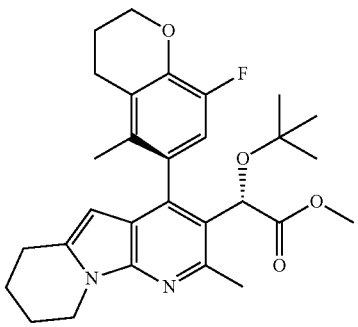

(2S)(M)-methyl 2-(tert-butoxy)-2-(-4-(8-fluoro-5-methylchroman-6-yl)-2-(4-hydroxybutyl)-6-methyl-1H-pyrrolo[2,3-b]pyridin-5-yl)acetate (27.4 mg, 0.053 mmol) was dissolved in dichloromethane (2 mL) and treated with 0.3 M mesyl chloride/dichloromethane (0.16 mL, 0.048 mmol) and 0.3 M triethylamine (0.16 mL, 0.47 mmol). The reaction stirred for 10 minutes at ambient temperature under nitrogen, was extracted with dichloromethane, dried over sodium sulfate, filtered, concentrated in vacuo. The crude material was dissolved in tetrahydrofuran (3 mL) and treated with potassium tert-butoxide (11.0 mg, 0.098 mmol) at room temperature under nitrogen. After stirring for 30 minutes, the reaction was treated with water (0.5 mL), extracted with dichloromethane, dried over sodium sulfate, filtered, concentrated under reduced pressure and purified by silica gel chromatography (0-20% methanol/dichloromethane) to afford the title compound (15.9 mg, 0.032 mmol, 60.4% yield). $^1$H NMR (400 MHz, CHLOROFORM-d) δ=6.74 (d, J=11.4 Hz, 1H), 5.57 (s, 1H), 5.13 (s, 1H), 4.34-4.27 (m, 2H), 4.26-4.20 (m, 2H), 3.58 (s, 3H), 2.88 (t, J=6.3 Hz, 2H), 2.79 (s, 3H), 2.75-2.69 (m, 2H), 2.20-2.12 (m, 2H), 2.07-1.99 (m, 2H), 1.91-1.84 (m, 2H), 1.82 (s, 3H), 1.11 (s, 9H). LC/MS (m/z) ES$^+$=495 (M+1).

Step D (2S)(M)-2-(tert-butoxy)-2-(-4-(8-fluoro-5-methyl-chroman-6-yl)-2-methyl-6,7,8,9-tetrahydropyrido[3,2-b]indolizin-3-yl)acetic acid

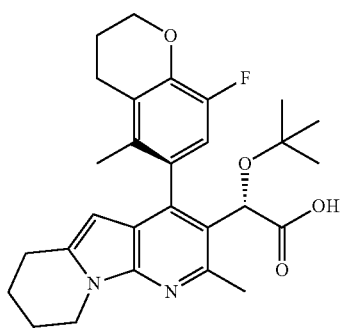

A solution of (2S)(M)-Methyl 2-(tert-butoxy)-2-(-4-(8-fluoro-5-methylchroman-6-yl)-2-methyl-6,7,8,9-tetrahydropyrido[3,2-b]indolizin-3-yl)acetate (15.9 mg, 0.032 mmol) in MeOH (2 mL) was treated with 1 M lithium hydroxide (2 mL, 2.000 mmol) and heated to 55° C. After 18 hours the reaction mixture was poured into 1M HCl and extracted with DCM. The organics were washed with brine, dried ($Na_2SO_4$), filtered and concentrated in vacuo. The residue was purified by reverse phase HPLC to afford the title compound (15.5 mg, 0.026 mmol, 79% yield). $^1$H NMR (400 MHz, CHLOROFORM-d) δ=6.70 (d, J=10.8 Hz, 1H), 5.82 (s, 1H), 5.18 (s, 1H), 4.48 (br. s., 2H), 4.31 (t, J=5.1 Hz, 2H), 2.95 (s, 3H), 2.93 (br. s., 2H), 2.78 (s, 1H), 2.75-2.64 (m, 2H), 2.21-2.04 (m, 4H), 1.92-1.84 (m, 2H), 1.78 (s, 3H), 1.12 (s, 9H). LC/MS (m/z) $ES^+$=481 (M+1).

Compounds in Table 3 (examples 30-78) were synthesized using the procedure described above with the appropriate boronic acids.

TABLE 3

| Example | Structure | MW | Observed Mass |
|---|---|---|---|
| 30 | 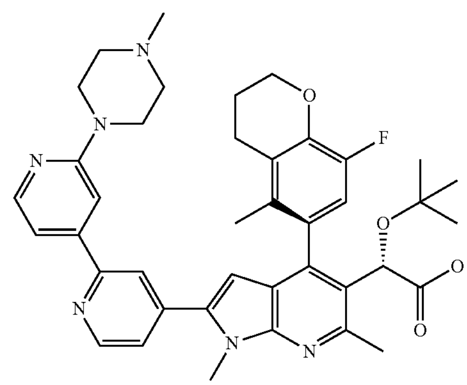 | 692.82 | 693 |
| 31 | 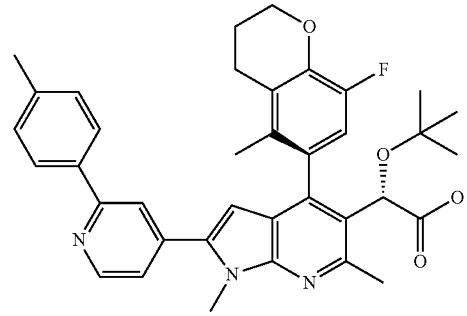 | 607.71 | 608 |

TABLE 3-continued

| Example | Structure | MW | Observed Mass |
|---|---|---|---|
| 32 | 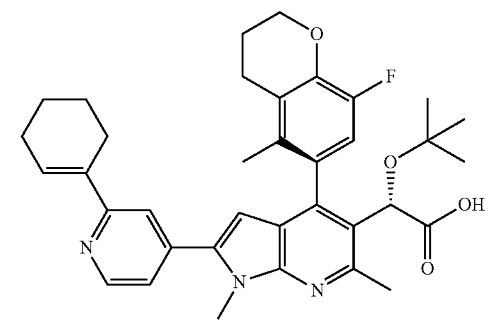 | 597.72 | 598 |
| 33 | 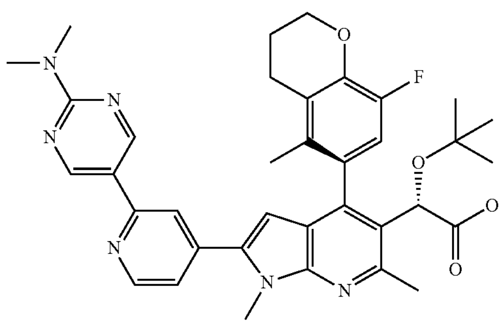 | 638.73 | 639 |
| 34 | 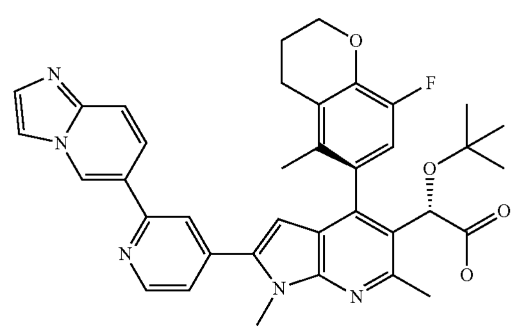 | 633.71 | 634 |
| 35 | 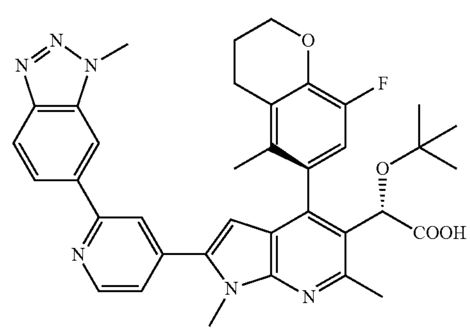 | 648.73 | 649 |

TABLE 3-continued

| Example | Structure | MW | Observed Mass |
|---|---|---|---|
| 36 | 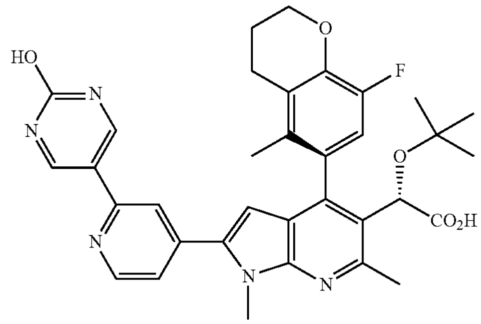 | 611.66 | 612 |
| 37 | 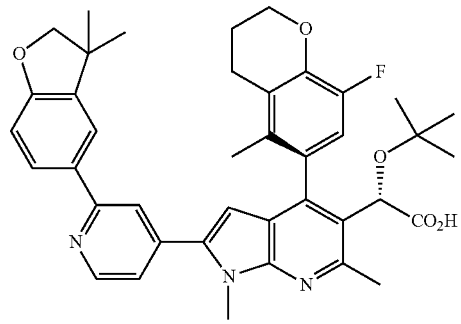 | 663.78 | 664 |
| 38 | 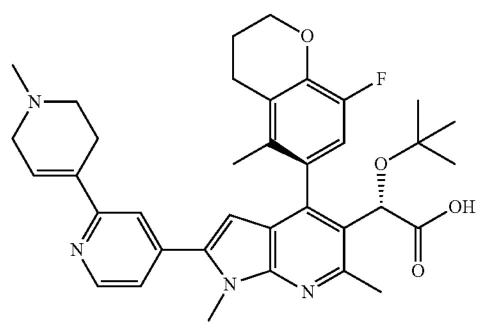 | 612.73 | 613 |
| 39 | 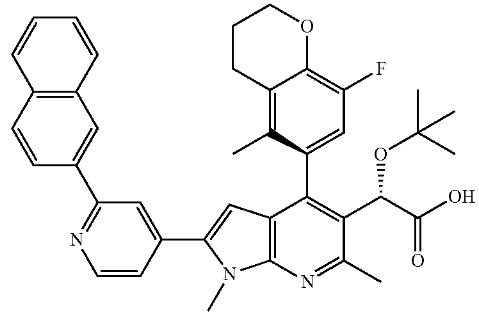 | 643.75 | 644 |

TABLE 3-continued

| Example | Structure | MW | Observed Mass |
|---------|-----------|-----|---------------|
| 40 | 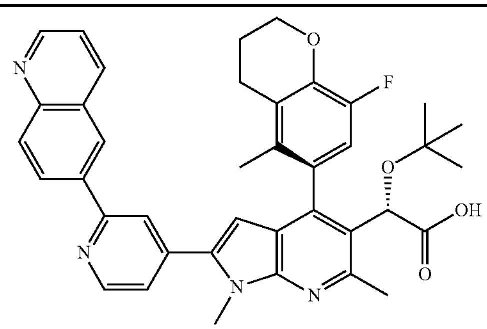 | 644.73 | 645 |
| 41 | 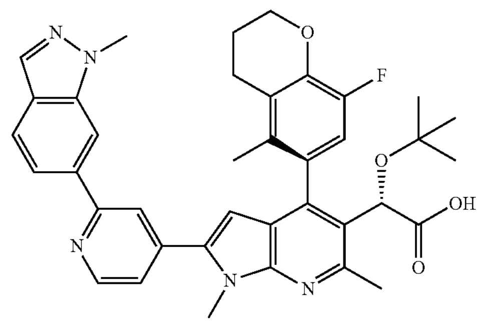 | 647.74 | 648 |
| 42 | 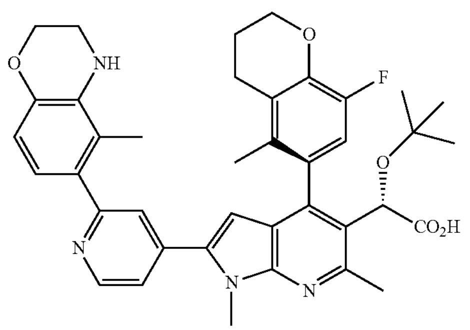 | 664.76 | 665 |
| 43 | 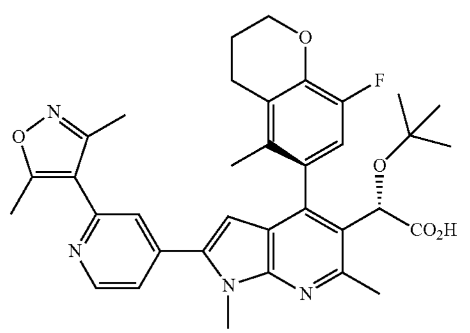 | 612.69 | 613 |
| 44 | 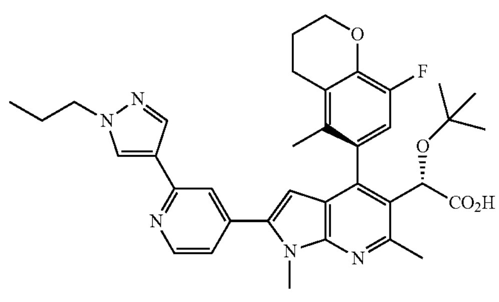 | 625.73 | 325 |

TABLE 3-continued
| Example | Structure | MW | Observed Mass |
|---------|-----------|------|---------------|
| 45 | 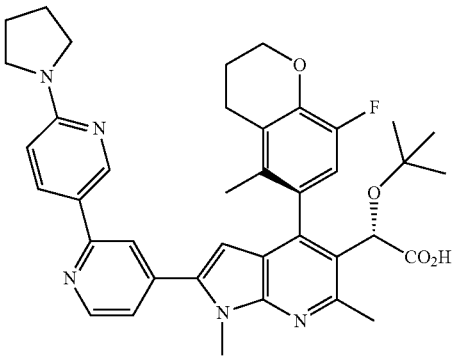 | 663.78 | 664 |
| 46 | 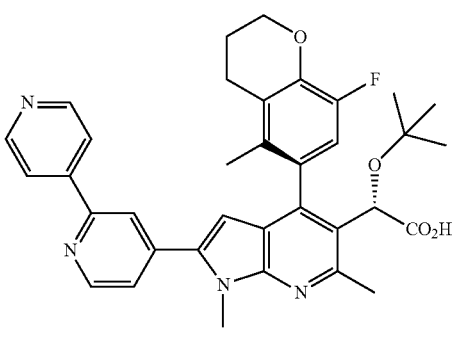 | 594.68 | 595 |
| 47 | 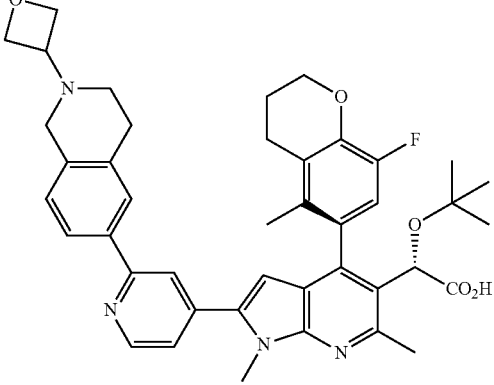 | 704.83 | 705 |
| 48 | 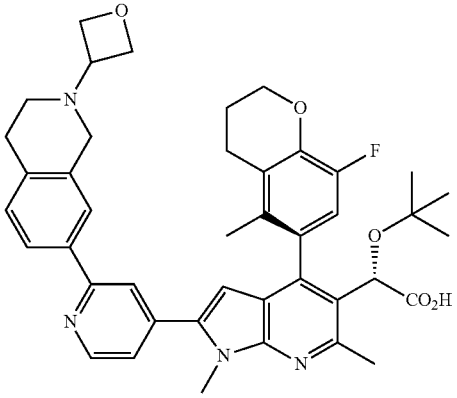 | 704.83 | 705 |

TABLE 3-continued

| Example | Structure | MW | Observed Mass |
|---------|-----------|------|---------------|
| 49 | 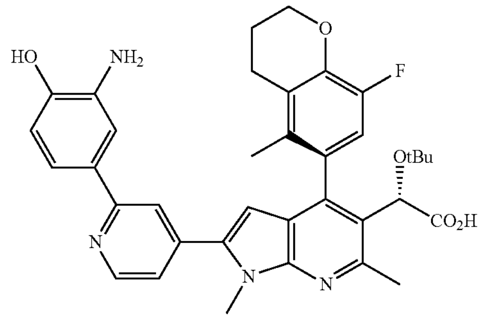 | 624.7 | 625 |
| 50 | 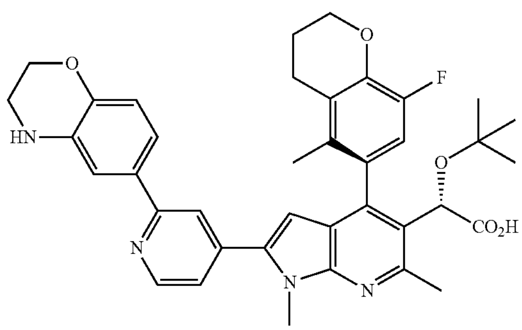 | 650.74 | 651 |
| 51 | 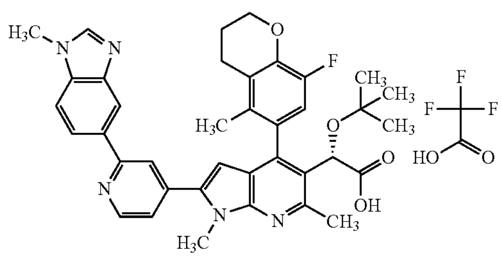 | 647.74 | 648 |
| 52 | 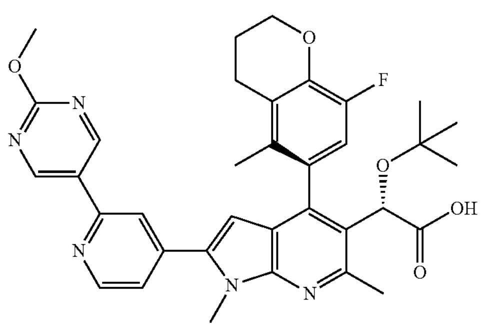 | 625.69 | 626 |
| 53 | 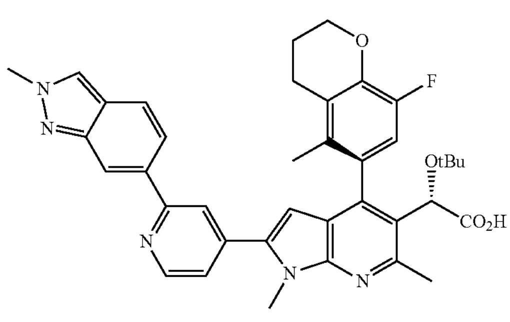 | 647.74 | 648 |

TABLE 3-continued

| Example | Structure | MW | Observed Mass |
|---|---|---|---|
| 54 | 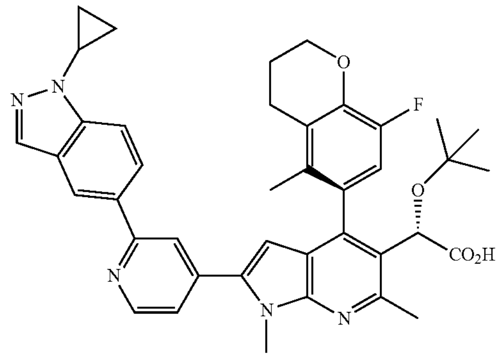 | 673.78 | 674 |
| 55 | 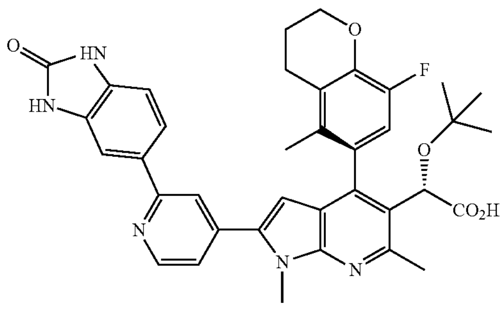 | 649.71 | 650 |
| 56 | 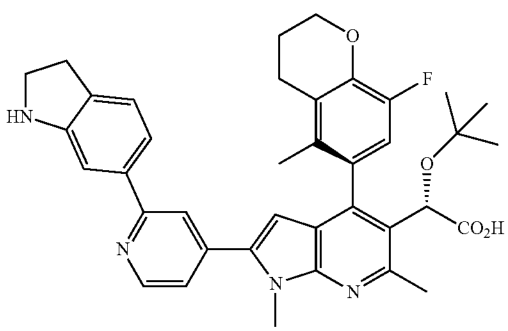 | 634.74 | 635 |
| 57 | 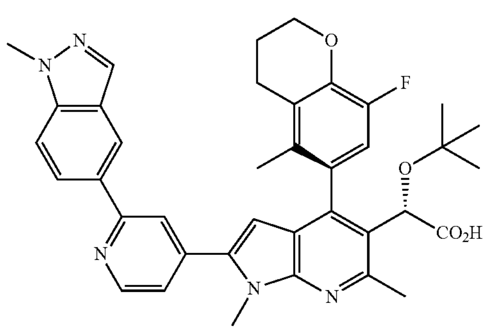 | 647.74 | 648 |

TABLE 3-continued

| Example | Structure | MW | Observed Mass |
|---|---|---|---|
| 58 | 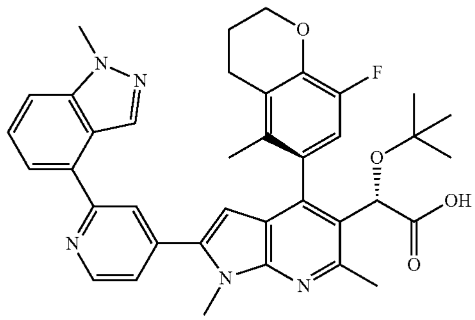 | 647.74 | 648 |
| 59 | 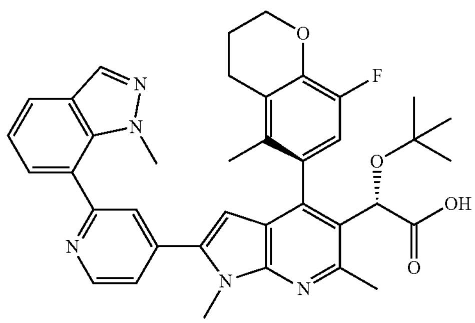 | 647.74 | 648 |
| 60 | 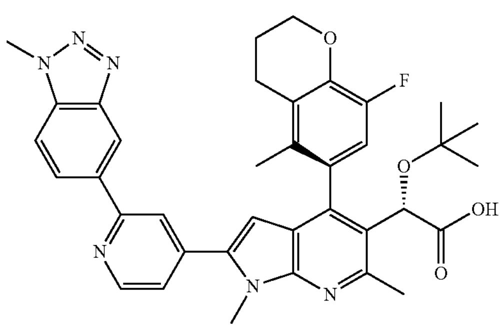 | 648.73 | 649 |
| 61 | 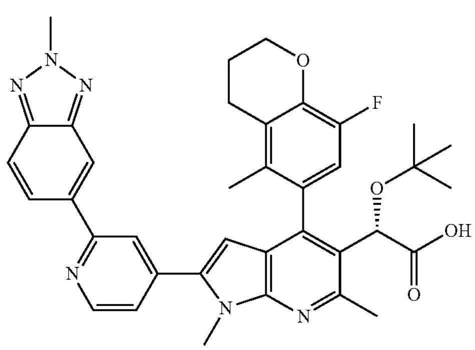 [SMILES: Cc1nc2c(cc(-c3ccnc(-c4ccc5nn(C)nc5c4)c3)n2C)c(-c2cc(F)c3c(c2C)CCCO3)c1[C@H](OC(C)(C)C)C(=O)O] | 648.73 | 649 |

TABLE 3-continued

| Example | Structure | MW | Observed Mass |
|---|---|---|---|
| 62 | 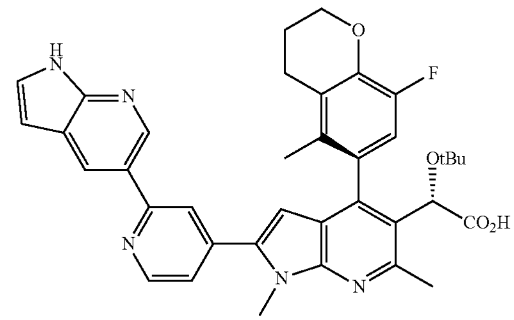 | 633.71 | 634 |
| 63 | 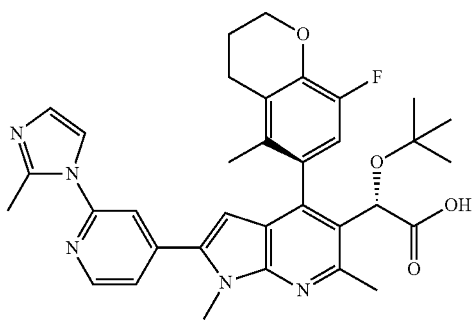 | 597.68 | 598 |
| 64 | 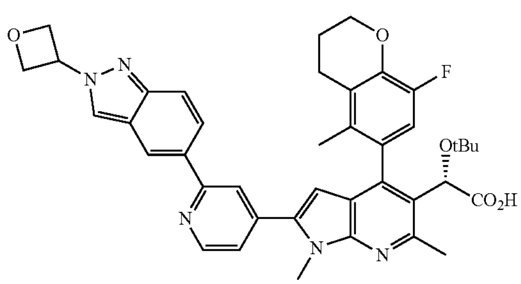 [SMILES: Cc1nc2c(cc(-c3ccnc(-c4ccc5nn(C6COC6)cc5c4)c3)n2C)c(-c2cc(F)c3c(c2C)CCCO3)c1[C@H](OC(C)(C)C)C(=O)O] | 689.77 | 690 |
| 65 | 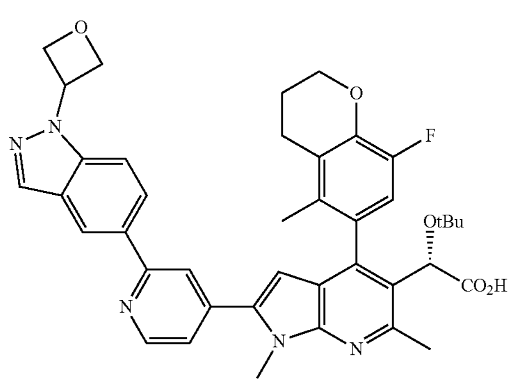 [SMILES: Cc1nc2c(cc(-c3ccnc(-c4ccc5c(cnn5C5COC5)c4)c3)n2C)c(-c2cc(F)c3c(c2C)CCCO3)c1[C@H](OC(C)(C)C)C(=O)O] | 689.77 | 690 |

TABLE 3-continued

| Example | Structure | MW | Observed Mass |
|---|---|---|---|
| 66 | 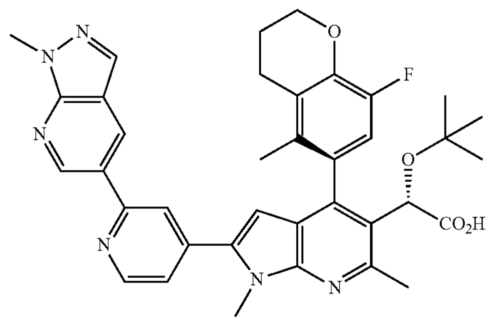 | 648.73 | 649 |
| 67 | 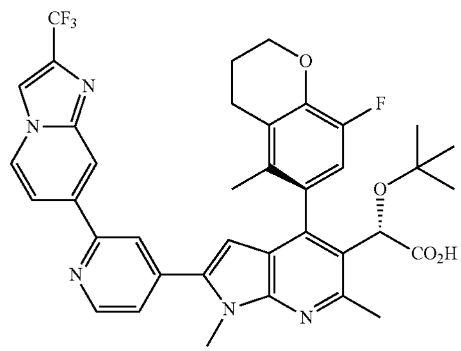 | 701.71 | 702 |
| 68 | 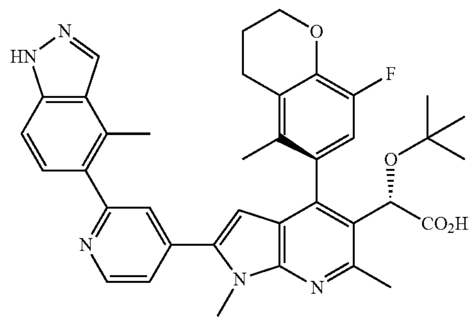 | 647.74 | 648 |
| 69 | 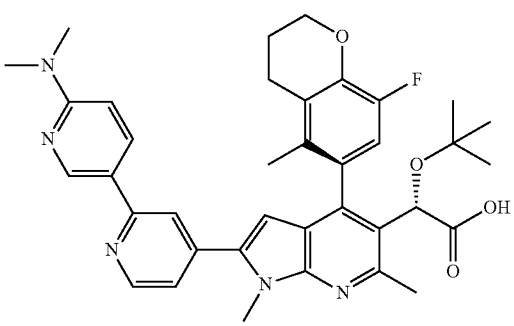 | 637.74 | 638 |

TABLE 3-continued

| Example | Structure | MW | Observed Mass |
|---|---|---|---|
| 70 | 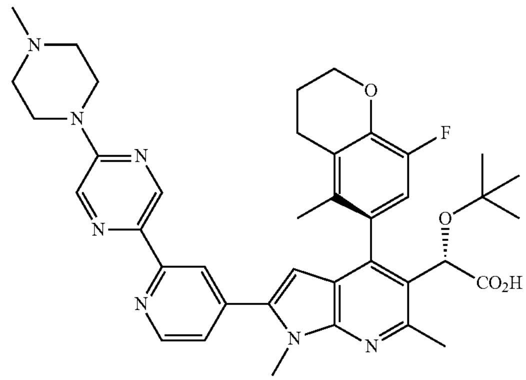 | 693.81 | 694 |
| 71 | 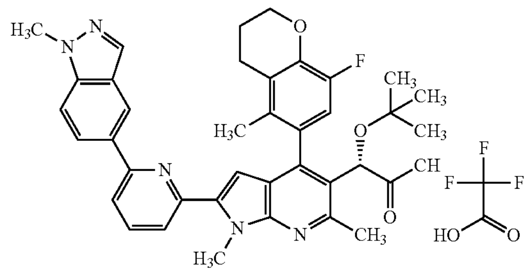 | 647.74 | 648 |
| 72 | 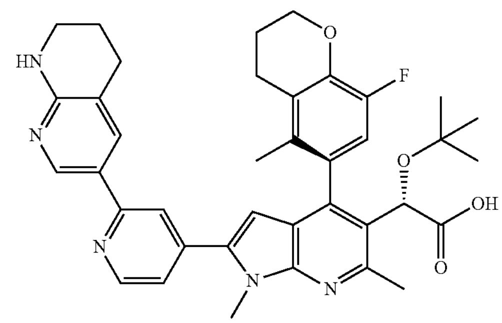 | 649.75 | 650 |
| 73 | 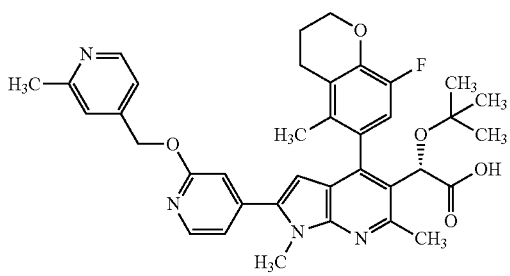 [SMILES: Cc1cc(COc2cc(-c3cc4c(-c5cc(F)c6c(c5C)CCCO6)c([C@H](OC(C)(C)C)C(=O)O)c(C)nc4n3C)ccn2)ccn1] | 638.73 | 639 |
| 74 | 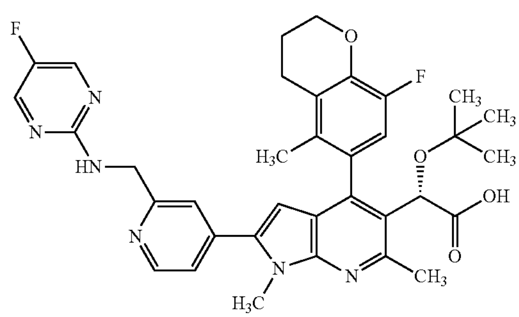 [SMILES: Cc1nc2c(cc(-c3ccnc(CNc4ncc(F)cn4)c3)n2C)c(-c2cc(F)c3c(c2C)CCCO3)c1[C@H](OC(C)(C)C)C(=O)O] | 642.69 | 643 |

TABLE 3-continued

| Example | Structure | MW | Observed Mass |
|---|---|---|---|
| 75 | 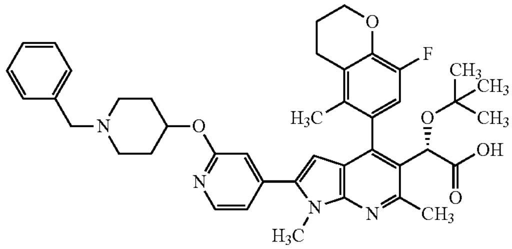 [SMILES: Cc1nc2c(cc(-c3ccnc(OC4CCN(Cc5ccccc5)CC4)c3)n2C)c(-c2cc(F)c3c(c2C)CCCO3)c1[C@H](OC(C)(C)C)C(=O)O] | 706.84 | 707 |
| 76 | 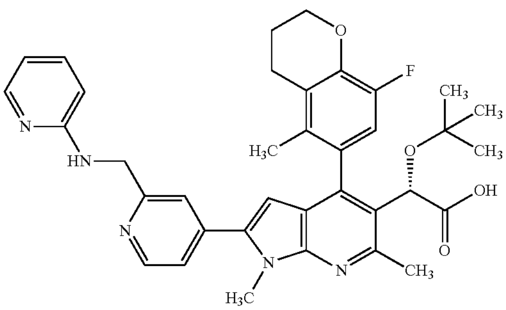 [SMILES: Cc1nc2c(cc(-c3ccnc(CNc4ccccn4)c3)n2C)c(-c2cc(F)c3c(c2C)CCCO3)c1[C@H](OC(C)(C)C)C(=O)O] | 623.72 | 624 |
| 77 | 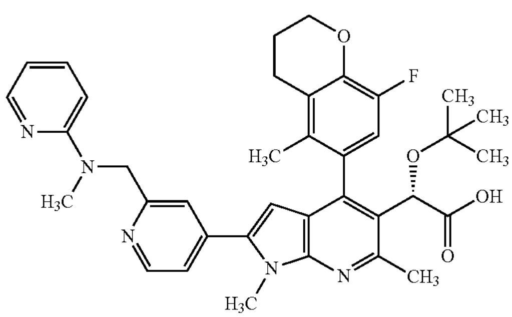 [SMILES: Cc1nc2c(cc(-c3ccnc(CN(C)c4ccccn4)c3)n2C)c(-c2cc(F)c3c(c2C)CCCO3)c1[C@H](OC(C)(C)C)C(=O)O] | 637.74 | 638 |
| 78 | 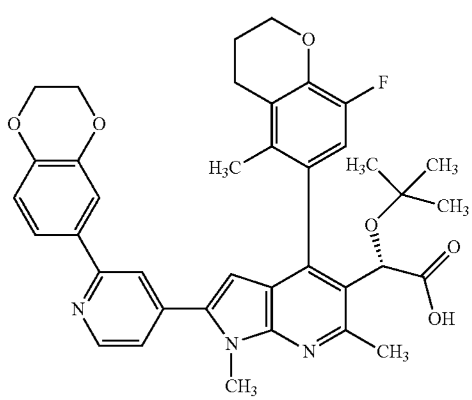 [SMILES: Cc1nc2c(cc(-c3ccnc(-c4ccc5c(c4)OCCO5)c3)n2C)c(-c2cc(F)c3c(c2C)CCCO3)c1[C@H](OC(C)(C)C)C(=O)O] | 651.72 | 652 |

General Scheme 7
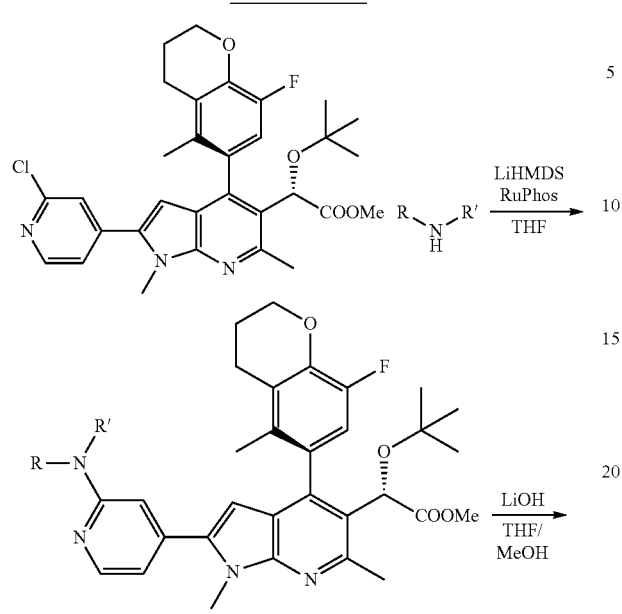
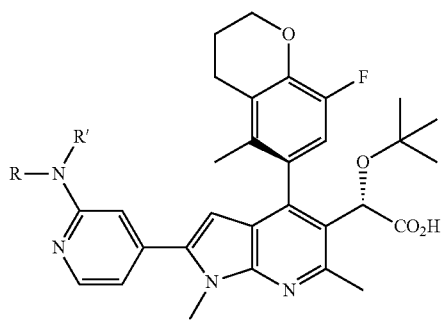
Compounds in Table 4 (examples 79-128) were synthesized using the procedure described in Example 10 with the appropriate amine.
TABLE 4
| Example | Structure | MW | Observed Mass |
|---|---|---|---|
| 79 | 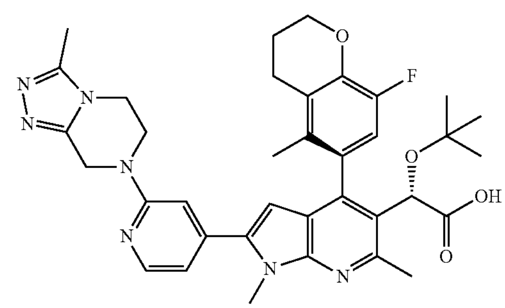 | 653.75 | 654 |
| 80 | 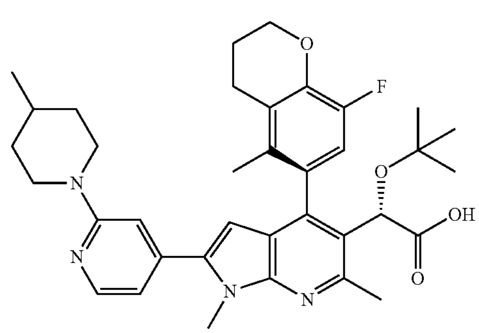 | 614.75 | 615 |

TABLE 4-continued

| Example | Structure | MW | Observed Mass |
|---|---|---|---|
| 81 | 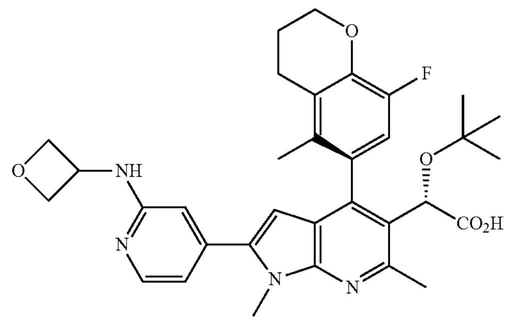 | 588.67 | 589 |
| 82 | 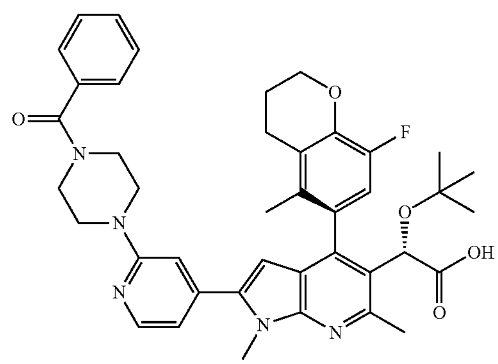 | 705.82 | 706 |
| 83 | 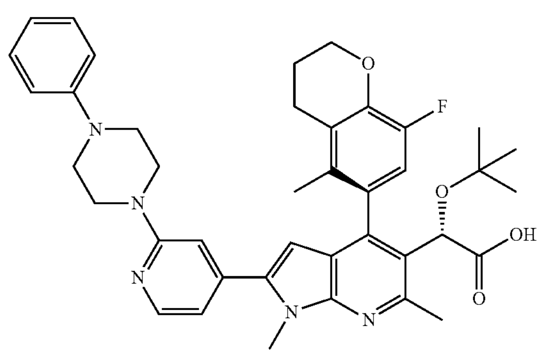 | 677.81 | 678 |
| 84 | 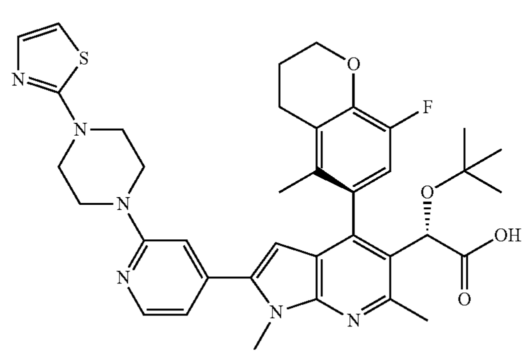 | 684.82 | 685 |

TABLE 4-continued

| Example | Structure | MW | Observed Mass |
|---|---|---|---|
| 85 | 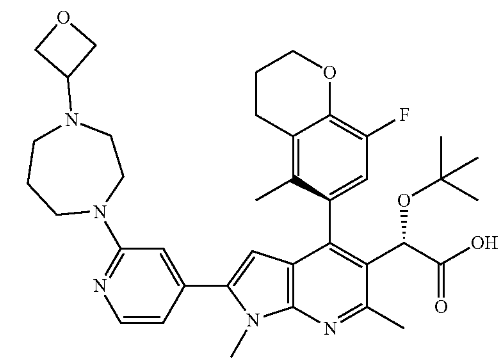 | 671.8 | 672 |
| 86 | 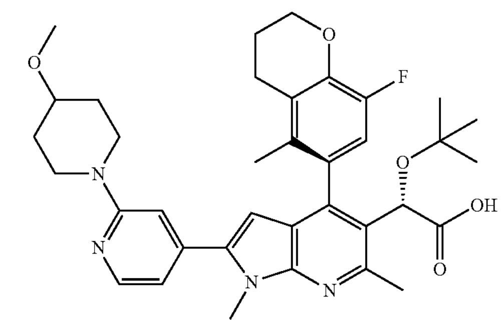 | 630.75 | 631 |
| 87 | 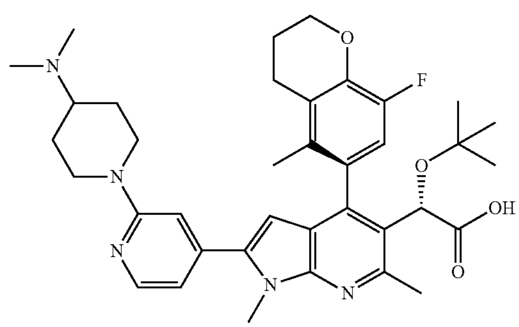 | 643.79 | 644 |
| 88 | 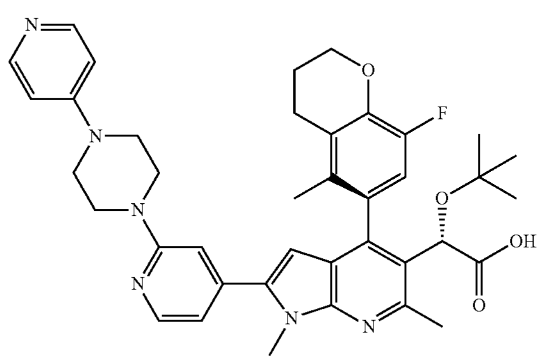 | 678.79 | 679 |

TABLE 4-continued

| Example | Structure | MW | Observed Mass |
|---|---|---|---|
| 89 | 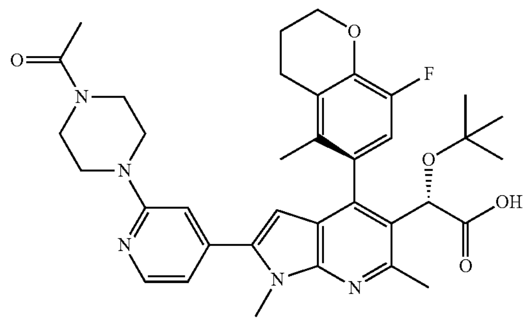 | 643.75 | 644 |
| 90 | 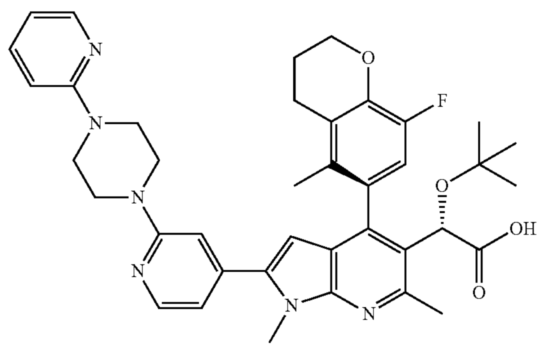 | 678.79 | 679 |
| 91 | 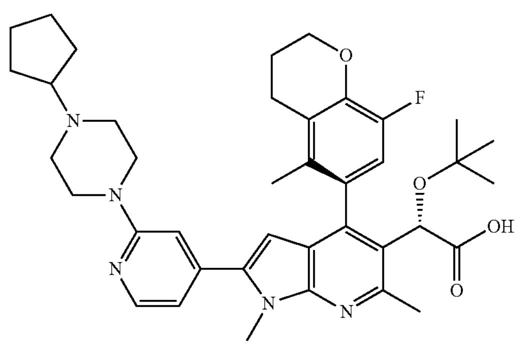 | 669.83 | 670 |
| 92 | 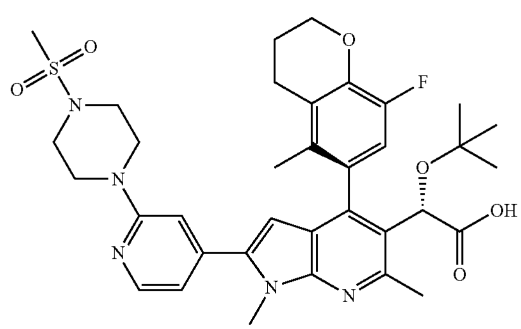 | 679.8 | 680 |

TABLE 4-continued

| Example | Structure | MW | Observed Mass |
|---|---|---|---|
| 93 | 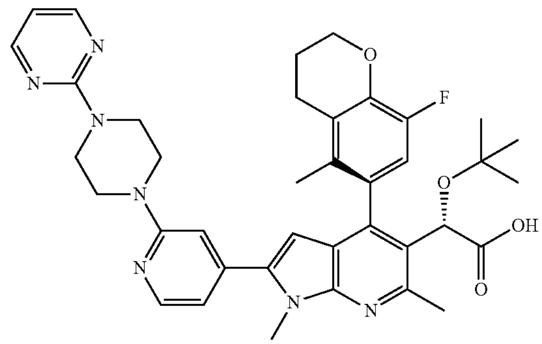 | 679.78 | 680 |
| 94 | 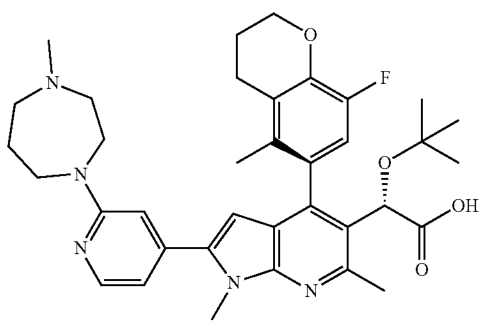 | 629.76 | 630 |
| 95 | 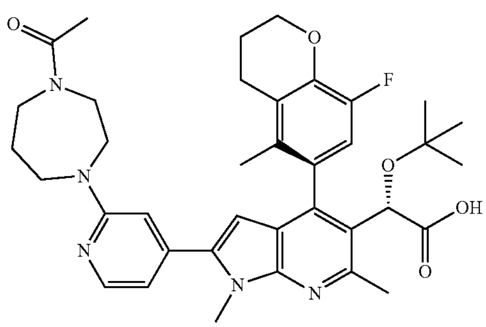 | 657.77 | 658 |
| 96 | 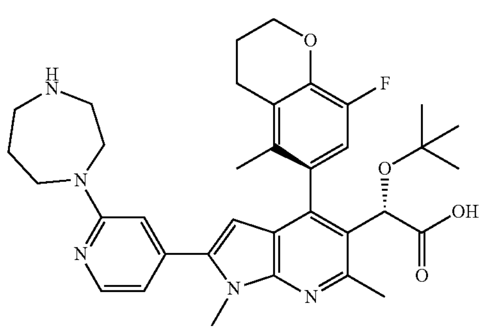 | 615.74 | 616 |

TABLE 4-continued

| Example | Structure | MW | Observed Mass |
|---|---|---|---|
| 97 | 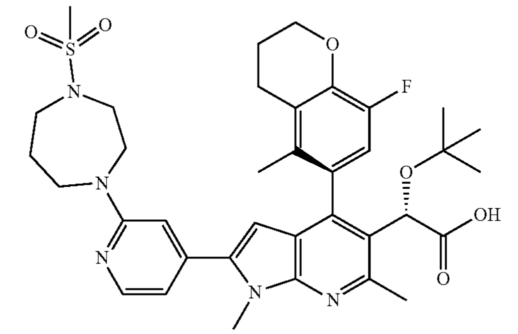 | 693.83 | 694 |
| 98 | 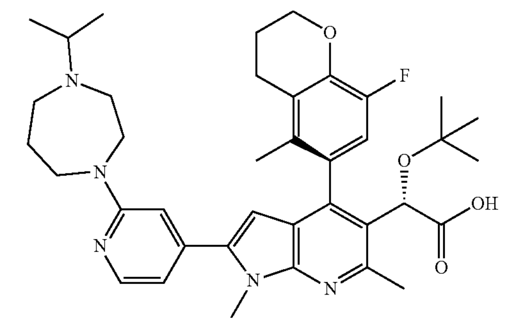 | 657.82 | 658 |
| 99 | 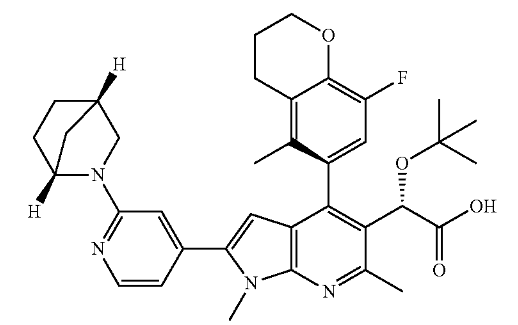 | 612.73 | 613 |
| 100 | 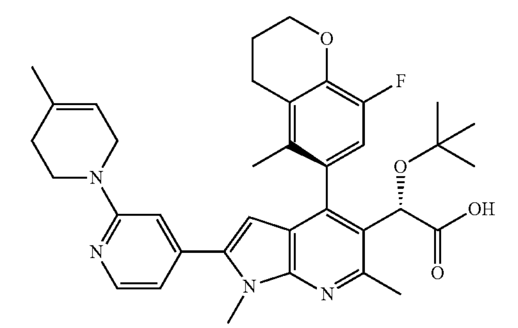 | 612.73 | 613 |
| 101 | 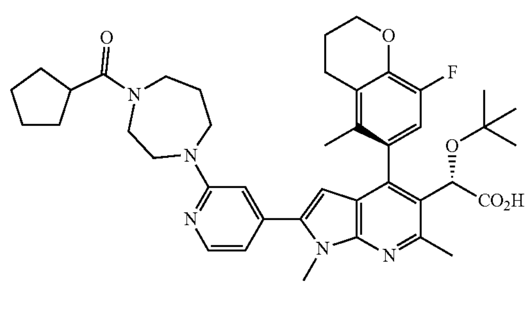 | 711.86 | 712 |

TABLE 4-continued

| Example | Structure | MW | Observed Mass |
|---------|-----------|-----|---------------|
| 102 | 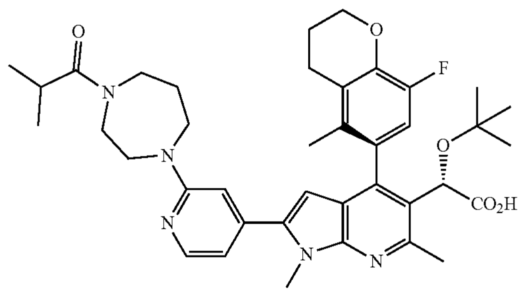 | 685.83 | 686 |
| 103 | 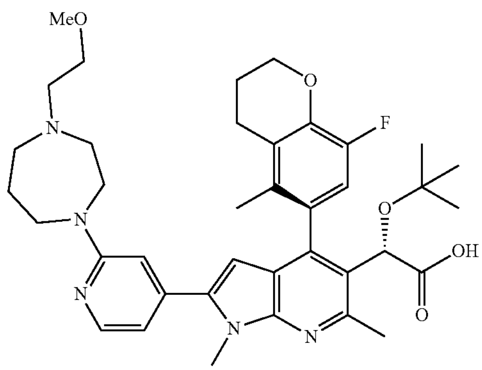 | 673.82 | 674 |
| 104 | 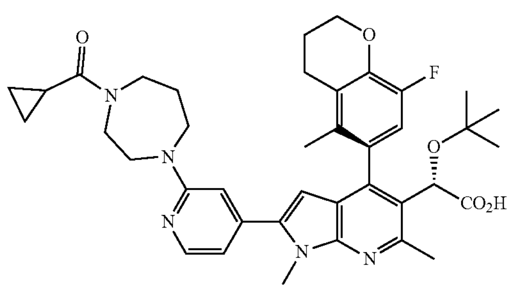 | 683.81 | 684 |
| 105 | 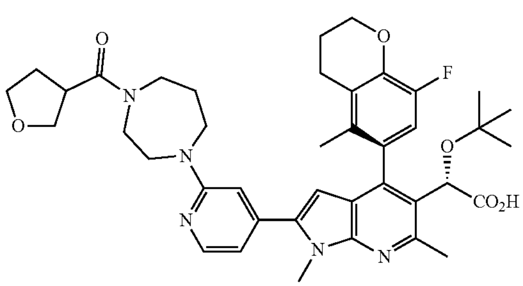 | 713.84 | 714 |
| 106 | 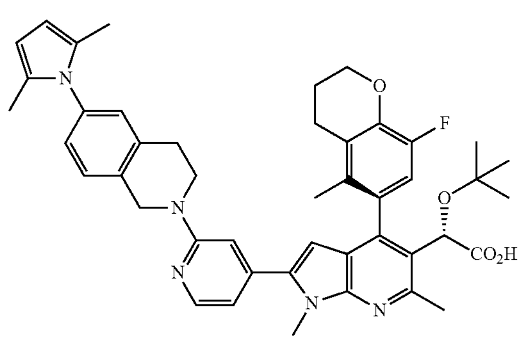 | 741.89 | 742 |

TABLE 4-continued

| Example | Structure | MW | Observed Mass |
|---------|-----------|------|------|
| 107 | 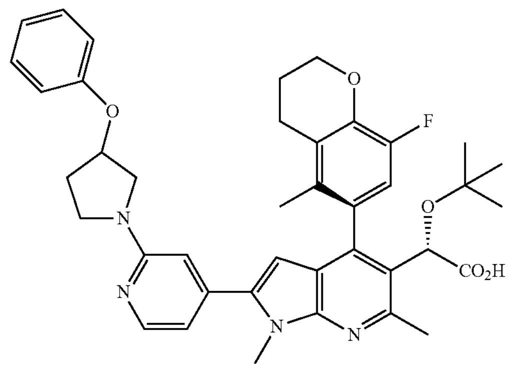 | 678.79 | 679 |
| 108 | 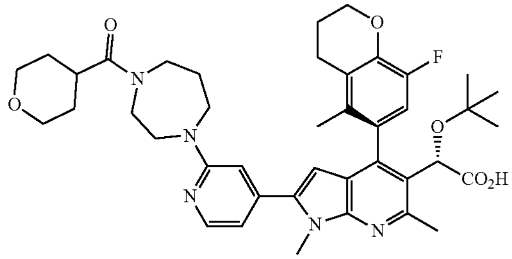 | 727.86 | 728 |
| 109 | 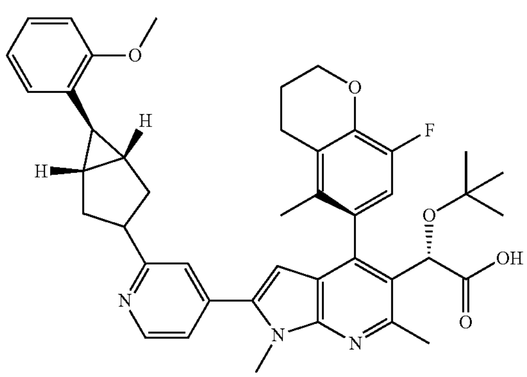 | 704.83 | 705 |
| 110 | 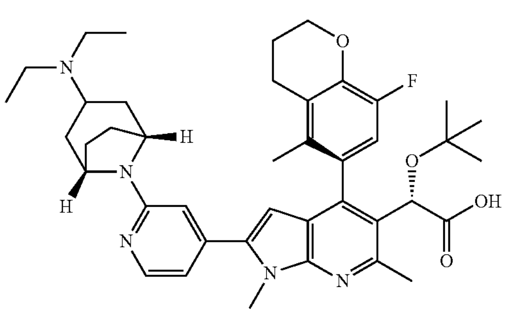 | 697.88 | 698 |

TABLE 4-continued

| Example | Structure | MW | Observed Mass |
|---|---|---|---|
| 111 | 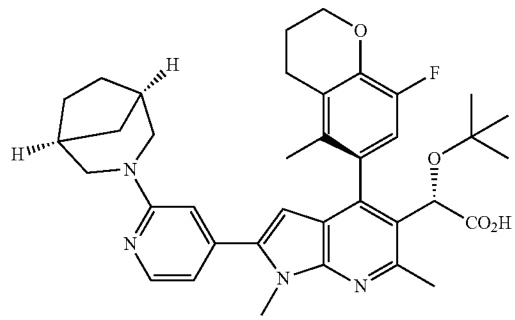 | 626.76 | 627 |
| 112 | 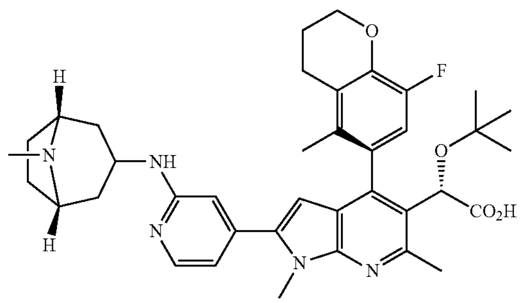 | 655.8 | 656 |
| 113 | 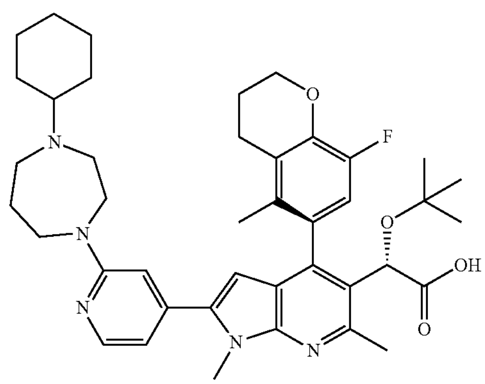 | 699.85 | 700 |
| 114 | 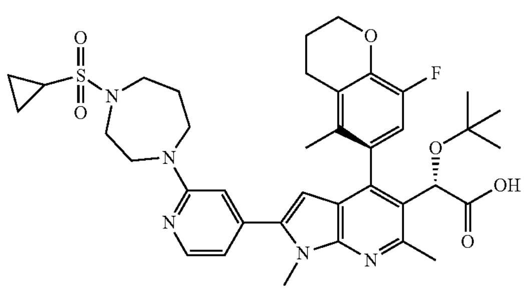 | 719.86 | 720 |
| 115 | 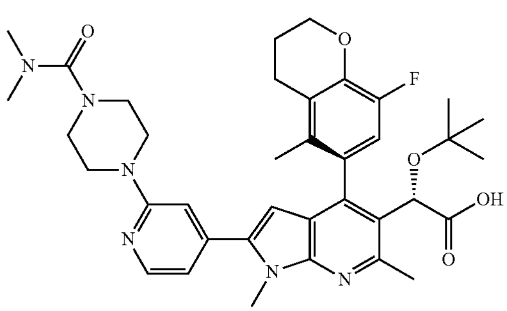 | 672.79 | 673 |

TABLE 4-continued

| Example | Structure | MW | Observed Mass |
|---|---|---|---|
| 116 | 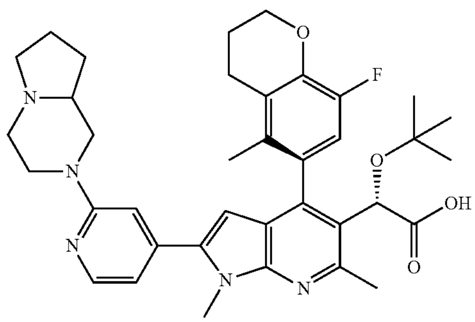 | 641.77 | 642 |
| 117 | 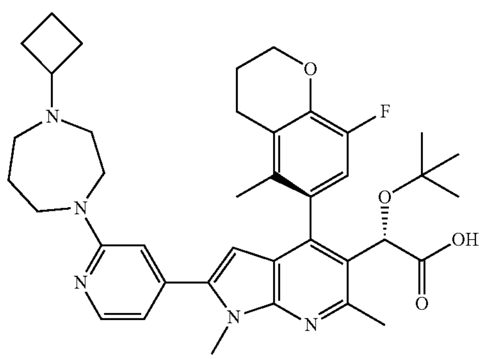 | 669.83 | 670 |
| 118 | 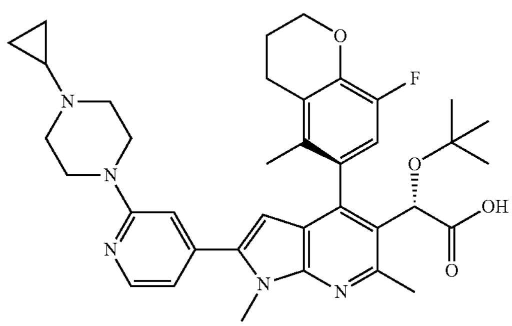 | 641.77 | 642 |
| 119 | 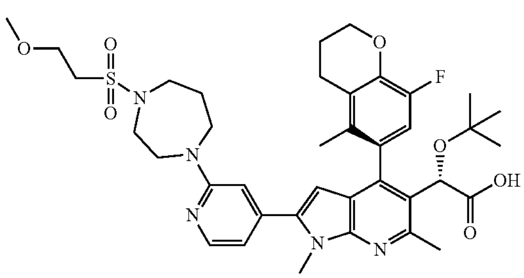 | 737.88 | 738 |

TABLE 4-continued

| Example | Structure | MW | Observed Mass |
|---|---|---|---|
| 120 | 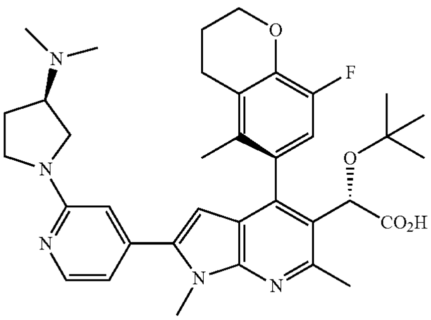 | 629.76 | 630 |
| 121 | 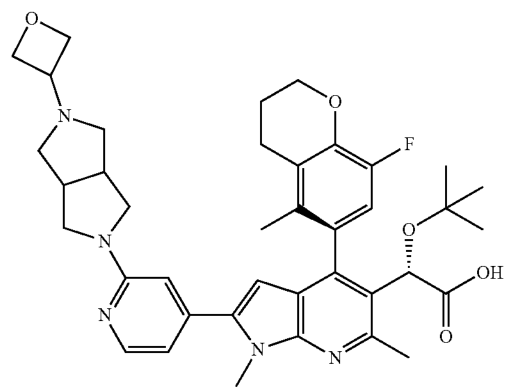 | 683.81 | 684 |
| 122 | 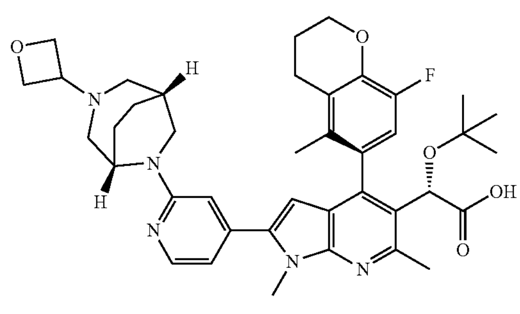 | 697.84 | 698 |
| 123 | 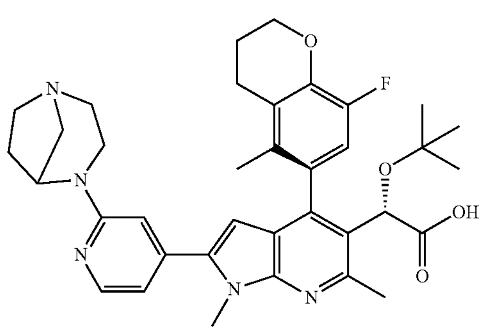 | 627.75 | 628 |

TABLE 4-continued

| Example | Structure | MW | Observed Mass |
|---|---|---|---|
| 124 | 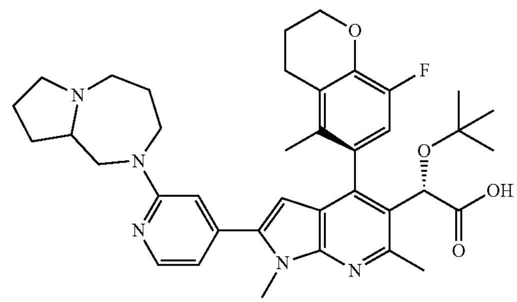 | 655.8 | 656 |
| 125 | 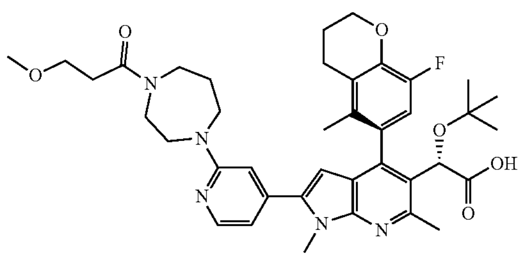 | 701.83 | 702 |
| 126 | 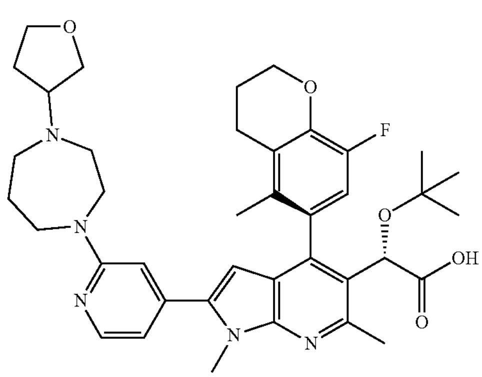 | 685.83 | 686 |
| 127 | 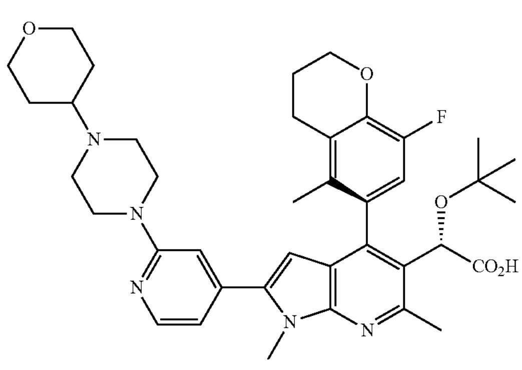 | 685.83 | 686 |

TABLE 4-continued

| Example | Structure | MW | Observed Mass |
|---------|-----------|-----|---------------|
| 128 | 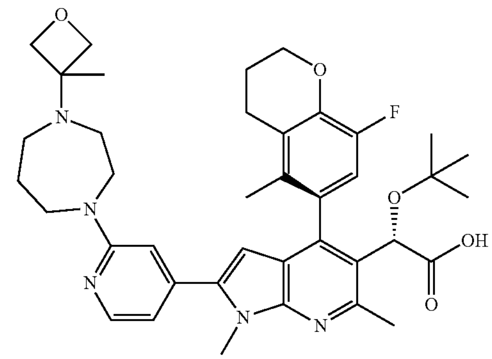 | 685.83 | 686 |

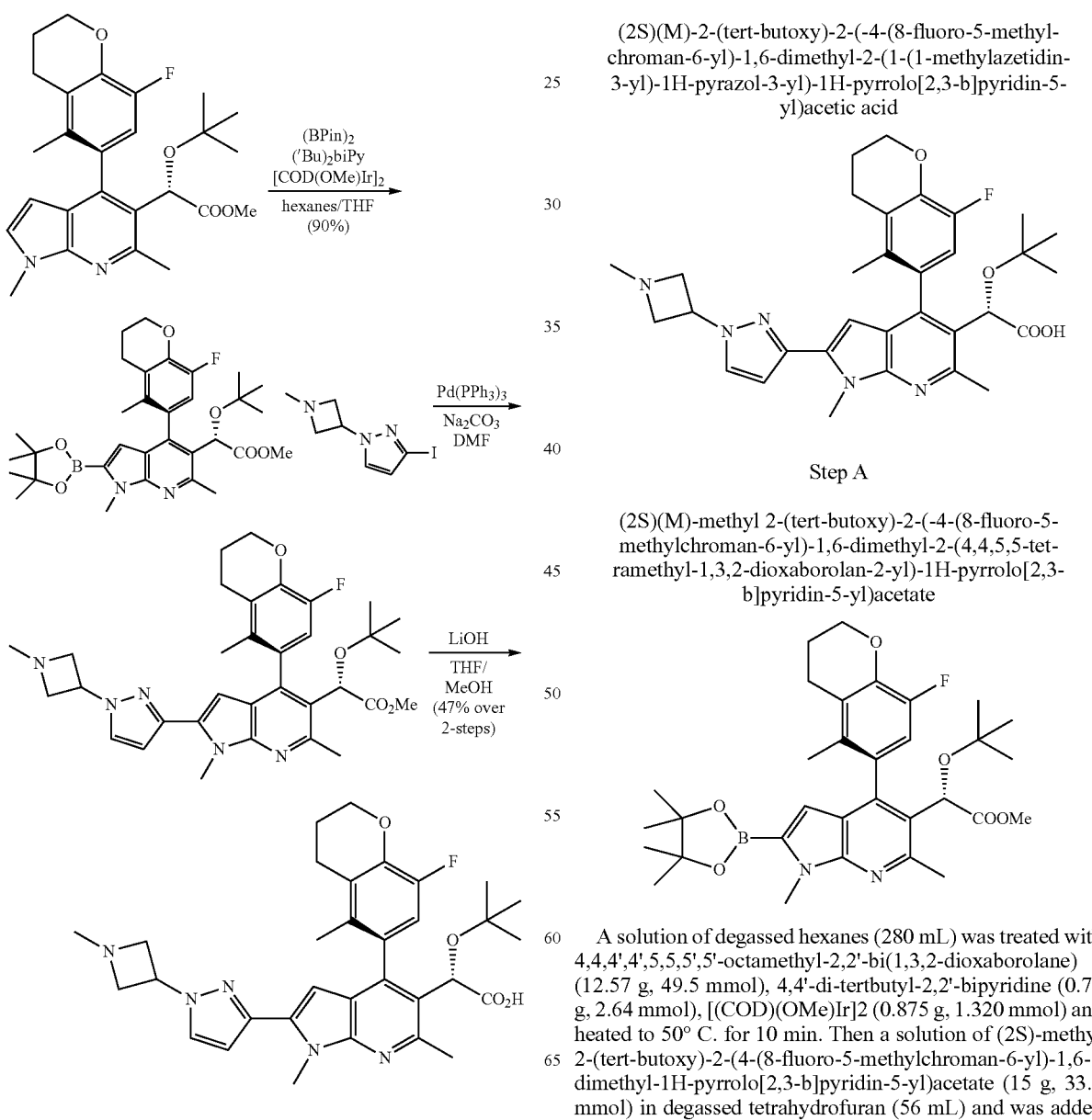

Example 129

(2S)(M)-2-(tert-butoxy)-2-(-4-(8-fluoro-5-methyl-chroman-6-yl)-1,6-dimethyl-2-(1-(1-methylazetidin-3-yl)-1H-pyrazol-3-yl)-1H-pyrrolo[2,3-b]pyridin-5-yl)acetic acid

Step A (2S)(M)-methyl 2-(tert-butoxy)-2-(-4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate A solution of degassed hexanes (280 mL) was treated with 4,4,4',4',5,5,5',5'-octamethyl-2,2'-bi(1,3,2-dioxaborolane) (12.57 g, 49.5 mmol), 4,4'-di-tertbutyl-2,2'-bipyridine (0.71 g, 2.64 mmol), [(COD)(OMe)Ir]2 (0.875 g, 1.320 mmol) and heated to 50° C. for 10 min. Then a solution of (2S)-methyl 2-(tert-butoxy)-2-(4-(8-fluoro-5-methylchroman-6-yl)-1,6-dimethyl-1H-pyrrolo[2,3-b]pyridin-5-yl)acetate (15 g, 33.0 mmol) in degassed tetrahydrofuran (56 mL) and was added and the reaction mixture was warmed to 90° C. After 30 min, the reaction mixture was cooled to ambient temperature and concentrated in vacuo. The residue was purified by silica gel chromatography (0-100% Ethyl acetate/hexanes) to afford the title compound (18 g, 31.0 mmol, 94% yield). $^1$H NMR (400 MHz, CHLOROFORM-d) δ ppm 1.09 (s, 9H) 1.32 (s, 12H) 1.76 (s, 3H) 2.09-2.18 (m, 2H) 2.67-2.73 (m, 2H) 2.80 (s, 3H) 3.57 (s, 3H) 4.02 (s, 3H) 4.28 (dd, J=5.76, 4.59 Hz, 2H) 5.13 (s, 1H) 6.47-6.50 (m, 1H) 6.71 (d, J=11.24 Hz, 1H). LC-MS: ES+MS; 581 (M+1).

Steps B/C (2S)(M)-2-(tert-butoxy)-2-(-4-(8-fluoro-5-methyl-chroman-6-yl)-1,6-dimethyl-2-(1-(1-methylazetidin-3-yl)-1H-pyrazol-3-yl)-1H-pyrrolo[2,3-b]pyridin-5-yl)acetic acid

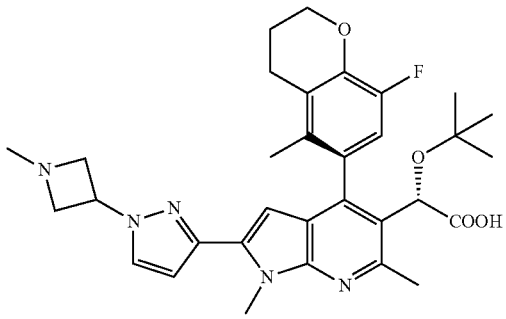

A mixture of (2S)(M)-methyl 2-(tert-butoxy)-2-(-4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate (40 mg, 0.069 mmol), 3-iodo-1-(1-methylazetidin-3-yl)-1H-pyrazole (25.6 mg, 0.083 mmol), Pd(PPh$_3$)$_4$ (7.96 mg, 6.89 μmol) and 2 M aqueous sodium carbonate (0.069 mL, 0.138 mmol) in N,N-Dimethylformamide (DMF) (1 mL) was degassed for 5 min (N$_2$) then sealed and heated at 70° C. for 40 min. Water was added and the mixture was extracted with EtOAc. The organic phase was dried (Na$_2$SO$_4$) and concentrated in vacuo. The residue was dissolved in THF (0.5 mL)/MeOH (0.5 mL) and LiOH monohydrate (20 mg) was added followed by water (0.25 mL) and heated to 70° C. After 3 h, the reaction mixture was filtered and purified by reverse phase HPLC to afford the title compound (27 mg, 0.033 mmol, 47.3% yield) as a yellow solid: $^1$H NMR (400 MHz, CHLOROFORM-d) δ ppm 1.12 (s, 9H) 1.85 (s, 3H) 2.15 (d, J=4.89 Hz, 2H) 2.63-2.78 (m, 2H) 3.02 (s, 3H) 3.13 (s, 3H) 4.12 (s, 3H) 4.30 (t, J=5.08 Hz, 2H) 4.33-4.43 (m, 2H) 4.97 (br. s., 2H) 5.21 (s, 1H) 5.50-5.57 (m, 1H) 6.11 (s, 1H) 6.72 (d, J=10.75 Hz, 1H) 7.83 (s, 2H) 12.55-12.81 (m, 1H). LC-MS: ES+MS; 576 (M+1).

Compounds in Table 5 (examples 130-144) were synthesized using the procedure described above with the appropriate aryl iodide.

TABLE 5

| Example | Structure | MW | Observed Mass |
|---|---|---|---|
| 130 | 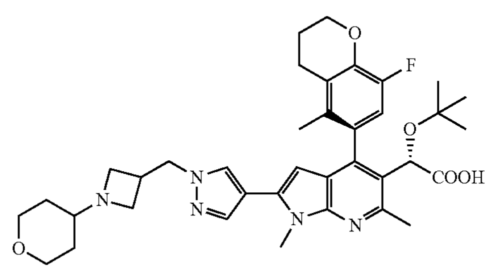 | 659.79 | 660 |
| 131 | 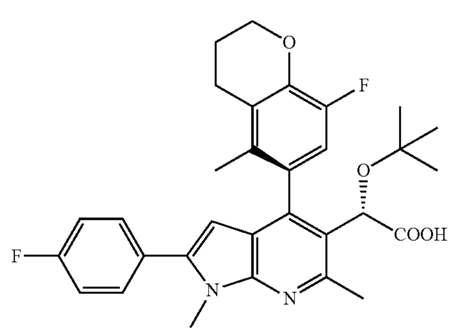 | 534.59 | 535 |

TABLE 5-continued

| Example | Structure | MW | Observed Mass |
|---------|-----------|------|--------|
| 132 | 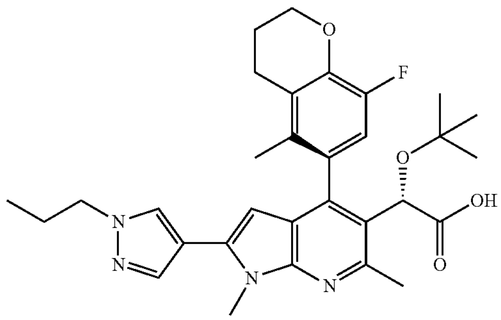 | 548.65 | 549 |
| 133 | 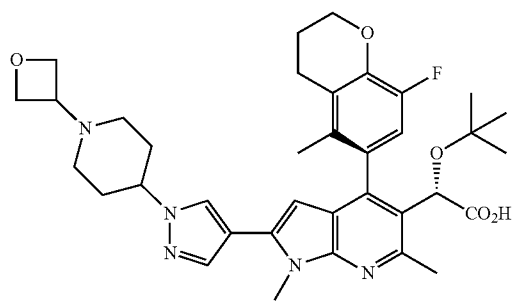 | 645.76 | 646 |
| 134 | 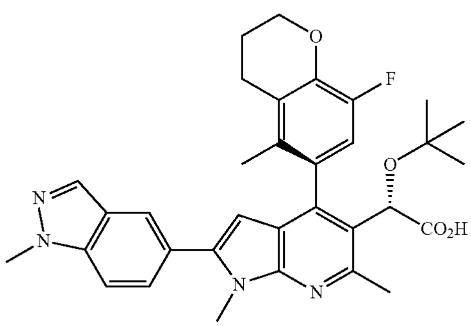 | 570.65 | 571 |
| 135 | 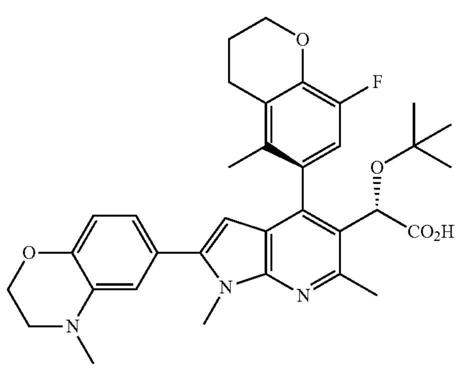 | 587.68 | 588 |

TABLE 5-continued

| Example | Structure | MW | Observed Mass |
|---|---|---|---|
| 136 | 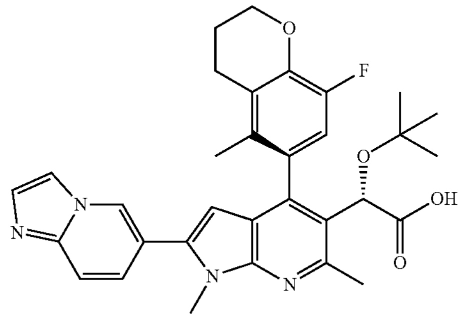 | 556.63 | 557 |
| 137 | 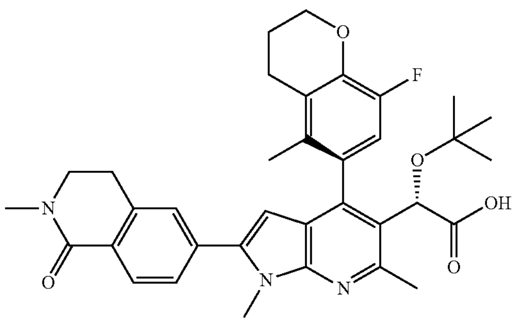 | 599.69 | 600 |
| 138 | 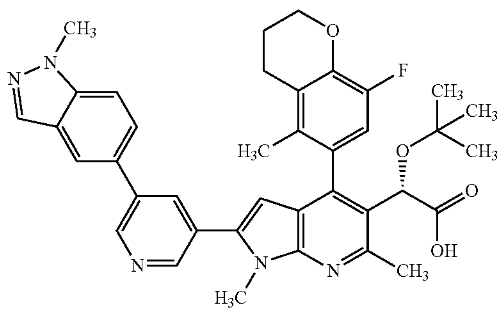 | 647.74 | 648 |
| 139 | 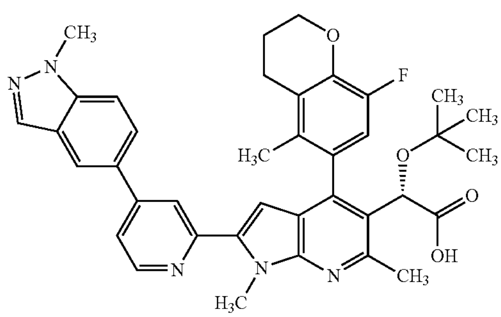 [SMILES: Cc1nc2c(cc(-c3cncc(-c4ccc5c(cnn5C)c4)c3)n2C)c(-c2cc(F)c3c(c2C)CCCO3)c1[C@H](OC(C)(C)C)C(=O)O] | 647.74 | 648 |
| 140 | 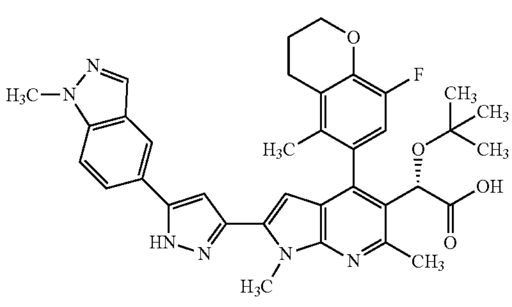 [SMILES: Cc1nc2c(cc(-c3cc(-c4ccc5c(cnn5C)c4)[nH]n3)n2C)c(-c2cc(F)c3c(c2C)CCCO3)c1[C@H](OC(C)(C)C)C(=O)O] | 636.72 | 637 |

TABLE 5-continued

| Example | Structure | MW | Observed Mass |
|---|---|---|---|
| 141 | 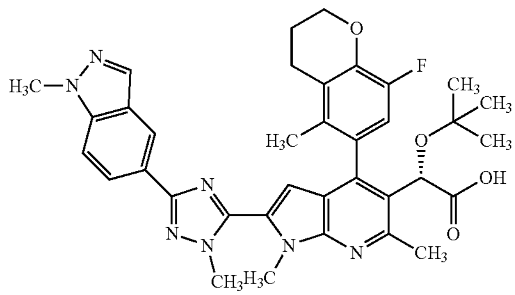 [SMILES: Cc1nc2c(cc(-c3nc(-c4ccc5c(cnn5C)c4)nn3C)n2C)c(-c2cc(F)c3c(c2C)CCCO3)c1[C@H](OC(C)(C)C)C(=O)O] | 651.73 | 652 |
| 142 | 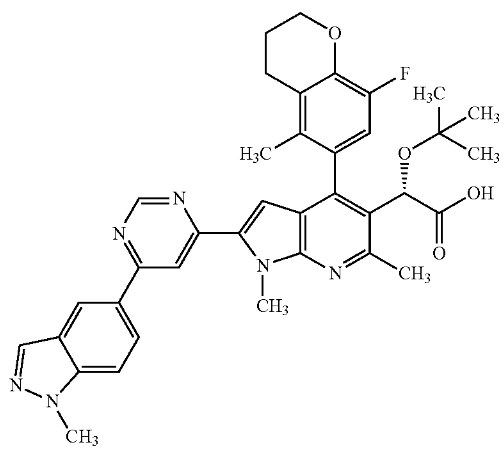 [SMILES: Cc1nc2c(cc(-c3cc(-c4ccc5c(cnn5C)c4)ncn3)n2C)c(-c2cc(F)c3c(c2C)CCCO3)c1[C@H](OC(C)(C)C)C(=O)O] | 648.73 | 649 |
| 143 | 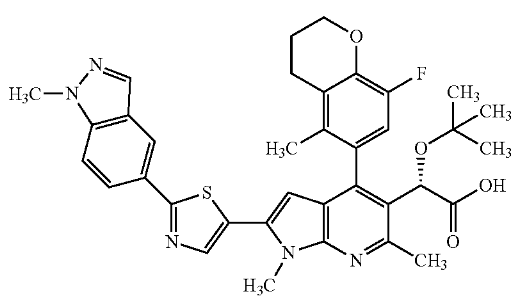 [SMILES: Cc1nc2c(cc(-c3cnc(-c4ccc5c(cnn5C)c4)s3)n2C)c(-c2cc(F)c3c(c2C)CCCO3)c1[C@H](OC(C)(C)C)C(=O)O] | 653.77 | 654 |
| 144 | 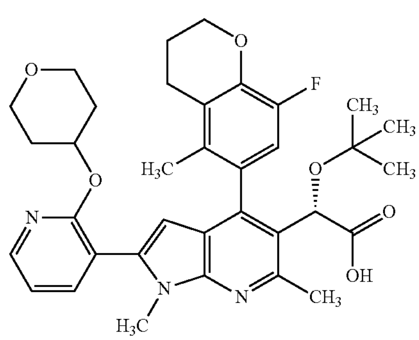 [SMILES: Cc1nc2c(cc(-c3cccnc3OC3CCOCC3)n2C)c(-c2cc(F)c3c(c2C)CCCO3)c1[C@H](OC(C)(C)C)C(=O)O] | 631.31 | 632 |

133

General Scheme 10

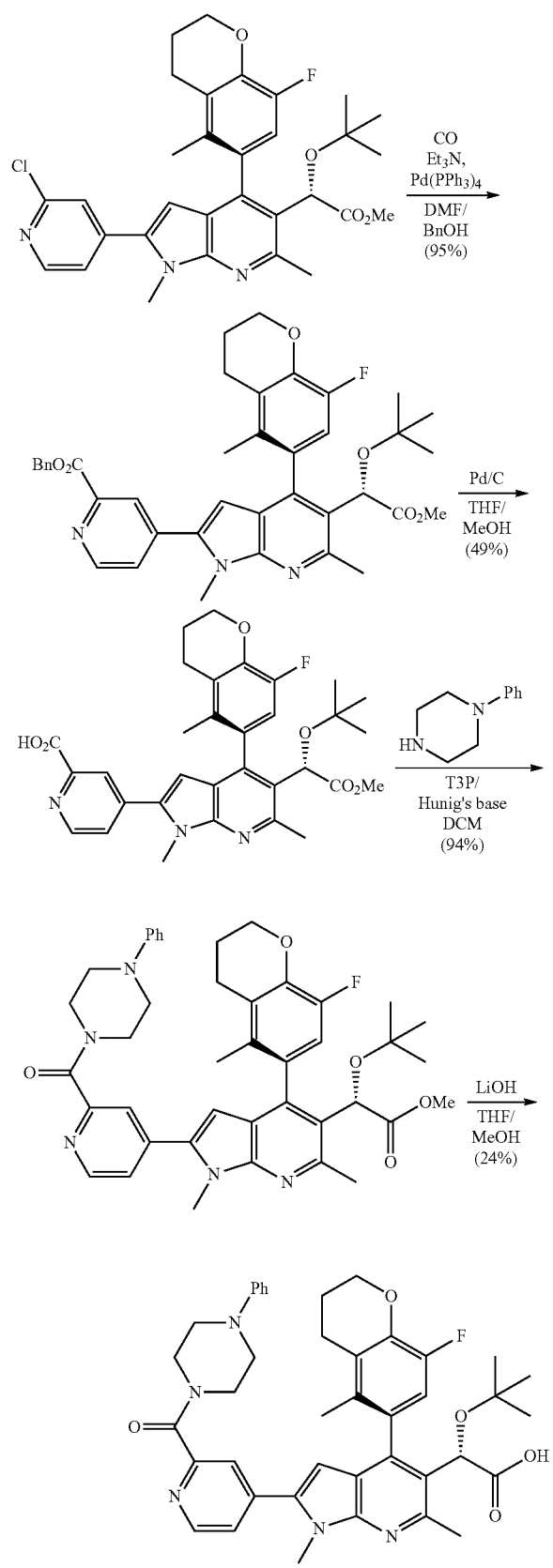

134

Example 145

(2S)(M)-2-(tert-butoxy)-2-(-4-(8-fluoro-5-methyl-chroman-6-yl)-1,6-dimethyl-2-(1-(1-methylazetidin-3-yl)-1H-pyrazol-3-yl)-1H-pyrrolo[2,3-b]pyridin-5-yl)acetic acid Step A (2S) (M)-Benzyl 4-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)picolinate A solution of (2S)(M)-methyl 2-(tert-butoxy)-2-(-2-(2-chloropyridin-4-yl)-4-(8-fluoro-5-methylchroman-6-yl)-1,6-dimethyl-1H-pyrrolo[2,3-b]pyridin-5-yl)acetate (120 mg, 0.212 mmol) in DMF (5 mL) and benzyl alcohol (0.1 mL) was treated with Et₃N (0.15 mL, 1.06 mmol) and degassed with N2 for 5 min. Pd(PPh₃)₄ (98 mg, 0.085 mmol) was added and the reaction mixture was heated placed under an atmosphere of CO (70 psi) and heated to 90° C. After 18 h, the reaction mixture was cooled to ambient temperature and concentrated in vacuo and purified by silica gel chromatography (0-100%

EtOAc-hexanes) to afford the title compound (112 mg, 0.16 mmol, 95%): LC-MS: ES+MS; 666 (M+1).

Step B (2S)(M)-4-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)picolinic acid

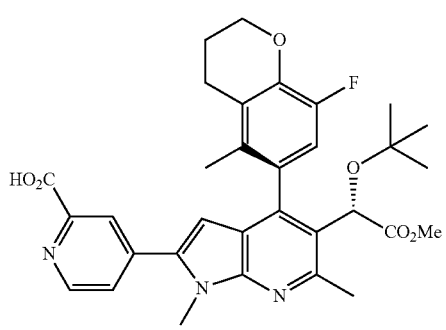

A solution of benzyl (2S)(M)-4-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)picolinate (112 mg, 0.16 mmol) in THF (3 mL) was degassed with $N_2$ for 5 min. Pd/C (63 mg) was added and the reaction mixture was placed under an atmosphere of $H_2$ (1 atm). After 4 h, the reaction mixture was filtered and the filtrate concentrated in vacuo to afford the title compound (68 mg, 0.12 mmol, 49% yield). LC-MS: ES+MS; 576 (M+1).

Step C (2S) (M)-Methyl 2-(tert-butoxy)-2-(-4-(8-fluoro-5-methylchroman-6-yl)-1,6-dimethyl-2-(2-(4-phenylpiperazine-1-carbonyl)pyridin-4-yl)-1H-pyrrolo[2,3-b]pyridin-5-yl)acetate

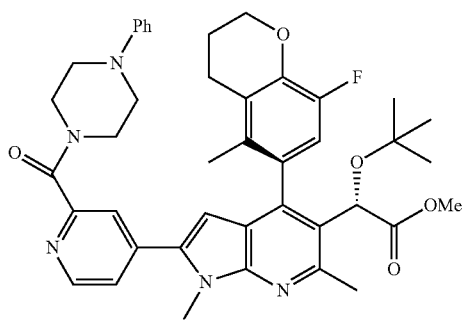

A solution of (2S)(M)-4-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)picolinic acid (31 mg, 0.054 mmol) and 1-phenylpiperazine (17.47 mg, 0.108 mmol) in DCM (3 mL) was added DIEA (0.056 mL, 0.323 mmol) and 2,4,6-tripropyl-1,3,5,2,4,6-trioxatriphosphinane 2,4,6-trioxide (0.024 mL, 0.081 mmol). After 20 min, the reaction mixture was poured into water and extracted with EtOAc. The organics were dried ($Na_2SO_4$), filtered and concentrated in vacuo to afford the title compound (41 mg, 0.054 mmol, 94%). LC-MS: ES+MS; 720 (M+1).

Step D (2S)(M)-2-(tert-butoxy)-2-(-4-(8-fluoro-5-methylchroman-6-yl)-1,6-dimethyl-2-(1-(1-methylazetidin-3-yl)-1H-pyrazol-3-yl)-1H-pyrrolo[2,3-b]pyridin-5-yl)acetic acid

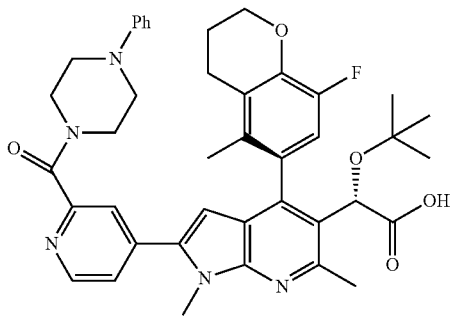

A solution of (2S)(M)-methyl 2-(tert-butoxy)-2-(-4-(8-fluoro-5-methylchroman-6-yl)-1,6-dimethyl-2-(2-(4-phenylpiperazine-1-carbonyl)pyridin-4-yl)-1H-pyrrolo[2,3-b]pyridin-5-yl)acetate (30 mg, 0.042 mmol) in THF (1.5 mL), Methanol (0.5 mL) and Water (0.5 mL) was treated with 1N LiOH (9.98 mg, 0.417 mmol) and heated to 60° C. After 2 h, the reaction mixture was poured into 1M HCl and extracted with EtOAc. The organics were dried ($MgSO_4$), filtered and concentrated in vacuo. The residue was purified by reverse phase HPLC to afford the title compound (13.3 mg, 24% yield): $^1$H NMR ($CD_3OD$): 8.71 (1H, d), 7.88 (1H, s), 7.50-7.55 (5H, m), 6.74 (1H, d, J=10.8), 6.38 (1H, s), 5.25 (1H, s), 4.31 (2H, m), 4.30 (2H, m), 4.10 (2H, m), 4.07 (3H, s), 3.60 (3H, s), 2.95 (3H, s), 2.73 (2H, m), 2.16 (2H, m), 1.84 (3H, s), 1.14 (9H, s). LC-MS: ES+MS; 706 (M+1).

Compounds in Table 6 (examples 146-153) were synthesized using the procedure described above with the appropriate amine.

TABLE 6

| Example | Structure | MW | Observed Mass |
|---|---|---|---|
| 146 | 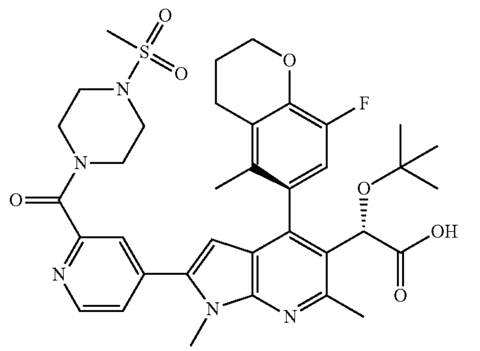 | 707.81 | 708 |
| 147 | 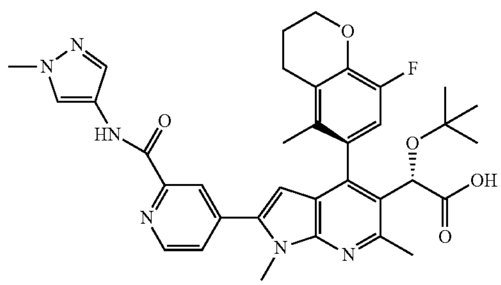 | 640.7 | 641 |
| 148 | 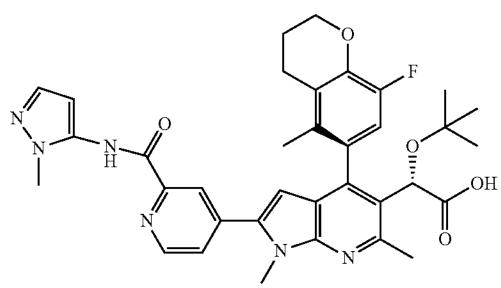 | 640.7 | 641 |
| 149 | 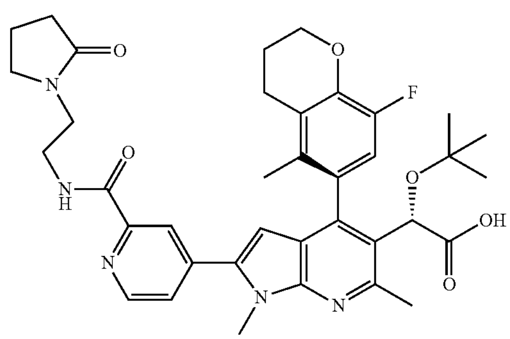 | 671.76 | 672 |
| 150 | 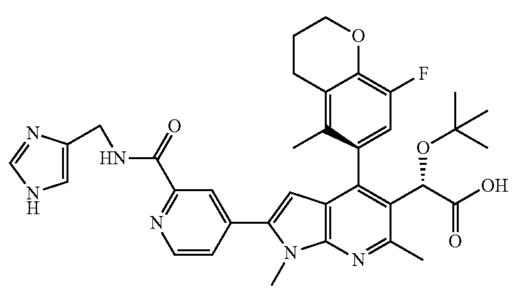 | 640.7 | 641 |

TABLE 6-continued
| Example | Structure | MW | Observed Mass |
|---|---|---|---|
| 151 | 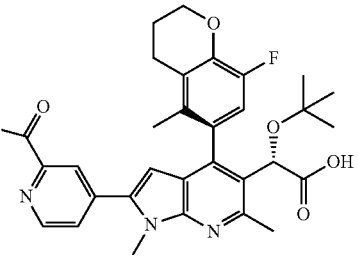 | 668.73 | 669 |
| 152 | 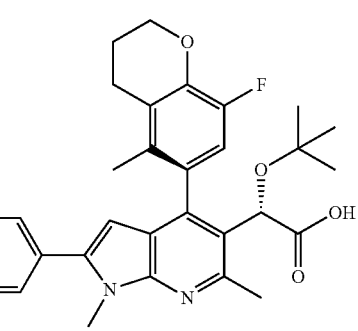 | 642.76 | 643 |
| 153 | 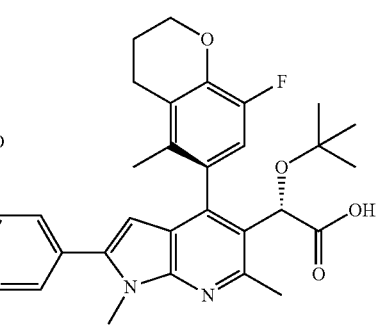 | 640.7 | 641 |
General Scheme 10
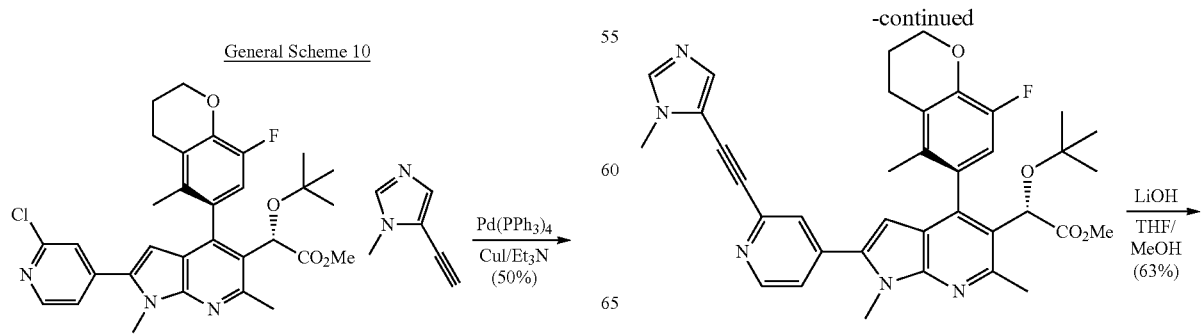

141

-continued

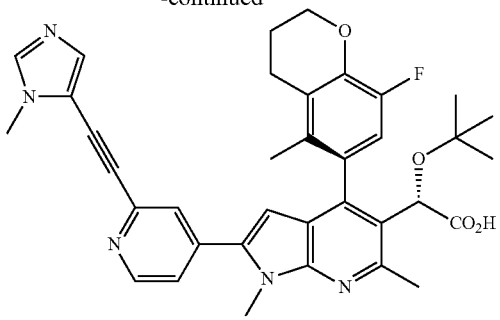

Example 154

(2S)(M)-2-(tert-butoxy)-2-(-4-(8-fluoro-5-methyl-chroman-6-yl)-1,6-dimethyl-2-(2-((1-methyl-1H-imidazol-5-yl)ethynyl)pyridin-4-yl)-1H-pyrrolo[2,3-b]pyridin-5-yl)acetic acid

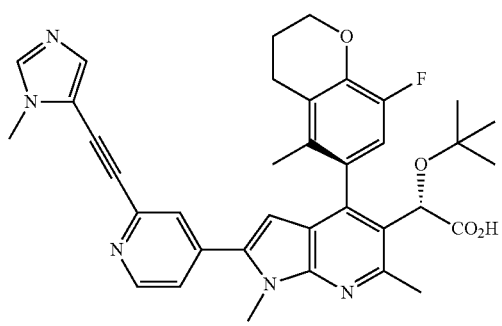

Step A (2S) (M)-Methyl 2-(tert-butoxy)-2-(-4-(8-fluoro-5-methylchroman-6-yl)-1,6-dimethyl-2-(2-(1-methyl-1H-imidazol-5-yl)ethynyl)pyridin-4-yl)-1H-pyrrolo[2,3-b]pyridin-5-yl)acetate

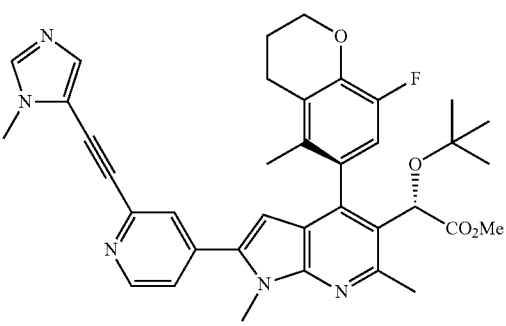

A solution of (2S)(M)-methyl 2-(tert-butoxy)-2-(2-(2-chloropyridin-4-yl)-4-(8-fluoro-5-methylchroman-6-yl)-1,6-dimethyl-1H-pyrrolo[2,3-b]pyridin-5-yl)acetate (30 mg,

142

0.053 mmol), 5-ethynyl-1-methyl-1H-imidazole (56.2 mg, 0.530 mmol), copper(I) iodide (2.019 mg, 10.60 μmol) and Pd(Ph$_3$P)$_4$ (12.25 mg, 10.60 μmol) in TEA (2 mL) was degassed under nitrogen for 10 min. The mixture was then heated to 80° C. for 7 h. The reaction mixture was cooled to ambient temperature, diluted with ethyl acetate, washed with NaHCO$_3$ sat. solution, dried over sodium sulfate and concentrated. The residue was purified by preparative TLC (DCM/MeOH 5%) to afford the title compound (17 mg, 50%). LC-MS: ES+MS; 636 (M+1).

Step B (2S)(M)-2-(tert-butoxy)-2-(-4-(8-fluoro-5-methyl-chroman-6-yl)-1,6-dimethyl-2-(2-((1-methyl-1H-imidazol-5-yl)ethynyl)pyridin-4-yl)-1H-pyrrolo[2,3-b]pyridin-5-yl)acetic acid

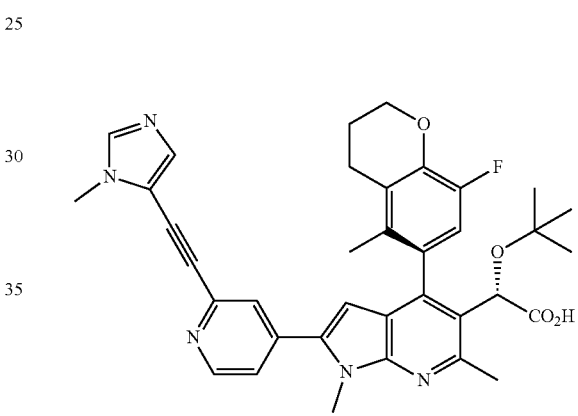

A solution of (2S)(M)-methyl 2-(tert-butoxy)-2-(-4-(8-fluoro-5-methylchroman-6-yl)-1,6-dimethyl-2-(2-((1-methyl-1H-imidazol-5-yl)ethynyl)pyridin-4-yl)-1H-pyrrolo[2,3-b]pyridin-5-yl)acetate (17 mg, 0.027 mmol) in THF (3 mL), Water (0.5 mL) was treated with LiOH (20 mg) and heated to 70° C. After 18 h, the reaction mixture was poured into 1M HCl and extracted with EtOAc. The organics were dried (MgSO$_4$), filtered and concentrated in vacuo. The residue was purified by reverse phase HPLC to afford the title compound (13 mg, 62% yield): $^1$H NMR (400 MHz, METHANOL-d$_4$) δ ppm 1.10 (s, 9H) 1.84 (s, 3H) 2.11 (br. s., 2H) 2.66-2.78 (m, 2H) 2.82 (s, 3H) 3.97 (s, 3H) 4.00 (s, 3H) 4.23 (t, J=5.08 Hz, 3H) 5.16 (s, 1H) 6.28 (s, 1H) 6.72 (d, J=11.33 Hz, 1H) 7.70 (dd, J=5.27, 1.76 Hz, 1H) 7.95 (d, J=0.98 Hz, 2H) 8.66 (d, J=5.27 Hz, 1H) 8.94 (br. s., 1H). LC-MS: ES+MS; 622 (M+1).

Compounds in Table 7 (examples 155-160) were synthesized using the procedure described above with the appropriate amine.

TABLE 7

| Example | Structure | MW | Observed Mass |
|---|---|---|---|
| 155 | 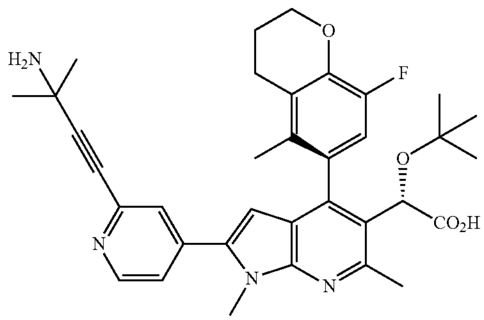 | 598.71 | 599 |
| 156 | 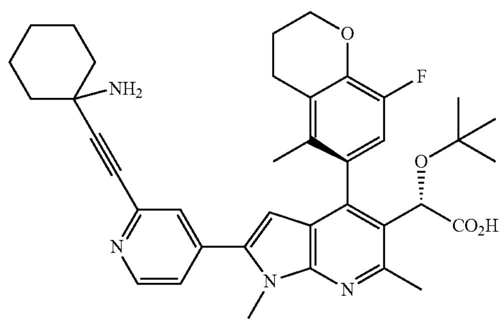 | 638.77 | 639 |
| 157 | 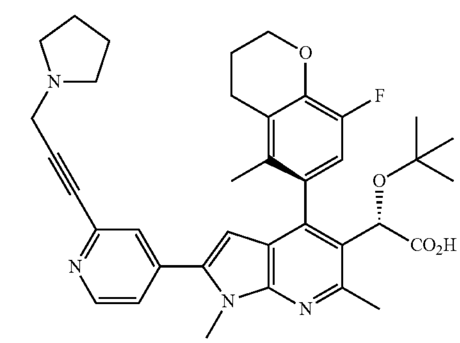 | 624.74 | 625 |
| 158 | 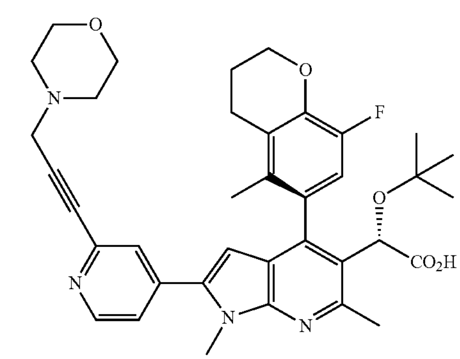 | 640.74 | 641 |

TABLE 7-continued
| Example | Structure | MW | Observed Mass |
|---|---|---|---|
| 159 | 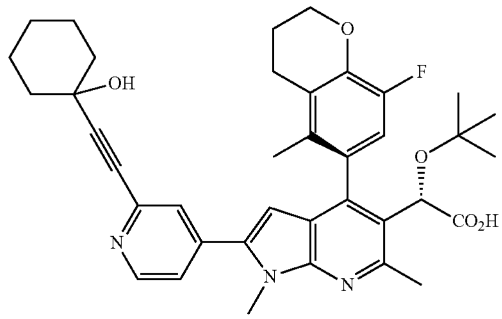 | 639.76 | 640 |
| 160 | 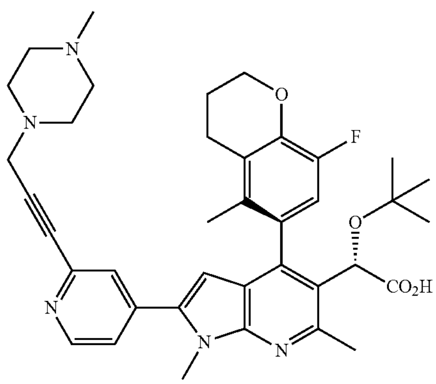 | 653.79 | 654 |
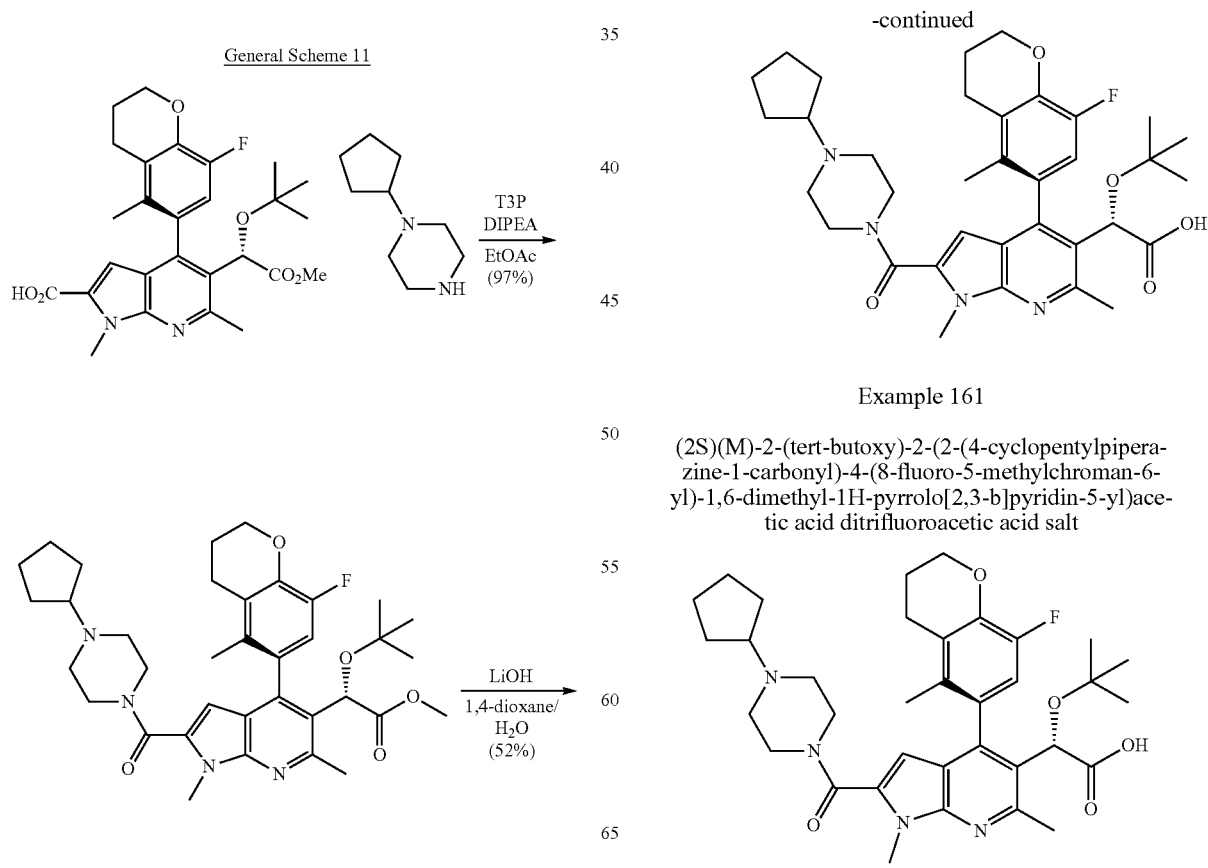
Example 161
(2S)(M)-2-(tert-butoxy)-2-(2-(4-cyclopentylpipera-zine-1-carbonyl)-4-(8-fluoro-5-methylchroman-6-yl)-1,6-dimethyl-1H-pyrrolo[2,3-b]pyridin-5-yl)ace-tic acid ditrifluoroacetic acid salt Step A (2S) (M)-Methyl 2-(tert-butoxy)-2-(2-(4-cyclopentylpiperazine-1-carbonyl)-4-(8-fluoro-5-methylchroman-6-yl)-1,6-dimethyl-1H-pyrrolo[2,3-b]pyridin-5-yl)acetate

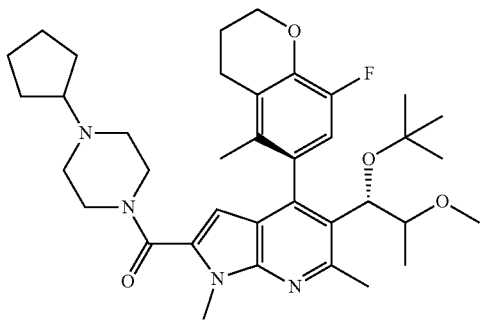

To a mixture of (2S)(M)-5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid (30 mg, 0.060 mmol) and 1-cyclopentylpiperazine (8.67 μL, 0.060 mmol) in ethyl acetate (1 mL) was added DIEA (0.026 mL, 0.150 mmol) followed by addition of 1-propanephosphonic acid cyclic anhydride (T3P) (0.072 mL, 0.120 mmol) as a 50% solution in ethyl acetate and stirred at room temperature for 30 min. Diluted with ethyl acetate, added water and saturated ammonium chloride and extracted with ethyl acetate. Organic phase was washed with brine, dried over $Na_2SO_4$, filtered and concentrated to give (2S)(M)-methyl 2-(tert-butoxy)-2-(2-(4-cyclopentylpiperazine-1-carbonyl)-4-(8-fluoro-5-methylchroman-6-yl)-1,6-dimethyl-1H-pyrrolo[2,3-b]pyridin-5-yl)acetate (37 mg, 97% yield) as a colorless oil. $^1$H NMR (400 MHz, CHLOROFORM-d) δ=6.74 (br. s., 1H), 5.99 (br. s., 1H), 5.14 (s, 1H), 4.32 (t, J=5.0 Hz, 2H), 3.93 (br. s., 3H), 3.78-3.88 (m, 1H), 3.59 (s, 3H), 2.78-2.86 (m, 3H), 2.74 (br. s., 2H), 2.53 (br. s., 2H), 2.17 (br. s., 2H), 1.89 (br. s., 2H), 1.78 (s, 3H), 1.57 (br. s., 12H), 1.06-1.17 (m, 9H); LC/MS (m/z) $ES^+$=635 (M+1).

Step B (2S)(M)-2-(tert-butoxy)-2-(2-(4-cyclopentylpiperazine-1-carbonyl)-4-(8-fluoro-5-methylchroman-6-yl)-1,6-dimethyl-1H-pyrrolo[2,3-b]pyridin-5-yl)acetic acid ditrifluoroacetic acid salt

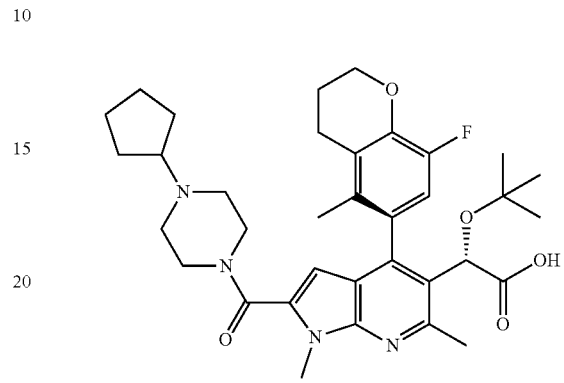

To a solution of (2S)(M)-methyl 2-(tert-butoxy)-2-(2-(4-cyclopentylpiperazine-1-carbonyl)-4-(8-fluoro-5-methylchroman-6-yl)-1,6-dimethyl-1H-pyrrolo[2,3-b]pyridin-5-yl) acetate (36 mg, 0.057 mmol) in 1,4-dioxane (1.76 mL) and water (0.235 mL) was added lithium hydroxide monohydrate (23.79 mg, 0.567 mmol). Heated at 75° C. overnight, concentrated, diluted with methanol and purified by reverse phase (10-100% acetonitrile/water/0.05% trifluoroacetic acid) to give the title compound (25 mg, 52% yield) as a white solid. $^1$H NMR (400 MHz, METHANOL-$d_4$) δ=6.70 (d, J=11.1 Hz, 1H), 6.17 (s, 1H), 5.12 (s, 1H), 4.53 (br. s., 2H), 4.22 (t, J=5.1 Hz, 2H), 3.89 (s, 3H), 3.32-3.69 (m, 5H), 3.10 (d, J=1.6 Hz, 2H), 2.79 (s, 3H), 2.59-2.76 (m, 2H), 1.99-2.22 (m, 4H), 1.76-1.84 (m, 5H), 1.67 (br. s., 4H), 1.08 (s, 9H); LC/MS (m/z) $ES^+$=621 (M+1).

Compounds in Table 8 (examples 162-280) were synthesized using the procedure described above with the appropriate amine.

TABLE 8

| Example | Structure | MW | Observed Mass |
|---|---|---|---|
| 162 | 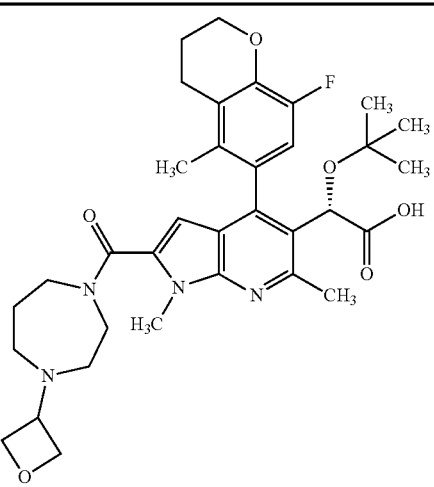 | 622.73 | 623 |

TABLE 8-continued

| Example | Structure | MW | Observed Mass |
|---------|-----------|-----|---------------|
| 163 | 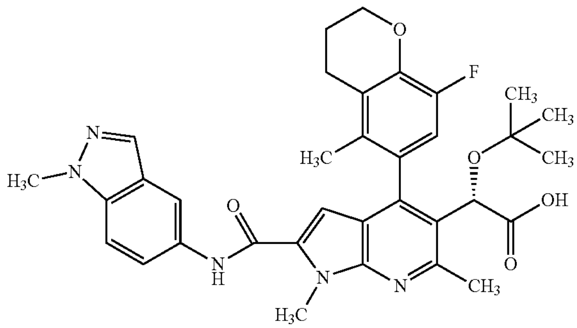 [SMILES: Cc1nc2c(cc(C(=O)Nc3ccc4c(cnn4C)c3)n2C)c(-c2cc(F)c3c(c2C)CCCO3)c1[C@H](OC(C)(C)C)C(=O)O] | 613.68 | 614 |
| 164 | 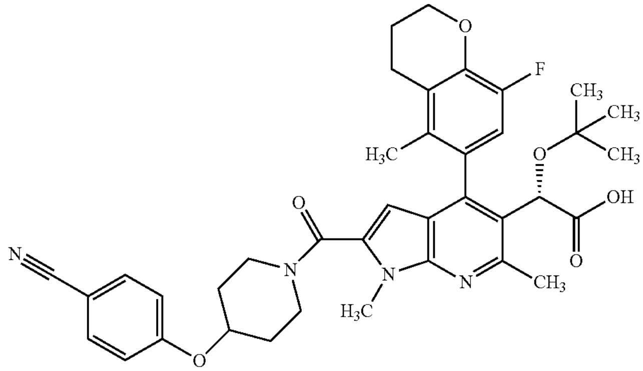 [SMILES: Cc1nc2c(cc(C(=O)N3CCC(Oc4ccc(C#N)cc4)CC3)n2C)c(-c2cc(F)c3c(c2C)CCCO3)c1[C@H](OC(C)(C)C)C(=O)O] | 668.75 | 669 |
| 165 | 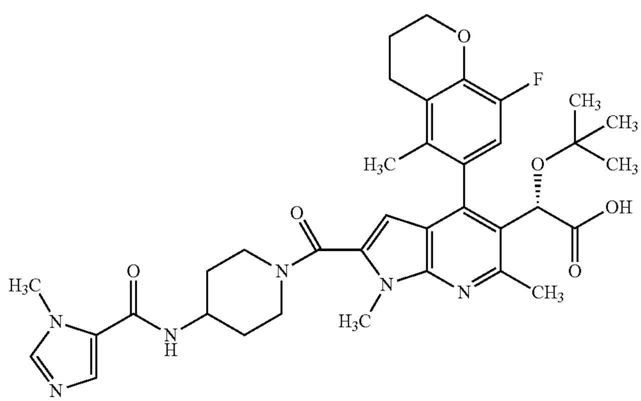 [SMILES: Cc1nc2c(cc(C(=O)N3CCC(NC(=O)c4cncn4C)CC3)n2C)c(-c2cc(F)c3c(c2C)CCCO3)c1[C@H](OC(C)(C)C)C(=O)O] | 674.76 | 675 |
| 166 | 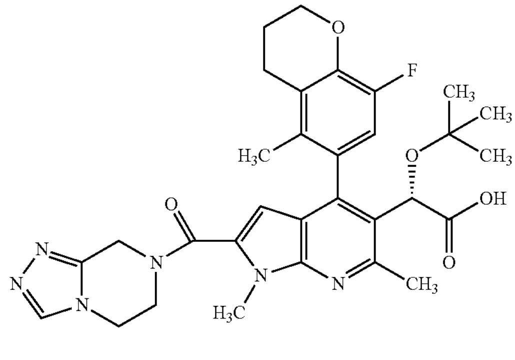 [SMILES: Cc1nc2c(cc(C(=O)N3CCn4cnnc4C3)n2C)c(-c2cc(F)c3c(c2C)CCCO3)c1[C@H](OC(C)(C)C)C(=O)O] | 590.65 | 591 |

TABLE 8-continued

| Example | Structure | MW | Observed Mass |
|---|---|---|---|
| 167 | 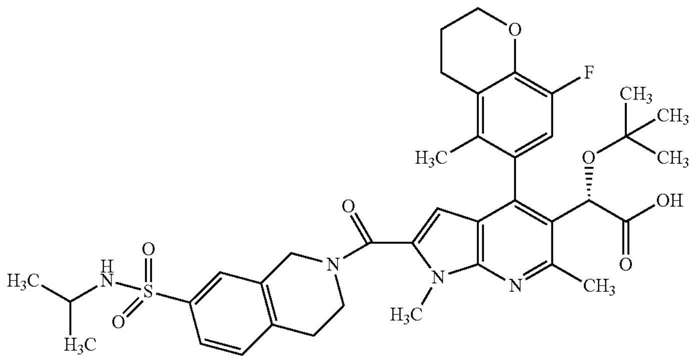 [SMILES: Cc1nc2c(cc(C(=O)N3CCc4ccc(S(=O)(=O)NC(C)C)cc4C3)n2C)c(-c2cc(F)c3c(c2C)CCCO3)c1[C@H](OC(C)(C)C)C(=O)O] | 720.85 | 721 |
| 168 | 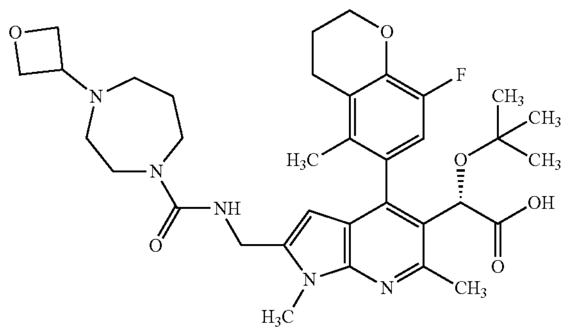 [SMILES: Cc1nc2c(cc(CNC(=O)N3CCCN(C4COC4)CC3)n2C)c(-c2cc(F)c3c(c2C)CCCO3)c1[C@H](OC(C)(C)C)C(=O)O] | 651.77 | 652 |
| 169 | 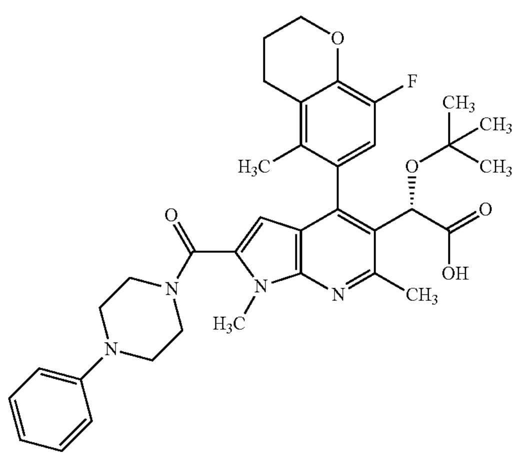 [SMILES: Cc1nc2c(cc(C(=O)N3CCN(c4ccccc4)CC3)n2C)c(-c2cc(F)c3c(c2C)CCCO3)c1[C@H](OC(C)(C)C)C(=O)O] | 629.72 | 630 |
| 170 | 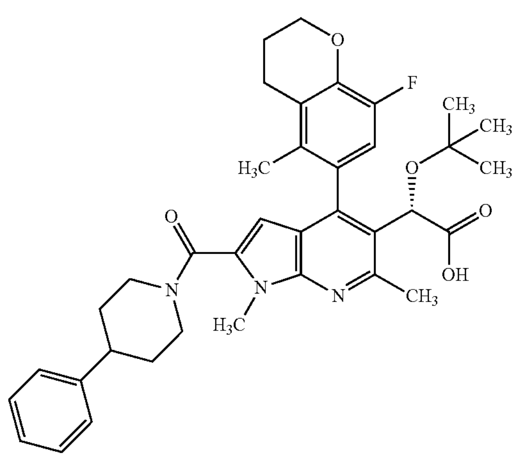 [SMILES: Cc1nc2c(cc(C(=O)N3CCC(c4ccccc4)CC3)n2C)c(-c2cc(F)c3c(c2C)CCCO3)c1[C@H](OC(C)(C)C)C(=O)O] | 627.74 | 628 |

TABLE 8-continued

| Example | Structure | MW | Observed Mass |
|---------|-----------|-----|---------------|
| 171 | 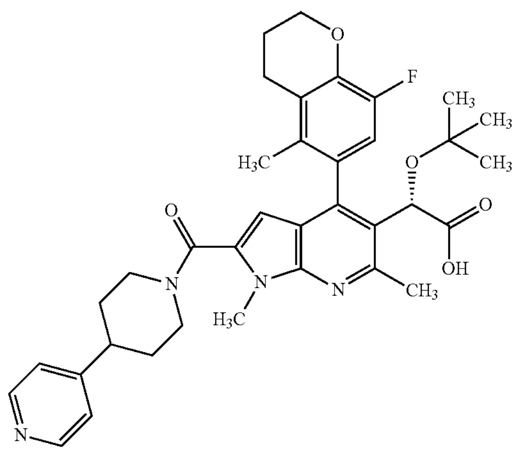 [SMILES: Cc1nc2c(cc(C(=O)N3CCC(c4ccncc4)CC3)n2C)c(-c2cc(F)c3c(c2C)CCCO3)c1[C@H](OC(C)(C)C)C(=O)O] | 628.73 | 630 |
| 172 | 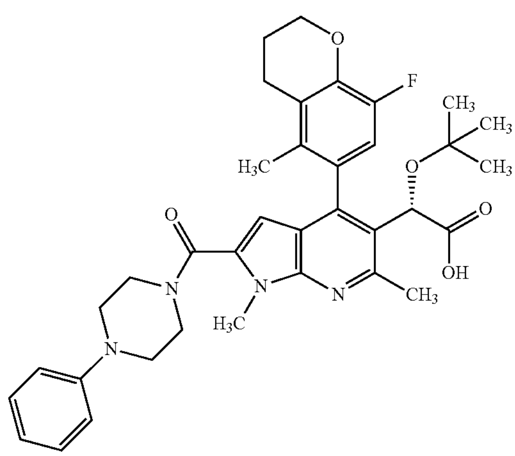 | 628.73 | 629 |
| 173 | 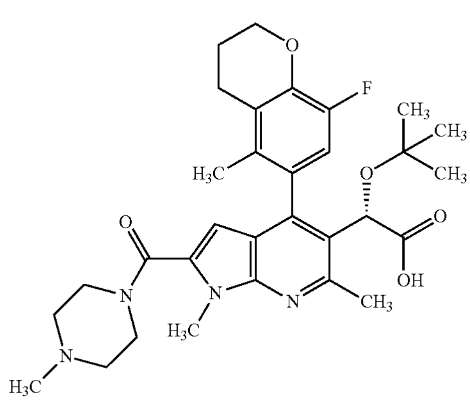 | 566.66 | 567 |

TABLE 8-continued

| Example | Structure | MW | Observed Mass |
|---|---|---|---|
| 174 | 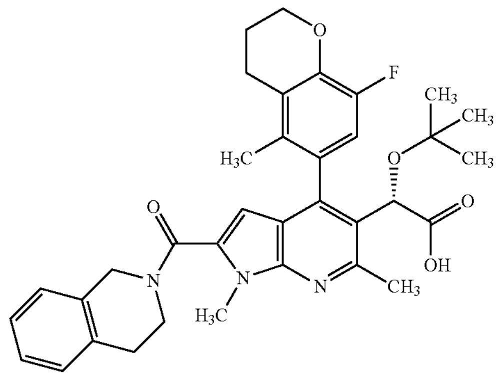 [SMILES: Cc1nc2c(cc(C(=O)N3CCc4ccccc4C3)n2C)c(-c2cc(F)c3c(c2C)CCCO3)c1[C@H](OC(C)(C)C)C(=O)O] | 599.69 | 600 |
| 175 | 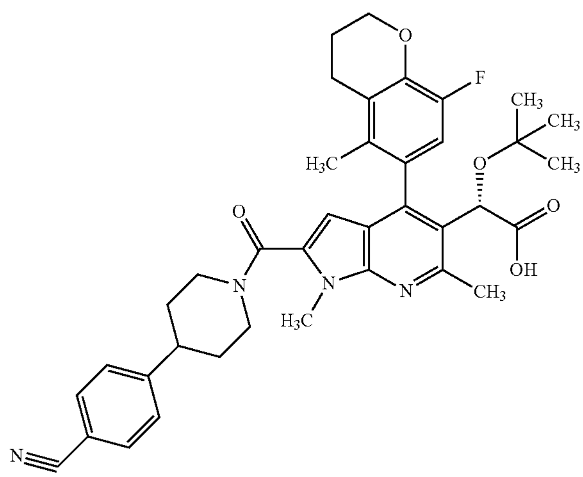 [SMILES: Cc1nc2c(cc(C(=O)N3CCC(c4ccc(C#N)cc4)CC3)n2C)c(-c2cc(F)c3c(c2C)CCCO3)c1[C@H](OC(C)(C)C)C(=O)O] | 652.75 | 653 |
| 176 | 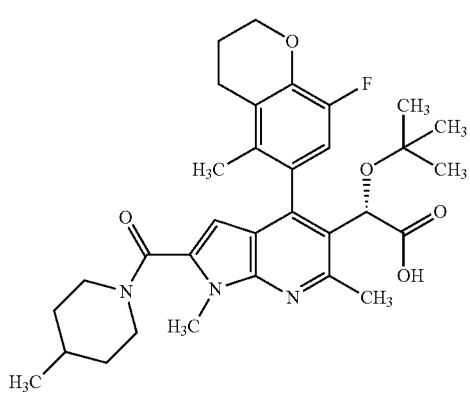 [SMILES: Cc1nc2c(cc(C(=O)N3CCC(C)CC3)n2C)c(-c2cc(F)c3c(c2C)CCCO3)c1[C@H](OC(C)(C)C)C(=O)O] | 565.68 | 566 |

TABLE 8-continued

| Example | Structure | MW | Observed Mass |
|---------|-----------|------|------|
| 177 | 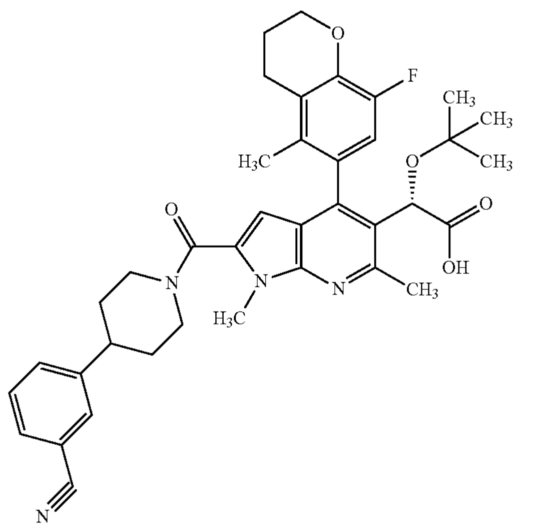 [SMILES: Cc1nc2c(cc(C(=O)N3CCC(c4cccc(C#N)c4)CC3)n2C)c(-c2cc(F)c3c(c2C)CCCO3)c1[C@H](OC(C)(C)C)C(=O)O] | 652.75 | 653 |
| 178 | 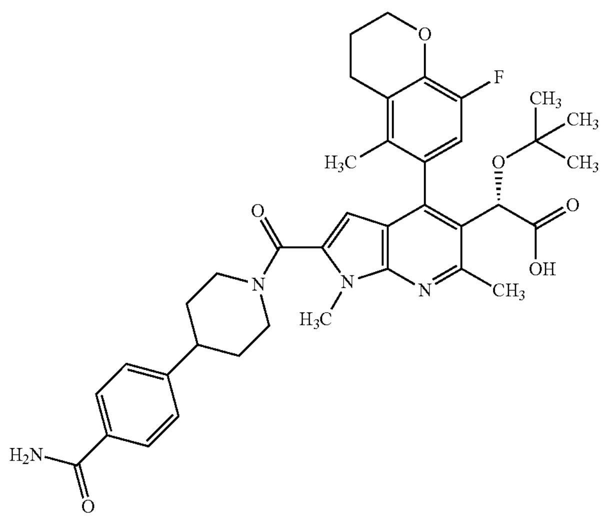 [SMILES: Cc1nc2c(cc(C(=O)N3CCC(c4ccc(C(N)=O)cc4)CC3)n2C)c(-c2cc(F)c3c(c2C)CCCO3)c1[C@H](OC(C)(C)C)C(=O)O] | 670.77 | 671 |
| 179 | 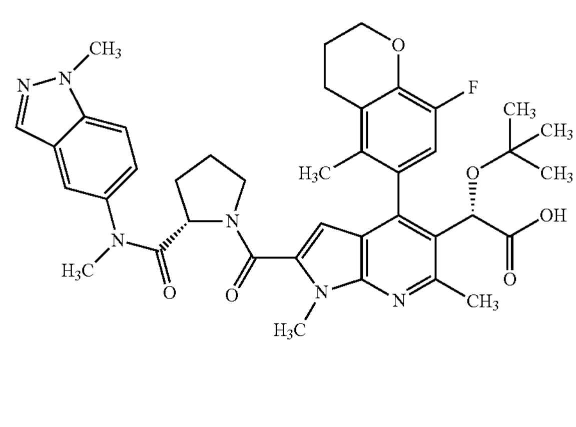 [SMILES: Cc1nc2c(cc(C(=O)N3CCC[C@H]3C(=O)N(C)c3ccc4c(cnn4C)c3)n2C)c(-c2cc(F)c3c(c2C)CCCO3)c1[C@H](OC(C)(C)C)C(=O)O] | 724.82 | 725 |

TABLE 8-continued

| Example | Structure | MW | Observed Mass |
|---|---|---|---|
| 180 | 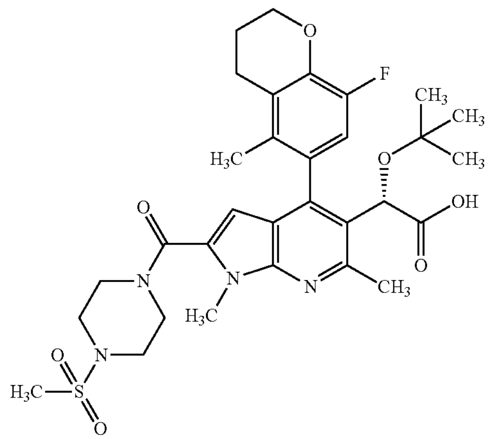 [SMILES: Cc1nc2c(cc(C(=O)N3CCN(S(C)(=O)=O)CC3)n2C)c(-c2cc(F)c3c(c2C)CCCO3)c1[C@H](OC(C)(C)C)C(=O)O] | 630.73 | 631 |
| 181 | 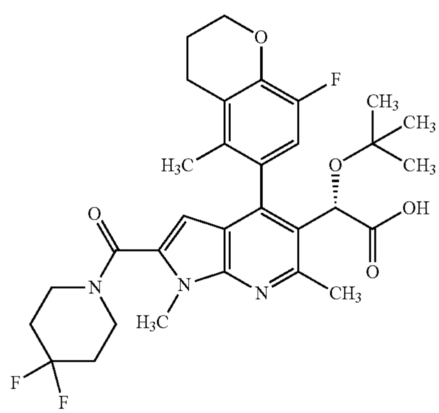 [SMILES: Cc1nc2c(cc(C(=O)N3CCC(F)(F)CC3)n2C)c(-c2cc(F)c3c(c2C)CCCO3)c1[C@H](OC(C)(C)C)C(=O)O] | 587.63 | 588 |
| 182 | 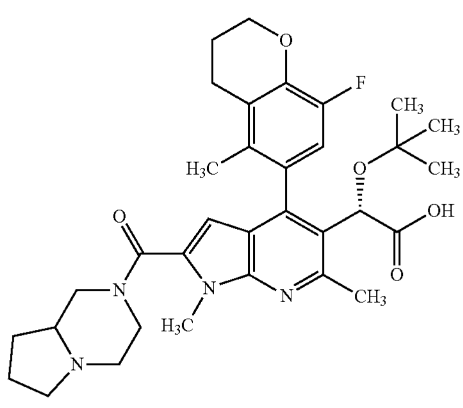 [SMILES: Cc1nc2c(cc(C(=O)N3CCN4CCCC4C3)n2C)c(-c2cc(F)c3c(c2C)CCCO3)c1[C@H](OC(C)(C)C)C(=O)O] | 592.7 | 593 |

TABLE 8-continued

| Example | Structure | MW | Observed Mass |
|---|---|---|---|
| 183 | 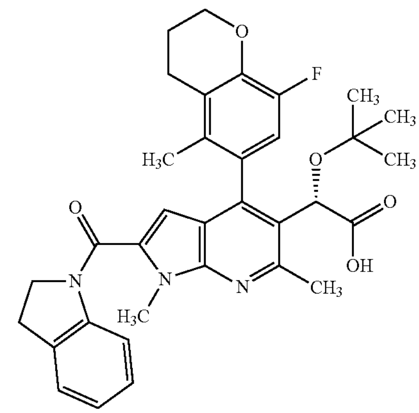 [SMILES: Cc1nc2c(cc(C(=O)N3CCc4ccccc43)n2C)c(-c2cc(F)c3c(c2C)CCCO3)c1[C@H](OC(C)(C)C)C(=O)O] | 585.67 | 586 |
| 184 | 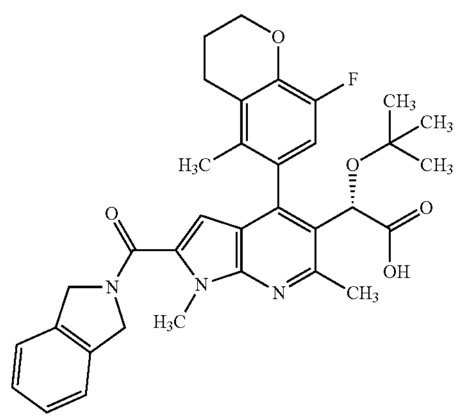 [SMILES: Cc1nc2c(cc(C(=O)N3Cc4ccccc4C3)n2C)c(-c2cc(F)c3c(c2C)CCCO3)c1[C@H](OC(C)(C)C)C(=O)O] | 585.67 | 586 |
| 185 | 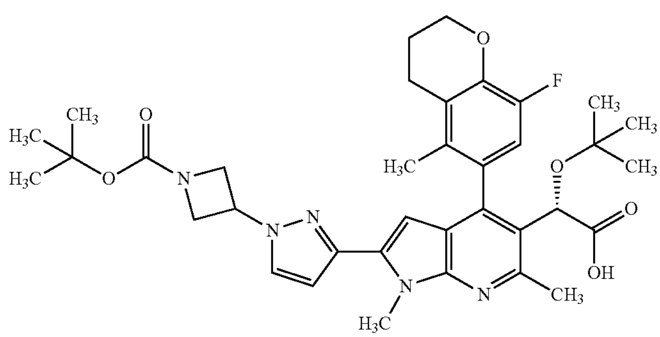 [SMILES: Cc1nc2c(cc(-c3ccn(C4CN(C(=O)OC(C)(C)C)C4)n3)n2C)c(-c2cc(F)c3c(c2C)CCCO3)c1[C@H](OC(C)(C)C)C(=O)O] | 661.76 | 662 |
| 186 | 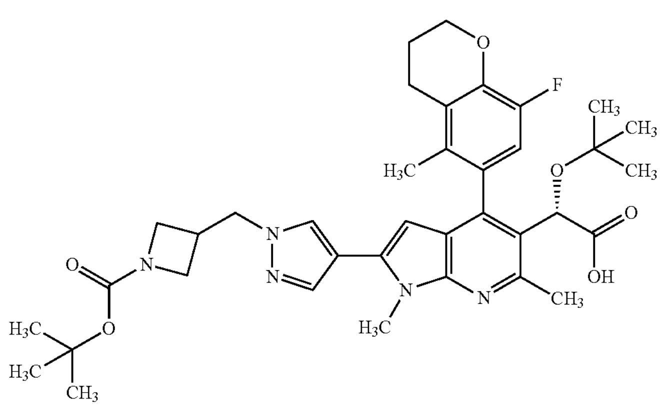 [SMILES: Cc1nc2c(cc(-c3cnn(CC4CN(C(=O)OC(C)(C)C)C4)c3)n2C)c(-c2cc(F)c3c(c2C)CCCO3)c1[C@H](OC(C)(C)C)C(=O)O] | 675.79 | 676 |

TABLE 8-continued

| Example | Structure | MW | Observed Mass |
|---|---|---|---|
| 187 | 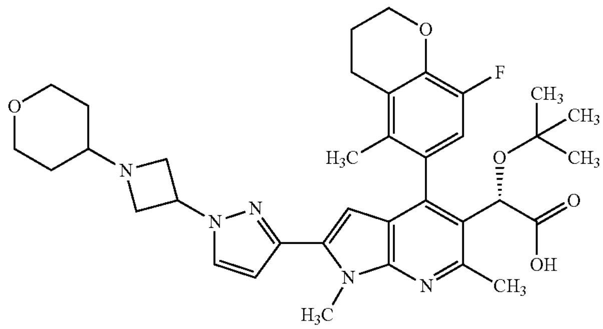 [SMILES: Cc1nc2c(cc(-c3ccn(C4CN(C5CCOCC5)C4)n3)n2C)c(-c2cc(F)c3c(c2C)CCCO3)c1[C@H](OC(C)(C)C)C(=O)O] | 645.76 | 646 |
| 188 | 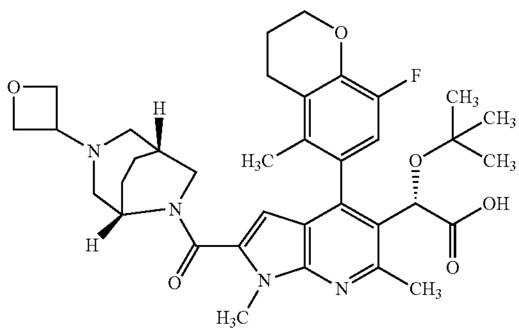 [SMILES: Cc1nc2c(cc(C(=O)N3C[C@@H]4CC[C@H]3CN(C3COC3)C4)n2C)c(-c2cc(F)c3c(c2C)CCCO3)c1[C@H](OC(C)(C)C)C(=O)O] | 648.76 | 649 |
| 189 | 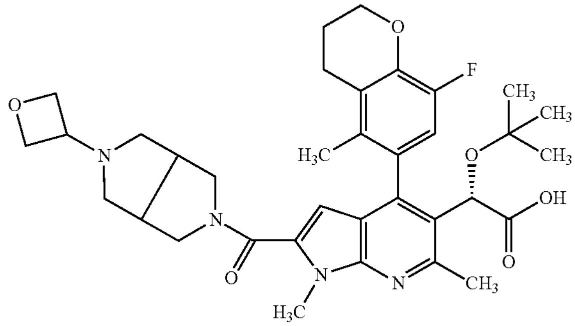 [SMILES: Cc1nc2c(cc(C(=O)N3CC4CN(C5COC5)CC4C3)n2C)c(-c2cc(F)c3c(c2C)CCCO3)c1[C@H](OC(C)(C)C)C(=O)O] | 634.74 | 635 |
| 190 | 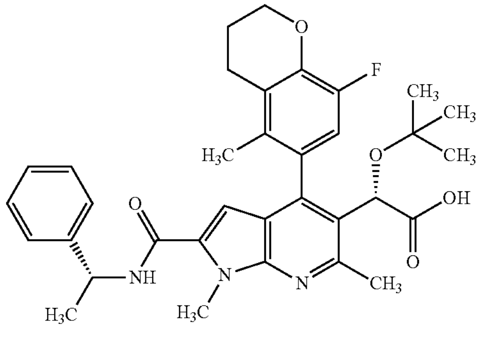 [SMILES: Cc1nc2c(cc(C(=O)N[C@H](C)c3ccccc3)n2C)c(-c2cc(F)c3c(c2C)CCCO3)c1[C@H](OC(C)(C)C)C(=O)O] | 587.68 | 588 |

TABLE 8-continued

| Example | Structure | MW | Observed Mass |
|---------|-----------|-----|---------------|
| 191 | 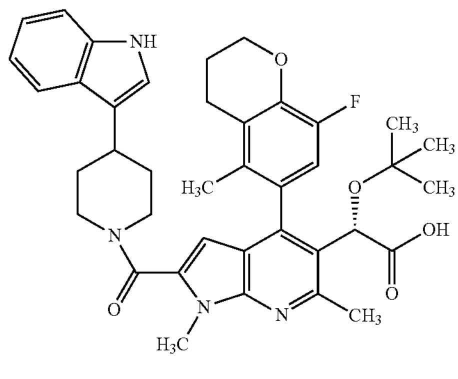 [SMILES: Cc1nc2c(cc(C(=O)N3CCC(c4c[nH]c5ccccc45)CC3)n2C)c(-c2cc(F)c3c(c2C)CCCO3)c1[C@H](OC(C)(C)C)C(=O)O] | 666.78 | 667 |
| 192 | 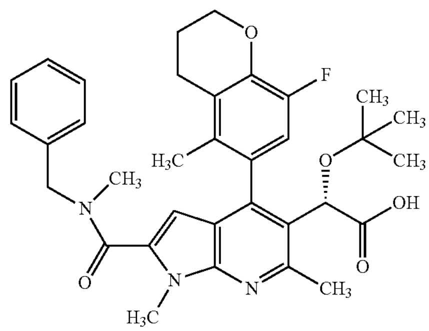 [SMILES: Cc1nc2c(cc(C(=O)N(C)Cc3ccccc3)n2C)c(-c2cc(F)c3c(c2C)CCCO3)c1[C@H](OC(C)(C)C)C(=O)O] | 587.68 | 588 |
| 193 | 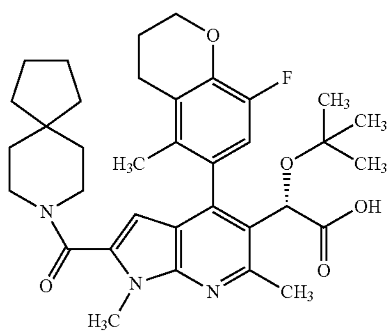 [SMILES: Cc1nc2c(cc(C(=O)N3CCC4(CCCC4)CC3)n2C)c(-c2cc(F)c3c(c2C)CCCO3)c1[C@H](OC(C)(C)C)C(=O)O] | 605.74 | 606 |
| 194 | 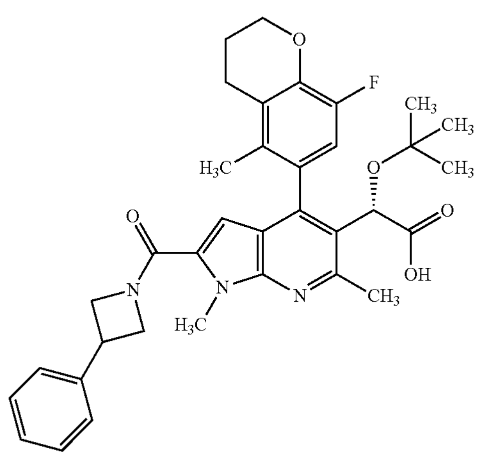 [SMILES: Cc1nc2c(cc(C(=O)N3CC(c4ccccc4)C3)n2C)c(-c2cc(F)c3c(c2C)CCCO3)c1[C@H](OC(C)(C)C)C(=O)O] | 599.69 | 600 |

TABLE 8-continued

| Example | Structure | MW | Observed Mass |
|---|---|---|---|
| 195 | 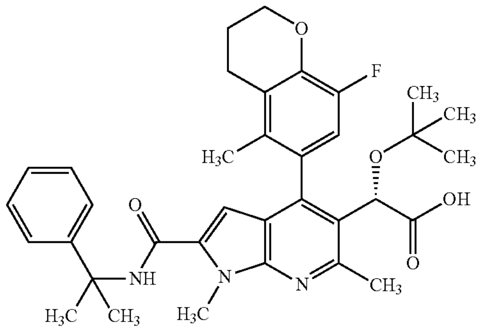 [SMILES: Cc1nc2c(cc(C(=O)NC(C)(C)c3ccccc3)n2C)c(-c2cc(F)c3c(c2C)CCCO3)c1[C@H](OC(C)(C)C)C(=O)O] | 601.71 | 602 |
| 196 | 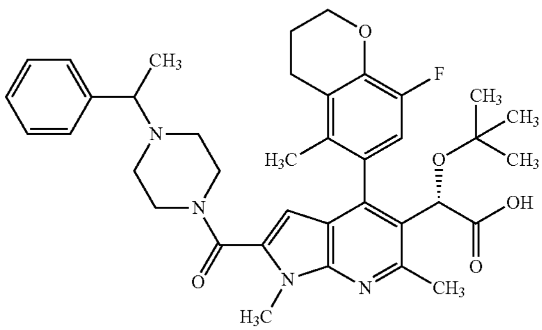 [SMILES: Cc1nc2c(cc(C(=O)N3CCN(C(C)c4ccccc4)CC3)n2C)c(-c2cc(F)c3c(c2C)CCCO3)c1[C@H](OC(C)(C)C)C(=O)O] | 656.79 | 657 |
| 197 | 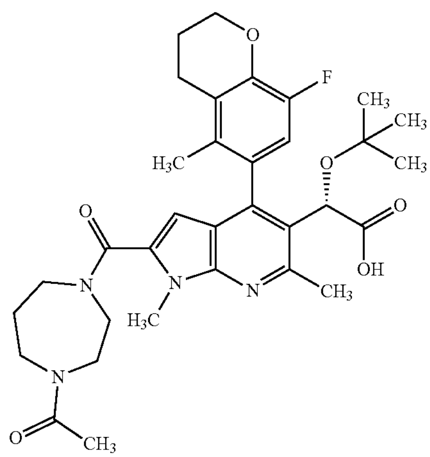 [SMILES: CC(=O)N1CCCN(C(=O)c2cc3c(-c4cc(F)c5c(c4C)CCCO5)c([C@H](OC(C)(C)C)C(=O)O)c(C)nc3n2C)CC1] | 608.7 | 609 |
| 198 | 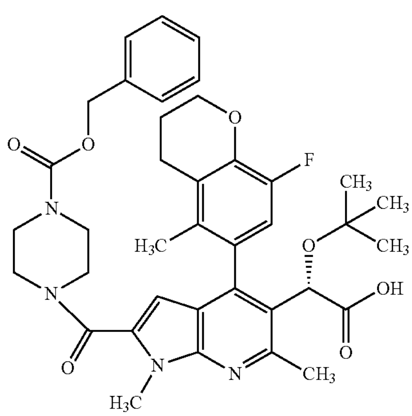 [SMILES: Cc1nc2c(cc(C(=O)N3CCN(C(=O)OCc4ccccc4)CC3)n2C)c(-c2cc(F)c3c(c2C)CCCO3)c1[C@H](OC(C)(C)C)C(=O)O] | 686.77 | 687 |

TABLE 8-continued

| Example | Structure | MW | Observed Mass |
|---|---|---|---|
| 199 | 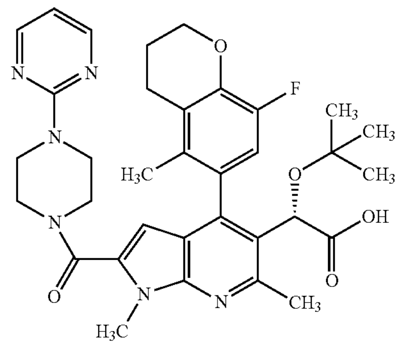 [SMILES: Cc1nc2c(cc(C(=O)N3CCN(c4ncccn4)CC3)n2C)c(-c2cc(F)c3c(c2C)CCCO3)c1[C@H](OC(C)(C)C)C(=O)O] | 630.71 | 631 |
| 200 | 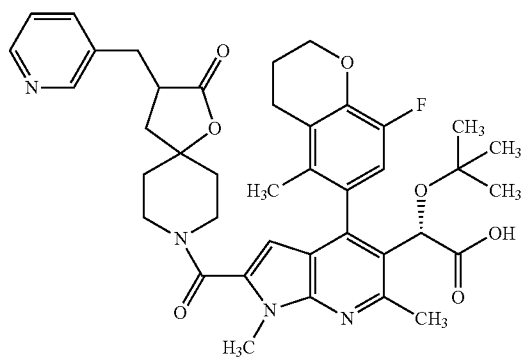 [SMILES: Cc1nc2c(cc(C(=O)N3CCC4(CC3)CC(Cc3cccnc3)C(=O)O4)n2C)c(-c2cc(F)c3c(c2C)CCCO3)c1[C@H](OC(C)(C)C)C(=O)O] | 712.81 | 713 |
| 201 | 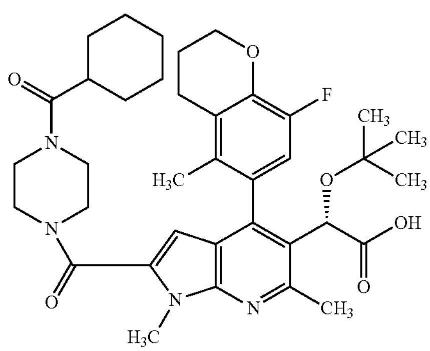 [SMILES: Cc1nc2c(cc(C(=O)N3CCN(C(=O)C4CCCCC4)CC3)n2C)c(-c2cc(F)c3c(c2C)CCCO3)c1[C@H](OC(C)(C)C)C(=O)O] | 662.79 | 663 |
| 202 | 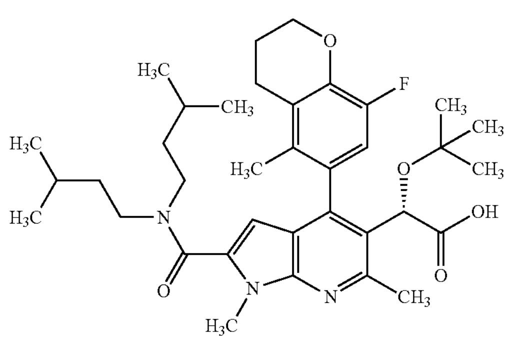 [SMILES: Cc1nc2c(cc(C(=O)N(CCC(C)C)CCC(C)C)n2C)c(-c2cc(F)c3c(c2C)CCCO3)c1[C@H](OC(C)(C)C)C(=O)O] | 623.8 | 624 |

TABLE 8-continued

| Example | Structure | MW | Observed Mass |
|---|---|---|---|
| 203 | 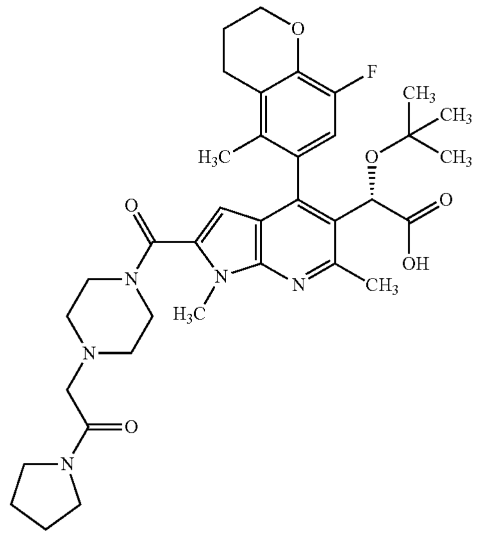 [SMILES: Cc1nc2c(cc(C(=O)N3CCN(CC(=O)N4CCCC4)CC3)n2C)c(-c2cc(F)c3c(c2C)CCCO3)c1[C@H](OC(C)(C)C)C(=O)O] | 663.78 | 664 |
| 204 | 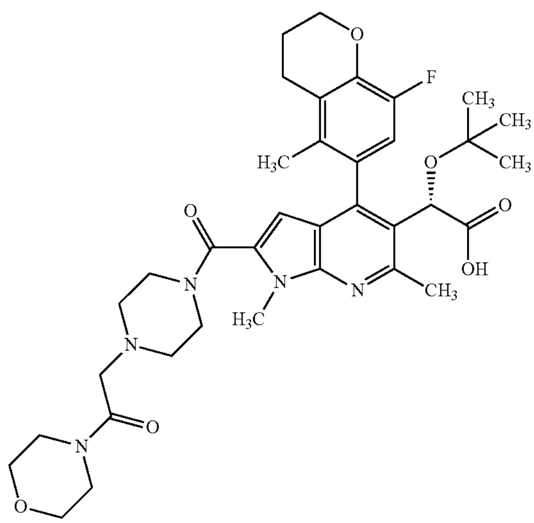 [SMILES: Cc1nc2c(cc(C(=O)N3CCN(CC(=O)N4CCOCC4)CC3)n2C)c(-c2cc(F)c3c(c2C)CCCO3)c1[C@H](OC(C)(C)C)C(=O)O] | 679.78 | 680 |
| 205 | 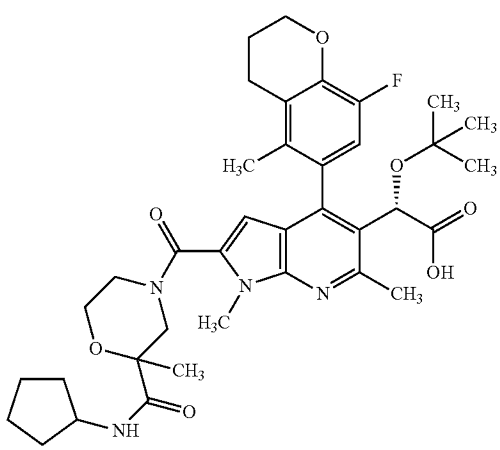 [SMILES: Cc1nc2c(cc(C(=O)N3CCOC(C)(C(=O)NC4CCCC4)C3)n2C)c(-c2cc(F)c3c(c2C)CCCO3)c1[C@H](OC(C)(C)C)C(=O)O] | 678.79 | 679 |

TABLE 8-continued

| Example | Structure | MW | Observed Mass |
|---|---|---|---|
| 206 | 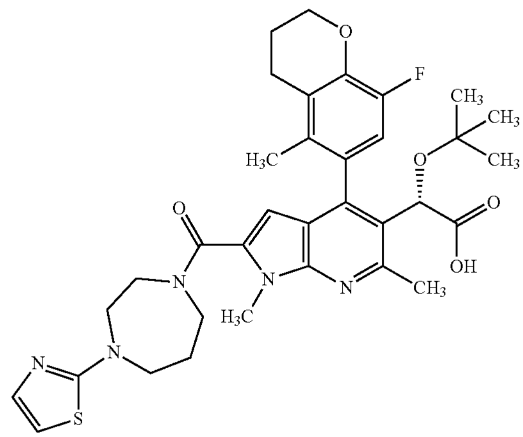 [SMILES: Cc1nc2c(cc(C(=O)N3CCCN(c4nccs4)CC3)n2C)c(-c2cc(F)c3c(c2C)CCCO3)c1[C@H](OC(C)(C)C)C(=O)O] | 649.78 | 650 |
| 207 | 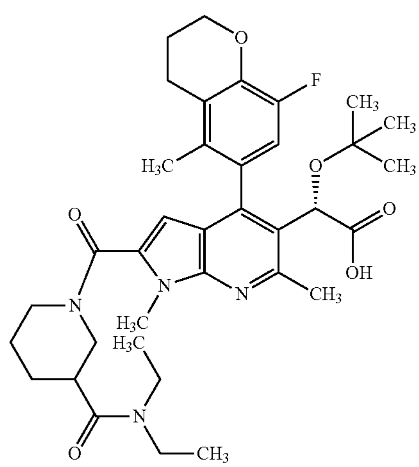 [SMILES: CCN(CC)C(=O)C1CCCN(C(=O)c2cc3c(-c4cc(F)c5c(c4C)CCCO5)c([C@H](OC(C)(C)C)C(=O)O)c(C)nc3n2C)C1] | 650.78 | 651 |
| 208 | 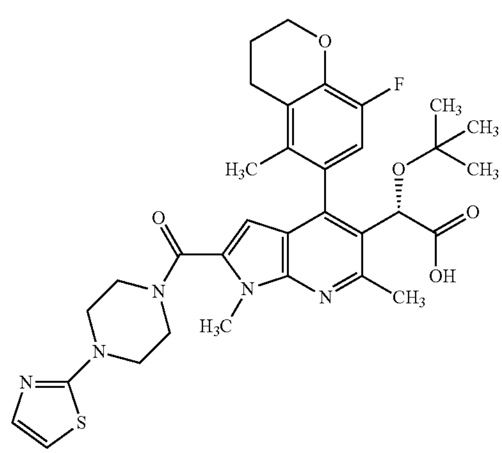 [SMILES: Cc1nc2c(cc(C(=O)N3CCN(c4nccs4)CC3)n2C)c(-c2cc(F)c3c(c2C)CCCO3)c1[C@H](OC(C)(C)C)C(=O)O] | 635.75 | 636 |

TABLE 8-continued

| Example | Structure | MW | Observed Mass |
|---------|-----------|-----|---------------|
| 209 | 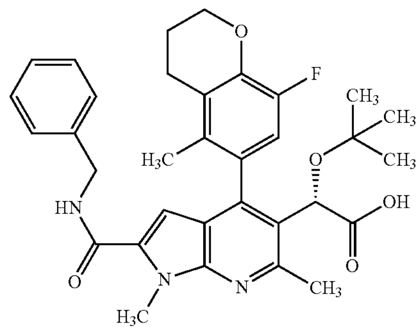 [SMILES: Cc1nc2c(cc(C(=O)NCc3ccccc3)n2C)c(-c2cc(F)c3c(c2C)CCCO3)c1[C@H](OC(C)(C)C)C(=O)O] | 573.65 | 574 |
| 210 | 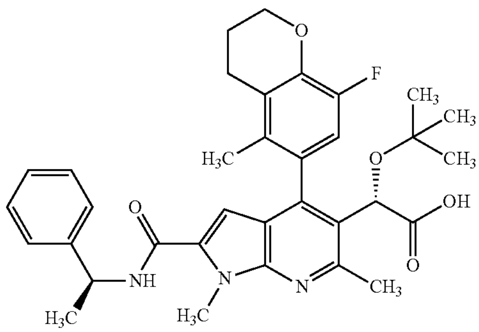 [SMILES: Cc1nc2c(cc(C(=O)N[C@@H](C)c3ccccc3)n2C)c(-c2cc(F)c3c(c2C)CCCO3)c1[C@H](OC(C)(C)C)C(=O)O] | 587.68 | 588 |
| 211 | 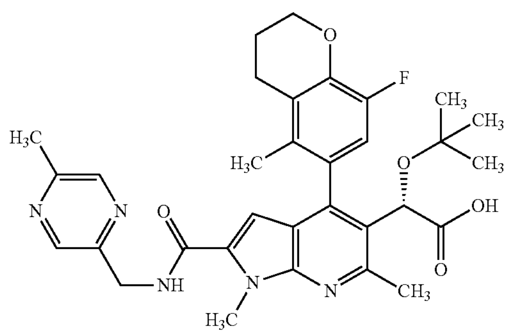 [SMILES: Cc1cnc(CNC(=O)c2cc3c(-c4cc(F)c5c(c4C)CCCO5)c([C@H](OC(C)(C)C)C(=O)O)c(C)nc3n2C)cn1] | 589.66 | 590 |
| 212 | 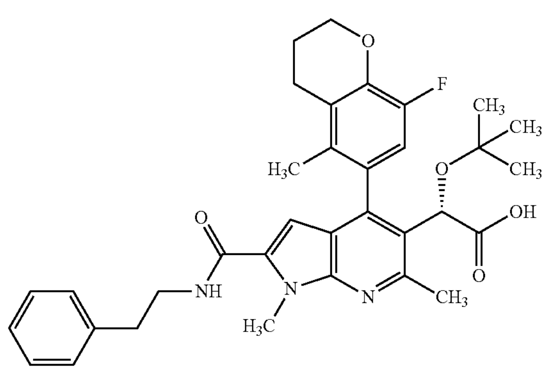 [SMILES: Cc1nc2c(cc(C(=O)NCCc3ccccc3)n2C)c(-c2cc(F)c3c(c2C)CCCO3)c1[C@H](OC(C)(C)C)C(=O)O] | 587.68 | 588 |

TABLE 8-continued

| Example | Structure | MW | Observed Mass |
|---------|-----------|-----|---------------|
| 213 | 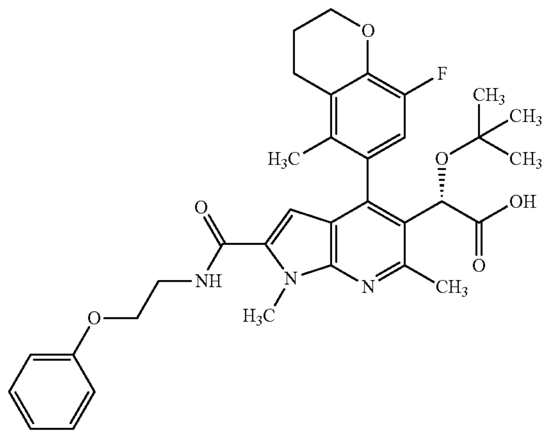 [SMILES: Cc1nc2c(cc(C(=O)NCCOc3ccccc3)n2C)c(-c2cc(F)c3c(c2C)CCCO3)c1[C@H](OC(C)(C)C)C(=O)O] | 603.68 | 604 |
| 214 | 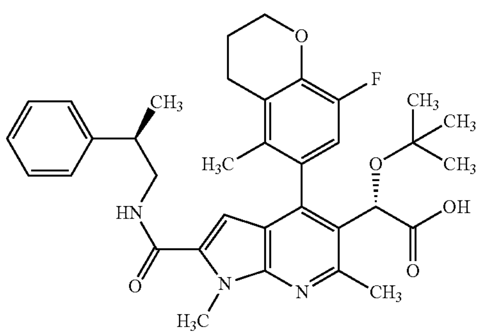 [SMILES: Cc1nc2c(cc(C(=O)NC[C@H](C)c3ccccc3)n2C)c(-c2cc(F)c3c(c2C)CCCO3)c1[C@H](OC(C)(C)C)C(=O)O] | 601.71 | 602 |
| 215 | 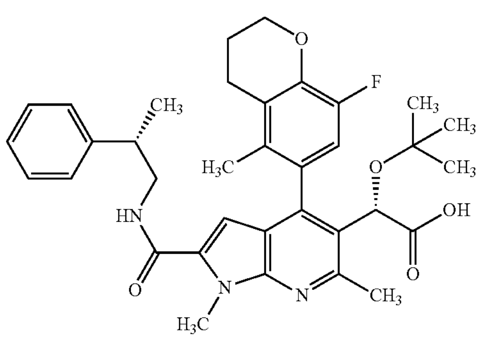 [SMILES: Cc1nc2c(cc(C(=O)NC[C@@H](C)c3ccccc3)n2C)c(-c2cc(F)c3c(c2C)CCCO3)c1[C@H](OC(C)(C)C)C(=O)O] | 601.71 | 602 |
| 216 | 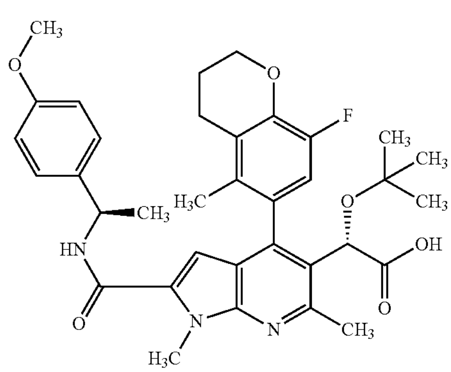 [SMILES: COc1ccc([C@@H](C)NC(=O)c2cc3c(-c4cc(F)c5c(c4C)CCCO5)c([C@H](OC(C)(C)C)C(=O)O)c(C)nc3n2C)cc1] | 617.71 | 618 |

TABLE 8-continued

| Example | Structure | MW | Observed Mass |
|---|---|---|---|
| 217 | 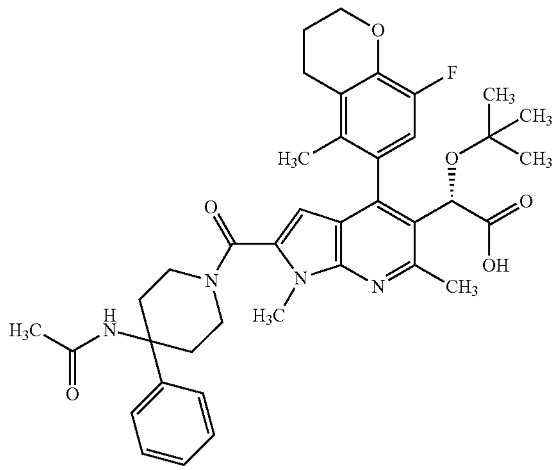 [SMILES: CC(=O)NC1(c2ccccc2)CCN(C(=O)c2cc3c(-c4cc(F)c5c(c4C)CCCO5)c([C@H](OC(C)(C)C)C(=O)O)c(C)nc3n2C)CC1] | 684.8 | 685 |
| 218 | 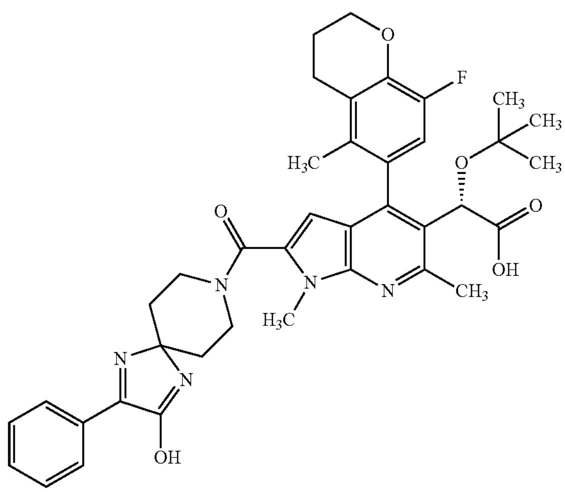 [SMILES: Cc1nc2c(cc(C(=O)N3CCC4(CC3)N=C(O)C(c3ccccc3)=N4)n2C)c(-c2cc(F)c3c(c2C)CCCO3)c1[C@H](OC(C)(C)C)C(=O)O] | 693.81 | 694 |
| 219 | 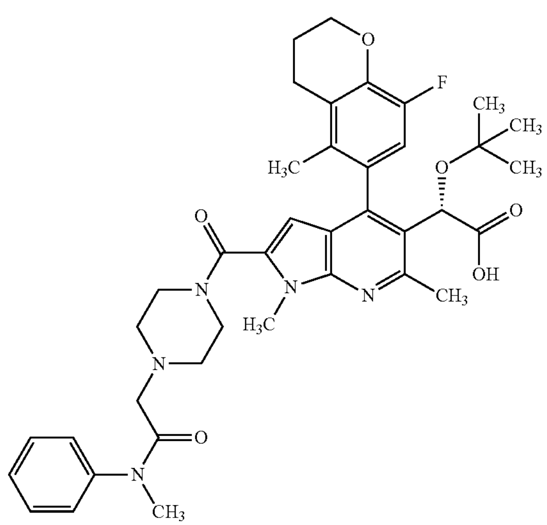 [SMILES: Cc1nc2c(cc(C(=O)N3CCN(CC(=O)N(C)c4ccccc4)CC3)n2C)c(-c2cc(F)c3c(c2C)CCCO3)c1[C@H](OC(C)(C)C)C(=O)O] | 699.81 | 700 |

TABLE 8-continued

| Example | Structure | MW | Observed Mass |
|---|---|---|---|
| 220 | 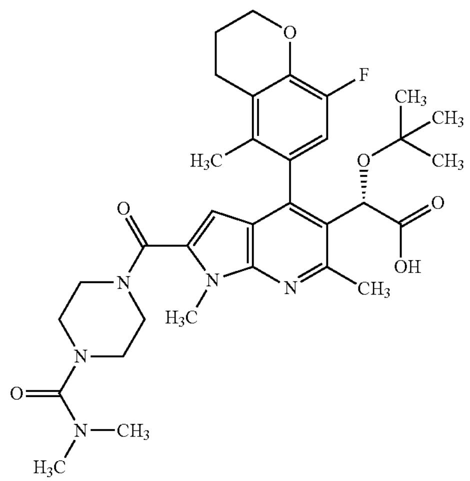 [SMILES: Cc1nc2c(cc(C(=O)N3CCN(C(=O)N(C)C)CC3)n2C)c(-c2cc(F)c3c(c2C)CCCO3)c1[C@H](OC(C)(C)C)C(=O)O] | 623.71 | 624 |
| 221 | 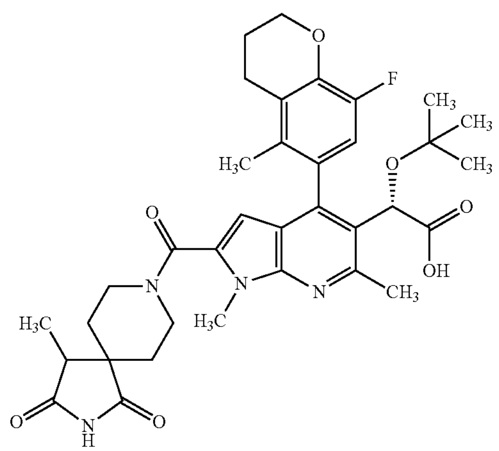 [SMILES: Cc1nc2c(cc(C(=O)N3CCC4(CC3)C(=O)NC(=O)C4C)n2C)c(-c2cc(F)c3c(c2C)CCCO3)c1[C@H](OC(C)(C)C)C(=O)O] | 649.71 | 650 |
| 222 | 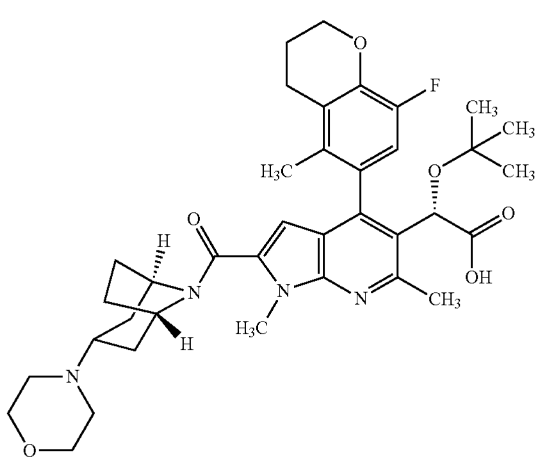 [SMILES: Cc1nc2c(cc(C(=O)N3[C@@H]4CC[C@H]3CC(N3CCOCC3)C4)n2C)c(-c2cc(F)c3c(c2C)CCCO3)c1[C@H](OC(C)(C)C)C(=O)O] | 662.79 | 663 |

TABLE 8-continued

| Example | Structure | MW | Observed Mass |
|---|---|---|---|
| 223 | 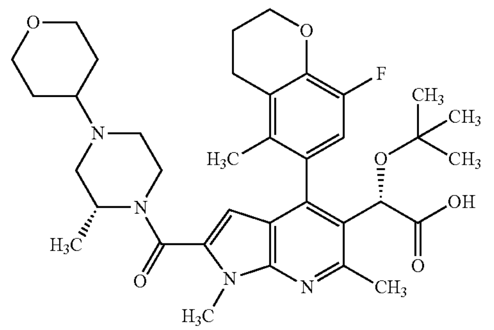 [SMILES: Cc1nc2c(cc(C(=O)N3CCN(C4CCOCC4)C[C@H]3C)n2C)c(-c2cc(F)c3c(c2C)CCCO3)c1[C@H](OC(C)(C)C)C(=O)O] | 650.78 | 651 |
| 224 | 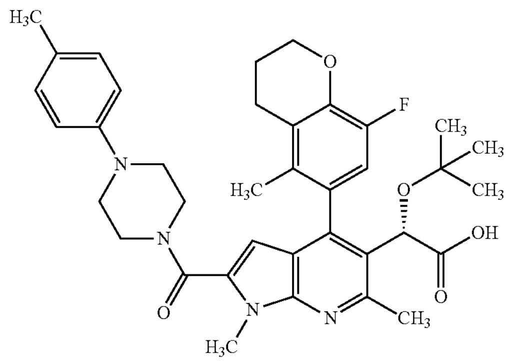 [SMILES: Cc1ccc(N2CCN(C(=O)c3cc4c(-c5cc(F)c6c(c5C)CCCO6)c([C@H](OC(C)(C)C)C(=O)O)c(C)nc4n3C)CC2)cc1] | 642.76 | 643 |
| 225 | 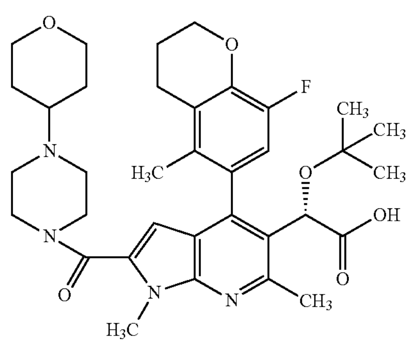 [SMILES: Cc1nc2c(cc(C(=O)N3CCN(C4CCOCC4)CC3)n2C)c(-c2cc(F)c3c(c2C)CCCO3)c1[C@H](OC(C)(C)C)C(=O)O] | 636.75 | 637 |
| 226 | 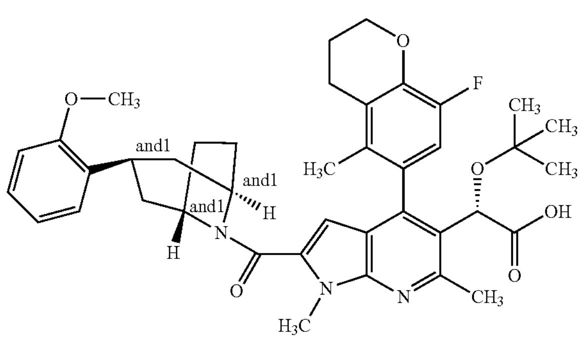 [SMILES: COc1ccccc1[C@H]1C[C@H]2CC[C@@H](C1)N2C(=O)c1cc2c(-c3cc(F)c4c(c3C)CCCO4)c([C@H](OC(C)(C)C)C(=O)O)c(C)nc2n1C] | 683.81 | 684 |

TABLE 8-continued

| Example | Structure | MW | Observed Mass |
|---|---|---|---|
| 227 | 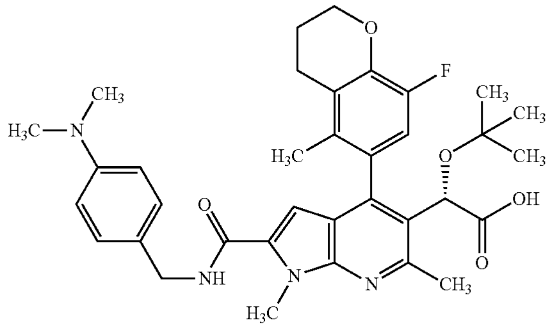 [SMILES: Cc1nc2c(cc(C(=O)NCc3ccc(N(C)C)cc3)n2C)c(-c2cc(F)c3c(c2C)CCCO3)c1[C@H](OC(C)(C)C)C(=O)O] | 616.72 | 617 |
| 228 | 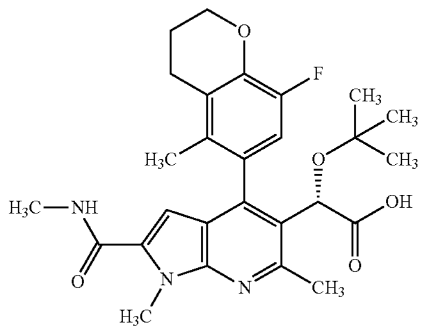 [SMILES: CNC(=O)c1cc2c(-c3cc(F)c4c(c3C)CCCO4)c([C@H](OC(C)(C)C)C(=O)O)c(C)nc2n1C] | 497.56 | 498 |
| 229 | 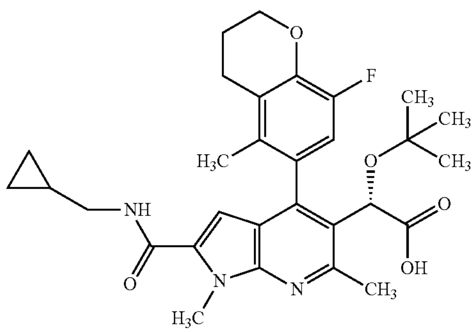 [SMILES: Cc1nc2c(cc(C(=O)NCC3CC3)n2C)c(-c2cc(F)c3c(c2C)CCCO3)c1[C@H](OC(C)(C)C)C(=O)O] | 537.62 | 538 |
| 230 | 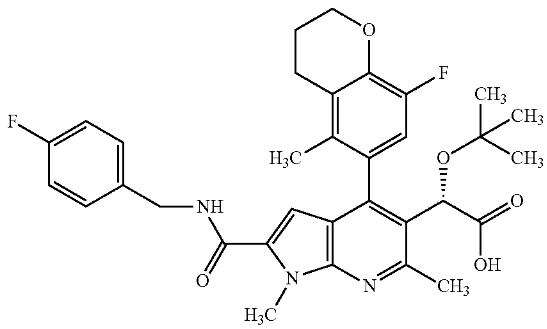 [SMILES: Cc1nc2c(cc(C(=O)NCc3ccc(F)cc3)n2C)c(-c2cc(F)c3c(c2C)CCCO3)c1[C@H](OC(C)(C)C)C(=O)O] | 591.64 | 592 |

TABLE 8-continued

| Example | Structure | MW | Observed Mass |
|---|---|---|---|
| 231 | 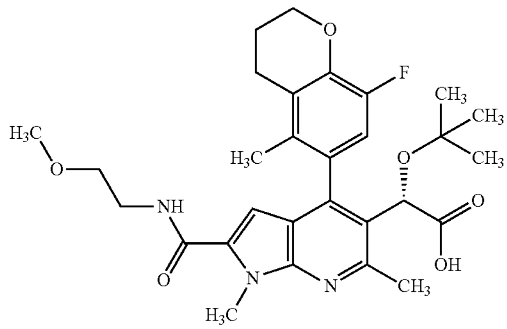 | 541.61 | 542 |
| 232 | 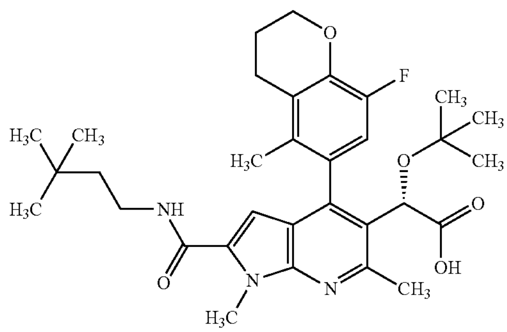 [SMILES: Cc1nc2c(cc(C(=O)NCCC(C)(C)C)n2C)c(-c2cc(F)c3c(c2C)CCCO3)c1[C@H](OC(C)(C)C)C(=O)O] | 567.69 | 568 |
| 233 | 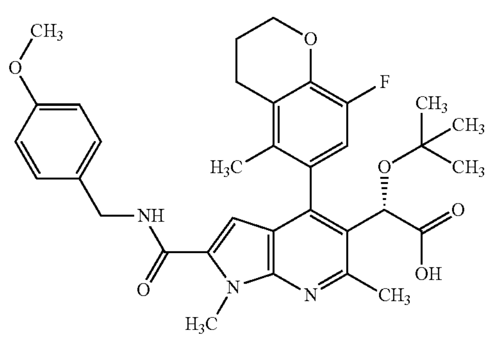 [SMILES: COc1ccc(CNC(=O)c2cc3c(-c4cc(F)c5c(c4C)CCCO5)c([C@H](OC(C)(C)C)C(=O)O)c(C)nc3n2C)cc1] | 603.68 | 604 |
| 234 | 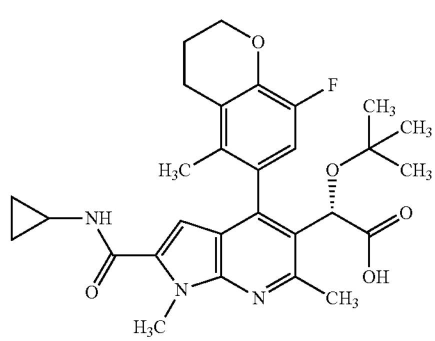 [SMILES: Cc1nc2c(cc(C(=O)NC3CC3)n2C)c(-c2cc(F)c3c(c2C)CCCO3)c1[C@H](OC(C)(C)C)C(=O)O] | 523.6 | 524 |

TABLE 8-continued
| Example | Structure | MW | Observed Mass |
|---------|-----------|-----|---------------|
| 235 | 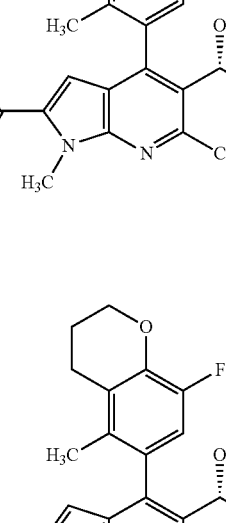 | 557.68 | 558 |
| 236 | 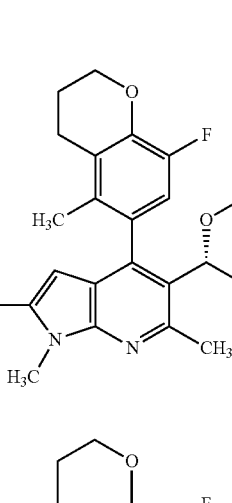 | 589.68 | 590 |
| 237 | 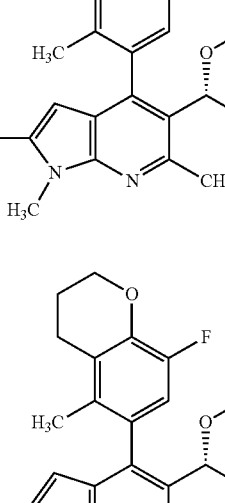 | 579.7 | 580 |
| 238 | 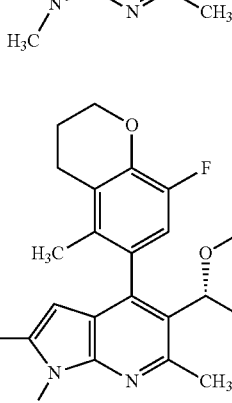 | 527.58 | 528 |

TABLE 8-continued

| Example | Structure | MW | Observed Mass |
|---|---|---|---|
| 239 | 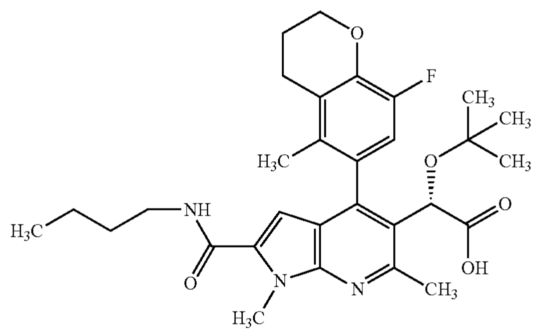 [SMILES: CCCCNC(=O)c1cc2c(-c3cc(F)c4c(c3C)CCCO4)c([C@H](OC(C)(C)C)C(=O)O)c(C)nc2n1C] | 539.64 | 540 |
| 240 | 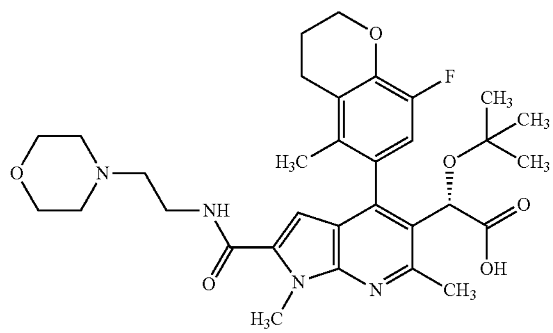 [SMILES: Cc1nc2c(cc(C(=O)NCCN3CCOCC3)n2C)c(-c2cc(F)c3c(c2C)CCCO3)c1[C@H](OC(C)(C)C)C(=O)O] | 596.69 | 597 |
| 241 | 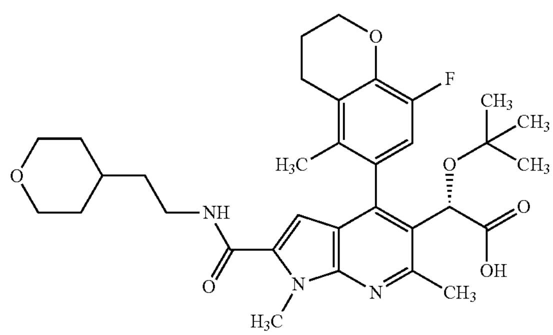 [SMILES: Cc1nc2c(cc(C(=O)NCCC3CCOCC3)n2C)c(-c2cc(F)c3c(c2C)CCCO3)c1[C@H](OC(C)(C)C)C(=O)O] | 595.7 | 596 |
| 242 | 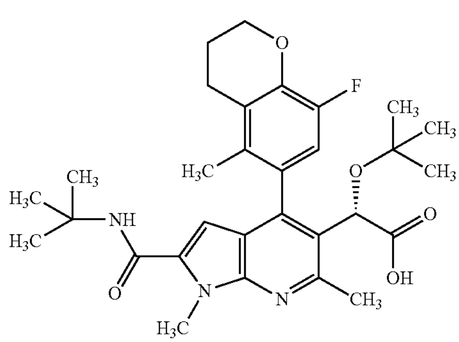 [SMILES: Cc1nc2c(cc(C(=O)NC(C)(C)C)n2C)c(-c2cc(F)c3c(c2C)CCCO3)c1[C@H](OC(C)(C)C)C(=O)O] | 539.64 | 540 |

TABLE 8-continued

| Example | Structure | MW | Observed Mass |
|---|---|---|---|
| 243 | 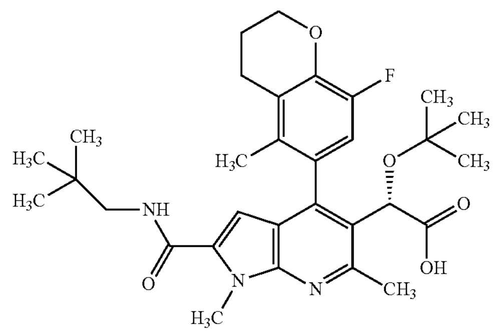 [SMILES: Cc1nc2c(cc(C(=O)NCC(C)(C)C)n2C)c(-c2cc(F)c3c(c2C)CCCO3)c1[C@H](OC(C)(C)C)C(=O)O] | 553.66 | 554 |
| 244 | 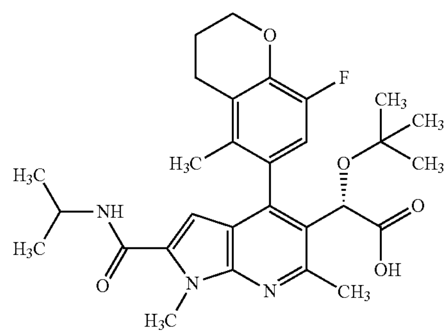 [SMILES: Cc1nc2c(cc(C(=O)NC(C)C)n2C)c(-c2cc(F)c3c(c2C)CCCO3)c1[C@H](OC(C)(C)C)C(=O)O] | 525.61 | 526 |
| 245 | 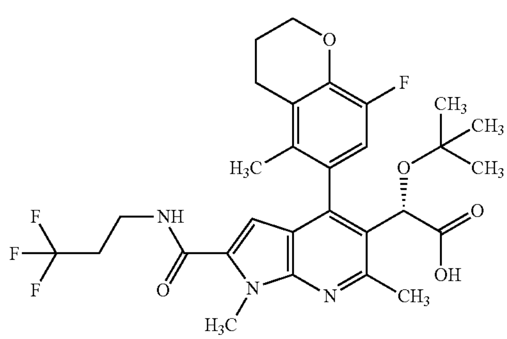 [SMILES: Cc1nc2c(cc(C(=O)NCCC(F)(F)F)n2C)c(-c2cc(F)c3c(c2C)CCCO3)c1[C@H](OC(C)(C)C)C(=O)O] | 579.58 | 580 |
| 246 | 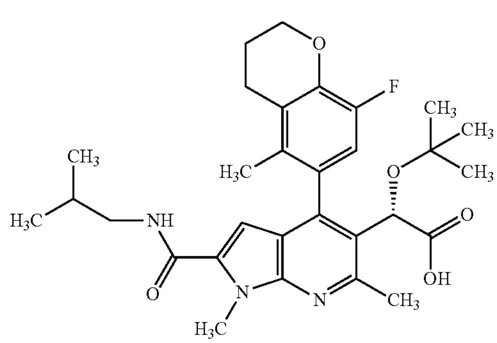 [SMILES: Cc1nc2c(cc(C(=O)NCC(C)C)n2C)c(-c2cc(F)c3c(c2C)CCCO3)c1[C@H](OC(C)(C)C)C(=O)O] | 539.64 | 540 |

TABLE 8-continued

| Example | Structure | MW | Observed Mass |
|---|---|---|---|
| 247 | 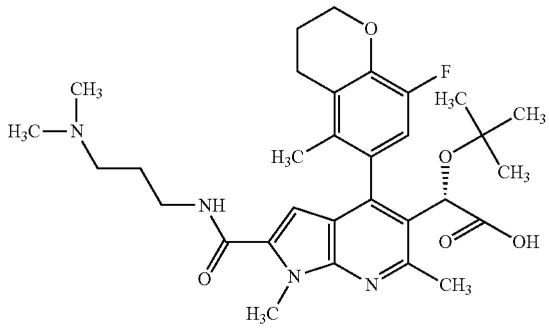 [SMILES: Cc1nc2c(cc(C(=O)NCCCN(C)C)n2C)c(-c2cc(F)c3c(c2C)CCCO3)c1[C@H](OC(C)(C)C)C(=O)O] | 568.68 | 569 |
| 248 | 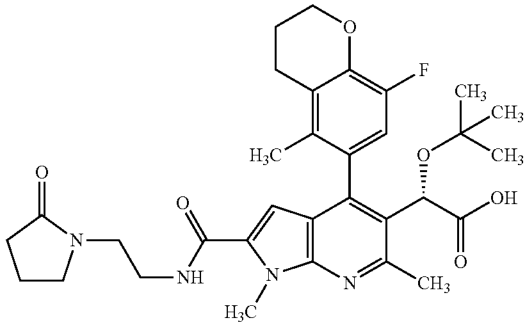 [SMILES: Cc1nc2c(cc(C(=O)NCCN3CCCC3=O)n2C)c(-c2cc(F)c3c(c2C)CCCO3)c1[C@H](OC(C)(C)C)C(=O)O] | 594.67 | 595 |
| 249 | 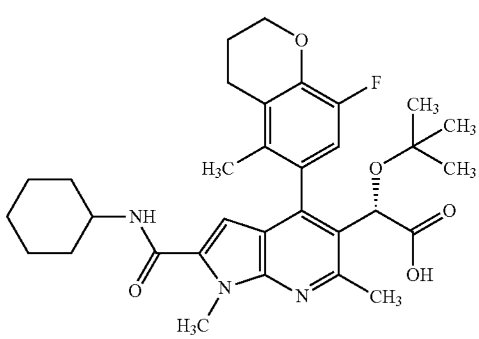 [SMILES: Cc1nc2c(cc(C(=O)NC3CCCCC3)n2C)c(-c2cc(F)c3c(c2C)CCCO3)c1[C@H](OC(C)(C)C)C(=O)O] | 565.68 | 566 |
| 250 | 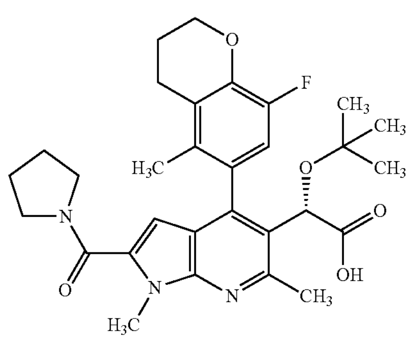 [SMILES: Cc1nc2c(cc(C(=O)N3CCCC3)n2C)c(-c2cc(F)c3c(c2C)CCCO3)c1[C@H](OC(C)(C)C)C(=O)O] | 537.62 | 538 |

TABLE 8-continued

| Example | Structure | MW | Observed Mass |
|---------|-----------|------|---------------|
| 251 | 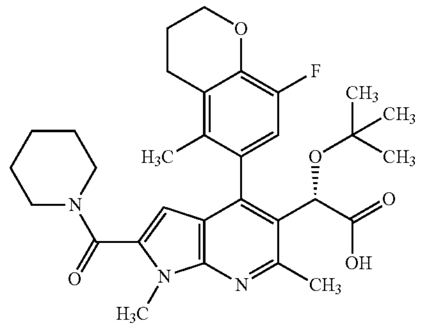 [SMILES: Cc1nc2c(cc(C(=O)N3CCCCC3)n2C)c(-c2cc(F)c3c(c2C)CCCO3)c1[C@H](OC(C)(C)C)C(=O)O] | 551.65 | 552 |
| 252 | 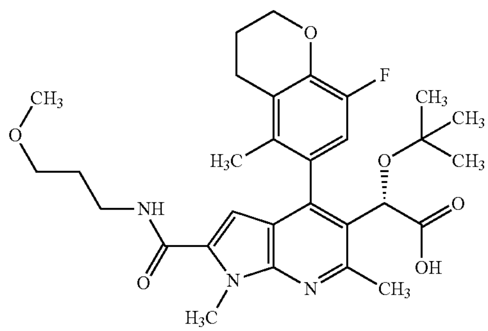 [SMILES: COCCCNC(=O)c1cc2c(-c3cc(F)c4c(c3C)CCCO4)c([C@H](OC(C)(C)C)C(=O)O)c(C)nc2n1C] | 555.64 | 556 |
| 253 | 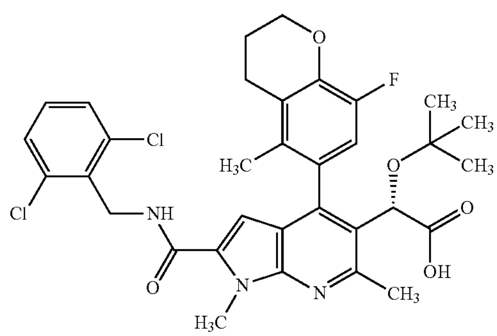 [SMILES: Cc1nc2c(cc(C(=O)NCc3c(Cl)cccc3Cl)n2C)c(-c2cc(F)c3c(c2C)CCCO3)c1[C@H](OC(C)(C)C)C(=O)O] | 642.19 | 643 |
| 254 | 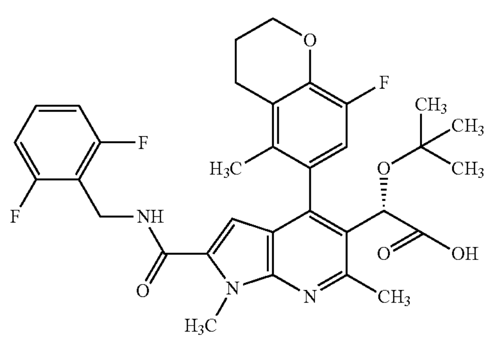 [SMILES: Cc1nc2c(cc(C(=O)NCc3c(F)cccc3F)n2C)c(-c2cc(F)c3c(c2C)CCCO3)c1[C@H](OC(C)(C)C)C(=O)O] | 609.64 | 610 |

TABLE 8-continued

| Example | Structure | MW | Observed Mass |
|---|---|---|---|
| 255 | 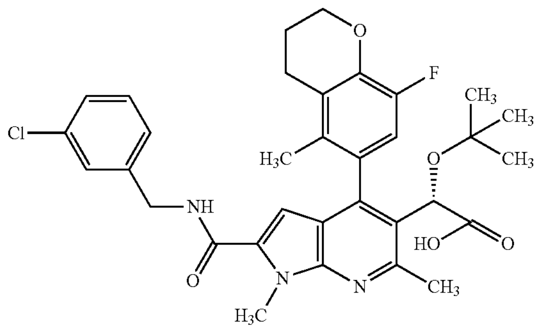 [SMILES: Cc1nc2c(cc(C(=O)NCc3cccc(Cl)c3)n2C)c(-c2cc(F)c3c(c2C)CCCO3)c1[C@H](OC(C)(C)C)C(=O)O] | 608.1 | 609 |
| 256 | 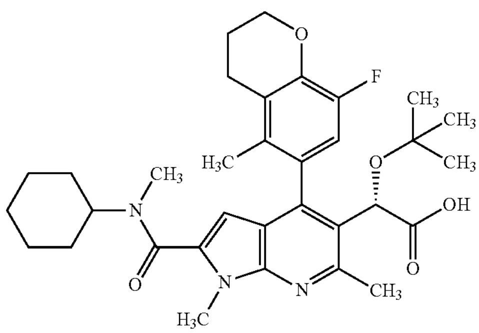 [SMILES: Cc1nc2c(cc(C(=O)N(C)C3CCCCC3)n2C)c(-c2cc(F)c3c(c2C)CCCO3)c1[C@H](OC(C)(C)C)C(=O)O] | 579.7 | 580 |
| 257 | 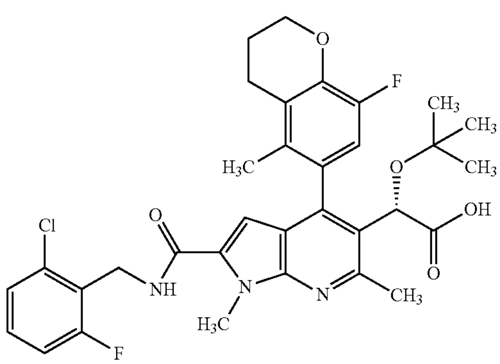 [SMILES: Cc1nc2c(cc(C(=O)NCc3c(F)cccc3Cl)n2C)c(-c2cc(F)c3c(c2C)CCCO3)c1[C@H](OC(C)(C)C)C(=O)O] | 626.09 | 627 |
| 258 | 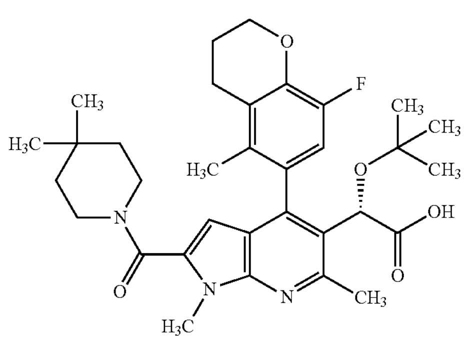 [SMILES: Cc1nc2c(cc(C(=O)N3CCC(C)(C)CC3)n2C)c(-c2cc(F)c3c(c2C)CCCO3)c1[C@H](OC(C)(C)C)C(=O)O] | 579.7 | 580 |

TABLE 8-continued
| Example | Structure | MW | Observed Mass |
|---|---|---|---|
| 259 | 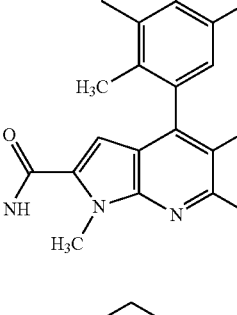 | 593.73 | 594 |
| 260 | 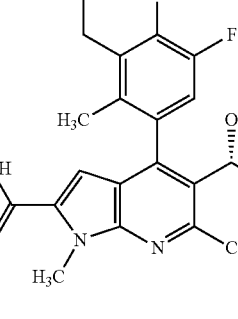 | 617.66 | 618 |
| 261 | 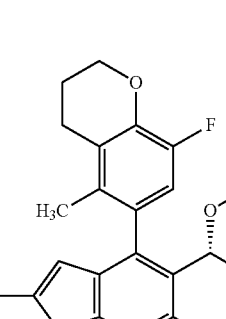 | 593.73 | 594 |
| 262 | 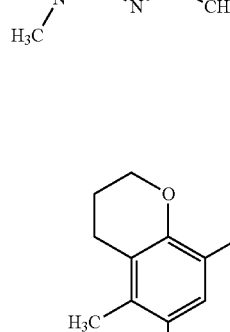 | 588.67 | 589 |

TABLE 8-continued

| Example | Structure | MW | Observed Mass |
|---|---|---|---|
| 263 | 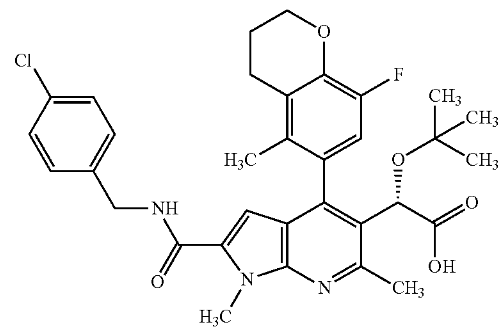 [SMILES: Cc1nc2c(cc(C(=O)NCc3ccc(Cl)cc3)n2C)c(-c2cc(F)c3c(c2C)CCCO3)c1[C@H](OC(C)(C)C)C(=O)O] | 607.23 | 608 |
| 264 | 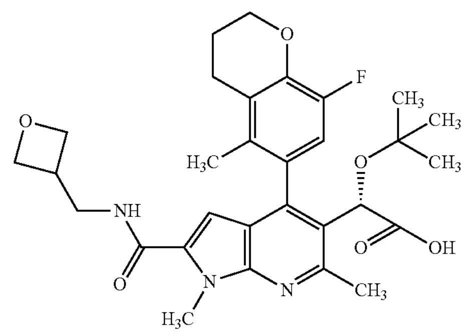 [SMILES: Cc1nc2c(cc(C(=O)NCC3COC3)n2C)c(-c2cc(F)c3c(c2C)CCCO3)c1[C@H](OC(C)(C)C)C(=O)O] | 553.62 | 554 |
| 265 | 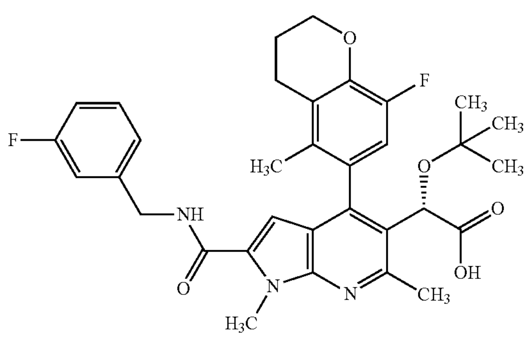 [SMILES: Cc1nc2c(cc(C(=O)NCc3cccc(F)c3)n2C)c(-c2cc(F)c3c(c2C)CCCO3)c1[C@H](OC(C)(C)C)C(=O)O] | 591.64 | 592 |
| 266 | 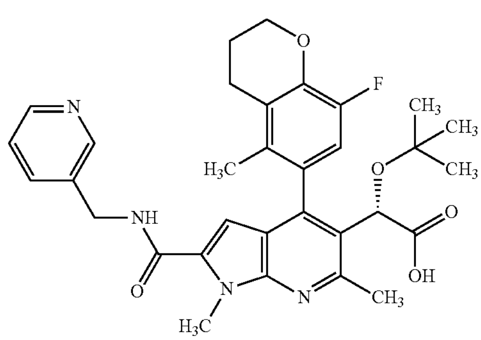 | 574.64 | 575 |

TABLE 8-continued

| Example | Structure | MW | Observed Mass |
|---|---|---|---|
| 267 | 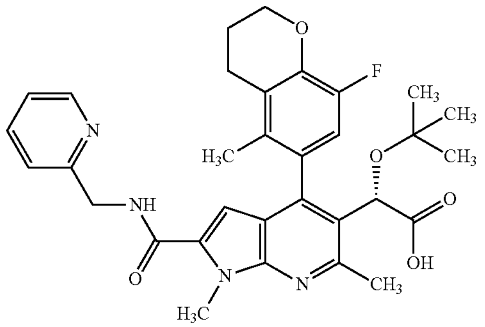 [SMILES: Cc1nc2c(cc(C(=O)NCc3ccccn3)n2C)c(-c2cc(F)c3c(c2C)CCCO3)c1[C@H](OC(C)(C)C)C(=O)O] | 574.64 | 575 |
| 268 | 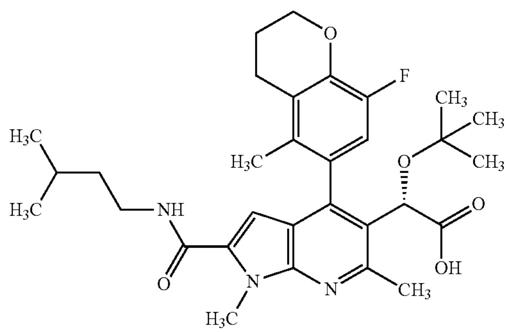 [SMILES: Cc1nc2c(cc(C(=O)NCCC(C)C)n2C)c(-c2cc(F)c3c(c2C)CCCO3)c1[C@H](OC(C)(C)C)C(=O)O] | 553.66 | 554 |
| 269 | 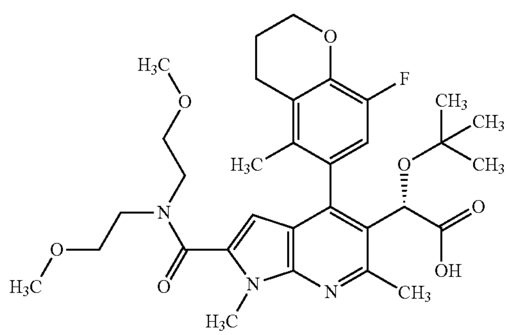 [SMILES: COCCN(CCOC)C(=O)c1cc2c(-c3cc(F)c4c(c3C)CCCO4)c([C@H](OC(C)(C)C)C(=O)O)c(C)nc2n1C] | 599.69 | 600 |
| 270 | 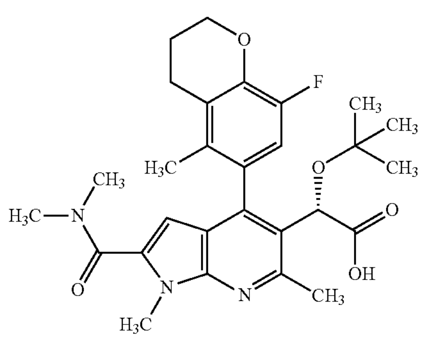 [SMILES: Cc1nc2c(cc(C(=O)N(C)C)n2C)c(-c2cc(F)c3c(c2C)CCCO3)c1[C@H](OC(C)(C)C)C(=O)O] | 511.59 | 512 |

TABLE 8-continued

| Example | Structure | MW | Observed Mass |
|---------|-----------|-----|---------------|
| 271 | 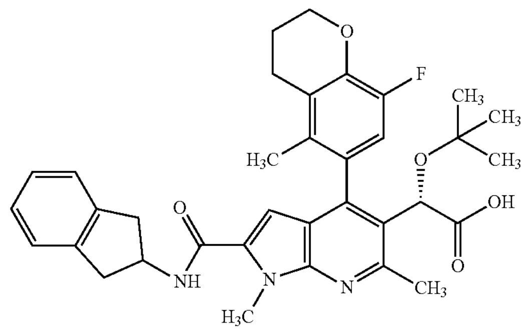 [SMILES: Cc1nc2c(cc(C(=O)NC3Cc4ccccc4C3)n2C)c(-c2cc(F)c3c(c2C)CCCO3)c1[C@H](OC(C)(C)C)C(=O)O] | 599.69 | 600 |
| 272 | 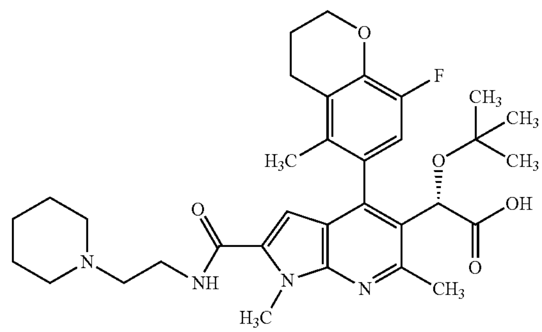 [SMILES: Cc1nc2c(cc(C(=O)NCCN3CCCCC3)n2C)c(-c2cc(F)c3c(c2C)CCCO3)c1[C@H](OC(C)(C)C)C(=O)O] | 594.72 | 595 |
| 273 | 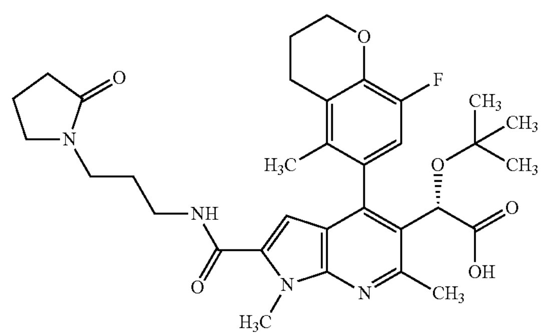 [SMILES: Cc1nc2c(cc(C(=O)NCCCN3CCCC3=O)n2C)c(-c2cc(F)c3c(c2C)CCCO3)c1[C@H](OC(C)(C)C)C(=O)O] | 608.7 | 609 |
| 274 | 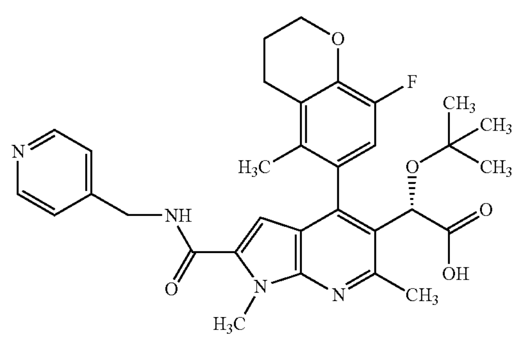 [SMILES: Cc1nc2c(cc(C(=O)NCc3ccncc3)n2C)c(-c2cc(F)c3c(c2C)CCCO3)c1[C@H](OC(C)(C)C)C(=O)O] | 574.64 | 575 |

TABLE 8-continued
| Example | Structure | MW | Observed Mass |
|---|---|---|---|
| 275 | 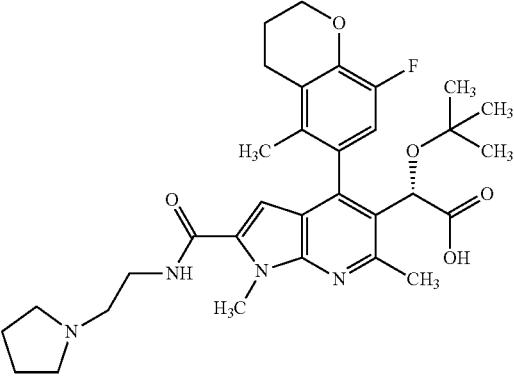 [SMILES: Cc1nc2c(cc(C(=O)NCCN3CCCC3)n2C)c(-c2cc(F)c3c(c2C)CCCO3)c1[C@H](OC(C)(C)C)C(=O)O] | 580.69 | 581 |
| 276 | 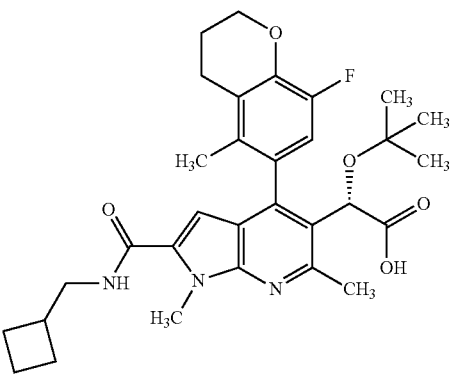 [SMILES: Cc1nc2c(cc(C(=O)NCC3CCC3)n2C)c(-c2cc(F)c3c(c2C)CCCO3)c1[C@H](OC(C)(C)C)C(=O)O] | 551.65 | 552 |
| 277 | 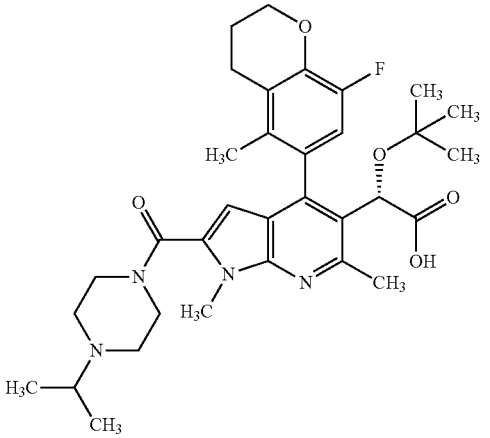 [SMILES: Cc1nc2c(cc(C(=O)N3CCN(C(C)C)CC3)n2C)c(-c2cc(F)c3c(c2C)CCCO3)c1[C@H](OC(C)(C)C)C(=O)O] | 594.72 | 595 |

TABLE 8-continued

| Example | Structure | MW | Observed Mass |
|---------|-----------|------|---------------|
| 278 | 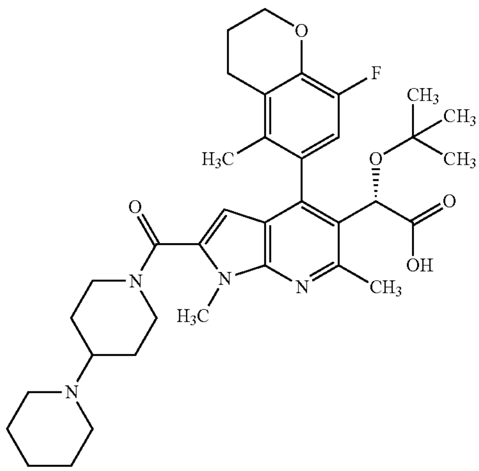 [SMILES: Cc1nc2c(cc(C(=O)N3CCC(N4CCCCC4)CC3)n2C)c(-c2cc(F)c3c(c2C)CCCO3)c1[C@H](OC(C)(C)C)C(=O)O] | 634.78 | 635 |
| 279 | 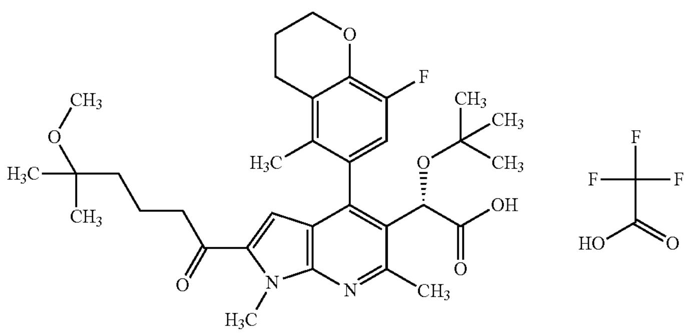 [SMILES: COC(C)(C)CCCC(=O)c1cc2c(-c3cc(F)c4c(c3C)CCCO4)c([C@H](OC(C)(C)C)C(=O)O)c(C)nc2n1C ; O=C(O)C(F)(F)F] | 583.69 | 584 |
| 280 | 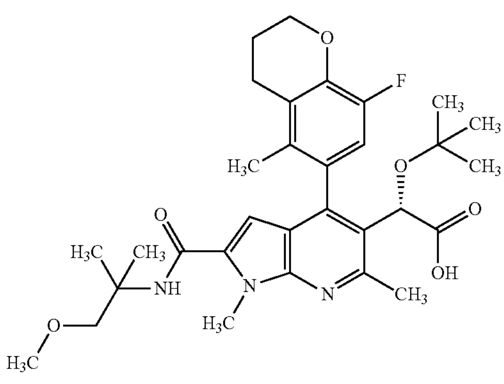 [SMILES: COCC(C)(C)NC(=O)c1cc2c(-c3cc(F)c4c(c3C)CCCO4)c([C@H](OC(C)(C)C)C(=O)O)c(C)nc2n1C] | 569.66 | 570 |

Example 281

(2S)(M)-2-(tert-butoxy)-2-(-4-(8-fluoro-5-methyl-chroman-6-yl)-1,6-dimethyl-2-(4-phenylpiperidine-1-carbonothioyl)-1H-pyrrolo[2,3-b]pyridin-5-yl)acetic acid

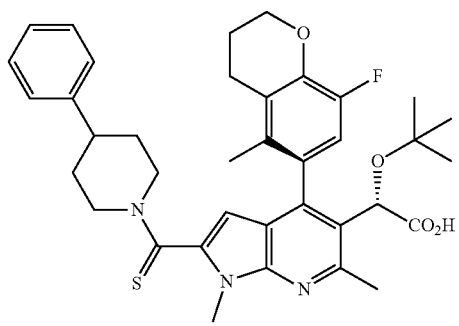

Step A (2S)(M)-Methyl-2-(tert-butoxy)-2-(-4-(8-fluoro-5-methylchroman-6-yl)-1,6-dimethyl-2-(4-phenylpiperidine-1-carbonothioyl)-1H-pyrrolo[2,3-b]pyridin-5-yl)acetic acid A solution of (2S)(M)-Methyl 2-(tert-butoxy)-2-(-4-(8-fluoro-5-methylchroman-6-yl)-1,6-dimethyl-2-(4-phenylpiperidine-1-carbonyl)-1H-pyrrolo[2,3-b]pyridin-5-yl)acetate (67 mg, 0.099 mmol) in Toluene (2 mL) was treated with Lawesson's reagent (20.68 mg, 0.050 mmol) and heated to 110° C. in a sealed vessel. After 3 h, the reaction mixture was concentrated in vacuo and purified by silica gel chromatography to afford the title compound (41.2 mg, 0.062 mmol, 62.5% yield) as a yellow foam.

Step B (2S)(M)-2-(tert-butoxy)-2-(-4-(8-fluoro-5-methyl-chroman-6-yl)-1,6-dimethyl-2-(4-phenylpiperidine-1-carbonothioyl)-1H-pyrrolo[2,3-b]pyridin-5-yl)acetic acid

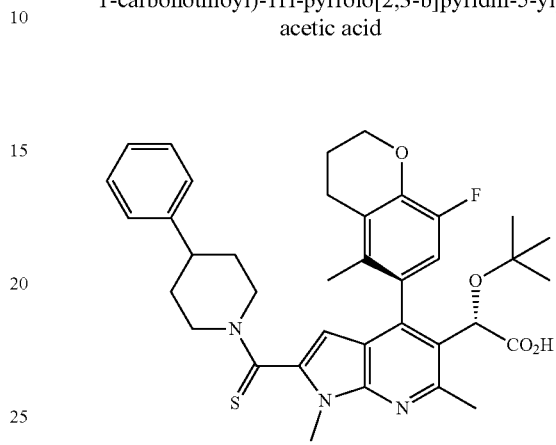

A solution of (2S)(M)-methyl 2-(tert-butoxy)-2-(-4-(8-fluoro-5-methylchroman-6-yl)-1,6-dimethyl-2-(4-phenylpiperidine-1-carbonothioyl)-1H-pyrrolo[2,3-b]pyridin-5-yl)acetate (39 mg, 0.059 mmol) in Tetrahydrofuran (THF) (0.5 mL)/Methanol (0.500 mL)/Water (0.25 mL) was treated with lithium hydroxide, monohydrate (24.9 mg, 0.593 mmol) and heated to 65° C. After 3 h, the reaction mixture was purified by reverse phase HPLC to afford the title compound (26.9 mg, 0.035 mmol, 59.3% yield) as a yellow solid.

General Scheme 12

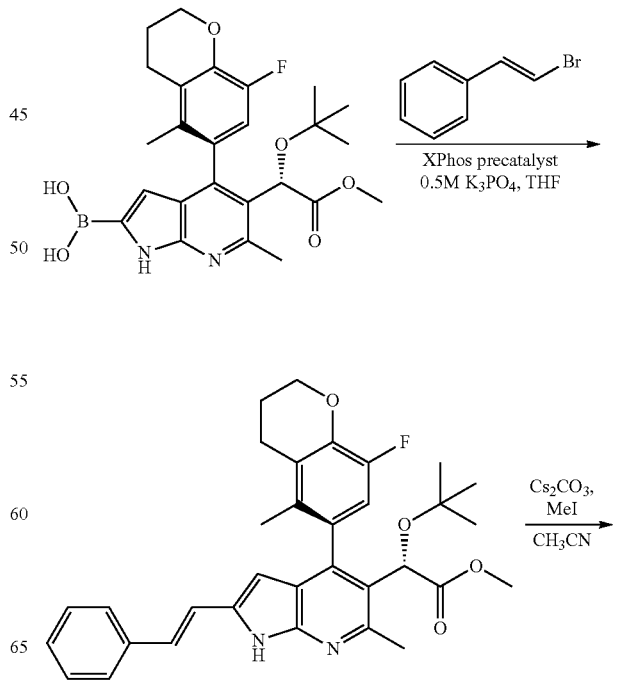

215
-continued

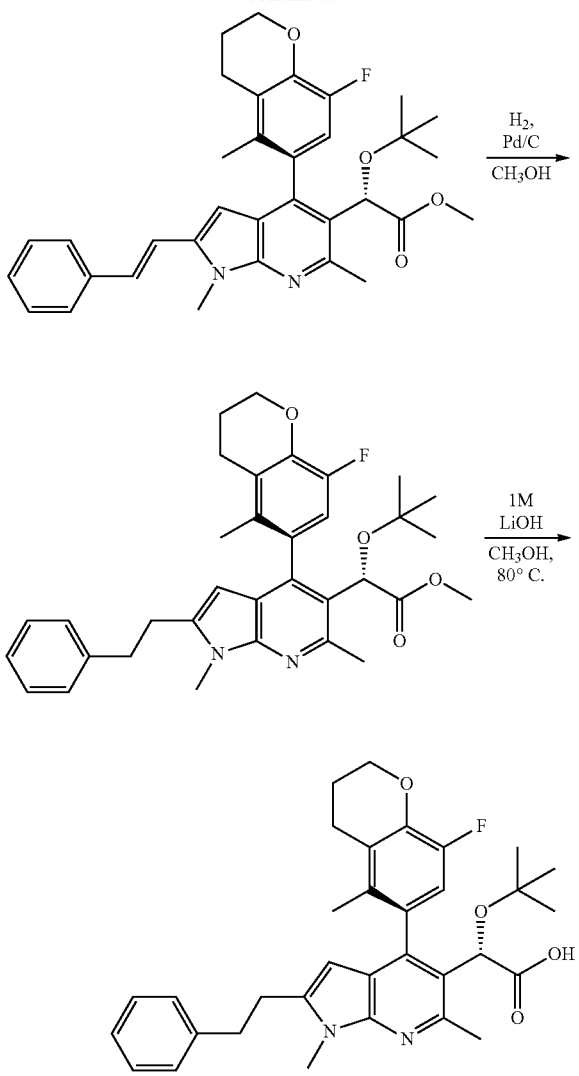

Example 282

(2S)(M)-2-(tert-butoxy)-2-(-4-(8-fluoro-5-methyl-chroman-6-yl)-1,6-dimethyl-2-phenethyl-1H-pyrrolo[2,3-b]pyridin-5-yl)acetic acid

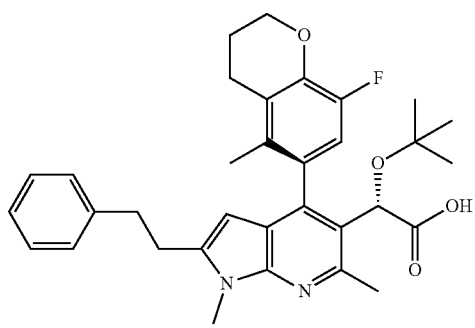

216

Step A (2S) (M)-Methyl 2-(tert-butoxy)-2-(-4-(8-fluoro-5-methylchroman-6-yl)-6-methyl-2-((E)-styryl)-1H-pyrrolo[2,3-b]pyridin-5-yl)acetate

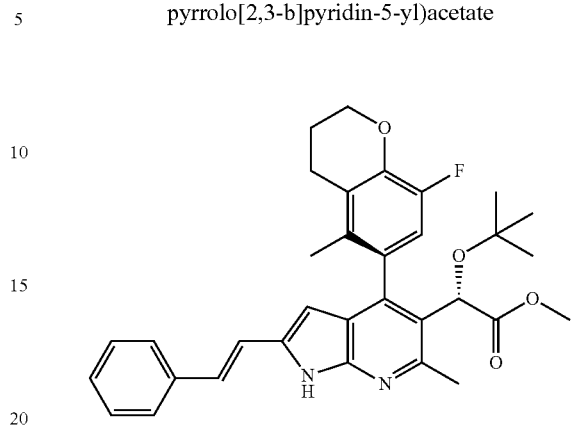

A solution of (2S)(M)-(-5-((S)-1-(tert-butoxy)-2-methoxy-2-oxoethyl)-4-(8-fluoro-5-methylchroman-6-yl)-6-methyl-1H-pyrrolo[2,3-b]pyridin-2-yl)boronic acid (60.3 mg, 0.106 mmol) and 1M (E)-(2-bromovinyl)benzene/tetrahydrofuran (0.11 mL, 0.117 mmol), and 0.5 M tripotassium phosphate (0.43 mL, 0.215 mmol) in THF (1.0 mL) was degassed with $N_2$ for 5 min. Chloro(2-dicyclohexylphosphino-2',4',6'-triisopropyl-1,1'-biphenyl)[2-(2-aminoethyl)phenyl)]palladium(II) (3.5 mg, 4.45 μmol) was added and the reaction mixture stirred at ambient temperature for 2 h. The reaction mixture was partitioned between EtOAc and water and the organics washed with brine, dried ($Na_2SO_4$), filtered and concentrated in vacuo. The residue was purified by silica gel chromatography (0-100% EtOAc-hexanes) to afford the title compound (50.5 mg, 0.093 mmol, 87.7% yield) as a mixture of E/Z isomers. $^1$H NMR (400 MHz, CHLOROFORM-d) δ=10.66 (br. s., 1H), 7.45 (d, J=7.4 Hz, 2H), 7.34 (t, J=7.7 Hz, 3H), 7.02 (s, 1H), 6.82 (d, J=11.2 Hz, 1H), 6.03 (s, 1H), 5.17 (s, 1H), 4.36-4.29 (m, 2H), 3.60 (s, 3H), 2.82 (s, 3H), 2.80-2.74 (m, 2H), 2.22-2.14 (m, 2H), 1.88 (s, 3H), 1.15 (s, 9H). LC/MS (m/z) ES$^+$=543.33 (M+1).

Step B (2S) (M)-Methyl 2-(tert-butoxy)-2-(-4-(8-fluoro-5-methylchroman-6-yl)-1,6-dimethyl-2-((E)-styryl)-1H-pyrrolo[2,3-b]pyridin-5-yl)acetate

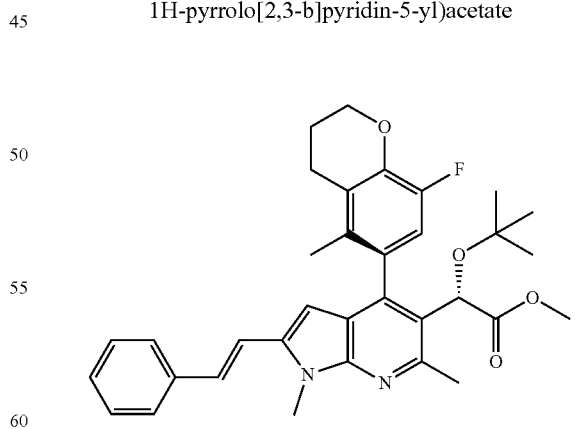

A solution of (2S)(M)-methyl 2-(tert-butoxy)-2-(4-(8-fluoro-5-methylchroman-6-yl)-6-methyl-2-((E)-styryl)-1H-pyrrolo[2,3-b]pyridin-5-yl)acetate (50.5 mg, 0.093 mmol) in Acetonitrile (0.652 mL) was treated with cesium carbonate (91 mg, 0.279 mmol) and iodomethane (0.279 mL, 0.084 mmol, 0.3 M in $CH_3CN$) and heated to 70° C. After 30 min, the reaction mixture was cooled to ambient temperature, diluted with dichloromethane, and extracted. The combined organics were washed with brine, dried over sodium sulfate and concentrated in vacuo to afford the title compound. 49.5 mg (86% yield). $^1$H NMR (400 MHz, CHLOROFORM-d) δ=$^1$H NMR (400 MHz, CHLOROFORM-d) d=7.49 (d, J=7.4 Hz, 2H), 7.36 (t, J=7.5 Hz, 2H), 7.29 (d, J=7.2 Hz, 1H), 7.11 (d, J=12.1 Hz, 1H), 6.76 (d, J=11.3 Hz, 1H), 6.21 (s, 1H), 5.30 (s, 1H), 5.14 (s, 1H), 4.33 (t, J=5.2 Hz, 2H), 4.11 (br. s., 2H), 3.61 (s, 3H), 2.95 (s, 2H), 2.76 (t, J=6.4 Hz, 2H), 2.23-2.15 (m, 2H), 1.83 (s, 3H), 1.12 (s, 9H). LC/MS (m/z) ES$^+$=557.59 (M+1).

Step C (2S)(M)-Methyl 2-(tert-butoxy)-2-(-4-(8-fluoro-5-methylchroman-6-yl)-1,6-dimethyl-2-phenethyl-1H-pyrrolo[2,3-b]pyridin-5-yl)acetate

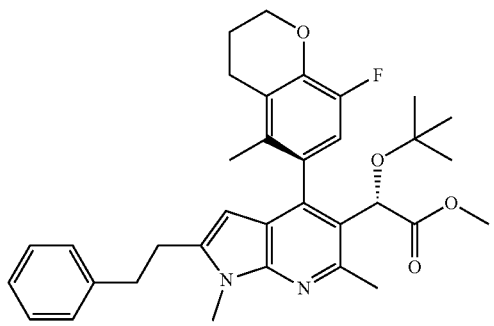

A solution of (2S)(M)-Methyl 2-(tert-butoxy)-2-((R)-4-(8-fluoro-5-methylchroman-6-yl)-1,6-dimethyl-2-((E)-styryl)-1H-pyrrolo[2,3-b]pyridin-5-yl)acetate (49.5 mg, 0.089 mmol) in MeOH (1 mL) was evacuated under vacuum and backfilled with nitrogen three times and treated with Palladium on carbon (34.1 mg, 0.320 mmol) and placed under an atmosphere of H$_2$ (1 atm). After 1 h, the reaction was filtered through a pad of Celite, washed with dichloromethane and methanol, concentrated under reduced pressure. The residue was purified by silica gel chromatography (0-20% methanol/dichloromethane gradient elution) to afford the title compound (37.4 mg, 0.067 mmol, 75.3% yield) as a yellow solid.

$^1$H NMR (400 MHz, CHLOROFORM-d) δ=7.32-7.27 (m, 2H), 7.24-7.15 (m, 3H), 6.75 (d, J=12.0 Hz, 1H), 5.65 (s, 1H), 5.13 (s, 1H), 4.31 (t, J=5.2 Hz, 2H), 3.75 (s, 3H), 3.58 (s, 3H), 2.99-2.95 (m, 4H), 2.80 (s, 3H), 2.77-2.71 (m, 2H), 2.21-2.12 (m, 2H), 2.07 (d, J=4.0 Hz, 1H), 1.79 (s, 3H), 1.12 (s, 9H). LC/MS (m/z) ES$^+$=559.31 (M+1).

Step D (S)(M)-2-(tert-Butoxy)-2-(-4-(8-fluoro-5-methyl-chroman-6-yl)-1,6-dimethyl-2-phenethyl-1H-pyrrolo[2,3-b]pyridin-5-yl)acetic acid

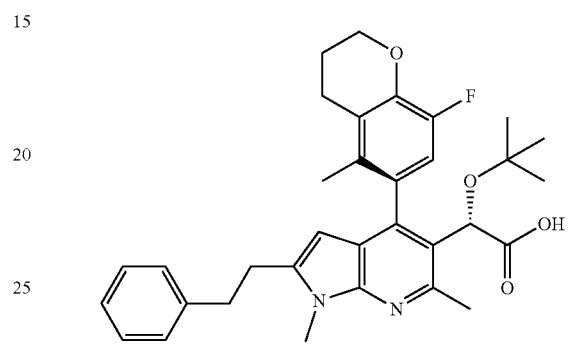

A solution of (2S)(M)-methyl 2-(tert-butoxy)-2-(4-(8-fluoro-5-methylchroman-6-yl)-1,6-dimethyl-2-phenethyl-1H-pyrrolo[2,3-b]pyridin-5-yl)acetate (37.4 mg, 0.067 mmol) in methanol (5.0 mL) was treated with lithium hydroxide (0.669 mL, 0.669 mmol) and heated to 80° C. After 18 h, the reaction mixture was cooled to ambient temperature and poured into 1M HCl. The solution was extracted with dichloromethane, dried over sodium sulfate and concentrated in vacuo. The residue was purified by reverse phase HPLC to afford the title compound (32.2 mg, 0.059 mmol, 88.1% yield). $^1$H NMR (400 MHz, CHLOROFORM-d) δ=7.30-7.24 (m, 2H), 7.22-7.13 (m, 3H), 6.78 (d, J=11.3 Hz, 1H), 5.68 (s, 1H), 5.20 (s, 1H), 4.28 (t, J=6.0 Hz, 2H), 3.74 (s, 3H), 2.96 (s, 4H), 2.77-2.66 (m, 5H), 2.18-2.08 (m, 2H), 1.87 (s, 3H), 1.10 (s, 9H). LC/MS (m/z) ES$^+$=545.33 (M+1).

Compounds in Table 9 (examples 283-287) were synthesized using the procedure described above with the appropriate vinyl bromide.

TABLE 9

| Example | Structure | MW | Observed Mass |
|---|---|---|---|
| 283 | 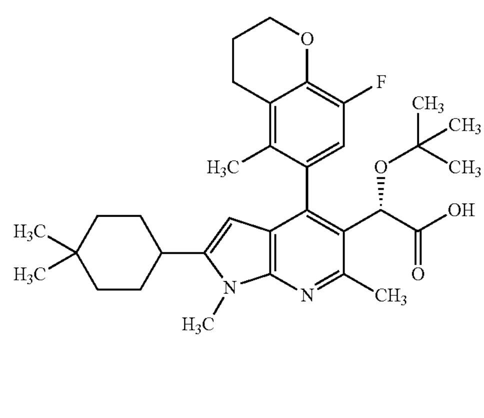 [SMILES: Cc1nc2c(cc(C3CCC(C)(C)CC3)n2C)c(-c2cc(F)c3c(c2C)CCCO3)c1[C@H](OC(C)(C)C)C(=O)O] | 550.7 | 551 |

TABLE 9-continued

| Example | Structure | MW | Observed Mass |
|---|---|---|---|
| 284 | 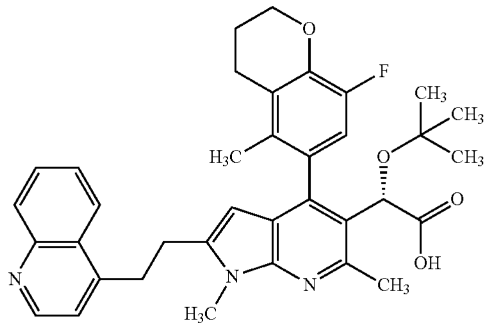 [SMILES: Cc1nc2c(cc(CCc3ccnc4ccccc34)n2C)c(-c2cc(F)c3c(c2C)CCCO3)c1[C@H](OC(C)(C)C)C(=O)O] | 595.7 | 596 |
| 285 | 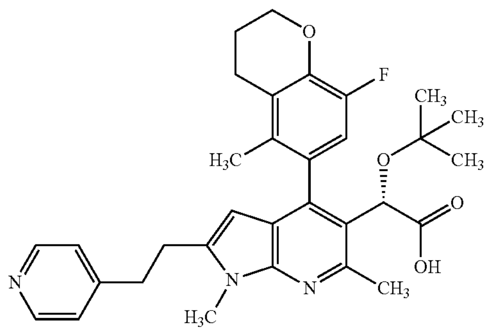 [SMILES: Cc1nc2c(cc(CCc3ccncc3)n2C)c(-c2cc(F)c3c(c2C)CCCO3)c1[C@H](OC(C)(C)C)C(=O)O] | 545.64 | 546 |
| 286 | 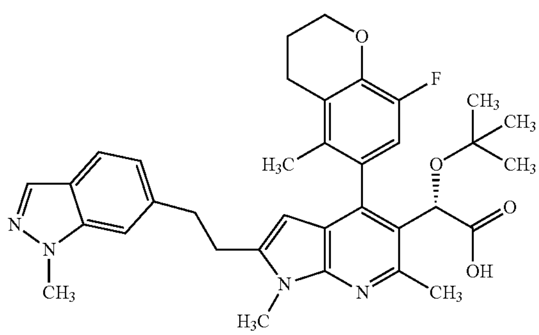 [SMILES: Cc1nc2c(cc(CCc3ccc4cnn(C)c4c3)n2C)c(-c2cc(F)c3c(c2C)CCCO3)c1[C@H](OC(C)(C)C)C(=O)O] | 598.71 | 599 |
| 287 | 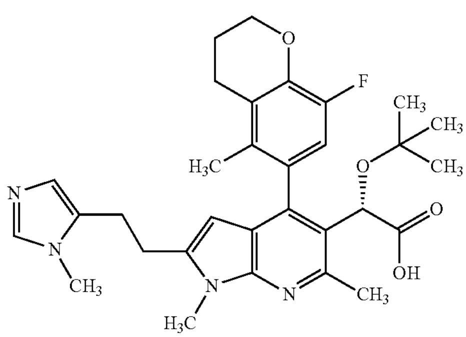 [SMILES: Cc1nc2c(cc(CCc3cncn3C)n2C)c(-c2cc(F)c3c(c2C)CCCO3)c1[C@H](OC(C)(C)C)C(=O)O] | 662.67 | 663 |

General Scheme 13

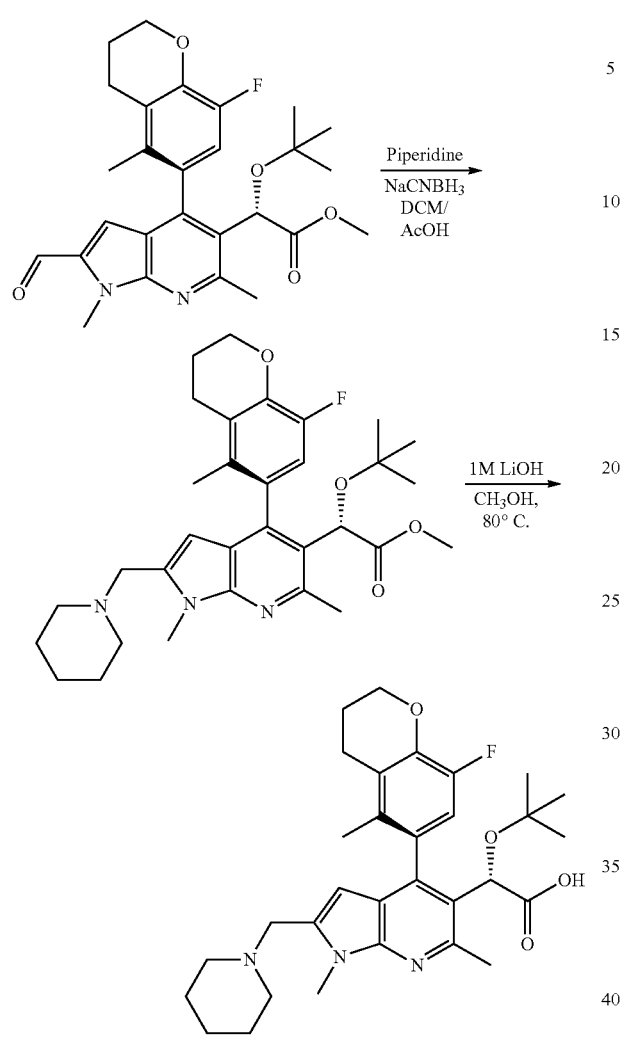

Example 288

(2S)(M)-2-(tert-butoxy)-2-(-4-(8-fluoro-5-methyl-chroman-6-yl)-1,6-dimethyl-2-(piperidin-1-ylmethyl)-1H-pyrrolo[2,3-b]pyridin-5-yl)acetic acid

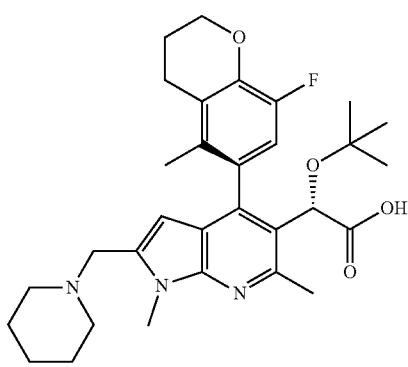

Step A (2S)(M)-methyl 2-(tert-butoxy)-2-(-4-(8-fluoro-5-methylchroman-6-yl)-1,6-dimethyl-2-(piperidin-1-ylmethyl)-1H-pyrrolo[2,3-b]pyridin-5-yl)acetate

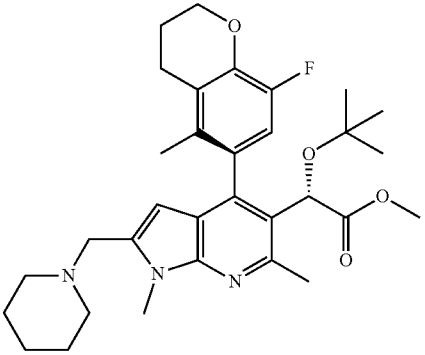

A solution of (2S)(M)-methyl 2-(tert-butoxy)-2-(-4-(8-fluoro-5-methylchroman-6-yl)-2-formyl-1,6-dimethyl-1H-pyrrolo[2,3-b]pyridin-5-yl)acetate (12 mg, 0.024 mmol) in DCM (0.2 mL) was treated with piperidine (0.01 mL, 0.10 mmol) and AcOH 0.01 mL, 0.175 mmol). After 2 h, the reaction mixture was diluted with DCM and washed with sat. aq. NaHCO$_3$. The organic layer was washed with brine, dried (Na$_2$SO$_4$), filtered and concentrated in vacuo to afford the title compound. LC/MS (m/z) ES$^+$=552 (M+1).

Step B (2S)(M)-2-(tert-butoxy)-2-(-4-(8-fluoro-5-methyl-chroman-6-yl)-1,6-dimethyl-2-(piperidin-1-ylmethyl)-1H-pyrrolo[2,3-b]pyridin-5-yl)acetic acid

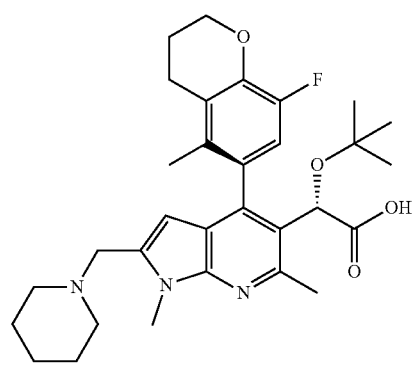

A solution of (2S)(M)-methyl 2-(tert-butoxy)-2-(-4-(8-fluoro-5-methylchroman-6-yl)-1,6-dimethyl-2-(piperidin-1-ylmethyl)-1H-pyrrolo[2,3-b]pyridin-5-yl)acetate (12 mg, 0.024 mmol) in MeOH (1 mL) was treated with LiOH (1 mL) and heated to 80° C. After 2 h, the reaction mixture was poured into 1M HCl and extracted with EtOAc. The organics were washed with brine, dried (MgSO$_4$), filtered and concentrated. The residue was purified by reverse phase HPLC to afford the title compound. $^1$H NMR (400 MHz, CHLOROFORM-d) δ 6.73 (m, 1H), 6.25 (s, 1H), 5.26 (s, 1H), 4.16-4.63 (m, 4H), 3.98 (s, 3H), 3.29-3.73 (m, 2H)(buried underneath water/TFA peak), 2.87 (s, 3H), 2.79-2.52 (m, 4H), 2.16 (m, 2H), 2.01-1.77 (m, 8H), 1.30 (m, 2H), 1.14 (s, 9H). LC/MS (m/z) ES$^+$=538 (M+1).

Compounds in Table 10 (examples 289-296) were synthesized using the procedure described above with the appropriate amine.

TABLE 10

| Example | Structure | MW | Observed Mass |
|---|---|---|---|
| 289 | 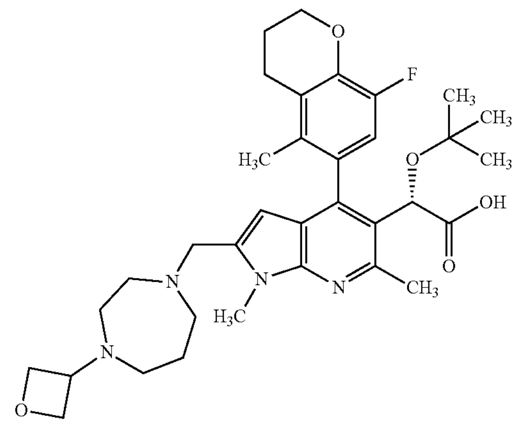 [SMILES: Cc1nc2c(cc(CN3CCCN(C4COC4)CC3)n2C)c(-c2cc(F)c3c(c2C)CCCO3)c1[C@H](OC(C)(C)C)C(=O)O] | 608.74 | 609 |
| 290 | 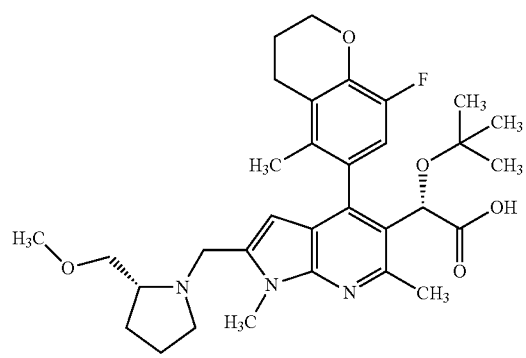 [SMILES: COC[C@H]1CCCN1Cc1cc2c(-c3cc(F)c4c(c3C)CCCO4)c([C@H](OC(C)(C)C)C(=O)O)c(C)nc2n1C] | 567.69 | 568 |
| 291 | 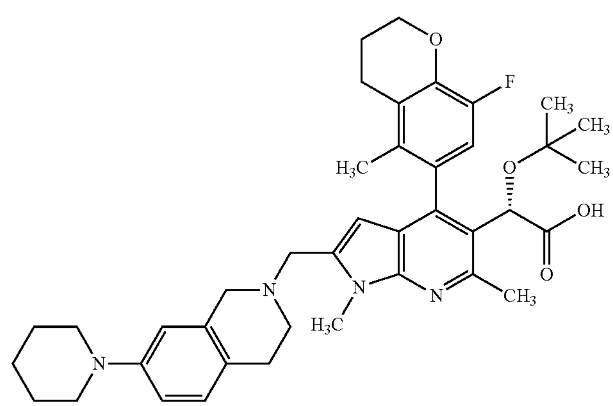 [SMILES: Cc1nc2c(cc(CN3CCc4ccc(N5CCCCC5)cc4C3)n2C)c(-c2cc(F)c3c(c2C)CCCO3)c1[C@H](OC(C)(C)C)C(=O)O] | 668.84 | 669 |

TABLE 10-continued

| Example | Structure | MW | Observed Mass |
|---|---|---|---|
| 292 | 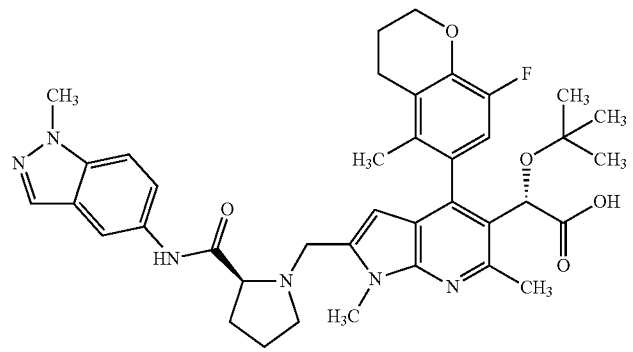 [SMILES: Cc1nc2c(cc(CN3CCC[C@H]3C(=O)Nc3ccc4c(cnn4C)c3)n2C)c(-c2cc(F)c3c(c2C)CCCO3)c1[C@H](OC(C)(C)C)C(=O)O] | 696.81 | 697 |
| 293 | 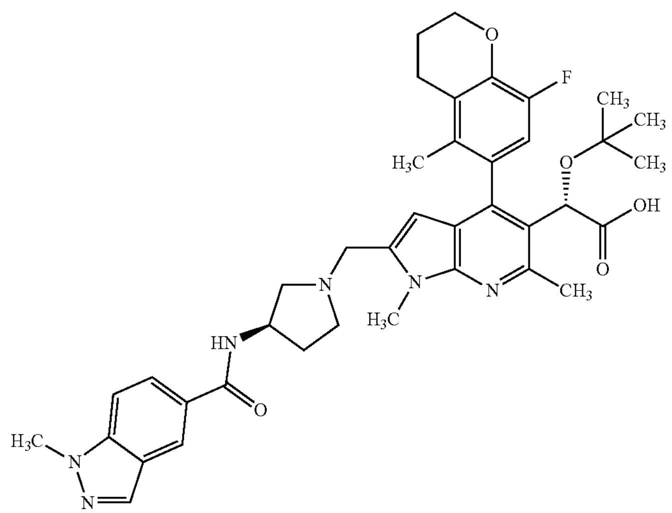 [SMILES: Cc1nc2c(cc(CN3CC[C@@H](NC(=O)c4ccc5c(cnn5C)c4)C3)n2C)c(-c2cc(F)c3c(c2C)CCCO3)c1[C@H](OC(C)(C)C)C(=O)O] | 696.81 | 697 |
| 294 | 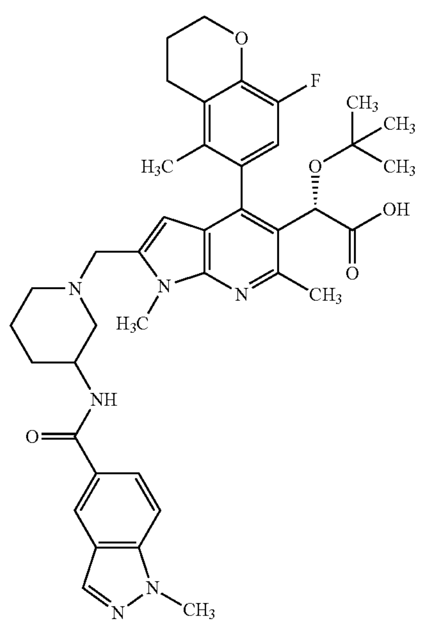 [SMILES: Cc1nc2c(cc(CN3CCCC(NC(=O)c4ccc5c(cnn5C)c4)C3)n2C)c(-c2cc(F)c3c(c2C)CCCO3)c1[C@H](OC(C)(C)C)C(=O)O] | 710.84 | 711 |

TABLE 10-continued
| Example | Structure | MW | Observed Mass |
|---|---|---|---|
| 295 | 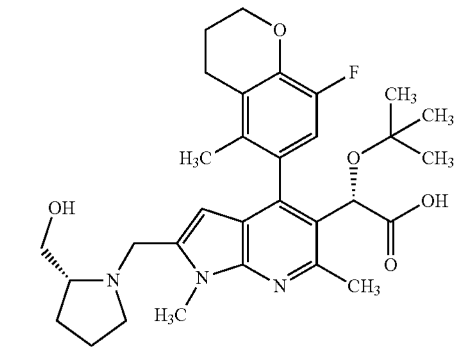 [SMILES: Cc1nc2c(cc(CN3CCC[C@@H]3CO)n2C)c(-c2cc(F)c3c(c2C)CCCO3)c1[C@H](OC(C)(C)C)C(=O)O] | 553.66 | 554 |
| 296 | 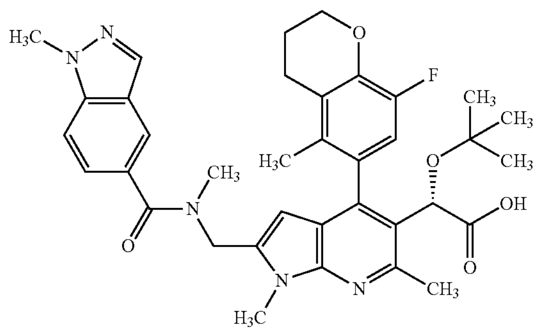 [SMILES: Cc1nc2c(cc(CN(C)C(=O)c3ccc4c(cnn4C)c3)n2C)c(-c2cc(F)c3c(c2C)CCCO3)c1[C@H](OC(C)(C)C)C(=O)O] | 641.73 | 642 |
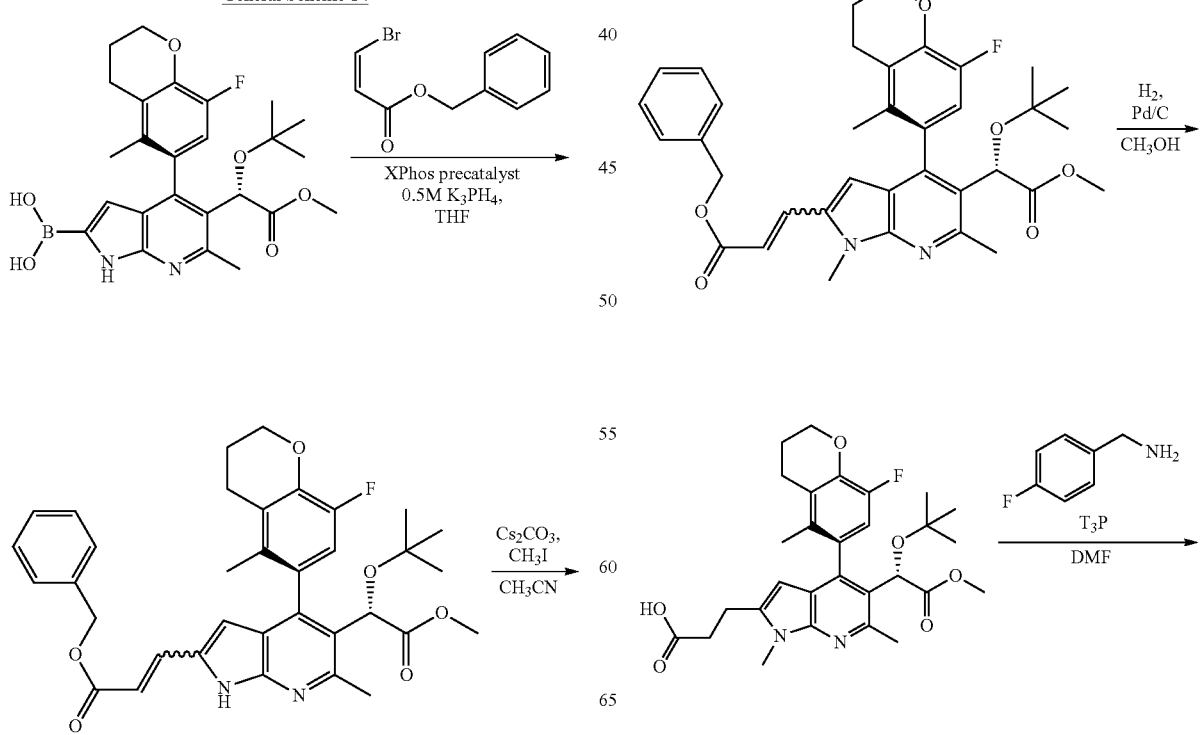
General Scheme 14

-continued

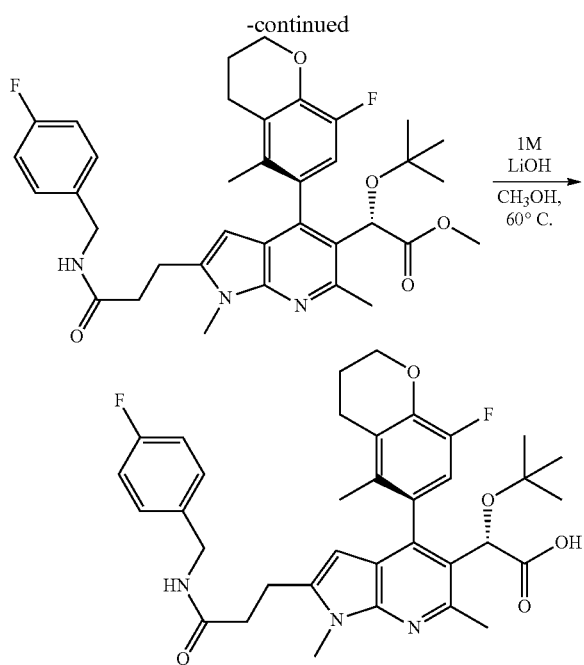

Example 297

(2S)(M) 2-(tert-butoxy)-2-((R)-4-(8-fluoro-5-methyl-chroman-6-yl)-2-(3-((4-fluorobenzyl)amino)-3-oxo-propyl)-1,6-dimethyl-1H-pyrrolo[2,3-b]pyridin-5-yl) acetic acid

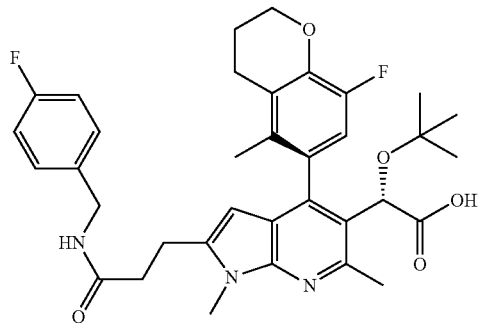

Step A (2S)(M) Benzyl 3-(-5-(-1-(tert-butoxy)-2-methoxy-2-oxoethyl)-4-(8-fluoro-5-methylchroman-6-yl)-6-methyl-1H-pyrrolo[2,3-b]pyridin-2-yl)acrylate

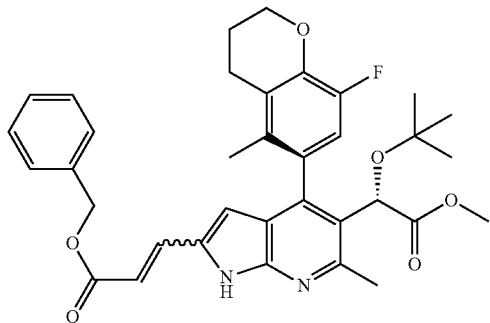

A solution of (2S)(M)(-5-(-1-(tert-butoxy)-2-methoxy-2-oxoethyl)-4-(8-fluoro-5-methylchroman-6-yl)-6-methyl-1H-pyrrolo[2,3-b]pyridin-2-yl)boronic acid (108.2 mg, 0.224 mmol), (Z)-benzyl 3-bromoacrylate (50.5 mg, 0.209 mmol), and tripotassium phosphate tripotassium phosphate (0.764 mL, 0.382 mmol, 0.5 M) in THF (2 mL) was degassed with $N_2$ for 5 min and treated with chloro(2-dicyclohexylphosphino-2',4',6'-triisopropyl-1,1'-biphenyl)[2-(2-aminoethyl)phenyl)]palladium(II) (15.0 mg, 0.019 mmol) and stirred at ambient temperature. After 18 h, the reaction mixture was diluted with DCM and the layers partitioned. The organic phase was washed with brine, dried ($Na_2SO_4$), filtered and concentrated in vacuo to afford the title compound. $^1$H NMR (400 MHz, CHLOROFORM-d) δ=12.02 (br. s., 1H), 7.45-7.28 (m, 5H), 6.77-6.70 (m, 2H), 6.13 (d, J=2.0 Hz, 1H), 5.79 (d, J=12.5 Hz, 1H), 5.23 (s, 2H), 5.11 (s, 1H), 4.29 (t, J=5.1 Hz, 2H), 3.59 (s, 3H), 2.80 (s, 3H), 2.75-2.68 (m, 2H), 2.18-2.10 (m, 2H), 1.11 (s, 9H). LC/MS (m/z) $ES^+$=601.20 (M+1).

Step B (2S)(M)-Benzyl-3-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)acrylate A solution of 3-((R)-5-((S)-1-(tert-butoxy)-2-methoxy-2-oxoethyl)-4-(8-fluoro-5-methylchroman-6-yl)-6-methyl-1H-pyrrolo[2,3-b]pyridin-2-yl)acrylate (144.3 mg, 0.240 mmol), and cesium carbonate (188.8 mg, 0.579 mmol) in acetonitrile (5 mL) was treated with iodomethane/acetonitrile (1.27 mL, 0.382 mmol, 0.3 M in $CH_3CN$) and heated to 70° C. After 4 h, the reaction mixture was diluted with DCM and the organics washed with water, brine, dried ($Na_2SO_4$), filtered and concentrated in vacuo. The residue was purified by silica gel chromatography to afford the title compound as a mixture of E and Z isomers (75.8 mg, 0.123 mmol, 50.4% yield over 2 steps). LC/MS (m/z) ES+=615.29 (M+1).

Step C (2S)(M)-3-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)propanoic acid

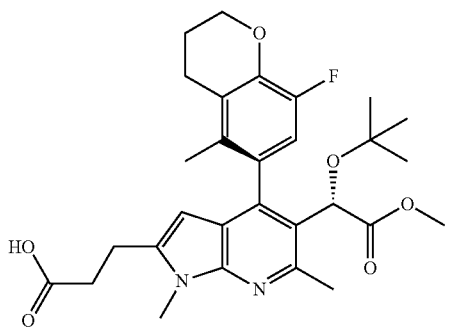

A solution of benzyl (2S)(M)-3-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)acrylate (75.8 mg, 0.123 mmol) and palladium on carbon (78.6 mg, 0.074 mmol) in methanol was degassed with $N_2$ 3× and then placed under an atmosphere of $H_2$ (1 atm). After 3 h, the reaction mixture was filtered and the filtrate concentrated in vacuo to afford the title compound. $^1$H NMR (400 MHz, CHLOROFORM-d) δ=6.65 (br. s., 1H), 5.52 (br. s., 1H), 5.07 (s, 1H), 4.33-4.19 (m, 2H), 3.57 (s, 3H), 3.54 (s, 3H), 2.73 (s, 3H), 2.69-2.60 (m, 2H), 2.52-2.41 (m, 2H), 2.08 (br. s., 2H), 1.71 (s, 3H), 1.08 (s, 9H). LC/MS (m/z) ES+=527.16 (M+1).

Step D (2S)(M)-methyl 2-(tert-butoxy)-2-(-4-(8-fluoro-5-methylchroman-6-yl)-2-(3-((4-fluorobenzyl)amino)-3-oxopropyl)-1,6-dimethyl-1H-pyrrolo[2,3-b]pyridin-5-yl)acetate

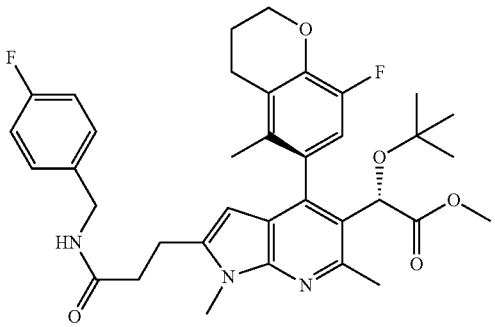

(2S)(M)-3-(-5-(-1-(tert-butoxy)-2-methoxy-2-oxoethyl)-4-(8-fluoro-5-methylchroman-6-yl)-1,6-dimethyl-1H-pyrrolo[2,3-b]pyridin-2-yl)propanoic acid (18.3 mg, 0.035 mmol) was dissolved in N,N-dimethylformamide (0.3 mL) and treated with N-ethyl-N-isopropylpropan-2-amine (0.110 mL, 0.033 mmol), (4-fluorophenyl)methanamine (0.070 mL, 0.035 mmol) and propylphosphonic anhydride solution (≥50 wt. % in ethyl acetate) (0.127 mL, 0.038 mmol). The reaction stirred at room temperature for 1 h, was extracted with dichloromethane, washed with brine, dried over sodium sulfate, concentrated under reduced pressure and purified on silica gel (0-20% methanol/dichloromethane) to afford the title compound (22.3 mg, 0.021 mmol, 60.0% yield). LC/MS (m/z) ES+=634.24 (M+1).

Step E (2S)(M)-2-(tert-butoxy)-2-(-4-(8-fluoro-5-methylchroman-6-yl)-2-(3-((4-fluorobenzyl)amino)-3-oxopropyl)-1,6-dimethyl-1H-pyrrolo[2,3-b]pyridin-5-yl)acetic acid

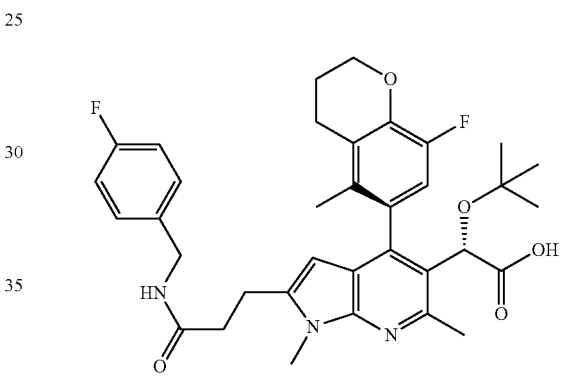

A solution of (2S)(M)-methyl 2-(tert-butoxy)-2-(-4-(8-fluoro-5-methylchroman-6-yl)-2-(3-((4-fluorobenzyl)amino)-3-oxopropyl)-1,6-dimethyl-1H-pyrrolo[2,3-b]pyridin-5-yl)acetate (22.3 mg, 0.035 mmol) and 1 M lithium hydroxide (2.0 mL, 2.0 mmol) in methanol (3.0 mL) was heated to 60° C. After 10 min, the reaction mixture was cooled to ambient temperature and poured into 1M HCl. The mixture was diluted with EtOAc and the layers partitioned. The organic phase was washed with brine, dried ($Na_2SO_4$), filtered and concentrated in vacuo. The residue was purified by reverse phase HPLC to afford the title compound (7.2 mg, 0.012 mmol, 33.0% yield). $^1$H NMR (400 MHz, CHLOROFORM-d) δ=7.19-7.16 (m, 2H), 7.01-6.95 (m, 2H), 6.68 (d, J=10.7 Hz, 2H), 6.01 (br. s., 2H), 5.87 (s, 1H), 5.31 (s, 1H), 5.20 (s, 1H), 4.39-4.28 (m, 5H), 3.97 (s, 3H), 3.11 (t, J=8.0 Hz, 2H), 2.92 (s, 3H), 2.78-2.66 (m, 2H), 2.58 (t, J=8.0 Hz, 2H), 2.19-2.13 (m, 2H), 1.80 (s, 3H), 1.13 (s, 9H). LC/MS (m/z) ES+=620.36.

Compounds in Table 11 (examples 298-299) were synthesized using the procedure described above with the appropriate amine.

TABLE 11
| Example | Structure | MW | Observed Mass |
|---|---|---|---|
| 298 | 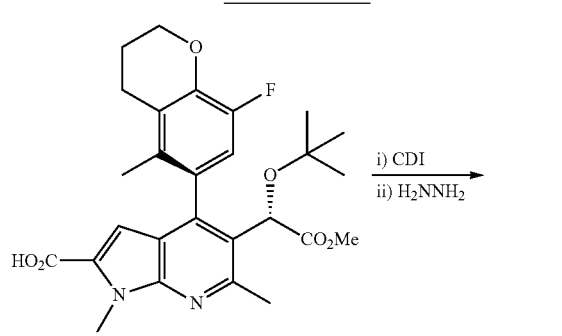 | 641.73 | 642 |
| 299 | 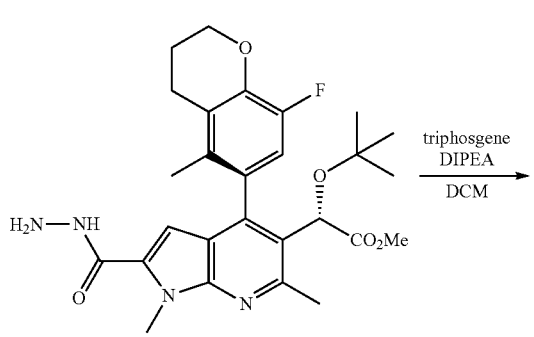 | 655.76 | 656 |
General Scheme 15
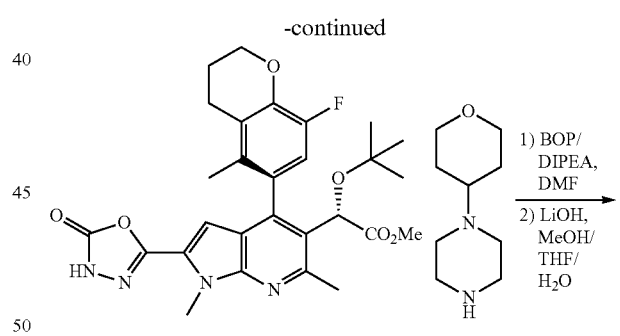
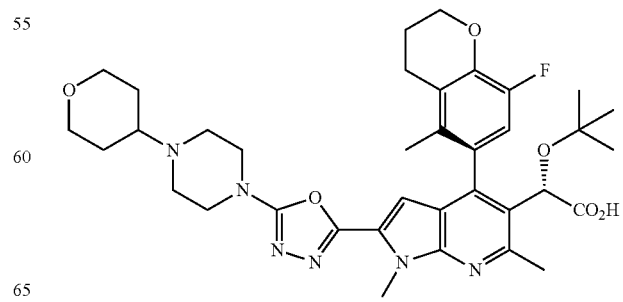

Example 300

(2S)(M)-2-(tert-butoxy)-2-(-4-(8-fluoro-5-methyl-chroman-6-yl)-1,6-dimethyl-2-(5-(4-(tetrahydro-2H-pyran-4-yl)piperazin-1-yl)-1,3,4-oxadiazol-2-yl)-1H-pyrrolo[2,3-B]pyridin-5-yl)acetic acid

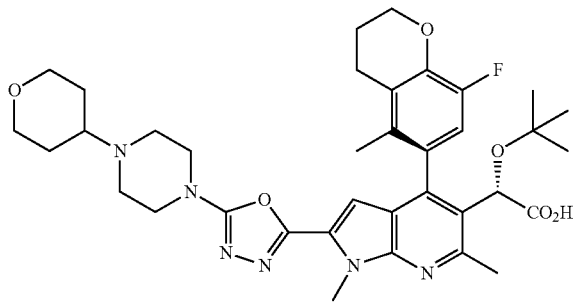

Step A (2S)(M) Benzyl 3-(-5-(-1-(tert-butoxy)-2-methoxy-2-oxoethyl)-4-(8-fluoro-5-methylchroman-6-yl)-6-methyl-1H-pyrrolo[2,3-b]pyridin-2-yl)acrylate

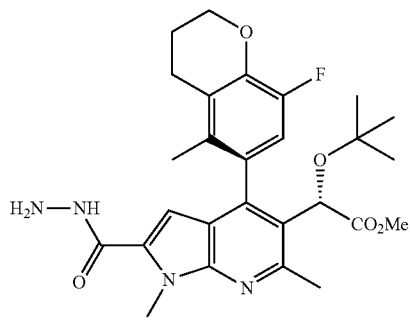

A solution of (2S)(M)-5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid (200 mg, 0.401 mmol) in Tetrahydrofuran (THF) (4.0 mL) was treated with CDI (260 mg, 1.605 mmol) and then heated to 60° C. After 25 min, the mixture was treated with hydrazine (0.126 mL, 4.01 mmol), stirred for 1 h, cooled and then concentrated in vacuo. The residue was purified by silica gel chromatography (0-10% DCM/MeOH gradient) to afford the title as a white solid. $^1$H NMR (400 MHz, CHLOROFORM-d) δ=7.19 (br. s., 1H), 6.74 (d, J=11.0 Hz, 1H), 6.22 (s, 1H), 5.14 (s, 1H), 4.32 (t, J=5.1 Hz, 2H), 4.13 (s, 3H), 3.99 (d, J=3.8 Hz, 2H), 3.61 (s, 3H), 2.83 (s, 3H), 2.79-2.68 (m, 2H), 2.26-2.08 (m, 2H), 1.79 (s, 3H), 1.12 (s, 9H); LC/MS (m/z) ES$^+$=513 (M+1).

Step B (2S)(M)-methyl 2-(tert-butoxy)-2-(-4-(8-fluoro-5-methylchroman-6-yl)-1,6-dimethyl-2-(5-oxo-4,5-dihydro-1,3,4-oxadiazol-2-yl)-1H-pyrrolo[2,3-b]pyridin-5-yl)acetate

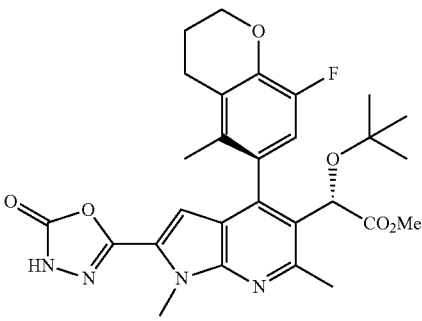

A solution of (2S)(M)-methyl 2-(tert-butoxy)-2-(4-(8-fluoro-5-methylchroman-6-yl)-2-(hydrazinecarbonyl)-1,6-dimethyl-1H-pyrrolo[2,3-b]pyridin-5-yl)acetate (159 mg, 0.310 mmol) and Hunig's base (0.108 mL, 0.620 mmol) in Dichloromethane (DCM) (5.0 mL) was treated with triphosgene (36.8 mg, 0.124 mmol) and stirred at ambient temperature for 20 min. The mixture was concentrated in vacuo and purified by silica gel chromatography (12 g column, 0-10% MeOH/DCM gradient) to afford the title compound as a white solid. $^1$H NMR (400 MHz, CHLOROFORM-d) d=8.90 (br. s., 1H), 6.74 (d, J=11.1 Hz, 1H), 6.52 (s, 1H), 5.19 (s, 1H), 4.36-4.29 (m, 2H), 4.09 (s, 3H), 3.62 (s, 3H), 2.86-2.81 (m, 3H), 2.79-2.70 (m, 2H), 2.24-2.11 (m, 2H), 1.81 (s, 3H), 1.14 (s, 9H); LC/MS (m/z) ES$^+$=539 (M+1).

Step C (2S)(M)-2-(tert-butoxy)-2-(-4-(8-fluoro-5-methyl-chroman-6-yl)-1,6-dimethyl-2-(5-(4-(tetrahydro-2H-pyran-4-yl)piperazin-1-yl)-1,3,4-oxadiazol-2-yl)-1H-pyrrolo[2,3-b]pyridin-5-yl)acetic acid

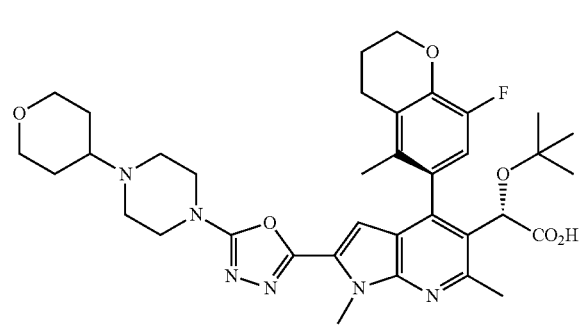

A solution of (2S)(M)-methyl 2-(tert-butoxy)-2-(4-(8-fluoro-5-methylchroman-6-yl)-1,6-dimethyl-2-(5-oxo-4,5-dihydro-1,3,4-oxadiazol-2-yl)-1H-pyrrolo[2,3-b]pyridin-5-yl)acetate (33.4 mg, 0.062 mmol) in N,N-

Dimethylformamide (DMF) (0.8 mL) was treated with Hunig's base (0.043 mL, 0.248 mmol) followed by 1-(tetrahydro-2H-pyran-4-yl)piperazine, 2 Hydrochloride (30.2 mg, 0.124 mmol) and then stirred for several minutes before adding BOP (30.2 mg, 0.068 mmol). The mixture was stirred overnight at ambient temperature. The mixture was purified directly by reverse phase HPLC to afford a yellow residue.

A solution of (2S)(M)-methyl 2-(tert-butoxy)-2-(4-(8-fluoro-5-methylchroman-6-yl)-1,6-dimethyl-2-(5-(4-(tetrahydro-2H-pyran-4-yl)piperazin-1-yl)-1,3,4-oxadiazol-2-yl)-1H-pyrrolo[2,3-b]pyridin-5-yl)acetate in methanol (0.4 mL), tetrahydrofuran (0.4 mL) and water (0.2 mL) was treated with lithium hydroxide monohydrate (20 mg, 0.477 mmol) and then irradiated in the microwave at 120° C. for 10 minutes. The mixture was purified directly by reverse phase HPLC to afford the title compound (21 mg, 0.023 mmol) as a white solid. $^1$H NMR (400 MHz, DMSO-d$_6$) δ=9.83 (br. s., 1H), 6.78 (d, J=11.3 Hz, 1H), 6.44 (s, 1H), 4.97 (s, 1H), 4.24 (t, J=5.1 Hz, 2H), 4.11 (s, 5H), 3.99 (dd, J=3.8, 11.3 Hz, 2H), 3.46 (br. s., 4H), 3.31 (t, J=11.5 Hz, 3H), 2.79-2.64 (m, 5H), 2.13-1.92 (m, 4H), 1.80 (s, 3H), 1.72-1.56 (m, 2H), 1.02 (s, 9H); LC/MS (m/z) ES$^+$=677 (M+1).

Compounds in Table 12 (examples 301-353) were synthesized using the procedure described above with the appropriate amine.

TABLE 12

| Example | Structure | MW | Observed Mass |
|---------|-----------|------|---------------|
| 301 | 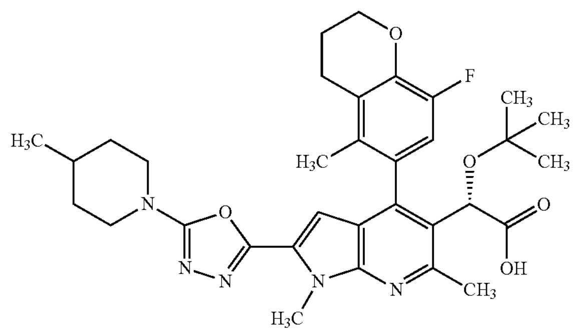 [SMILES: Cc1nc2c(cc(-c3nnc(N4CCC(C)CC4)o3)n2C)c(-c2cc(F)c3c(c2C)CCCO3)c1[C@H](OC(C)(C)C)C(=O)O] | 605.7 | 606 |
| 302 | 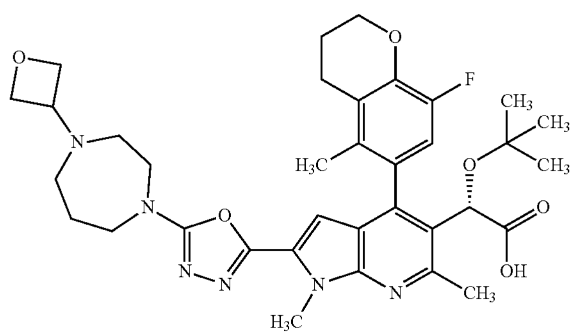 [SMILES: Cc1nc2c(cc(-c3nnc(N4CCCN(C5COC5)CC4)o3)n2C)c(-c2cc(F)c3c(c2C)CCCO3)c1[C@H](OC(C)(C)C)C(=O)O] | 662.75 | 663 |
| 303 | 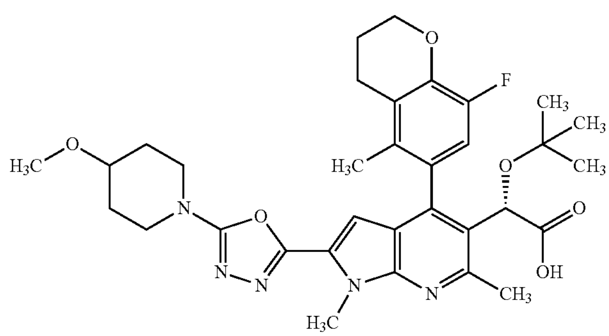 [SMILES: COC1CCN(c2nnc(-c3cc4c(-c5cc(F)c6c(c5C)CCCO6)c([C@H](OC(C)(C)C)C(=O)O)c(C)nc4n3C)o2)CC1] | 621.7 | 622 |

TABLE 12-continued

| Example | Structure | MW | Observed Mass |
|---|---|---|---|
| 304 | 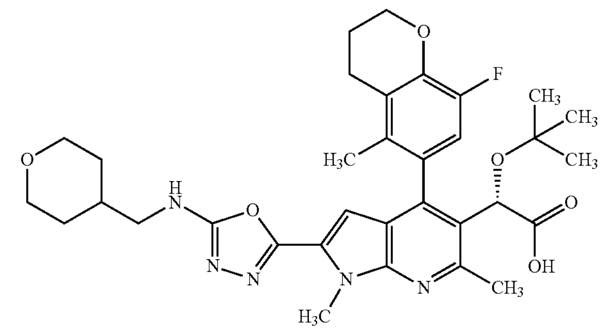 [SMILES: Cc1nc2c(cc(-c3nnc(NCC4CCOCC4)o3)n2C)c(-c2cc(F)c3c(c2C)CCCO3)c1[C@H](OC(C)(C)C)C(=O)O] | 621.7 | 622 |
| 305 | 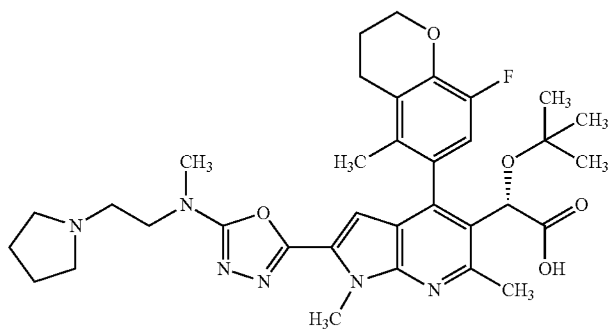 [SMILES: Cc1nc2c(cc(-c3nnc(N(C)CCN4CCCC4)o3)n2C)c(-c2cc(F)c3c(c2C)CCCO3)c1[C@H](OC(C)(C)C)C(=O)O] | 634.74 | 635 |
| 306 | 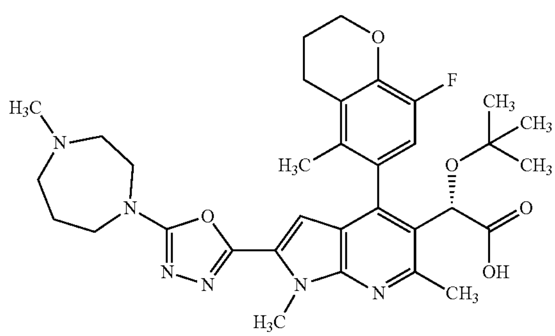 [SMILES: Cc1nc2c(cc(-c3nnc(N4CCCN(C)CC4)o3)n2C)c(-c2cc(F)c3c(c2C)CCCO3)c1[C@H](OC(C)(C)C)C(=O)O] | 620.71 | 621 |
| 307 | 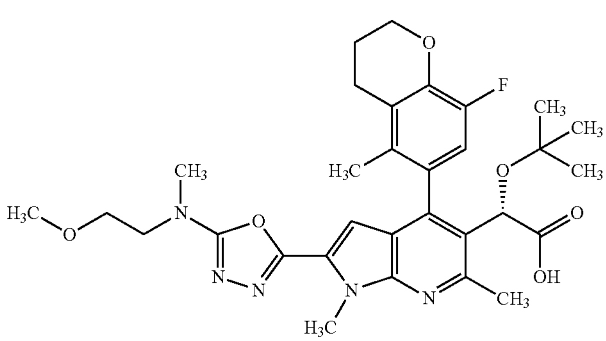 [SMILES: COCCN(C)c1nnc(-c2cc3c(-c4cc(F)c5c(c4C)CCCO5)c([C@H](OC(C)(C)C)C(=O)O)c(C)nc3n2C)o1] | 595.66 | 596 |

TABLE 12-continued

| Example | Structure | MW | Observed Mass |
|---------|-----------|-----|---------------|
| 308 | 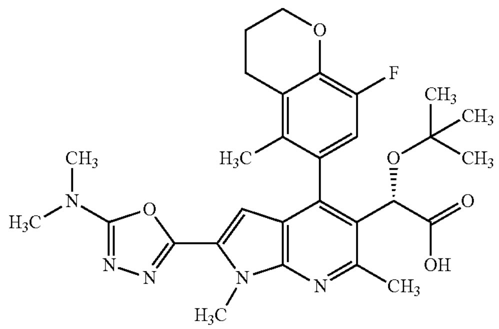 [SMILES: Cc1nc2c(cc(-c3nnc(N(C)C)o3)n2C)c(-c2cc(F)c3c(c2C)CCCO3)c1[C@H](OC(C)(C)C)C(=O)O] | 551.61 | 552 |
| 309 | 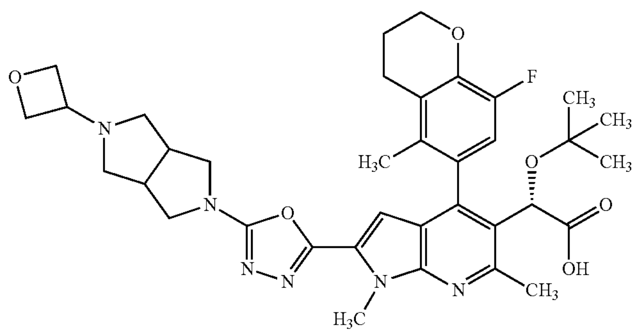 [SMILES: Cc1nc2c(cc(-c3nnc(N4CC5CN(C6COC6)CC5C4)o3)n2C)c(-c2cc(F)c3c(c2C)CCCO3)c1[C@H](OC(C)(C)C)C(=O)O] | 674.76 | 675 |
| 310 | 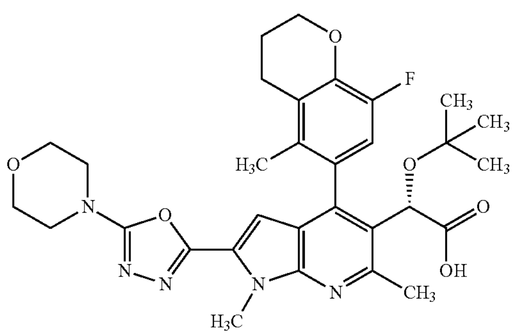 [SMILES: Cc1nc2c(cc(-c3nnc(N4CCOCC4)o3)n2C)c(-c2cc(F)c3c(c2C)CCCO3)c1[C@H](OC(C)(C)C)C(=O)O] | 593.65 | 594 |
| 311 | 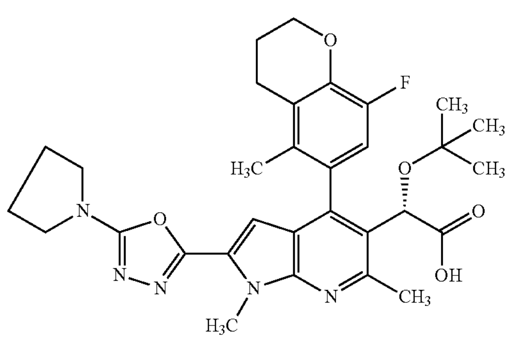 [SMILES: Cc1nc2c(cc(-c3nnc(N4CCCC4)o3)n2C)c(-c2cc(F)c3c(c2C)CCCO3)c1[C@H](OC(C)(C)C)C(=O)O] | 577.65 | 578 |

TABLE 12-continued

| Example | Structure | MW | Observed Mass |
|---|---|---|---|
| 312 | 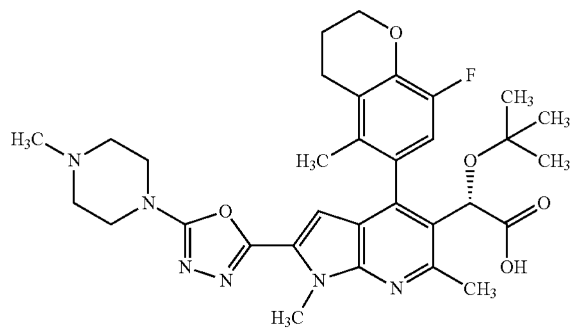 | 606.69 | 607 |
| 313 | 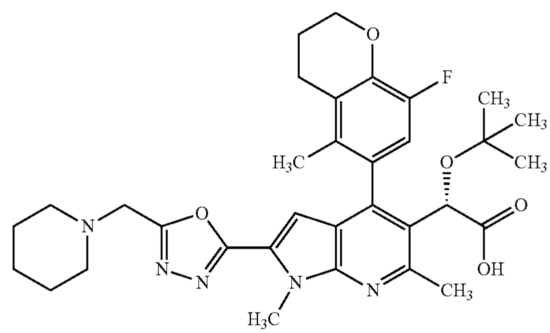 [SMILES: Cc1nc2c(cc(-c3nnc(CN4CCCCC4)o3)n2C)c(-c2cc(F)c3c(c2C)CCCO3)c1[C@H](OC(C)(C)C)C(=O)O] | 605.7 | 606 |
| 314 | 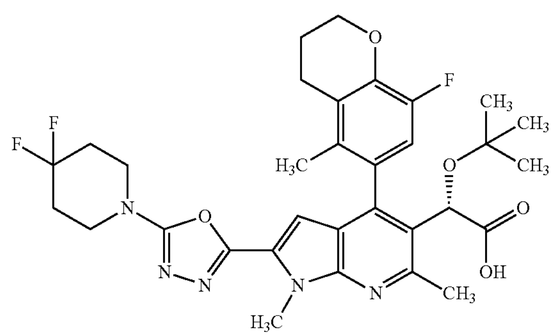 [SMILES: Cc1nc2c(cc(-c3nnc(N4CCC(F)(F)CC4)o3)n2C)c(-c2cc(F)c3c(c2C)CCCO3)c1[C@H](OC(C)(C)C)C(=O)O] | 627.65 | 628 |
| 315 | 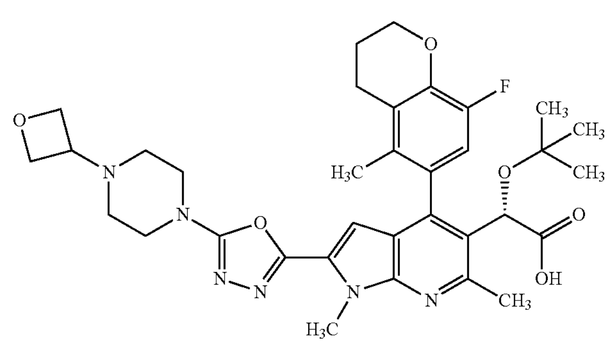 [SMILES: Cc1nc2c(cc(-c3nnc(N4CCN(C5COC5)CC4)o3)n2C)c(-c2cc(F)c3c(c2C)CCCO3)c1[C@H](OC(C)(C)C)C(=O)O] | 648.72 | 649 |

TABLE 12-continued

| Example | Structure | MW | Observed Mass |
|---|---|---|---|
| 316 | 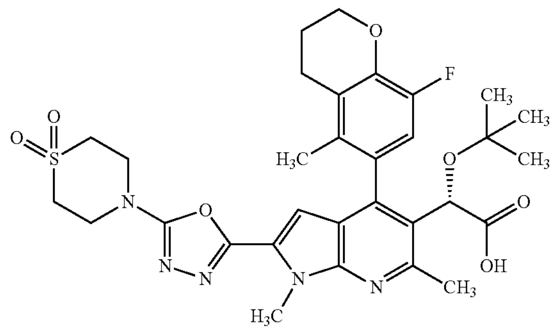 [SMILES: Cc1nc2c(cc(-c3nnc(N4CCS(=O)(=O)CC4)o3)n2C)c(-c2cc(F)c3c(c2C)CCCO3)c1[C@H](OC(C)(C)C)C(=O)O] | 641.71 | 642 |
| 317 | 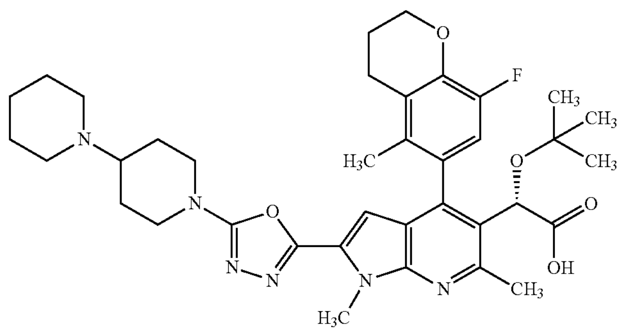 [SMILES: Cc1nc2c(cc(-c3nnc(N4CCC(N5CCCCC5)CC4)o3)n2C)c(-c2cc(F)c3c(c2C)CCCO3)c1[C@H](OC(C)(C)C)C(=O)O] | 674.8 | 675 |
| 318 | 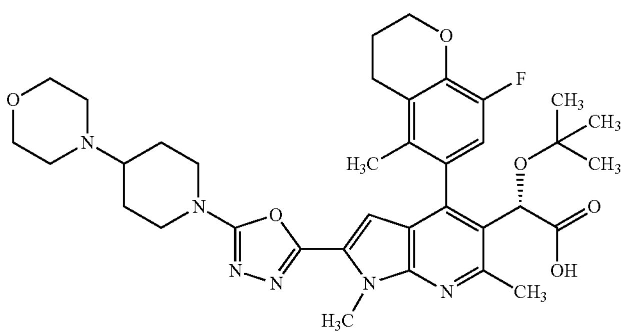 [SMILES: Cc1nc2c(cc(-c3nnc(N4CCC(N5CCOCC5)CC4)o3)n2C)c(-c2cc(F)c3c(c2C)CCCO3)c1[C@H](OC(C)(C)C)C(=O)O] | 676.78 | 677 |
| 319 | 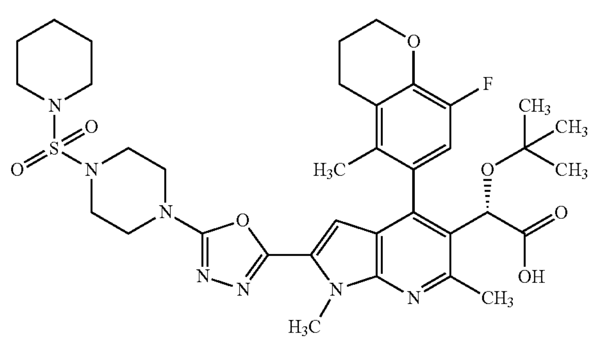 [SMILES: Cc1nc2c(cc(-c3nnc(N4CCN(S(=O)(=O)N5CCCCC5)CC4)o3)n2C)c(-c2cc(F)c3c(c2C)CCCO3)c1[C@H](OC(C)(C)C)C(=O)O] | 739.86 | 740 |

TABLE 12-continued

| Example | Structure | MW | Observed Mass |
|---------|-----------|------|---------------|
| 320 | 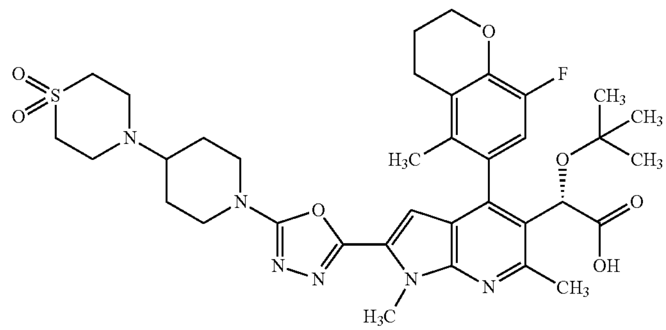 [SMILES: Cc1nc2c(cc(-c3nnc(N4CCC(N5CCS(=O)(=O)CC5)CC4)o3)n2C)c(-c2cc(F)c3c(c2C)CCCO3)c1[C@H](OC(C)(C)C)C(=O)O] | 724.84 | 725 |
| 321 | 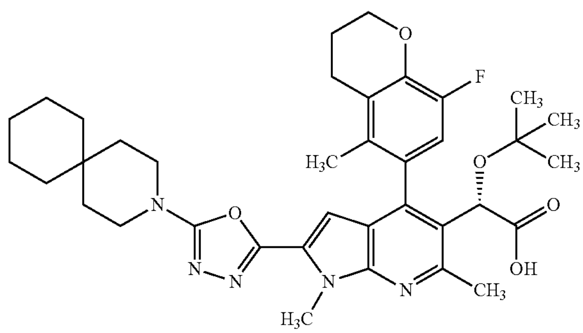 [SMILES: Cc1nc2c(cc(-c3nnc(N4CCC5(CCCCC5)CC4)o3)n2C)c(-c2cc(F)c3c(c2C)CCCO3)c1[C@H](OC(C)(C)C)C(=O)O] | 659.79 | 660 |
| 322 | 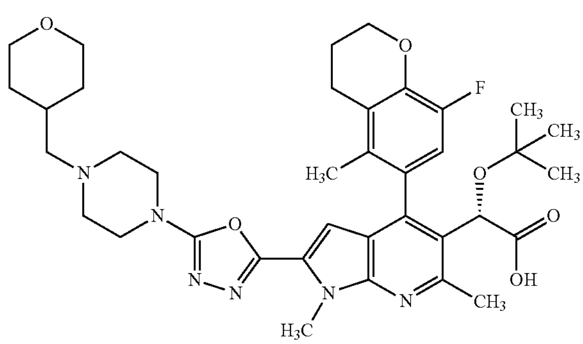 [SMILES: Cc1nc2c(cc(-c3nnc(N4CCN(CC5CCOCC5)CC4)o3)n2C)c(-c2cc(F)c3c(c2C)CCCO3)c1[C@H](OC(C)(C)C)C(=O)O] | 690.8 | 691 |
| 323 | 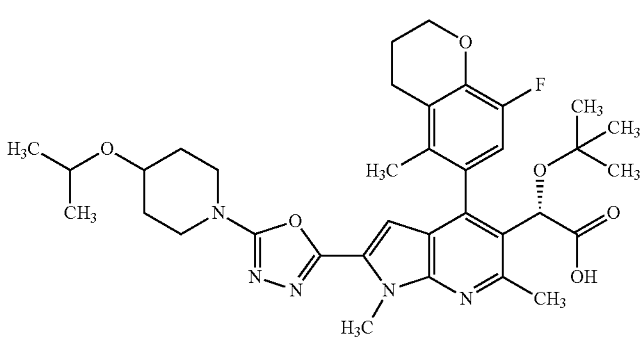 [SMILES: Cc1nc2c(cc(-c3nnc(N4CCC(OC(C)C)CC4)o3)n2C)c(-c2cc(F)c3c(c2C)CCCO3)c1[C@H](OC(C)(C)C)C(=O)O] | 649.75 | 650 |

TABLE 12-continued

| Example | Structure | MW | Observed Mass |
|---|---|---|---|
| 324 | 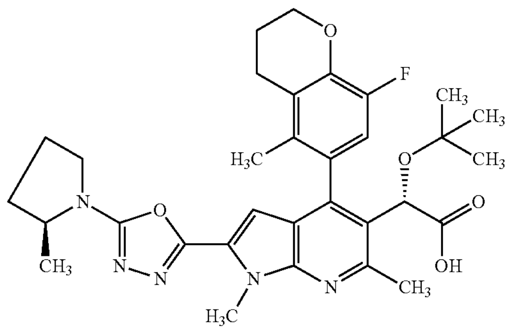 [SMILES: Cc1nc2c(cc(-c3nnc(N4CCC[C@@H]4C)o3)n2C)c(-c2cc(F)c3c(c2C)CCCO3)c1[C@H](OC(C)(C)C)C(=O)O] | 591.67 | 592 |
| 325 | 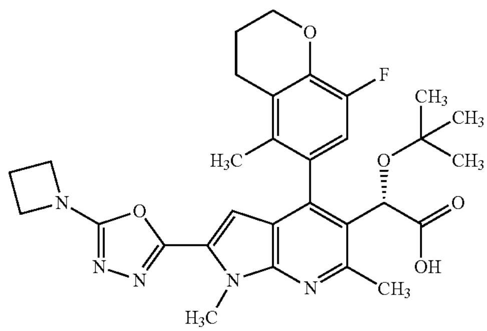 [SMILES: Cc1nc2c(cc(-c3nnc(N4CCC4)o3)n2C)c(-c2cc(F)c3c(c2C)CCCO3)c1[C@H](OC(C)(C)C)C(=O)O] | 563.62 | 564 |
| 326 | 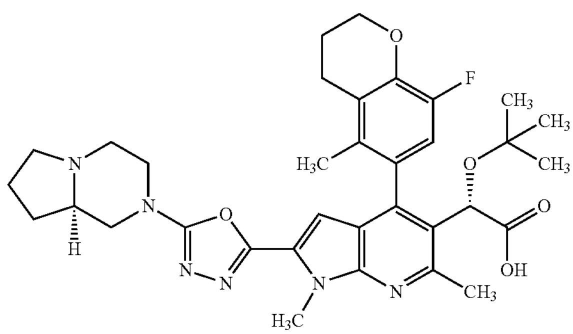 [SMILES: Cc1nc2c(cc(-c3nnc(N4CCN5CCC[C@@H]5C4)o3)n2C)c(-c2cc(F)c3c(c2C)CCCO3)c1[C@H](OC(C)(C)C)C(=O)O] | 632.72 | 633 |
| 327 | 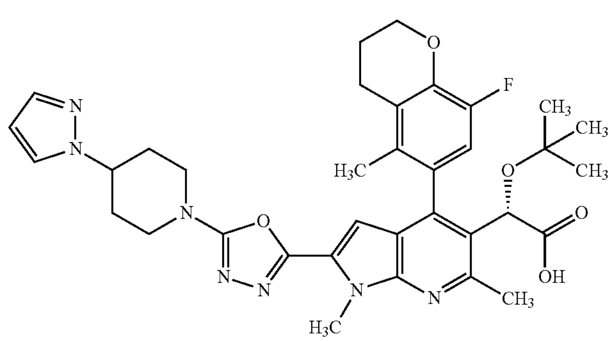 [SMILES: Cc1nc2c(cc(-c3nnc(N4CCC(n5cccn5)CC4)o3)n2C)c(-c2cc(F)c3c(c2C)CCCO3)c1[C@H](OC(C)(C)C)C(=O)O] | 657.73 | 658 |

TABLE 12-continued

| Example | Structure | MW | Observed Mass |
|---|---|---|---|
| 328 | 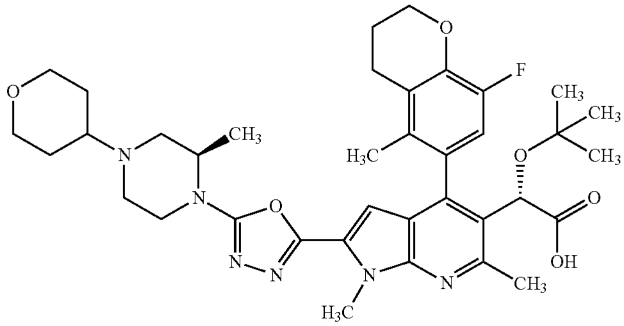 [SMILES: Cc1nc2c(cc(-c3nnc(N4CCN(C5CCOCC5)C[C@H]4C)o3)n2C)c(-c2cc(F)c3c(c2C)CCCO3)c1[C@H](OC(C)(C)C)C(=O)O] | 690.8 | 691 |
| 329 | 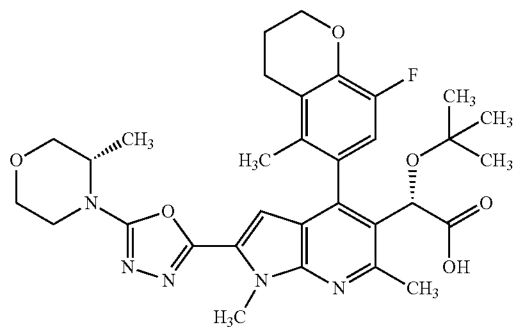 [SMILES: Cc1nc2c(cc(-c3nnc(N4CCOC[C@@H]4C)o3)n2C)c(-c2cc(F)c3c(c2C)CCCO3)c1[C@H](OC(C)(C)C)C(=O)O] | 607.67 | 608 |
| 330 | 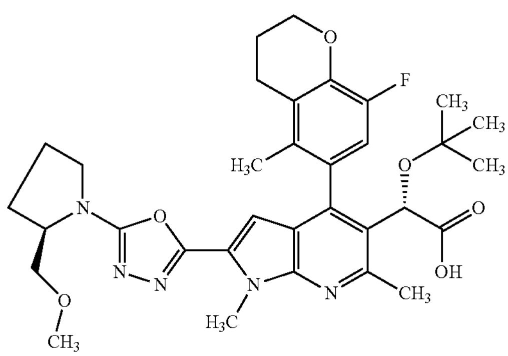 [SMILES: COC[C@H]1CCCN1c1nnc(-c2cc3c(-c4cc(F)c5c(c4C)CCCO5)c([C@H](OC(C)(C)C)C(=O)O)c(C)nc3n2C)o1] | 621.7 | 622 |
| 331 | 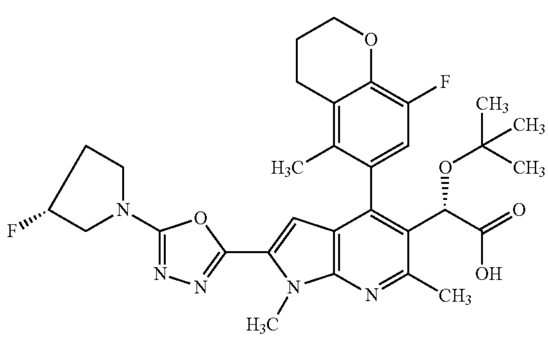 [SMILES: Cc1nc2c(cc(-c3nnc(N4CC[C@@H](F)C4)o3)n2C)c(-c2cc(F)c3c(c2C)CCCO3)c1[C@H](OC(C)(C)C)C(=O)O] | 595.64 | 596 |

TABLE 12-continued

| Example | Structure | MW | Observed Mass |
|---|---|---|---|
| 332 | 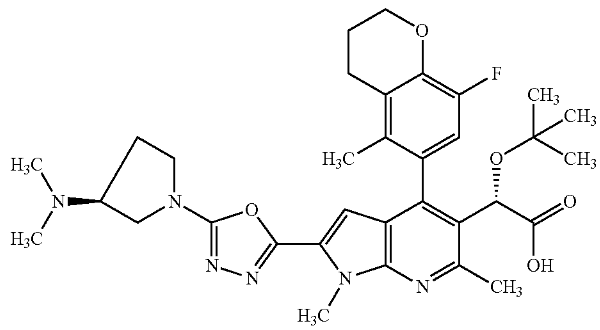 [SMILES: Cc1nc2c(cc(-c3nnc(N4CC[C@H](N(C)C)C4)o3)n2C)c(-c2cc(F)c3c(c2C)CCCO3)c1[C@H](OC(C)(C)C)C(=O)O] | 620.71 | 621 |
| 333 | 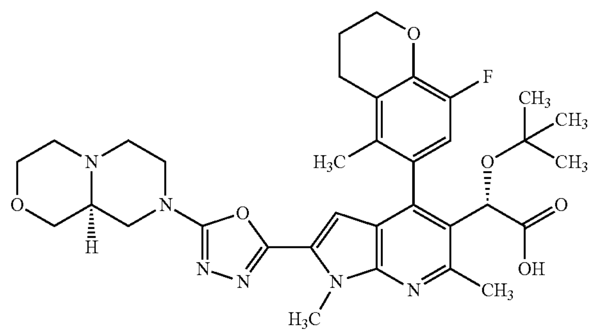 [SMILES: Cc1nc2c(cc(-c3nnc(N4CCN5CCOC[C@@H]5C4)o3)n2C)c(-c2cc(F)c3c(c2C)CCCO3)c1[C@H](OC(C)(C)C)C(=O)O] | 648.72 | 649 |
| 334 | 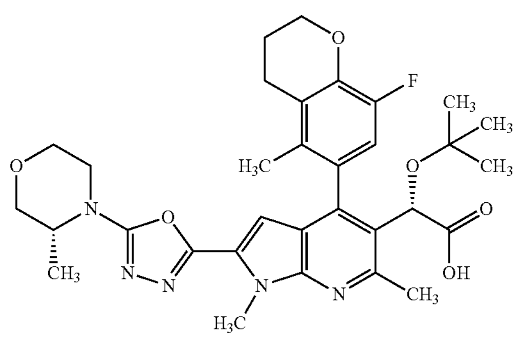 [SMILES: Cc1nc2c(cc(-c3nnc(N4CCOC[C@H]4C)o3)n2C)c(-c2cc(F)c3c(c2C)CCCO3)c1[C@H](OC(C)(C)C)C(=O)O] | 607.67 | 608 |
| 335 | 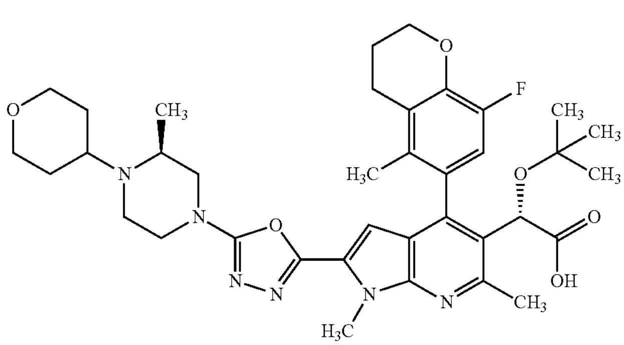 [SMILES: Cc1nc2c(cc(-c3nnc(N4CCN(C5CCOCC5)[C@@H](C)C4)o3)n2C)c(-c2cc(F)c3c(c2C)CCCO3)c1[C@H](OC(C)(C)C)C(=O)O] | 690.8 | 691 |

TABLE 12-continued

| Example | Structure | MW | Observed Mass |
|---------|-----------|------|------|
| 336 | 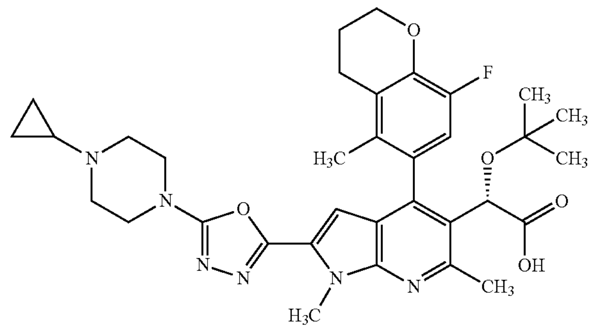 [SMILES: Cc1nc2c(cc(-c3nnc(N4CCN(C5CC5)CC4)o3)n2C)c(-c2cc(F)c3c(c2C)CCCO3)c1[C@H](OC(C)(C)C)C(=O)O] | 632.72 | 633 |
| 337 | 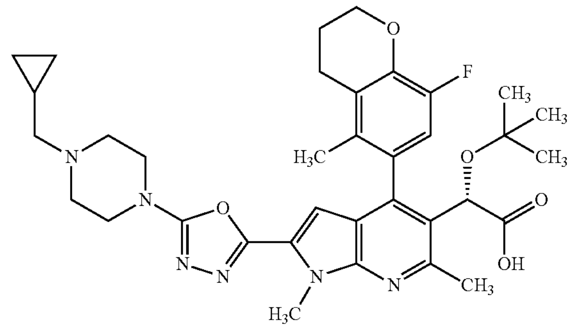 [SMILES: Cc1nc2c(cc(-c3nnc(N4CCN(CC5CC5)CC4)o3)n2C)c(-c2cc(F)c3c(c2C)CCCO3)c1[C@H](OC(C)(C)C)C(=O)O] | 646.75 | 647 |
| 338 | 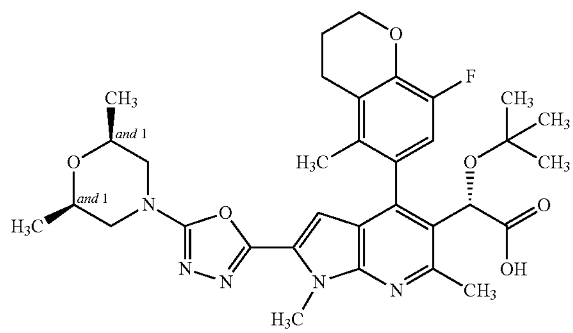 [SMILES: Cc1nc2c(cc(-c3nnc(N4C[C@@H](C)O[C@@H](C)C4)o3)n2C)c(-c2cc(F)c3c(c2C)CCCO3)c1[C@H](OC(C)(C)C)C(=O)O] | 621.7 | 622 |
| 339 | 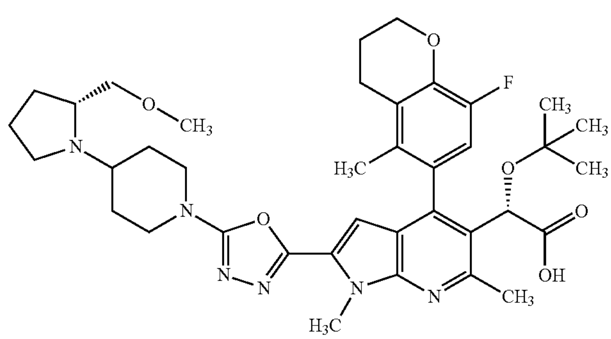 [SMILES: COC[C@H]1CCCN1C1CCN(c2nnc(-c3cc4c(-c5cc(F)c6c(c5C)CCCO6)c([C@H](OC(C)(C)C)C(=O)O)c(C)nc4n3C)o2)CC1] | 704.83 | 705 |

TABLE 12-continued

| Example | Structure | MW | Observed Mass |
|---------|-----------|------|---------------|
| 340 | 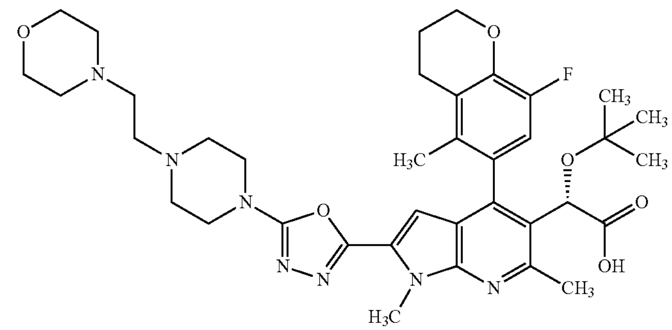 [SMILES: Cc1nc2c(cc(-c3nnc(N4CCN(CCN5CCOCC5)CC4)o3)n2C)c(-c2cc(F)c3c(c2C)CCCO3)c1[C@H](OC(C)(C)C)C(=O)O] | 705.82 | 706 |
| 341 | 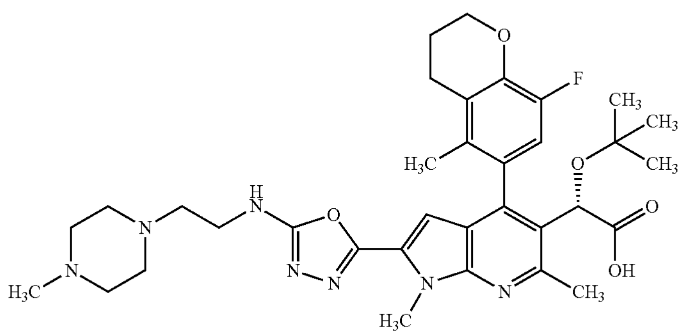 [SMILES: Cc1nc2c(cc(-c3nnc(NCCN4CCN(C)CC4)o3)n2C)c(-c2cc(F)c3c(c2C)CCCO3)c1[C@H](OC(C)(C)C)C(=O)O] | 649.76 | 650 |
| 342 | 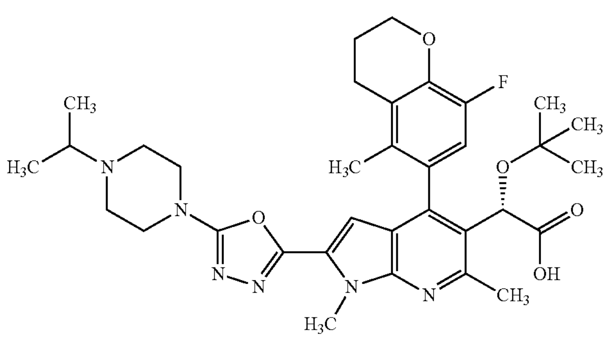 [SMILES: Cc1nc2c(cc(-c3nnc(N4CCN(C(C)C)CC4)o3)n2C)c(-c2cc(F)c3c(c2C)CCCO3)c1[C@H](OC(C)(C)C)C(=O)O] | 634.74 | 635 |
| 343 | 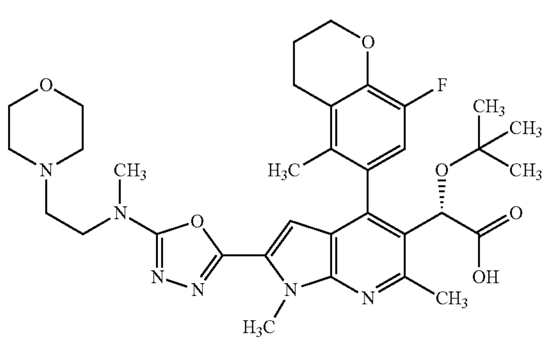 [SMILES: Cc1nc2c(cc(-c3nnc(N(C)CCN4CCOCC4)o3)n2C)c(-c2cc(F)c3c(c2C)CCCO3)c1[C@H](OC(C)(C)C)C(=O)O] | 650.74 | 651 |

TABLE 12-continued

| Example | Structure | MW | Observed Mass |
|---|---|---|---|
| 344 | 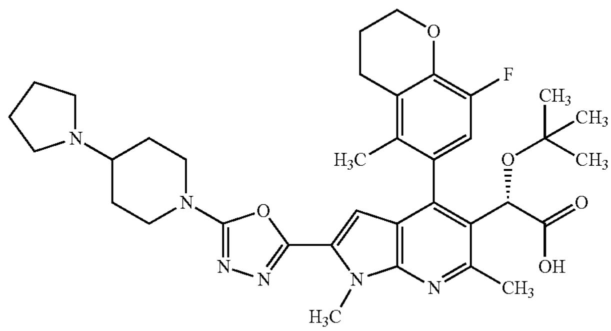 [SMILES: Cc1nc2c(cc(-c3nnc(N4CCC(N5CCCC5)CC4)o3)n2C)c(-c2cc(F)c3c(c2C)CCCO3)c1[C@H](OC(C)(C)C)C(=O)O] | 660.78 | 661 |
| 345 | 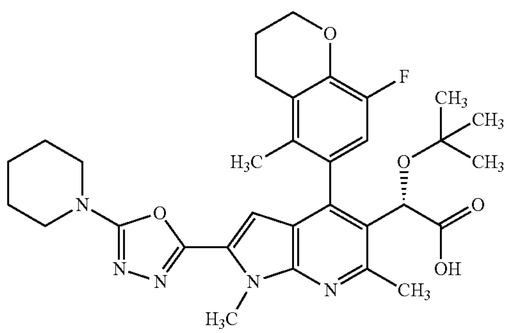 [SMILES: Cc1nc2c(cc(-c3nnc(N4CCCCC4)o3)n2C)c(-c2cc(F)c3c(c2C)CCCO3)c1[C@H](OC(C)(C)C)C(=O)O] | 591.67 | 592 |
| 346 | 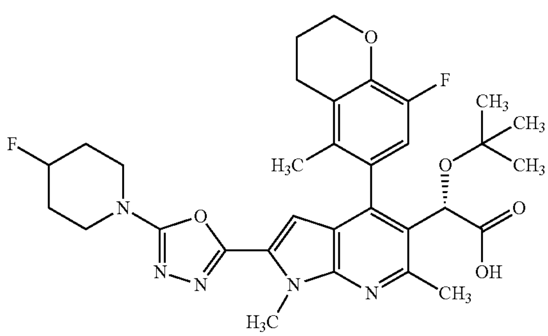 | 609.66 | 610 |
| 347 | 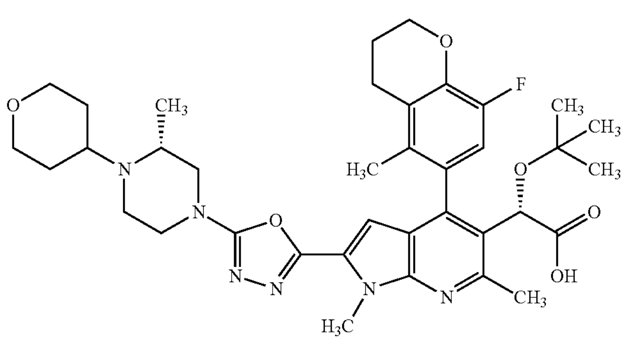 [SMILES: Cc1nc2c(cc(-c3nnc(N4CCN(C5CCOCC5)[C@H](C)C4)o3)n2C)c(-c2cc(F)c3c(c2C)CCCO3)c1[C@H](OC(C)(C)C)C(=O)O] | 690.8 | 691 |

TABLE 12-continued

| Example | Structure | MW | Observed Mass |
|---|---|---|---|
| 348 | 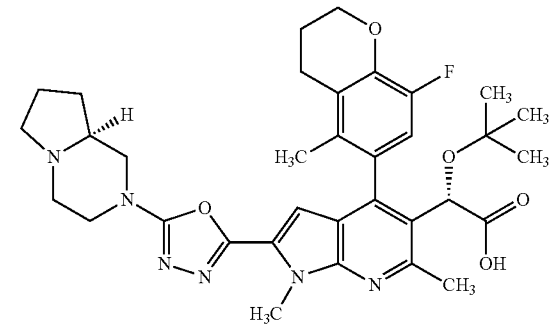 [SMILES: Cc1nc2c(cc(-c3nnc(N4CCN5CCC[C@H]5C4)o3)n2C)c(-c2cc(F)c3c(c2C)CCCO3)c1[C@H](OC(C)(C)C)C(=O)O] | 632.72 | 633 |
| 349 | 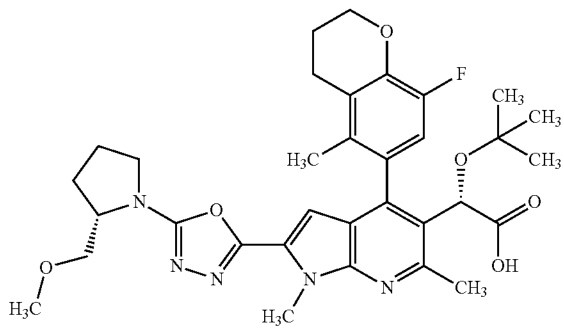 [SMILES: COC[C@@H]1CCCN1c1nnc(-c2cc3c(-c4cc(F)c5c(c4C)CCCO5)c([C@H](OC(C)(C)C)C(=O)O)c(C)nc3n2C)o1] | 621.7 | 622 |
| 350 | 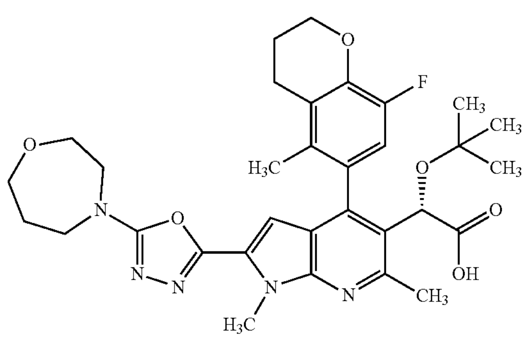 [SMILES: Cc1nc2c(cc(-c3nnc(N4CCCOCC4)o3)n2C)c(-c2cc(F)c3c(c2C)CCCO3)c1[C@H](OC(C)(C)C)C(=O)O] | 607.67 | 608 |
| 351 | 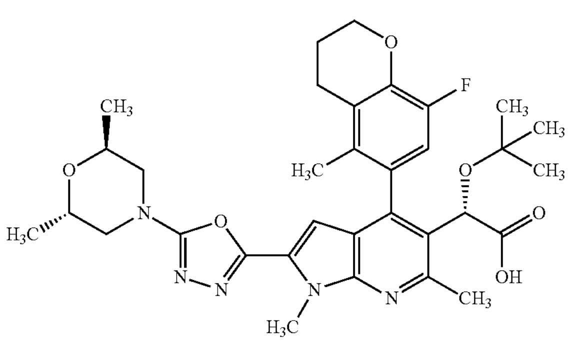 [SMILES: Cc1nc2c(cc(-c3nnc(N4C[C@H](C)O[C@@H](C)C4)o3)n2C)c(-c2cc(F)c3c(c2C)CCCO3)c1[C@H](OC(C)(C)C)C(=O)O] | 621.7 | 622 |

TABLE 12-continued

| Example | Structure | MW | Observed Mass |
|---------|-----------|------|---------------|
| 352 | 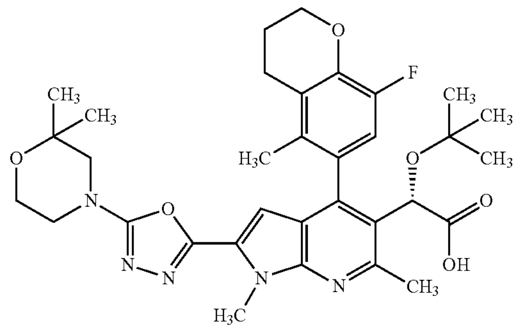 [SMILES: Cc1nc2c(cc(-c3nnc(N4CCOC(C)(C)C4)o3)n2C)c(-c2cc(F)c3c(c2C)CCCO3)c1[C@H](OC(C)(C)C)C(=O)O] | 621.7 | 622 |
| 353 | 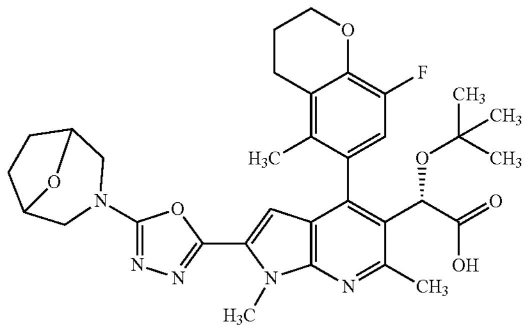 [SMILES: Cc1nc2c(cc(-c3nnc(N4CC5CCC(C4)O5)o3)n2C)c(-c2cc(F)c3c(c2C)CCCO3)c1[C@H](OC(C)(C)C)C(=O)O] | 619.68 | 620 |

Example 354

(2S)(M)-2-(tert-butoxy)-2-(4-(8-fluoro-5-methyl-chroman-6-yl)-1,6-dimethyl-2-(3-(1-methyl-1H-indazol-5-yl)-1,2,4-oxadiazol-5-yl)-1H-pyrrolo[2,3-b]pyridin-5-yl)acetic acid

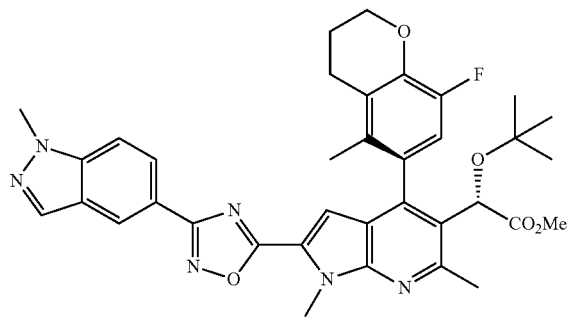

Step A

N'-hydroxy-1-methyl-1H-indazole-5-carboximidamide

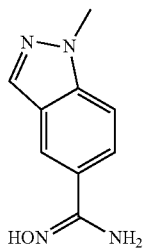

A solution of 1-methyl-1H-indazole-5-carbonitrile (205 mg, 1.304 mmol), hydroxylamine hydrochloride (363 mg, 5.22 mmol) and sodium bicarbonate (548 mg, 6.52 mmol) in Methanol (6 mL) was heated to 60 degrees for 90 min. The reaction mixture was cooled to ambient temperature and partitioned between EtOAc and water. The aqueous layer was extracted with EtOAc, and the combined organics washed with brine, dried ($Na_2SO_4$) and concentrated to afford the crude N'-hydroxy-1-methyl-1H-indazole-5-carboximidamide (174 mg, 0.915 mmol, 70% yield). $^1$H NMR (400 MHz, CHLOROFORM-d) δ ppm 1.15-1.38 (m, 6H) 2.13 (s, 3H) 4.18 (dq, J=19.59, 7.15 Hz, 4H) 4.98 (br. s., 1H) 8.90 (br. s., 1H). LC/MS (m/z) ES$^+$=191 (M+1).

Step B (2S) (M)-methyl 2-(tert-butoxy)-2-(-4-(8-fluoro-5-methylchroman-6-yl)-1,6-dimethyl-2-(3-(1-methyl-1H-indazol-5-yl)-1,2,4-oxadiazol-5-yl)-1H-pyrrolo[2,3-b]pyridin-5-yl)acetate

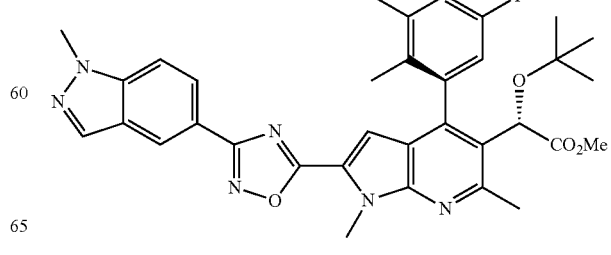

A solution of (2S)(M)-5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid (30.0 mg, 0.060 mmol) in N,N-Dimethylformamide (DMF) (0.6 mL) was treated sequentially with HOBT (11.98 mg, 0.078 mmol) and EDCl (12.14 mg, 0.078 mmol). The mixture was stirred for 20 minutes at ambient temperature. N'-hydroxy-1-methyl-1H-indazole-5-carboximidamide (14.88 mg, 0.078 mmol) was added and the mixture was heated to 90° C. for 18 hours and then allowed to stir at ambient temperature for 66 hours. The mixture was purified directly by reverse phase HPLC to afford the title compound (17 mg, 0.027 mmol) as a white solid. $^1$H NMR (400 MHz, CHLOROFORM-d) δ=8.61 (s, 1H), 8.19 (dd, J=1.4, 8.8 Hz, 1H), 8.11 (s, 1H), 7.51 (d, J=9.0 Hz, 1H), 6.92 (s, 1H), 6.78 (d, J=11.1 Hz, 1H), 5.20 (s, 1H), 4.40 (s, 3H), 4.37-4.32 (m, 2H), 4.14 (s, 3H), 3.63 (s, 3H), 2.89 (s, 3H), 2.77 (t, J=6.4 Hz, 2H), 2.26-2.12 (m, 2H), 1.84 (s, 3H), 1.15 (s, 9H); LC/MS (m/z) ES$^+$=653 (M+1).

Step C (2S)(M)-2-(tert-butoxy)-2-(4-(8-fluoro-5-methyl-chroman-6-yl)-1,6-dimethyl-2-(3-(1-methyl-1H-indazol-5-yl)-1,2,4-oxadiazol-5-yl)-1H-pyrrolo[2,3-b]pyridin-5-yl)acetic acid

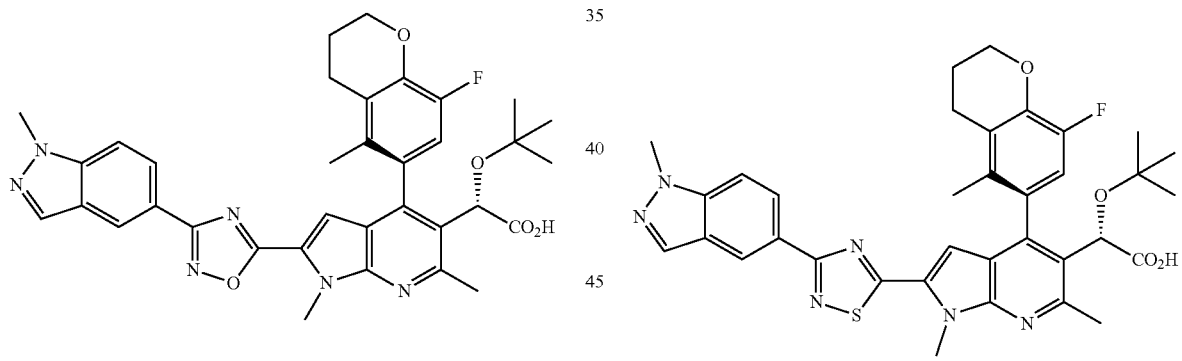

A solution of (2S)(M)-methyl 2-(tert-butoxy)-2-(-4-(8-fluoro-5-methylchroman-6-yl)-1,6-dimethyl-2-(3-(1-methyl-1H-indazol-5-yl)-1,2,4-oxadiazol-5-yl)-1H-pyrrolo[2,3-b]pyridin-5-yl)acetate (17 mg, 0.027 mmol) in Methanol (0.4 mL), Tetrahydrofuran (THF) (0.4 mL) and Water (0.2 mL) was treated with lithium hydroxide monohydrate (15.6 mg, 0.372 mmol) and then irradiated in the microwave at 120° C. for 10 minutes. The mixture was purified directly by reverse phase HPLC to afford the title product as a white solid (12 mg, 0.019 mmol, 70%). $^1$H NMR (400 MHz, CHLOROFORM-d) δ=8.62 (s, 1H), 8.20 (d, J=8.8 Hz, 1H), 8.12 (s, 1H), 7.52 (d, J=8.8 Hz, 1H), 6.95 (s, 1H), 6.83 (d, J=11.3 Hz, 1H), 5.28 (s, 1H), 4.40 (s, 3H), 4.37-4.27 (m, 2H), 4.15 (s, 3H), 2.83 (s, 3H), 2.76 (t, J=6.4 Hz, 2H), 2.23-2.11 (m, 2H), 1.94 (s, 3H), 1.16 (s, 9H); LC/MS (m/z) ES$^+$=639 (M+1).

Example 355

(2S)(M)-2-(tert-butoxy)-2-(-4-(8-fluoro-5-methyl-chroman-6-yl)-1,6-dimethyl-2-(3-(1-methyl-1H-indazol-5-yl)-1,2,4-thiadiazol-5-yl)-1H-pyrrolo[2,3-b]pyridin-5-yl)acetic acid

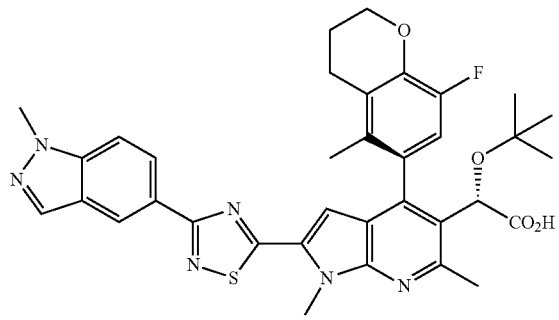

Steps A & B (2S)(M)-2-(tert-butoxy)-2-(-4-(8-fluoro-5-methyl-chroman-6-yl)-1,6-dimethyl-2-(3-(1-methyl-1H-indazol-5-yl)-1,2,4-thiadiazol-5-yl)-1H-pyrrolo[2,3-b]pyridin-5-yl)acetic acid A mixture of (2S)(M)-methyl 2-(tert-butoxy)-2-(2-(3-chloro-1,2,4-thiadiazol-5-yl)-4-(8-fluoro-5-methylchroman-6-yl)-1,6-dimethyl-1H-pyrrolo[2,3-b]pyridin-5-yl)acetate (20 mg, 0.035 mmol), (1-methyl-1H-indazol-5-yl)boronic acid (6.14 mg, 0.035 mmol) and Na$_2$CO$_3$ (0.052 mL, 0.105 mmol) in N,N-Dimethylformamide (DMF) (2 mL) was degassed with N$_2$ for 5 min. Pd(Ph$_3$P)$_4$ (8.07 mg, 6.98 µmol) was added and the reaction mixture was warmed to 90° C. After 30 min, the reaction mixture was cooled to ambient temperature and diluted with EtOAc. The organics were washed with sat. aq. NaHCO$_3$, brine, dried (Na$_2$SO$_4$), filtered and concentrated in vacuo to afford (2S)(M)-methyl 2-(tert-butoxy)-2-(-4-(8-fluoro-5-methylchroman-6-yl)-1,6-dimethyl-2-(3-(1-methyl-1H-indazol-5-yl)-1,2,4-thiadiazol-5-yl)-1H-pyrrolo[2,3-b]pyridin-5-yl)acetate as a solid. LC/MS (m/z) ES$^+$=669 (M+1). The residue was dissolved in MeOH (2 mL) and water (0.5 mL) and treated with LiOH (20 mg) and heated to 70° C. After 16 h, the reaction mixture was purified by reverse phase HPLC to afford the title compound (10 mg, 0.011 mmol, 33%) as a solid. $^1$H NMR (400 MHz, METHANOL-d$_4$) δ ppm 1.01 (s, 1H) 1.14 (s, 8H) 1.89 (s, 3H) 2.16 (br. s., 2H) 2.74-2.83 (m, 2H) 2.86 (s, 3H) 4.12 (s, 3H) 4.24-4.33 (m, 2H) 4.39 (s, 3H) 5.14-5.24 (m, 1H) 6.71 (s, 1H) 6.77 (d, 1H) 7.67 (d, J=8.78 Hz, 1H) 8.16 (s, 1H) 8.44 (d, J=8.53 Hz, 1H) 8.81 (s, 1H). LC/MS (m/z) ES$^+$=655 (M+1).

Example 356

(2S)(M)-2-(tert-butoxy)-2-(-4-(8-fluoro-5-methyl-chroman-6-yl)-1,6-dimethyl-2-(5-(1-methyl-1H-indazol-5-yl)-1,3,4-thiadiazol-2-yl)-1H-pyrrolo[2,3-b]pyridin-5-yl)acetic acid

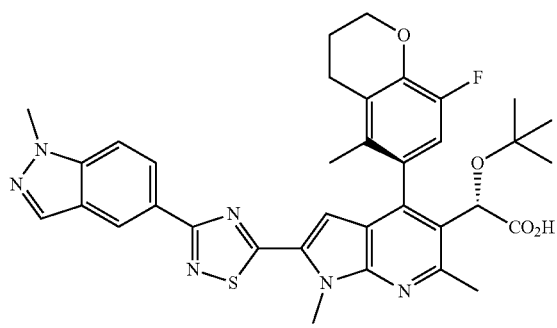

Step A (2S)(M)-2-(-2-(5-bromo-1,3,4-thiadiazol-2-yl)-4-(8-fluoro-5-methylchroman-6-yl)-1,6-dimethyl-1H-pyrrolo[2,3-b]pyridin-5-yl)-2-(tert-butoxy)acetic acid

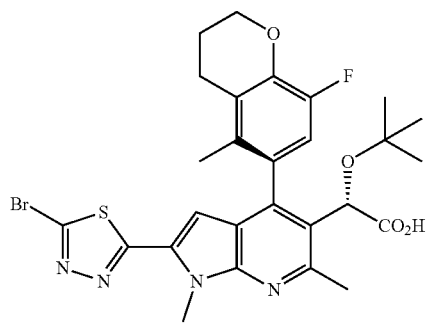

A solution of 2,5-dibromo-1,3,4-thiadiazole (46.2 mg, 0.189 mmol), (2S)(M)-methyl 2-(tert-butoxy)-2-(4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate (100 mg, 0.172 mmol) and Na$_2$CO$_3$ (0.258 mL, 0.517 mmol) in N,N-Dimethylformamide (DMF) (2 mL) was degassed with N$_2$ for 5 min. Pd(Ph$_3$P)$_4$ (39.8 mg, 0.034 mmol) was added and the mixture was stirred at 75° C. for 30 min. The reaction mixture was cooled to ambient temperature and diluted with EtOAc. The organics were washed with sat. aq. NaHCO$_3$, brine, dried (Na$_2$SO$_4$), filtered and concentrated in vacuo. The residue was purified by preparative TLC (MeOH/DCM 5%) to afford the title compound (45 mg). as a solid. LC/MS (m/z) ES$^+$=669 (M+1).

Steps B & C (2S)(M)-2-(tert-butoxy)-2-(-4-(8-fluoro-5-methyl-chroman-6-yl)-1,6-dimethyl-2-(5-(1-methyl-1H-indazol-5-yl)-1,3,4-thiadiazol-2-yl)-1H-pyrrolo[2,3-b]pyridin-5-yl)acetic acid

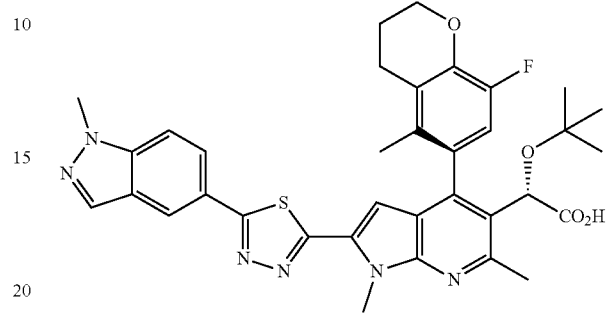

A mixture of (2S)(M)-methyl 2-(2-(5-bromo-1,3,4-thiadiazol-2-yl)-4-(8-fluoro-5-methylchroman-6-yl)-1,6-dimethyl-1H-pyrrolo[2,3-b]pyridin-5-yl)-2-(tert-butoxy)acetate (36 mg, 0.058 mmol), (1-methyl-1H-indazol-5-yl)boronic acid (15.39 mg, 0.087 mmol) and Na$_2$CO$_3$ (0.087 mL, 0.175 mmol) in N,N-Dimethylformamide (DMF) (2 mL) was degassed with N$_2$ for 5 min. Pd(Ph$_3$P)$_4$ (8.07 mg, 6.98 μmol) was added and the reaction mixture was warmed to 90° C. for 30 min. The reaction mixture was cooled to ambient temperature and diluted with EtOAc. The organics were washed with sat. aq. NaHCO$_3$, brine, dried (Na$_2$SO$_4$), filtered and concentrated in vacuo to afford (2S)(M)-methyl 2-(tert-butoxy)-2-(-4-(8-fluoro-5-methylchroman-6-yl)-1,6-dimethyl-2-(5-(1-methyl-1H-indazol-5-yl)-1,3,4-thiadiazol-2-yl)-1H-pyrrolo[2,3-b]pyridin-5-yl)acetate. LC/MS (m/z) ES$^+$=669 (M+1). The residue was dissolved in MeOH (2 mL) and water (0.5 mL) and treated with LiOH (20 mg) and heated to 70° C. After 16 h, the reaction mixture was purified by reverse phase HPLC to afford the title compound (11 mg, 0.012 mmol, 21%) as a solid. $^1$H NMR (400 MHz, METHANOL-d$_4$) δ ppm 1.13 (s, 9H) 1.88 (s, 3H) 2.06-2.25 (m, 2H) 2.73-2.83 (m, 2H) 2.88 (s, 3H) 4.07 (s, 3H) 4.25 (s, 3H) 4.29 (t, J=5.14 Hz, 2H) 5.20 (s, 1H) 6.57 (s, 1H) 6.79 (d, J=11.04 Hz, 1H) 7.62 (d, J=9.03 Hz, 1H) 8.02 (dd, J=8.91, 1.63 Hz, 1H) 8.10 (s, 1H) 8.33 (s, 1H). LC/MS (m/z) ES$^+$=655 (M+1).

Example 357

(2S)(M)-2-(tert-butoxy)-2-(-4-(8-fluoro-5-methyl-chroman-6-yl)-1,6-dimethyl-2-(5-(1-methyl-H-indazol-5-yl)-1,2,4-thiadiazol-3-yl)-1H-pyrrolo[2,3-b]pyridin-5-yl)acetic acid

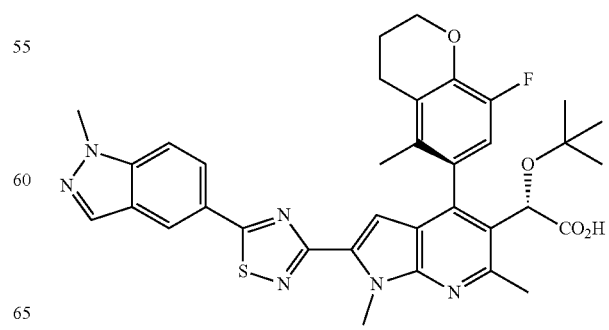

Step A

3-Chloro-5-(1-methyl-1H-indazol-5-yl)-1,2,4-thiadiazole

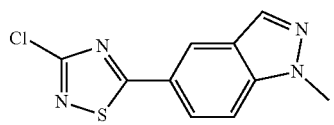

A solution of 3,5-dichloro-1,2,4-thiadiazole (100 mg, 0.645 mmol), Na$_2$CO$_3$ (0.968 mL, 1.935 mmol) and (1-methyl-1H-indazol-5-yl)boronic acid (114 mg, 0.645 mmol) in DMF (4 mL) was degassed under N$_2$ for 10 min. Pd(Ph$_3$P)$_4$ (149 mg, 0.129 mmol) was added and the mixture was stirred at 80° C. for 2 h. The reaction mixture was cooled to ambient temperature and diluted with EtOAc. The organics were washed with water, brine, dried (Na$_2$SO$_4$), filtered and concentrated in vacuo. The residue was purified by preparative TLC (5% MeOH/DCM) to afford the title compound as a solid. $^1$H NMR (400 MHz, CHLOROFORM-d) δ ppm 4.12 (s, 3H) 7.50 (d, J=8.79 Hz, 1H) 7.94 (d, J=8.79 Hz, 1H) 8.11 (s, 1H) 8.39 (s, 1H). LC/MS (m/z) ES$^+$=251(M+1).

Steps B & C

(2S)(M)-2-(tert-butoxy)-2-(-4-(8-fluoro-5-methylchroman-6-yl)-1,6-dimethyl-2-(5-(1-methyl-1H-indazol-5-yl)-1,2,4-thiadiazol-3-yl)-1H-pyrrolo[2,3-b]pyridin-5-yl)acetic acid

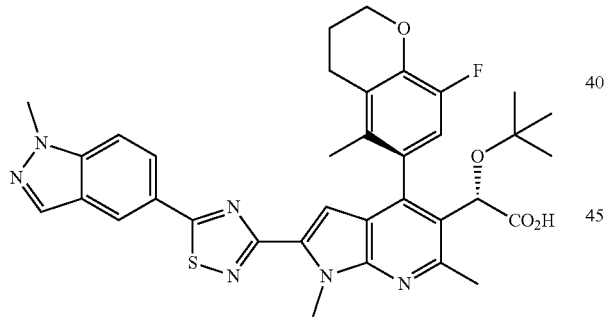

A solution of 3-chloro-5-(1-methyl-1H-indazol-5-yl)-1,2,4-thiadiazole (43.2 mg, 0.172 mmol), (2S)(M)-methyl 2-(tert-butoxy)-2-(4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate (100 mg, 0.172 mmol) and Na2CO3 (0.258 mL, 0.517 mmol) in N,N-Dimethylformamide (DMF) (2 mL) was degassed and added Pd(Ph$_3$P)$_4$ (39.8 mg, 0.034 mmol) and the mixture was stirred at 75° C. for 30 min. The reaction mixture was cooled to ambient temperature and diluted with EtOAc. The organics were washed with sat. aq. NaHCO$_3$, brine, dried (Na$_2$SO$_4$), filtered and concentrated in vacuo to afford (2S)(M)-methyl 2-(tert-butoxy)-2-(-4-(8-fluoro-5-methylchroman-6-yl)-1,6-dimethyl-2-(5-(1-methyl-1H-indazol-5-yl)-1,2,4-thiadiazol-3-yl)-1H-pyrrolo[2,3-b]pyridin-5-yl)acetate. LC/MS (m/z) ES$^+$=669 (M+1). The residue was dissolved in MeOH (2 mL) and water (0.5 mL) and treated with LiOH (20 mg) and heated to 70° C. After 16 h, the reaction mixture was purified by reverse phase HPLC to afford the title compound (5 mg, 0.0076 mmol, 4%) as a solid. $^1$H NMR (400 MHz, METHANOL-d$_4$) d ppm 1.11 (s, 9H) 1.29 (s, 3H) 1.94 (s, 3H) 2.17 (br. s., 3H) 2.81 (d, J=4.77 Hz, 3H) 2.88 (s, 3H) 4.11 (s, 3H) 4.27-4.33 (m, 2H) 4.35 (s, 3H) 5.11 (s, 1H) 5.49 (s, 1H) 6.73-6.87 (m, 2H) 7.69 (d, J=8.78 Hz, 1H) 8.08 (dd, J=8.91, 1.13 Hz, 1H) 8.16 (s, 1H) 8.56 (s, 1H). LC/MS (m/z) ES$^+$=655 (M+1).

Example 358

(2S)(M)-2-(tert-butoxy)-2-(4-(8-fluoro-5-methylchroman-6-yl)-1,6-dimethyl-2-(4-(4-(tetrahydro-2H-pyran-4-yl)piperazin-1-yl)pyrimidin-2-yl)-1H-pyrrolo[2,3-b]pyridin-5-yl)acetic acid

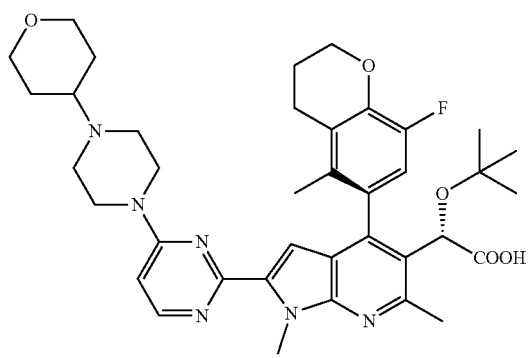

Step A

2-bromo-4-(4-(tetrahydro-2H-pyran-4-yl)piperazin-1-yl)pyrimidine

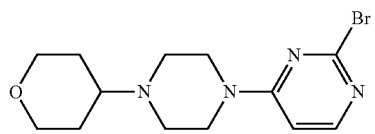 [SMILES: Brc1nccc(N2CCN(C3CCOCC3)CC2)n1]

A solution of 2,4-dibromopyrimidine (50 mg, 0.210 mmol) and 1-(tetrahydro-2H-pyran-4-yl)piperazine, 2 Hydrochloride (51.1 mg, 0.210 mmol) in Ethanol (1 mL) was treated with DIPEA (0.147 mL, 0.841 mmol) and DMAP (cat.) and stirred at ambient temperature for 1 h. The reaction mixture was concentrated in vacuo and triturated with water, filtered and the solid washed with water then dried in vacuo to provide 2-bromo-4-(4-(tetrahydro-2H-pyran-4-yl)piperazin-1-yl)pyrimidine (43 mg, 0.130 mmol, 61.9% yield) as an off-white solid. $^1$H NMR (400 MHz, CHLOROFORM-d) δ ppm 1.54 (s, 2H) 1.73 (br. s., 2H) 2.48 (br. s., 1H) 2.61 (br. s., 4H) 3.38 (t, J=11.24 Hz, 2H) 3.65 (br. s., 4H) 4.02 (br. s., 2H) 6.40 (d, J=6.25 Hz, 1H) 7.95 (d, J=5.86 Hz, 1H). LC/MS (m/z) ES$^+$=327 (M+1).

Step B (2S)(M)-Methyl-2-(tert-butoxy)-2-(4-(8-fluoro-5-methylchroman-6-yl)-1,6-dimethyl-2-(4-(4-(tetrahydro-2H-pyran-4-yl)piperazin-1-yl)pyrimidin-2-yl)-1H-pyrrolo[2,3-b]pyridin-5-yl)acetic acid

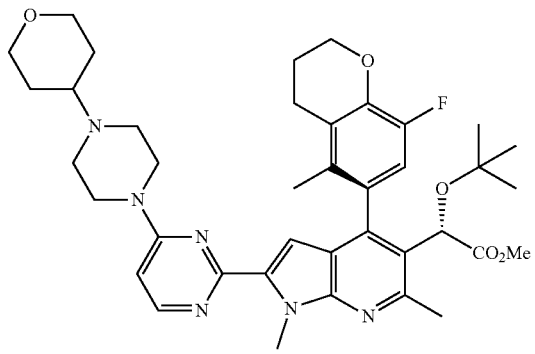

A solution of (2S)(M)-methyl 2-(tert-butoxy)-2-(4-(8-fluoro-5-methylchroman-6-yl)-1,6-dimethyl-2-(4,4,5,5-tetramethyl-1,3,2-dioxaborolan-2-yl)-1H-pyrrolo[2,3-b]pyridin-5-yl)acetate (50 mg, 0.082 mmol), 2-bromo-4-(4-(tetrahydro-2H-pyran-4-yl)piperazin-1-yl)pyrimidine (32.1 mg, 0.098 mmol), and sodium carbonate (0.082 mL, 0.164 mmol) (2M/water) in N,N-Dimethylformamide (DMF) (1 mL) was degassed with N₂ for 5 min. Pd(PPh₃)₄ (9.46 mg, 8.18 µmol) was added and the reaction mixture placed in a 90° C. oil bath. After 1 h, the reaction mixture was cooled to ambient temperature and diluted with EtOAc. The organics were washed with water, brine, dried (Na₂SO₄), filtered and concentrated in vacuo. The residue was purified by silica gel chromatography (5% MeOH/DCM) to afford the title compound (36 mg, 0.044 mmol, 53.4% yield) as a yellow foam. ¹H NMR (400 MHz, CHLOROFORM-d) δ ppm 1.11 (s, 9H). 1.55 (br. s., 4H) 1.69-1.90 (m, 5H) 2.14 (d, J=4.10 Hz, 2H) 2.48 (br. s., 1H) 2.56-2.76 (m, 7H) 2.82 (s, 3H) 3.30-3.47 (m, 2H) 3.59 (s, 3H) 3.61-3.79 (m, 4H) 3.94-4.11 (m, 2H) 4.18- 4.38 (m, 3H) 5.15 (s, 1H) 6.66-6.85 (m, 2H) 8.24 (d, J=5.86 Hz, 1H). LC/MS (m/z) ES⁺=701 (M+1).

Step C (2S)(M)-2-(tert-butoxy)-2-(4-(8-fluoro-5-methylchroman-6-yl)-1,6-dimethyl-2-(4-(4-(tetrahydro-2H-pyran-4-yl)piperazin-1-yl)pyrimidin-2-yl)-1H-pyrrolo[2,3-b]pyridin-5-yl)acetic acid

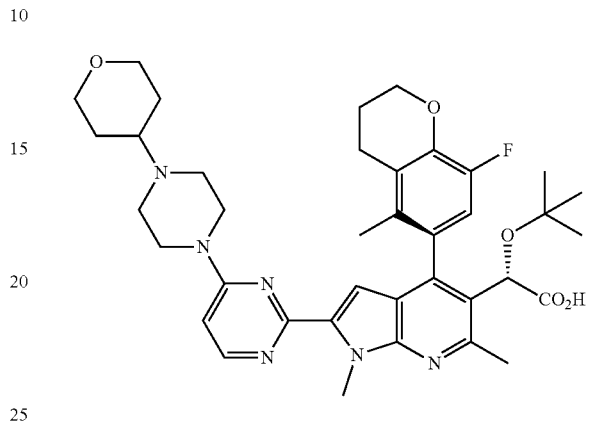

A solution of (2S)(M)-methyl 2-(tert-butoxy)-2-(4-(8-fluoro-5-methylchroman-6-yl)-1,6-dimethyl-2-(4-(4-(tetrahydro-2H-pyran-4-yl)piperazin-1-yl)pyrimidin-2-yl)-1H-pyrrolo[2,3-b]pyridin-5-yl)acetate (36 mg, 0.049 mmol) in Tetrahydrofuran (THF) (0.4 mL)/Methanol (0.4 mL)/Water (0.2 mL) was treated with lithium hydroxide, hydrate (10 mg, 0.238 mmol) and stirred at 65° C. for 2.5 h. The reaction mixture was purified by reverse phase HPLC to afford the title compound (28.8 mg, 0.031 mmol, 63.9% yield) as a yellow foam. ¹H NMR (400 MHz, DMSO-d₆) δ ppm 1.03 (s, 9H) 1.65 (d, J=7.62 Hz, 2H) 1.79 (s, 3H) 1.92-2.14 (m, 4H) 2.64-2.79 (m, 5H) 3.16 (br. s., 2H) 3.24-3.41 (m, 4H) 3.42-3.57 (m, 1H) 3.65 (br. s., 2H) 3.99 (d, J=7.23 Hz, 2H) 4.20 (s, 3H) 4.24 (t, J=5.08 Hz, 2H) 4.61 (br. s., 2H) 4.99 (s, 1H) 6.67 (s, 1H) 6.78 (d, J=11.33 Hz, 1H) 6.94 (d, J=6.44 Hz, 1H) 8.37 (d, J=6.25 Hz, 1H) 12.5 (br s, 1H). LC/MS (m/z) ES⁺=687 (M+1).

Compounds in Table 13 (examples 359-366) were synthesized using the procedure described above with the appropriate amine.

TABLE 13

| Example | Structure | MW | Observed Mass |
|---|---|---|---|
| 359 | 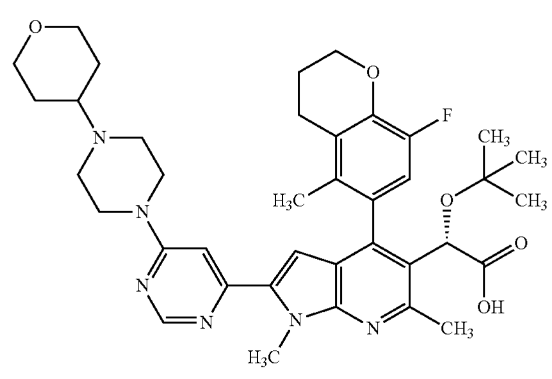 | 686.82 | 687 |

TABLE 13-continued

| Example | Structure | MW | Observed Mass |
|---|---|---|---|
| 360 | 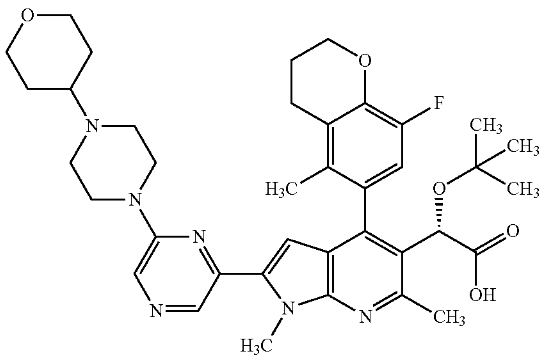 [SMILES: Cc1nc2c(cc(-c3cncc(N4CCN(C5CCOCC5)CC4)n3)n2C)c(-c2cc(F)c3c(c2C)CCCO3)c1[C@H](OC(C)(C)C)C(=O)O] | 686.82 | 687 |
| 361 | 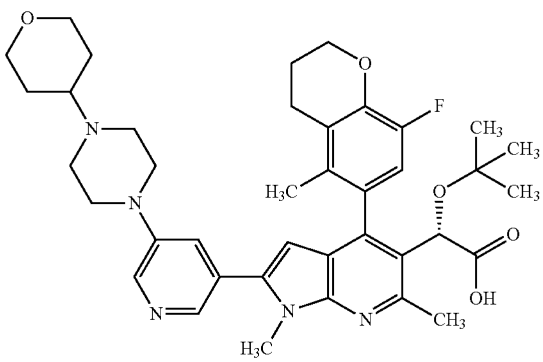 [SMILES: Cc1nc2c(cc(-c3cncc(N4CCN(C5CCOCC5)CC4)c3)n2C)c(-c2cc(F)c3c(c2C)CCCO3)c1[C@H](OC(C)(C)C)C(=O)O] | 685.83 | 686 |
| 362 | 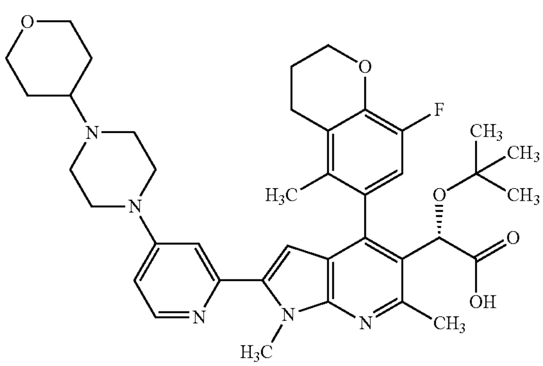 [SMILES: Cc1nc2c(cc(-c3cc(N4CCN(C5CCOCC5)CC4)ccn3)n2C)c(-c2cc(F)c3c(c2C)CCCO3)c1[C@H](OC(C)(C)C)C(=O)O] | 685.83 | 686 |
| 363 | 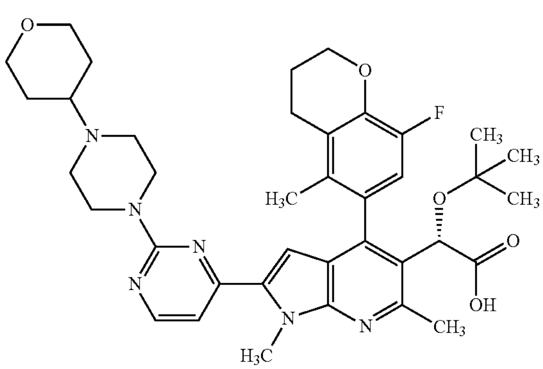 | 686.82 | 687 |

TABLE 13-continued

| Example | Structure | MW | Observed Mass |
|---|---|---|---|
| 364 | 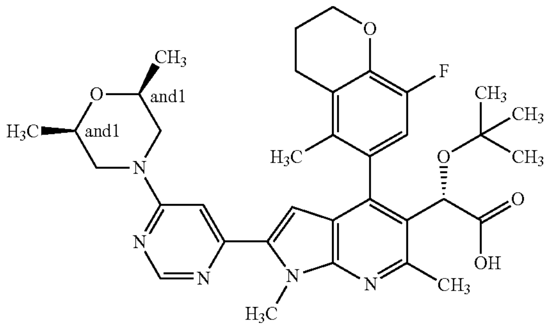 [SMILES: Cc1nc2c(cc(-c3cc(N4C[C@@H](C)O[C@@H](C)C4)ncn3)n2C)c(-c2cc(F)c3c(c2C)CCCO3)c1[C@H](OC(C)(C)C)C(=O)O] | 631.74 | 632 |
| 365 | 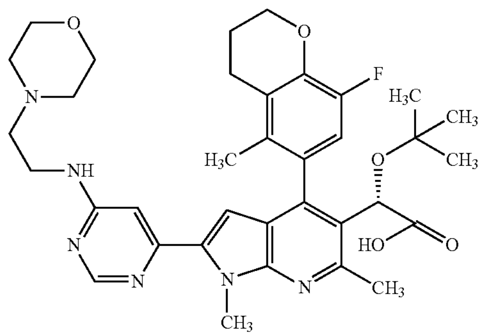 [SMILES: Cc1nc2c(cc(-c3cc(NCCN4CCOCC4)ncn3)n2C)c(-c2cc(F)c3c(c2C)CCCO3)c1[C@H](OC(C)(C)C)C(=O)O] | 646.75 | 647 |
| 366 | 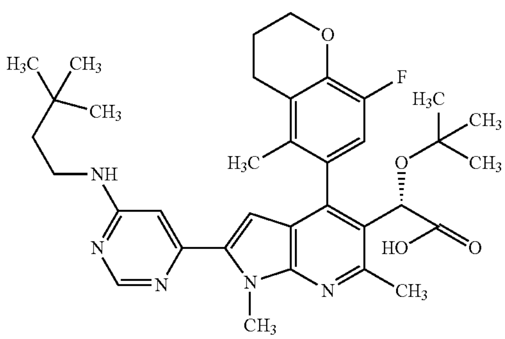 [SMILES: Cc1nc2c(cc(-c3cc(NCCC(C)(C)C)ncn3)n2C)c(-c2cc(F)c3c(c2C)CCCO3)c1[C@H](OC(C)(C)C)C(=O)O] | 617.75 | 618 |

Compounds in Table 14 (examples 367-409) were synthesized using the above procedures with the appropriate amine.

TABLE 14

| Example | Structure | MW | Observed Mass |
|---|---|---|---|
| 367 | 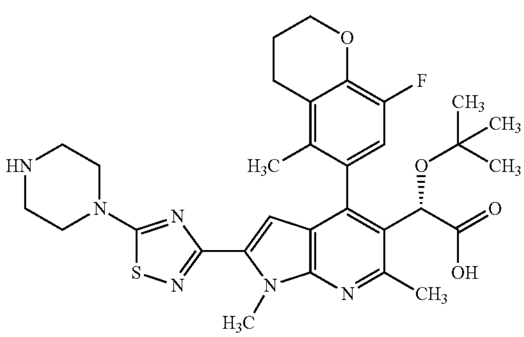 [SMILES: Cc1nc2c(cc(-c3nsc(N4CCNCC4)n3)n2C)c(-c2cc(F)c3c(c2C)CCCO3)c1[C@H](OC(C)(C)C)C(=O)O] | 608.73 | 609 |

TABLE 14-continued

| Example | Structure | MW | Observed Mass |
|---|---|---|---|
| 368 | 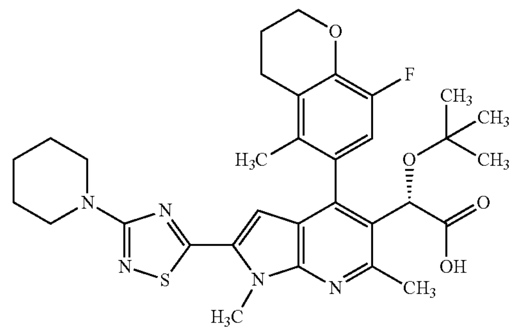 [SMILES: Cc1nc2c(cc(-c3nc(N4CCCCC4)ns3)n2C)c(-c2cc(F)c3c(c2C)CCCO3)c1[C@H](OC(C)(C)C)C(=O)O] | 607.74 | 608 |
| 369 | 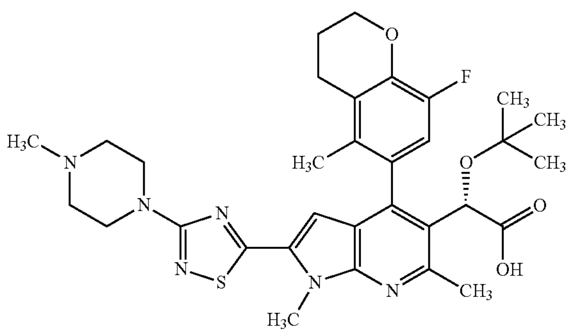 | 622.75 | 623 |
| 370 | 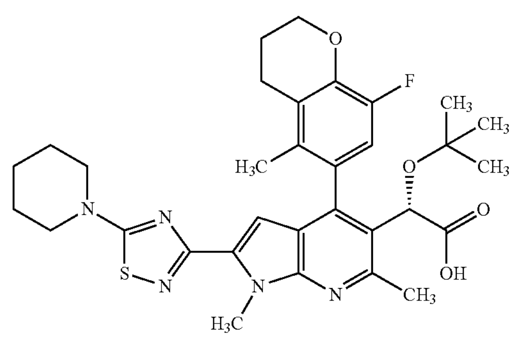 [SMILES: Cc1nc2c(cc(-c3nsc(N4CCCCC4)n3)n2C)c(-c2cc(F)c3c(c2C)CCCO3)c1[C@H](OC(C)(C)C)C(=O)O] | 607.74 | 608 |
| 371 | 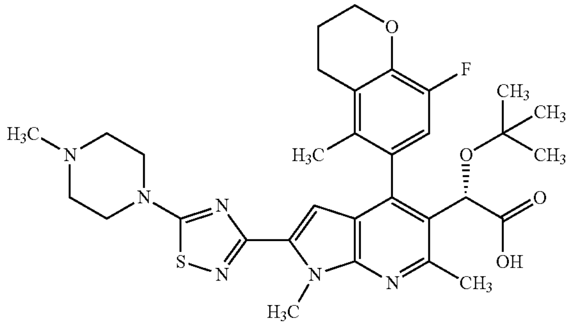 | 622.75 | 623 |

TABLE 14-continued

| Example | Structure | MW | Observed Mass |
|---|---|---|---|
| 372 | 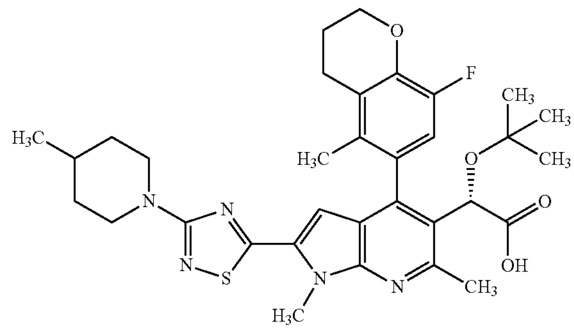 [SMILES: Cc1nc2c(cc(-c3nc(N4CCC(C)CC4)ns3)n2C)c(-c2cc(F)c3c(c2C)CCCO3)c1[C@H](OC(C)(C)C)C(=O)O] | 621.76 | 622 |
| 373 | 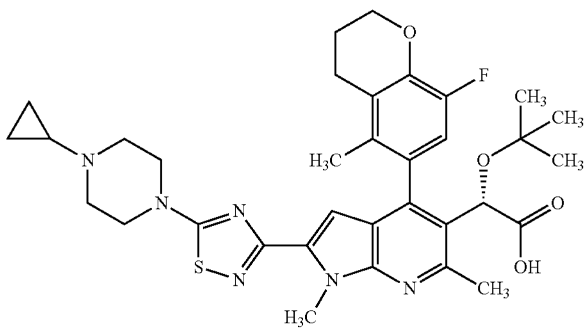 [SMILES: Cc1nc2c(cc(-c3nsc(N4CCN(C5CC5)CC4)n3)n2C)c(-c2cc(F)c3c(c2C)CCCO3)c1[C@H](OC(C)(C)C)C(=O)O] | 648.79 | 649 |
| 374 | 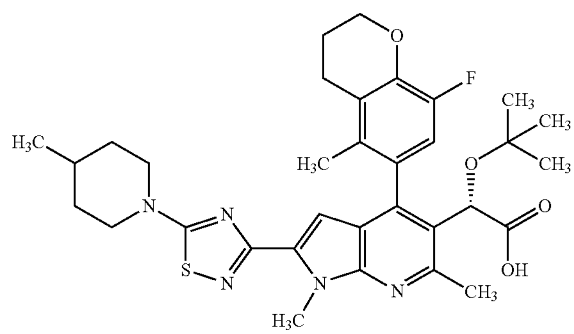 [SMILES: Cc1nc2c(cc(-c3nsc(N4CCC(C)CC4)n3)n2C)c(-c2cc(F)c3c(c2C)CCCO3)c1[C@H](OC(C)(C)C)C(=O)O] | 621.76 | 622 |
| 375 | 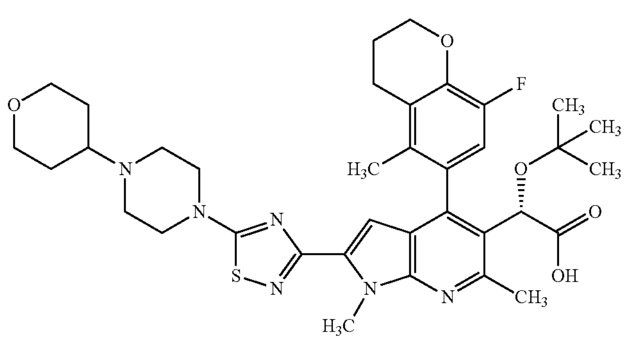 [SMILES: Cc1nc2c(cc(-c3nsc(N4CCN(C5CCOCC5)CC4)n3)n2C)c(-c2cc(F)c3c(c2C)CCCO3)c1[C@H](OC(C)(C)C)C(=O)O] | 692.84 | 693 |

TABLE 14-continued

| Example | Structure | MW | Observed Mass |
|---|---|---|---|
| 376 | 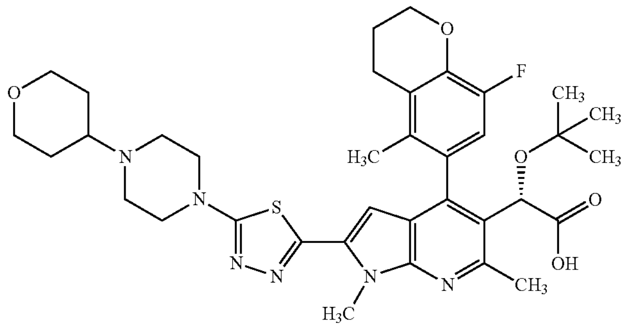 [SMILES: Cc1nc2c(cc(-c3nnc(N4CCN(C5CCOCC5)CC4)s3)n2C)c(-c2cc(F)c3c(c2C)CCCO3)c1[C@H](OC(C)(C)C)C(=O)O] | 692.84 | 693 |
| 377 | 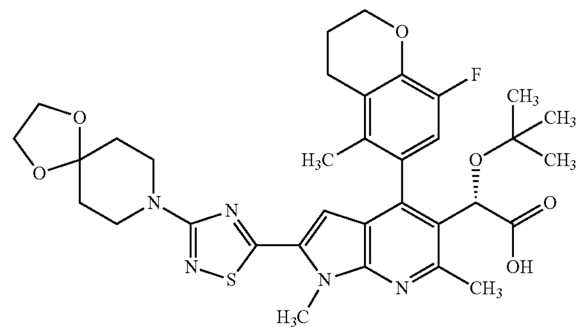 [SMILES: Cc1nc2c(cc(-c3nc(N4CCC5(CC4)OCCO5)ns3)n2C)c(-c2cc(F)c3c(c2C)CCCO3)c1[C@H](OC(C)(C)C)C(=O)O] | 665.78 | 666 |
| 378 | 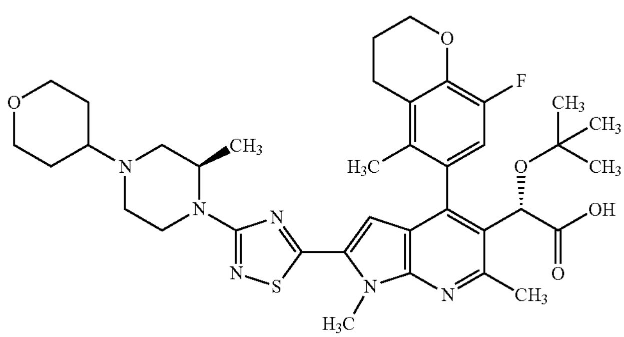 [SMILES: Cc1nc2c(cc(-c3nc(N4CCN(C5CCOCC5)C[C@H]4C)ns3)n2C)c(-c2cc(F)c3c(c2C)CCCO3)c1[C@H](OC(C)(C)C)C(=O)O] | 706.87 | 707 |
| 379 | 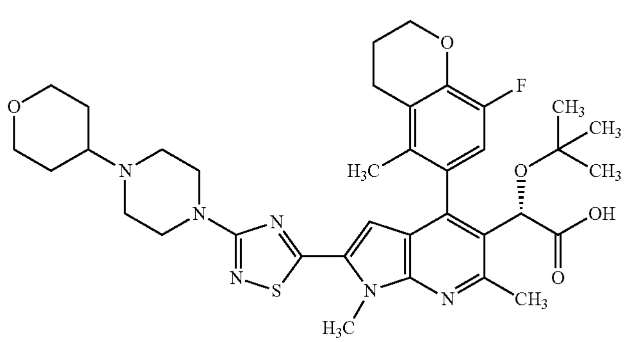 [SMILES: Cc1nc2c(cc(-c3nc(N4CCN(C5CCOCC5)CC4)ns3)n2C)c(-c2cc(F)c3c(c2C)CCCO3)c1[C@H](OC(C)(C)C)C(=O)O] | 692.84 | 693 |

TABLE 14-continued

| Example | Structure | MW | Observed Mass |
|---|---|---|---|
| 380 | 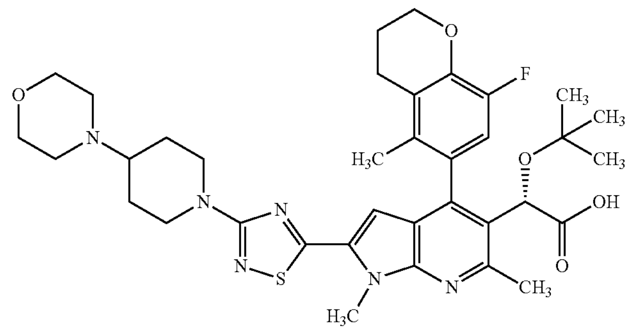 | 692.84 | 693 |
| 381 | 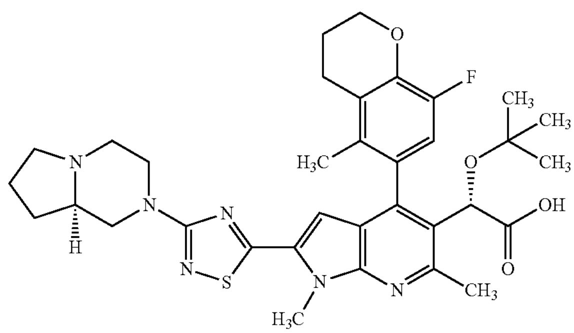 [SMILES: Cc1nc2c(cc(-c3nc(N4CCN5CCC[C@@H]5C4)ns3)n2C)c(-c2cc(F)c3c(c2C)CCCO3)c1[C@H](OC(C)(C)C)C(=O)O] | 648.79 | 649 |
| 382 | 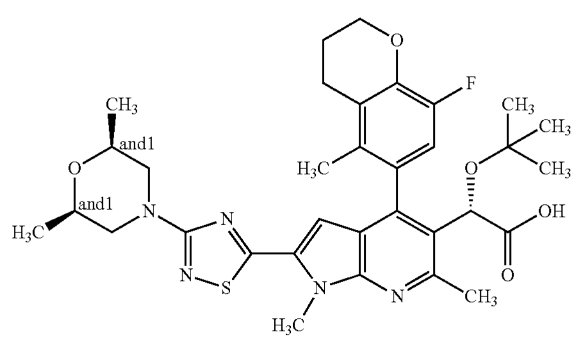 [SMILES: Cc1nc2c(cc(-c3nc(N4C[C@@H](C)O[C@@H](C)C4)ns3)n2C)c(-c2cc(F)c3c(c2C)CCCO3)c1[C@H](OC(C)(C)C)C(=O)O] | 637.76 | 638 |
| 383 | 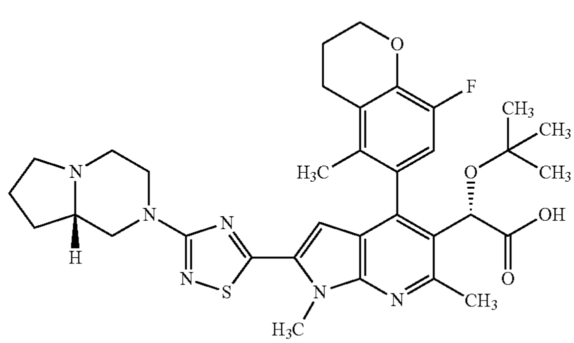 [SMILES: Cc1nc2c(cc(-c3nc(N4CCN5CCC[C@H]5C4)ns3)n2C)c(-c2cc(F)c3c(c2C)CCCO3)c1[C@H](OC(C)(C)C)C(=O)O] | 648.79 | 649 |

TABLE 14-continued

| Example | Structure | MW | Observed Mass |
|---|---|---|---|
| 384 | 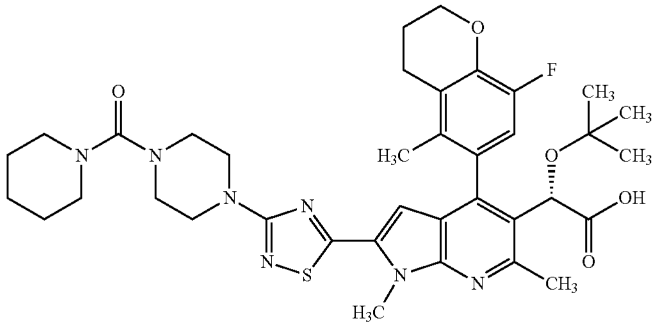 [SMILES: Cc1nc2c(cc(-c3nc(N4CCN(C(=O)N5CCCCC5)CC4)ns3)n2C)c(-c2cc(F)c3c(c2C)CCCO3)c1[C@H](OC(C)(C)C)C(=O)O] | 719.87 | 720 |
| 385 | 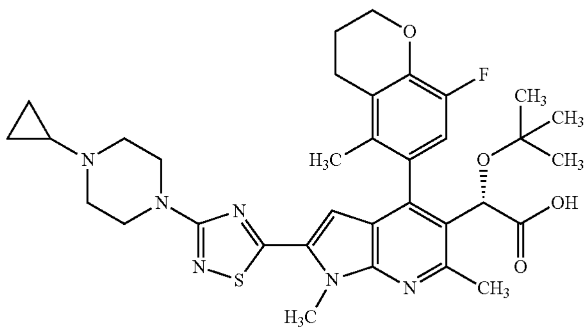 [SMILES: Cc1nc2c(cc(-c3nc(N4CCN(C5CC5)CC4)ns3)n2C)c(-c2cc(F)c3c(c2C)CCCO3)c1[C@H](OC(C)(C)C)C(=O)O] | 648.79 | 649 |
| 386 | 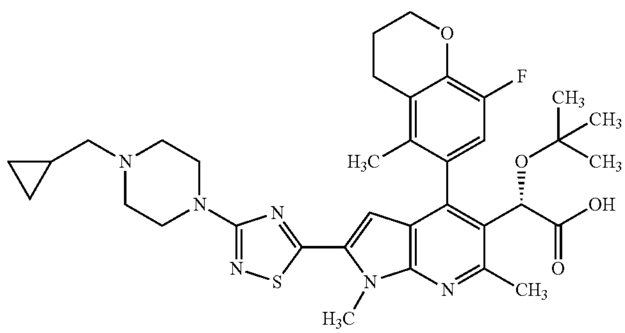 [SMILES: Cc1nc2c(cc(-c3nc(N4CCN(CC5CC5)CC4)ns3)n2C)c(-c2cc(F)c3c(c2C)CCCO3)c1[C@H](OC(C)(C)C)C(=O)O] | 662.82 | 663 |
| 387 | 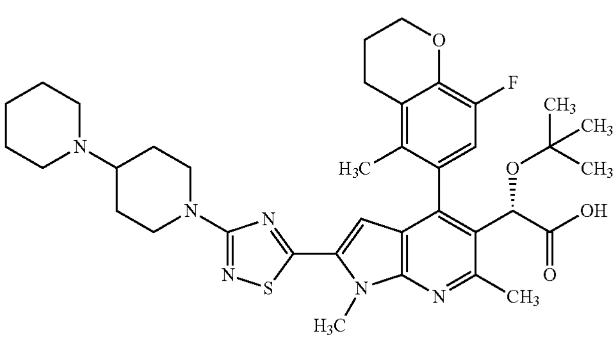 [SMILES: Cc1nc2c(cc(-c3nc(N4CCC(N5CCCCC5)CC4)ns3)n2C)c(-c2cc(F)c3c(c2C)CCCO3)c1[C@H](OC(C)(C)C)C(=O)O] | 690.87 | 691 |

TABLE 14-continued

| Example | Structure | MW | Observed Mass |
|---|---|---|---|
| 388 | 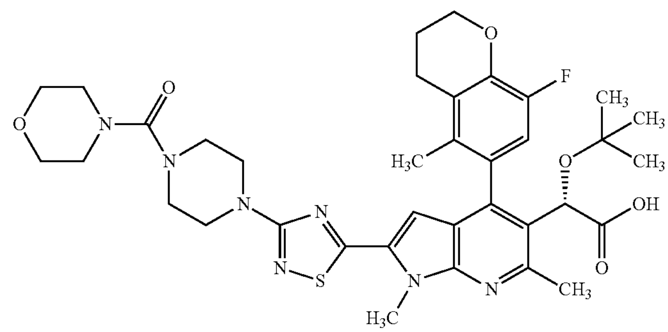 | 721.84 | 722 |
| 389 | 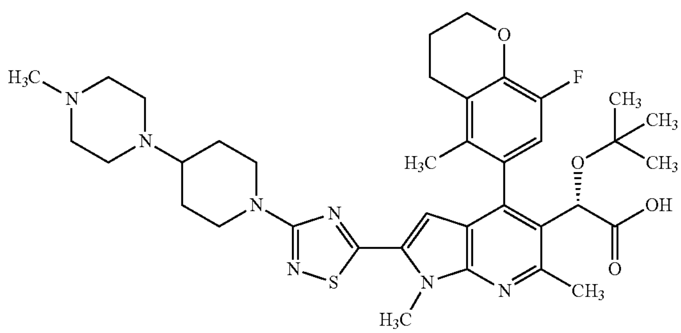 [SMILES: Cc1nc2c(cc(-c3nc(N4CCC(N5CCN(C)CC5)CC4)ns3)n2C)c(-c2cc(F)c3c(c2C)CCCO3)c1[C@H](OC(C)(C)C)C(=O)O] | 705.88 | 706 |
| 390 | 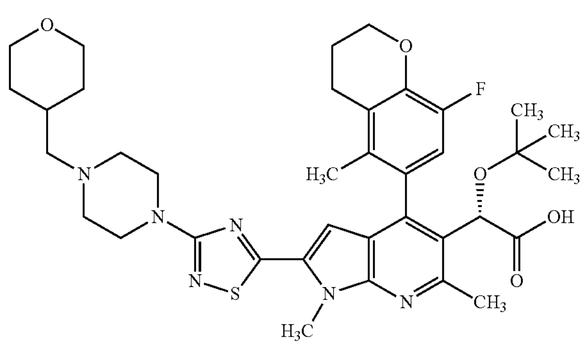 [SMILES: Cc1nc2c(cc(-c3nc(N4CCN(CC5CCOCC5)CC4)ns3)n2C)c(-c2cc(F)c3c(c2C)CCCO3)c1[C@H](OC(C)(C)C)C(=O)O] | 706.87 | 707 |
| 391 | 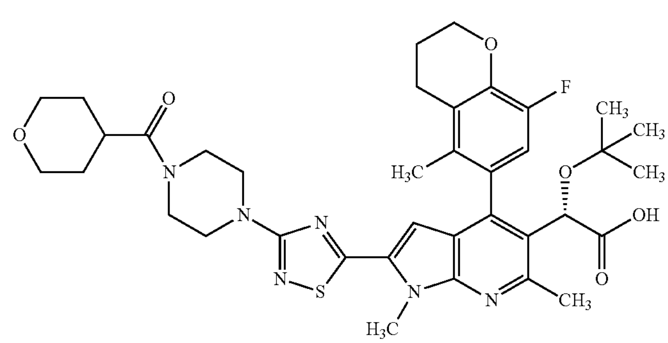 [SMILES: Cc1nc2c(cc(-c3nc(N4CCN(C(=O)C5CCOCC5)CC4)ns3)n2C)c(-c2cc(F)c3c(c2C)CCCO3)c1[C@H](OC(C)(C)C)C(=O)O] | 720.85 | 721 |

| Example | Structure | MW | Observed Mass |
|---------|-----------|------|------|
| 392 | 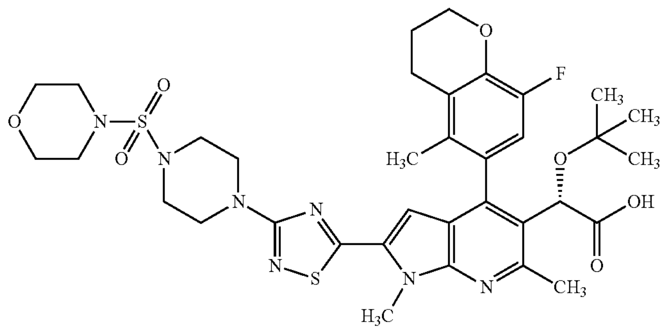 [SMILES: Cc1nc2c(cc(-c3nc(N4CCN(S(=O)(=O)N5CCOCC5)CC4)ns3)n2C)c(-c2cc(F)c3c(c2C)CCCO3)c1[C@H](OC(C)(C)C)C(=O)O] | 757.9 | 758 |
| 393 | 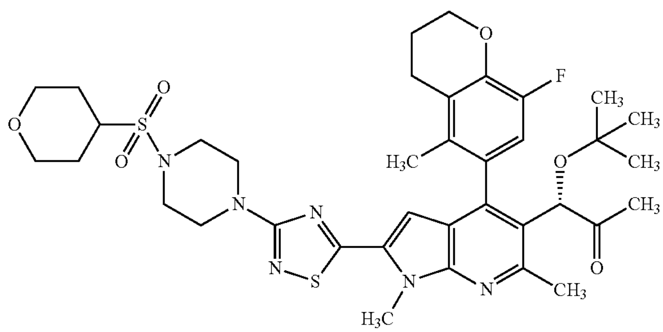 | 756.91 | 757 |
| 394 | 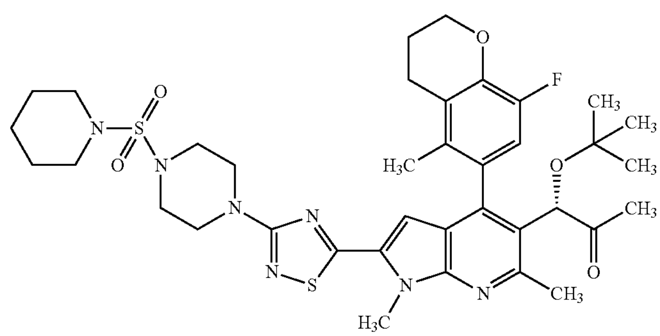 [SMILES: CC(=O)[C@@H](OC(C)(C)C)c1c(C)nc2c(cc(-c3nc(N4CCN(S(=O)(=O)N5CCCCC5)CC4)ns3)n2C)c1-c1cc(F)c2c(c1C)CCCO2] | 755.92 | 756 |
| 395 | 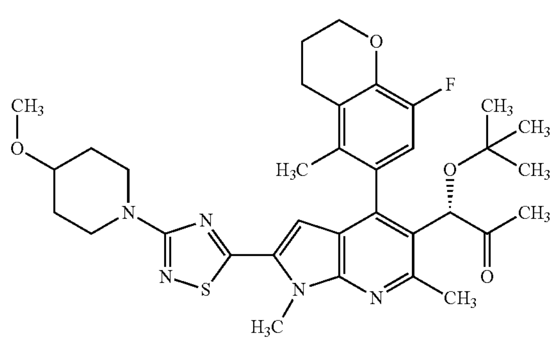 [SMILES: COC1CCN(c2nsc(-c3cc4c(-c5cc(F)c6c(c5C)CCCO6)c([C@H](OC(C)(C)C)C(C)=O)c(C)nc4n3C)n2)CC1] | 637.76 | 638 |

TABLE 14-continued

| Example | Structure | MW | Observed Mass |
|---|---|---|---|
| 396 | 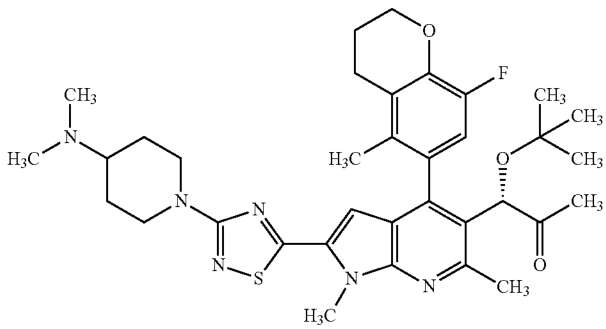 [SMILES: CC(=O)[C@@H](OC(C)(C)C)c1c(C)nc2c(cc(-c3nc(N4CCC(N(C)C)CC4)ns3)n2C)c1-c1cc(F)c2c(c1C)CCCO2] | 650.81 | 651 |
| 397 | 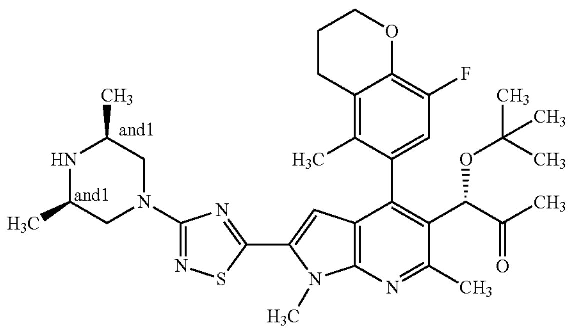 | 636.78 | 637 |
| 398 | 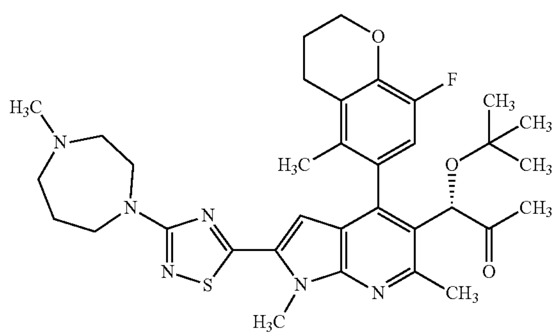 [SMILES: CC(=O)[C@@H](OC(C)(C)C)c1c(C)nc2c(cc(-c3nc(N4CCCN(C)CC4)ns3)n2C)c1-c1cc(F)c2c(c1C)CCCO2] | 636.78 | 637 |
| 399 | 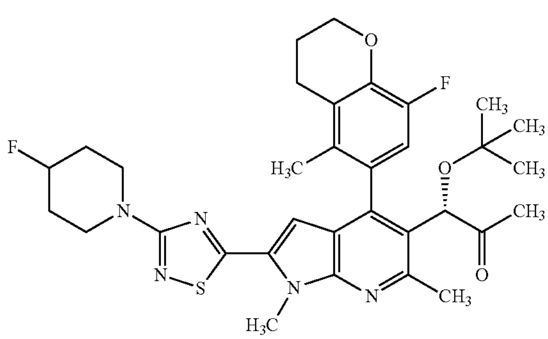 [SMILES: CC(=O)[C@@H](OC(C)(C)C)c1c(C)nc2c(cc(-c3nc(N4CCC(F)CC4)ns3)n2C)c1-c1cc(F)c2c(c1C)CCCO2] | 625.73 | 626 |

TABLE 14-continued
| Example | Structure | MW | Observed Mass |
|---|---|---|---|
| 400 | 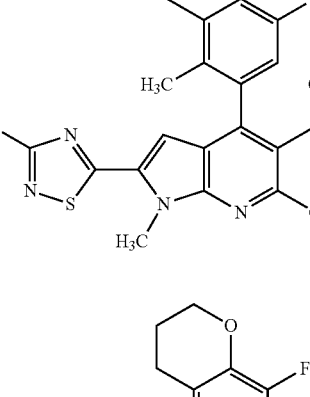 | 650.81 | 651 |
| 401 | 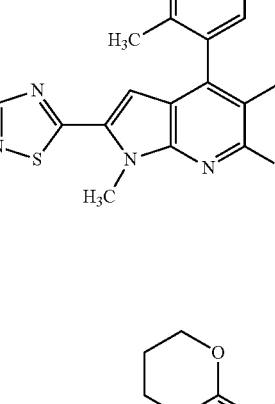 | 636.78 | 637 |
| 402 | 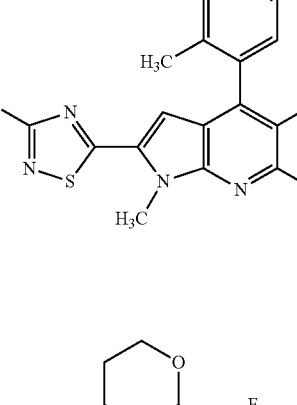 | 676.84 | 677 |
| 403 | 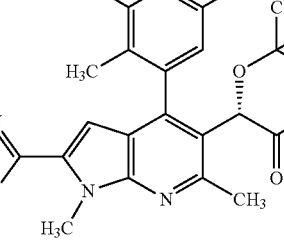 | 579.68 | 580 |

TABLE 14-continued

| Example | Structure | MW | Observed Mass |
|---|---|---|---|
| 404 | 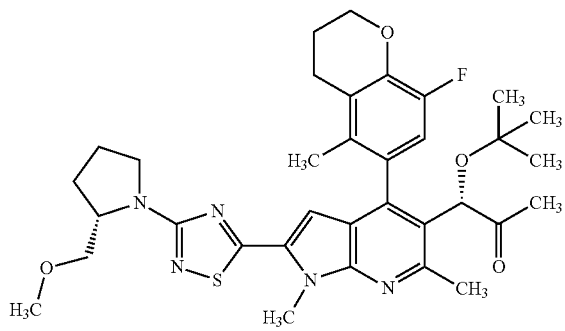 [SMILES: COC[C@@H]1CCCN1c1nsc(-c2cc3c(-c4cc(F)c5c(c4C)CCCO5)c([C@H](OC(C)(C)C)C(C)=O)c(C)nc3n2C)n1] | 637.76 | 638 |
| 405 | 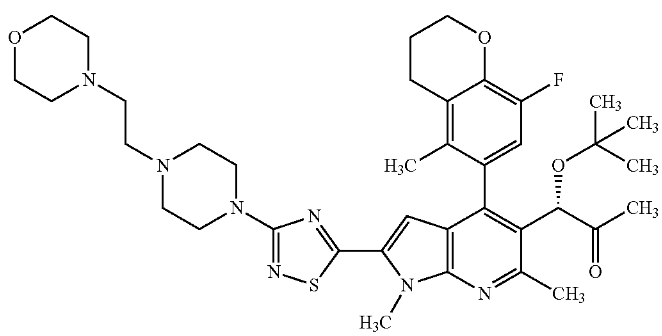 [SMILES: CC(=O)[C@@H](OC(C)(C)C)c1c(C)nc2c(cc(-c3nc(N4CCN(CCN5CCOCC5)CC4)ns3)n2C)c1-c1cc(F)c2c(c1C)CCCO2] | 721.88 | 722 |
| 406 | 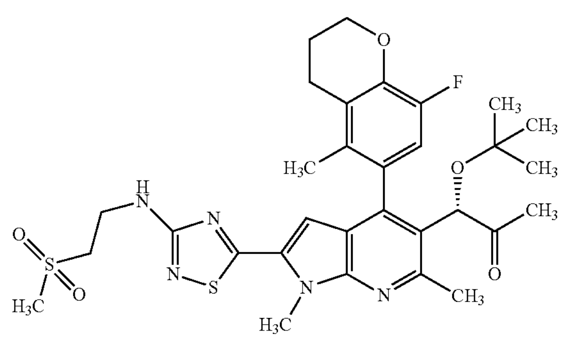 [SMILES: CC(=O)[C@@H](OC(C)(C)C)c1c(C)nc2c(cc(-c3nc(NCCS(C)(=O)=O)ns3)n2C)c1-c1cc(F)c2c(c1C)CCCO2] | 645.76 | 646 |
| 407 | 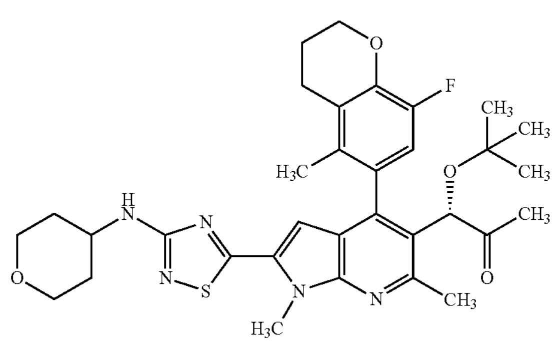 [SMILES: CC(=O)[C@@H](OC(C)(C)C)c1c(C)nc2c(cc(-c3nc(NC4CCOCC4)ns3)n2C)c1-c1cc(F)c2c(c1C)CCCO2] | 623.74 | 624 |

| Example | Structure | MW | Observed Mass |
|---|---|---|---|
| 408 | 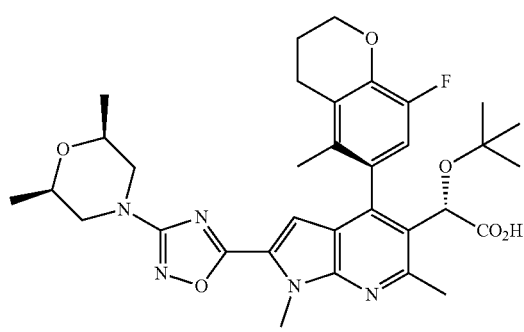 | 691.86 | 692 |
| 409 | 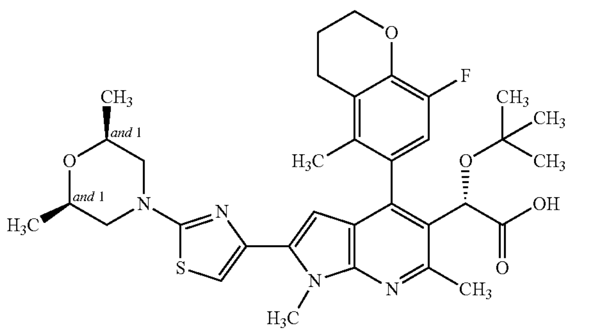 [SMILES: Cc1nc2c(cc(-c3csc(N4C[C@@H](C)O[C@@H](C)C4)n3)n2C)c(-c2cc(F)c3c(c2C)CCCO3)c1[C@H](OC(C)(C)C)C(=O)O] | 636.78 | 637 |

Example 410

(2S)(M)-2-(tert-butoxy)-2-(-2-(3-((2S,6R)-2,6-dimethylmorpholino)-1,2,4-oxadiazol-5-yl)-4-(8-fluoro-5-methylchroman-6-yl)-1,6-dimethyl-1H-pyrrolo[2,3-b]pyridin-5-yl)acetic acid

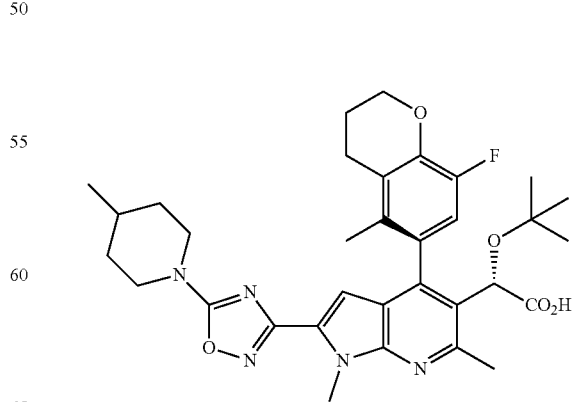

Example 410 was made in a manner similar to Example 27 except using cis-2,6-dimethylmorpholine as the amine.

$^1$H NMR (400 MHz, Chloroform-d) δ ppm=6.81 (s, 1H), 6.77 (d, J=10.9 Hz, 1H), 5.22 (s, 1H), 4.34-4.29 (m, 2H), 4.26 (s, 3H), 3.84 (d, J=12.5 Hz, 2H), 3.80-3.71 (m, 2H), 2.83 (s, 3H), 2.78-2.65 (m, 4H), 2.22-2.09 (m, 2H), 1.84 (s, 3H), 1.24 (d, J=6.1 Hz, 6H), 1.13 (s, 9H); LC/MS (m/z) ES$^+$=622.2 (M+1).

Example 411

(2S)(M)-2-(tert-butoxy)-2-(-4-(8-fluoro-5-methylchroman-6-yl)-1,6-dimethyl-2-(5-(4-methylpiperidin-1-yl)-1,2,4-oxadiazol-3-yl)-1H-pyrrolo[2,3-b]pyridin-5-yl)acetic acid

Step A (2S) (M)-methyl 2-(tert-butoxy)-2-((2-carbamoyl-4-(8-fluoro-5-methylchroman-6-yl)-1,6-dimethyl-1H-pyrrolo[2,3-b]pyridin-5-yl)acetate

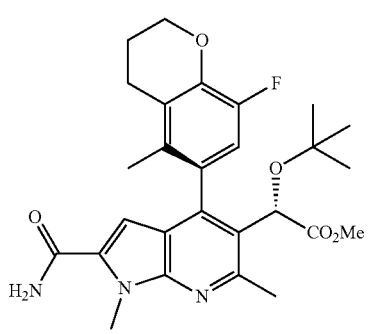

A solution of (2S)(M)-5-(-1-(tert-butoxy)-2-methoxy-2-oxoethyl)-4-(8-fluoro-5-methylchroman-6-yl)-1,6-dimethyl-1H-pyrrolo[2,3-b]pyridine-2-carboxylic acid (300 mg, 0.602 mmol) and CDI (240 mg, 1.480 mmol) in Tetrahydrofuran (THF) (6.0 mL) was heated to 65° C. for 10 minutes. The mixture was then cooled to 0° C. and treated with saturated NH$_3$ in THF (6.0 mL) in a sealed vessel and allowed to warm to ambient temperature. After 18 h, the reaction mixture was concentrated in vacuo. The residue was dissolved in EtOAc, washed with 1N HCl, followed by brine, dried over Na$_2$SO$_4$, filtered and concentrated to afford the title compound (297 mg, 0.59 mmol, 99%) as a white solid. $^1$H NMR (400 MHz, CHLOROFORM-d) d=6.74 (d, J=11.1 Hz, 1H), 6.28 (s, 1H), 5.13 (s, 1H), 4.31 (t, J=5.2 Hz, 2H), 4.15 (s, 3H), 3.60 (s, 3H), 2.86-2.80 (m, 3H), 2.78-2.67 (m, 2H), 2.21-2.09 (m, 2H), 1.80 (s, 3H), 1.15-1.06 (m, 9H); LC/MS (m/z) ES$^+$=498 (M+1).

Step B (2S) (M)-methyl 2-(tert-butoxy)-2-(-2-cyano-4-(8-fluoro-5-methylchroman-6-yl)-1,6-dimethyl-1H-pyrrolo[2,3-b]pyridin-5-yl)acetate

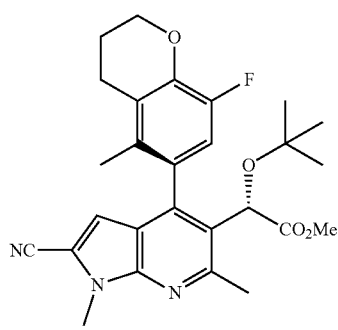

An ice cold solution of (2S)(M)-methyl 2-(tert-butoxy)-2-(2-carbamoyl-4-(8-fluoro-5-methylchroman-6-yl)-1,6-dimethyl-1H-pyrrolo[2,3-b]pyridin-5-yl)acetate (297 mg, 0.597 mmol) and triethylamine (0.125 mL, 0.895 mmol) in Tetrahydrofuran (THF) (8.0 mL) was treated slowly with TFAA (0.093 mL, 0.657 mmol) and then stirred at ambient temperature for 25 minutes. The mixture concentrated, then diluted with EtOAc, washed with water, dried over Na$_2$SO$_4$, filtered and concentrated in vacuo. The residue was purified on silica gel (0-30% hexanes/EtOAc) to afford the title compound (215 mg, 0.45 mmol, 75%) as an off-white residue. $^1$H NMR (400 MHz, CHLOROFORM-d) d=6.71 (d, J=11.1 Hz, 1H), 6.57 (s, 1H), 5.15 (s, 1H), 4.32 (t, J=5.2 Hz, 2H), 3.98 (s, 3H), 3.61 (s, 3H), 2.86-2.79 (m, 3H), 2.79-2.64 (m, 2H), 2.17 (dd, J=3.3, 6.1 Hz, 2H), 1.78 (s, 3H), 1.15-1.06 (m, 9H); LC/MS (m/z) ES$^+$=480 (M+1).

Step C (2S)(M)-methyl 2-(tert-butoxy)-2-(4-(8-fluoro-5-methylchroman-6-yl)-2-(N'-hydroxycarbamimidoyl)-1,6-dimethyl-1H-pyrrolo[2,3-b]pyridin-5-yl)acetate

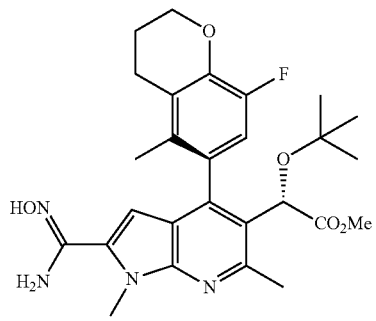

A mixture of (2S)(M)-methyl 2-(tert-butoxy)-2-(2-cyano-4-(8-fluoro-5-methylchroman-6-yl)-1,6-dimethyl-1H-pyrrolo[2,3-b]pyridin-5-yl)acetate (215 mg, 0.448 mmol), hydroxylamine hydrochloride (125 mg, 1.793 mmol) and sodium bicarbonate (188 mg, 2.242 mmol) in Methanol (6.0 mL) was heated to 60° C. for two hours. The mixture was concentrated in vacuo and then partitioned between EtOAc and water. The aq. phase was extracted with EtOAc, the combined extracts were dried over Na$_2$SO$_4$, filtered and concentrated to afford the title compound (230 mg, 0.449 mmol, 100%) a white solid. $^1$H NMR (400 MHz, CHLOROFORM-d) d=6.75 (d, J=11.3 Hz, 1H), 6.14 (s, 1H), 5.15 (s, 1H), 4.77 (br. s., 2H), 4.31 (t, J=5.2 Hz, 2H), 4.03 (s, 3H), 3.60 (s, 3H), 2.86-2.79 (m, 3H), 2.79-2.64 (m, 2H), 2.26-2.03 (m, 2H), 1.80 (s, 3H), 1.19-1.04 (m, 9H); LC/MS (m/z) ES$^+$=513 (M+1).

Step D (2S)(M)-Methyl-2-(tert-butoxy)-2-(-4-(8-fluoro-5-methylchroman-6-yl)-1,6-dimethyl-2-(5-(4-methylpiperidin-1-yl)-1,2,4-oxadiazol-3-yl)-1H-pyrrolo[2,3-b]pyridin-5-yl)acetic acid

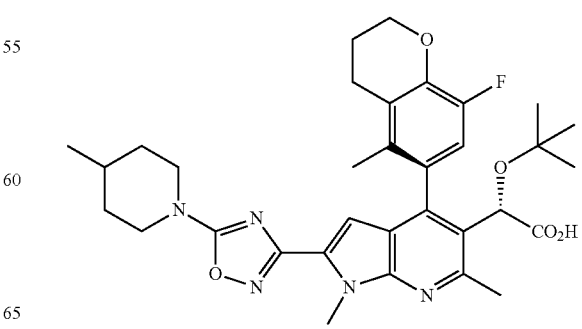

A solution of (2S)(M)-methyl 2-(tert-butoxy)-2-(4-(8-fluoro-5-methylchroman-6-yl)-2-(N'-hydroxycarbamimidoyl)-1,6-dimethyl-1H-pyrrolo[2,3-b]pyridin-5-yl)acetate (21.0 mg, 0.041 mmol) in 1,4-dioxane (1.0 mL) and N-methyl-2-pyrrolidone (0.1 mL) was treated with pyridine (6.60 µL, 0.082 mmol) and trichloroacetyl chloride (5.52 µL, 0.049 mmol) and the mixture was allowed to stir at ambient temperature overnight. The mixture was diluted with ethyl acetate, washed with saturated sodium bicarbonate, followed by brine, dried over sodium sulfate, filtered and concentrated in vacuo to afford a yellow residue (26 mg). The residue was dissolved in 4-methylpiperidine (0.7 mL) and irradiated in the microwave at 100° C. until the reaction was judged complete by LCMS (10-15 minutes). The mixture was concentrated and then purified directly by reverse phase chromatography to afford a white solid (4.7 mg, 19%). $^1$H NMR (400 MHz, CHLOROFORM-d) d=6.75 (d, J=11.3 Hz, 1H), 6.59 (s, 1H), 5.15 (s, 1H), 4.31 (t, J=5.2 Hz, 2H), 4.24-4.11 (m, 5H), 3.61 (s, 3H), 3.09 (td, J=2.5, 12.8 Hz, 2H), 2.84 (s, 3H), 2.77-2.66 (m, 2H), 2.17 (d, J=4.1 Hz, 2H), 1.78-1.65 (m, 5H), 1.37-1.19 (m, 3H), 1.12 (s, 9H), 0.99 (d, 3H); LC/MS (m/z) ES$^+$=620 (M+1).

Step E (2S)(M)-2-(tert-butoxy)-2-(-4-(8-fluoro-5-methylchroman-6-yl)-1,6-dimethyl-2-(5-(4-methylpiperidin-1-yl)-1,2,4-oxadiazol-3-yl)-1H-pyrrolo[2,3-b]pyridin-5-yl)acetic acid

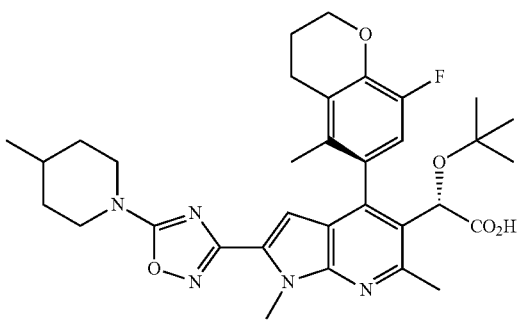

A mixture of (2S)(M)-methyl 2-(tert-butoxy)-2-(4-(8-fluoro-5-methylchroman-6-yl)-1,6-dimethyl-2-(5-(4-methylpiperidin-1-yl)-1,2,4-oxadiazol-3-yl)-1H-pyrrolo[2,3-b]pyridin-5-yl)acetate (6.50 mg, 10.49 µmol) and lithium hydroxide monohydrate (15.00 mg, 0.358 mmol) in Methanol (0.4 mL), Tetrahydrofuran (THF) (0.4 mL) and Water (0.2 mL) was irradiated in the microwave at 120° C. for 10 minutes. The reaction mixture was purified by reverse phase HPLC to afford the title compound (5.4 mg, 8.92 µmol, 85%). $^1$H NMR (400 MHz, CHLOROFORM-d) δ=6.79 (d, J=11.1 Hz, 1H), 6.63 (s, 1H), 5.23 (s, 1H), 4.30 (t, J=5.1 Hz, 2H), 4.23-4.11 (m, 5H), 3.09 (td, J=2.3, 12.8 Hz, 2H), 2.79 (s, 3H), 2.70 (q, J=6.5 Hz, 2H), 2.14 (dd, J=3.7, 6.1 Hz, 2H), 1.88 (s, 3H), 1.75 (d, J=11.9 Hz, 2H), 1.69-1.54 (m, 1H), 1.37-1.18 (m, 2H), 1.12 (s, 9H), 0.99 (d, J=6.4 Hz, 3H); LC/MS (m/z) ES$^+$=606 (M+1).

Example 412

(2S)(M)-2-(tert-butoxy)-2-(-4-(8-fluoro-5-methylchroman-6-yl)-1,6-dimethyl-2-yl)-methyl-1H-indazole-5-carboxamido)methyl)-1H-pyrrolo[2,3-b]pyridin-5-yl)acetic acid

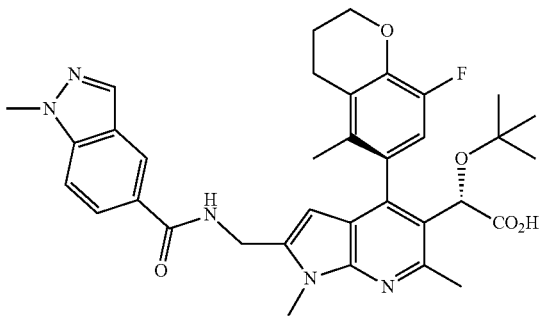

Step A (2S)(M)-methyl 2(-2-(aminomethyl)-4-(8-fluoro-5-methylchroman-6-yl)-1,6-dimethyl-1H-pyrrolo[2,3-b]pyridin-5-yl)-2-(tert-butoxy)acetate

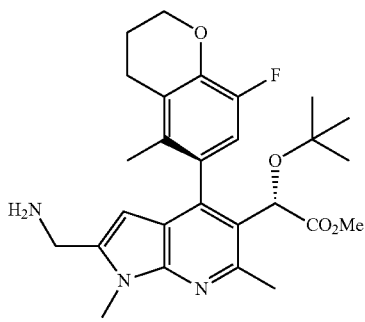

A solution of (2S)(M)-methyl 2-(tert-butoxy)-2-(-2-cyano-4-(8-fluoro-5-methylchroman-6-yl)-1,6-dimethyl-1H-pyrrolo[2,3-b]pyridin-5-yl)acetate (35.8 mg, 0.075 mmol) in Methanol (600 µl) and Tetrahydrofuran (THF) (200 µl) was treated with HCl (4N in dioxane) (22.40 µl, 0.090 mmol) and Pd/C, degussa type (7.94 mg, 7.47 µmol), purged and backfilled with N$_2$ 3×, H$_2$ 3×, and stirred under H$_2$ (50 psi) at ambient temperature overnight. The mixture was filtered through acrodisc psf ptfe 0.45 um, washed with MeOH and concentrated. Purification with reverse phase HPLC afforded the title compound (25 mg, 0.052 mmol, 69.3% yield) as light yellow oil. LC/MS (m/z) ES+=484 (M+1).

Step B (2S)(M)-methyl 2-(tert-butoxy)-2-(-4-(8-fluoro-5-methylchroman-6-yl)-1,6-dimethyl-2-((1-methyl-H-indazole-5-carboxamido)methyl)-1H-pyrrolo[2,3-b]pyridin-5-yl)acetate

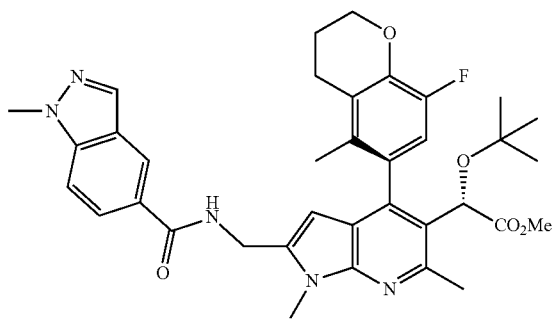

A solution of (2S)(M)-methyl 2-(-2-(aminomethyl)-4-(8-fluoro-5-methylchroman-6-yl)-1,6-dimethyl-1H-pyrrolo[2,3-b]pyridin-5-yl)-2-(tert-butoxy)acetate (25 mg, 0.052 mmol) in N,N-Dimethylformamide (DMF) (1 mL) was treated with DIEA (36.3 µl, 0.208 mmol), 1-methyl-1H-indazole-5-carboxylic acid (10.99 mg, 0.0624 mmol), and HATU (23.73 mg, 0.0624 mmol). After stirring at ambient temperature for 1 h, the mixture was diluted with sat. NaHCO$_3$, extracted with EtOAc, washed with brine, dried over Na$_2$SO$_4$, filtered, and concentrated. Purification by silica gel chromatography (0-10% MeOH/DCM) afforded the title compound (25 mg, 0.052 mmol, 69%) as a yellow oil. LC/MS (m/z) ES+=642 (M+1).

Step C (2S)(M)-2-(tert-butoxy)-2-(-4-(8-fluoro-5-methylchroman-6-yl)-1,6-dimethyl-2-(1-methyl-1H-indazole-5-carboxamido)methyl)-1H-pyrrolo[2,3-b]pyridin-5-yl)acetate

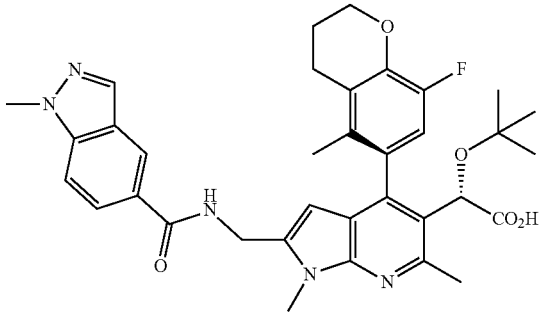

A solution of (2S)(M)-methyl 2-(tert-butoxy)-2-(-4-(8-fluoro-5-methylchroman-6-yl)-1,6-dimethyl-2-((1-methyl-1H-indazole-5-carboxamido)methyl)-1H-pyrrolo[2,3-b]pyridin-5-yl)acetate (28 mg, 0.044 mmol) in Methanol (500 µl) and Tetrahydrofuran (THF) (500 µl) was treated with 4M LiOH (110 µl, 0.44 mmol) and irradiated in microwave at 120° C. for 20 min. The mixture was concentrated, dissolved in MeOH, filtered through acrodisc psf ptfe 0.45 um, and purified with reverse phase HPLC to give the title compound (15.4 mg, 0.020 mmol, 27.3% yield) as white solid. $^1$H NMR (400 MHz, CHLOROFORM-d) δ ppm 8.21 (s, 1H), 7.98 (s, 1H), 7.83 (d, J=8.8 Hz, 1H), 7.38 (d, J=8.8 Hz, 1H), 7.17 (t, J=5.1 Hz, 1H), 6.68 (d, J=10.8 Hz, 1H), 6.16-6.12 (m, 1H), 5.17 (s, 1H), 4.79 (d, J=5.0 Hz, 2H), 4.28 (t, J=5.0 Hz, 2H), 4.12-4.03 (m, 3H), 3.99 (s, 3H), 2.95-2.81 (m, 3H), 2.67 (q, J=5.7 Hz, 2H), 2.12 (d, J=4.5 Hz, 2H), 1.82-1.70 (m, 3H), 1.16-0.94 (m, 9H); LCMS (m/z) ES+=628.5 (M+1).

Example 413

(2S)(M)-2-(tert-butoxy)-2-(-4-(8-fluoro-5-methylchroman-6-yl)-2-((E)-3-((2-methoxyethyl)amino)-3-oxoprop-1-en-1-yl)-1,6-dimethyl-1H-pyrrolo[2,3-b]pyridin-5-yl)acetic acid

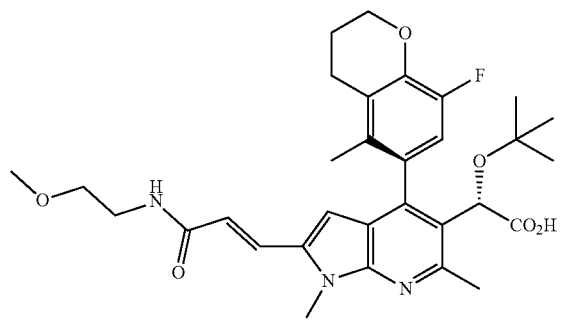

Step A (2S)(M)-2-(tert-butoxy)-2-(-2-((E)-3-ethoxy-3-oxoprop-1-en-1-yl)-4-(8-fluoro-5-methylchroman-6-yl)-1,6-dimethyl-1H-pyrrolo[2,3-b]pyridin-5-yl)acetic acid

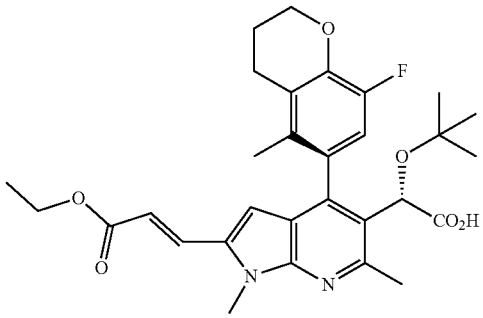

An ice cold solution of methyl 2-(diethoxyphosphoryl)acetate (1.742 g, 8.29 mmol), lithium chloride (0.351 g, 8.29 mmol), lithium chloride (0.351 g, 8.29 mmol), DBU (1.249 mL, 8.29 mmol) in Acetonitrile (20 mL) was stirred for 20 min. Then (2S)(M)-methyl 2-(tert-butoxy)-2-(-4-(8-fluoro-5-methylchroman-6-yl)-2-formyl-1,6-dimethyl-1H-pyrrolo[2,3-b]pyridin-5-yl)acetate (1 g, 2.072 mmol) in CH$_3$CN (2 mL) was added and the mixture was maintained at 0° C. for 10 min and allowed to warm to ambient temperature. After 2 h, sat. aq. NH₄Cl was added and the mixture extracted with EtOAc. The organics were washed with brine, dried (Na₂SO₄), filtered and concentrated in vacuo. The residue was purified by silica gel chromatography (30% EtOAc/hexanes to afford the title compound (1.0 g, 1.86 mmol, 90% yield) as a light yellow foam. LCMS (m/z) ES⁺=539 (M+1).

Step B (2S)(E)(M)-3-(-5-(tert-butoxy(carboxy)methyl)-4-(8-fluoro-5-methylchroman-6-yl)-1,6-dimethyl-1H-pyrrolo[2,3-b]pyridin-2-yl)acrylic acid

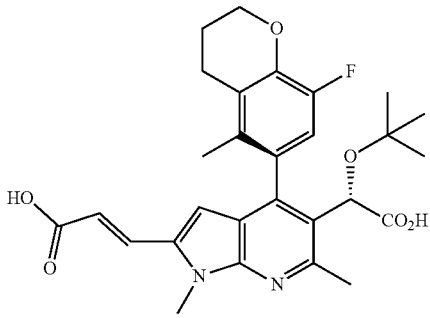

A solution of (2S)(M)-2-(tert-butoxy)-2-(-2-((E)-3-ethoxy-3-oxoprop-1-en-1-yl)-4-(8-fluoro-5-methylchroman-6-yl)-1,6-dimethyl-1H-pyrrolo[2,3-b]pyridin-5-yl)acetic acid (950 mg, 1.764 mmol) in Methanol (0.9 mL) and Tetrahydrofuran (THF) (0.9 mL) was treated with lithium hydroxide monohydrate (333 mg, 7.94 mmol) in Water (0.3 mL) at ambient temperature. After 50 min, the reaction mixture was poured into 1M HCl and extracted with EtOAc. The organics were washed with brine, dried (Na₂SO₄), filtered and concentrated in vacuo to afford the title compound (940 mg, 1.613 mmol, 91% yield) as yellow foam. LCMS (m/z) ES⁺=525 (M+1).

Step C (2S)(M)-Methyl-2-(tert-butoxy)-2-(-4-(8-fluoro-5-methylchroman-6-yl)-2-((E)-3-(2-methoxyethyl)amino)-3-oxoprop-1-en-1-yl)-1,6-dimethyl-1H-pyrrolo[2,3-b]pyridin-5-yl)acetic acid

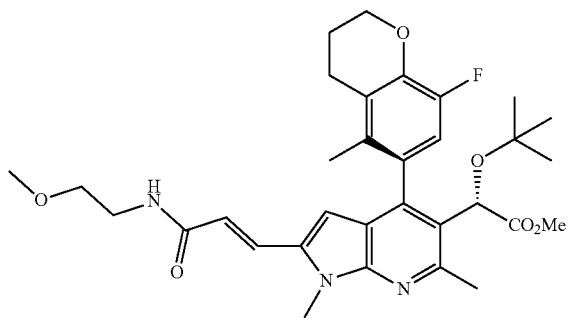

A solution of (2S)(E)(M)-3-(-5-(-tert-butoxy(carboxy)methyl)-4-(8-fluoro-5-methylchroman-6-yl)-1,6-dimethyl-1H-pyrrolo[2,3-b]pyridin-2-yl)acrylic acid (120 mg, 0.229 mmol), 2-methoxyethanamine (17.18 mg, 0.229 mmol) and DIPEA (0.040 mL, 0.229 mmol) was treated with HATU (261 mg, 0.686 mmol). After 2 h, the reaction mixture was diluted with EtOAc and washed with 1 N HCl. The organics were washed with brine, dried (Na₂SO₄), filtered and concentrated in vacuo. The residue was purified by silica gel chromatography (10% MeOH/DCM) to afford the title compound (80 mg, 0.131 mmol, 57.1% yield) as an off-white solid. LCMS (m/z) ES⁺=582 (M+1).

Step D (2S)(M)-2-(tert-butoxy)-2-(-4-(8-fluoro-5-methylchroman-6-yl)-2-((E)-3-((2-methoxyethyl)amino)-3-oxoprop-1-en-1-yl)-1,6-dimethyl-1H-pyrrolo[2,3-b]pyridin-5-yl)acetic acid

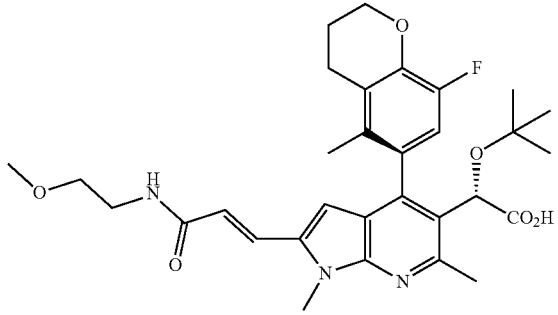

A solution of (2S)(M)-methyl 2-(tert-butoxy)-2-(-4-(8-fluoro-5-methylchroman-6-yl)-2-((E)-3-((2-methoxyethyl)amino)-3-oxoprop-1-en-1-yl)-1,6-dimethyl-1H-pyrrolo[2,3-b]pyridin-5-yl)acetate (80 mg, 0.138 mmol), in Tetrahydrofuran (THF) (0.7 mL), Water (0.350 mL) and Methanol (0.7 mL) was treated with lithium hydroxide monohydrate (28.9 mg, 0.688 mmol) and warmed to 60° C. After 18 h, the reaction mixture was acidified with TFA (2 drops) and then concentrated. The residue was purified by silica gel chromatography (0-15% MeOH/DCM) to afford the title compound (75 mg, 0.091 mmol, 66.5% yield) as an off-white solid. LCMS (m/z) ES⁺=582 (M+1).

Compounds in Table 15 (examples 414-419) were synthesized using the above procedures with the appropriate amine.

TABLE 15

| Example | Structure | MW | Observed Mass |
|---|---|---|---|
| 414 | 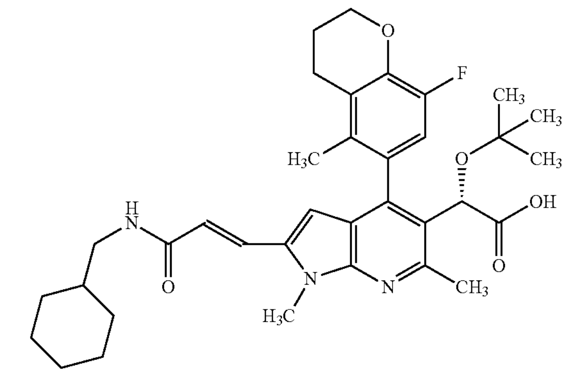 [SMILES: Cc1nc2c(cc(/C=C/C(=O)NCC3CCCCC3)n2C)c(-c2cc(F)c3c(c2C)CCCO3)c1[C@H](OC(C)(C)C)C(=O)O] | 605.74 | 606 |
| 415 | 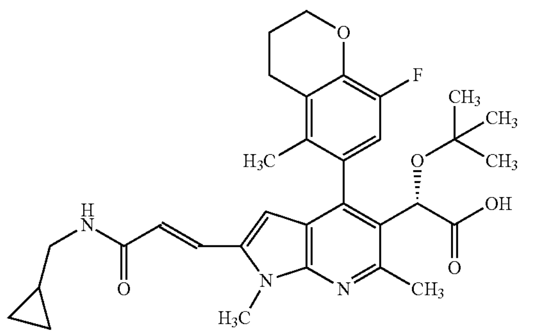 [SMILES: Cc1nc2c(cc(/C=C/C(=O)NCC3CC3)n2C)c(-c2cc(F)c3c(c2C)CCCO3)c1[C@H](OC(C)(C)C)C(=O)O] | 563.66 | 564 |
| 416 | 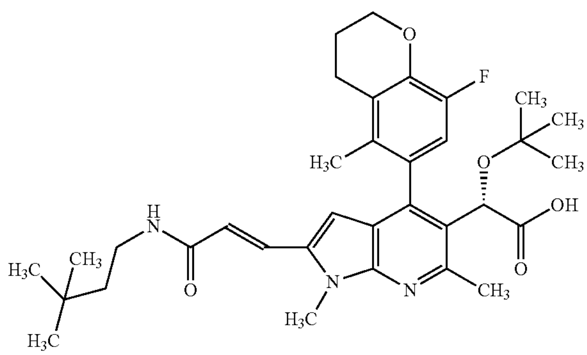 [SMILES: Cc1nc2c(cc(/C=C/C(=O)NCCC(C)(C)C)n2C)c(-c2cc(F)c3c(c2C)CCCO3)c1[C@H](OC(C)(C)C)C(=O)O] | 593.73 | 594 |
| 417 | 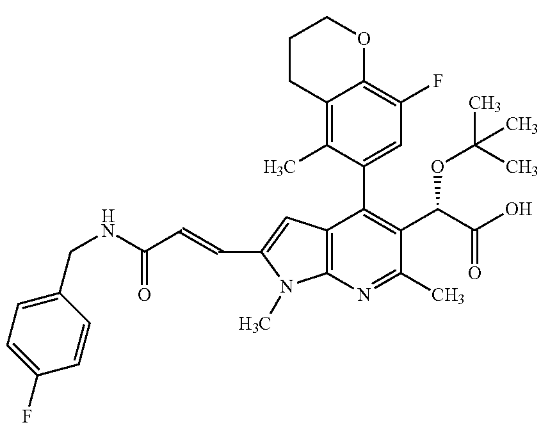 [SMILES: Cc1nc2c(cc(/C=C/C(=O)NCc3ccc(F)cc3)n2C)c(-c2cc(F)c3c(c2C)CCCO3)c1[C@H](OC(C)(C)C)C(=O)O] | 617.68 | 618 |

TABLE 15-continued

| Example | Structure | MW | Observed Mass |
|---------|-----------|------|----|
| 418 | 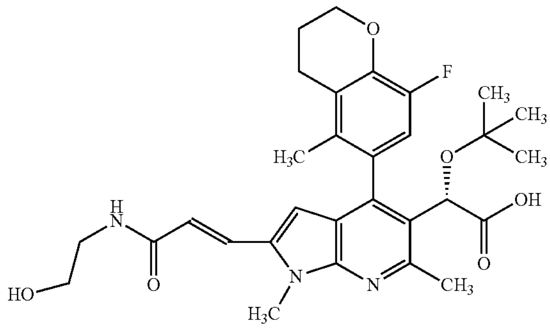 [SMILES: Cc1nc2c(cc(/C=C/C(=O)NCCO)n2C)c(-c2cc(F)c3c(c2C)CCCO3)c1[C@H](OC(C)(C)C)C(=O)O] | 553.62 | 554 |
| 419 | 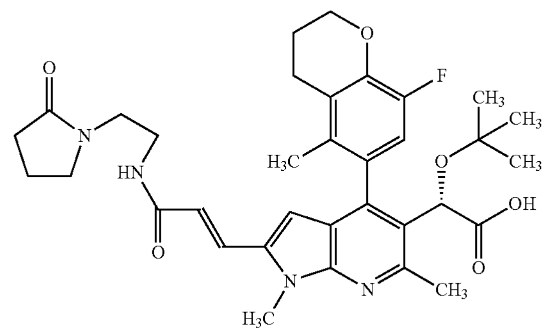 [SMILES: Cc1nc2c(cc(/C=C/C(=O)NCCN3CCCC3=O)n2C)c(-c2cc(F)c3c(c2C)CCCO3)c1[C@H](OC(C)(C)C)C(=O)O] | 620.71 | 621 |

Example 420

(2S)(M)-2-(-2-(2-(benzylamino)-2-oxoacetyl)-4-(8-fluoro-5-methylchroman-6-yl)-1,6-dimethyl-1H-pyrrolo[2,3-b]pyridin-5-yl)-2-(tert-butoxy)acetic acid

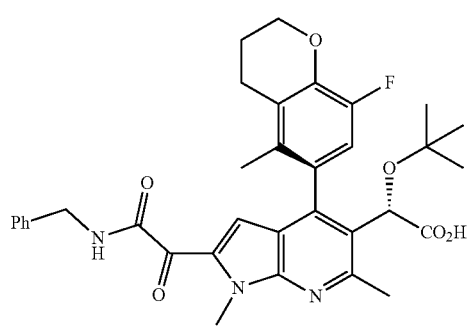

Step A (2S) (M)-Methyl 2-(tert-butoxy)-2-(-2-ethynyl-4-(8-fluoro-5-methylchroman-6-yl)-1,6-dimethyl-1H-pyrrolo[2,3-b]pyridin-5-yl)acetate

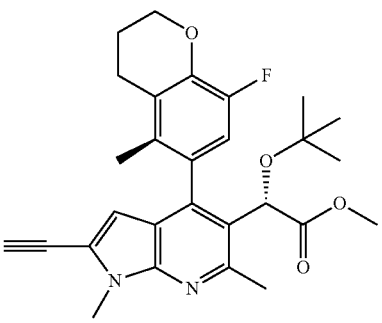

A mixture of $K_3PO_4$ (1058 mg, 4.98 mmol) and 4-acetamidobenzenesulfonyl azide (599 mg, 2.492 mmol) in N,N-Dimethylacetamide (DMA) (9 mL) was treated with dimethyl (2-oxopropyl)phosphonate (0.344 mL, 2.492 mmol) and stirred at ambient temperature for 20 min. The reaction was treated with a solution of (2S)(M)-Methyl 2-(tert-butoxy)-2-(-4-(8-fluoro-5-methylchroman-6-yl)-2-formyl-1,6- dimethyl-1H-pyrrolo[2,3-b]pyridin-5-yl)acetate (902 mg, 1.869 mmol) in Dichloromethane (DCM) (5.4 mL) and Methanol (3.6 mL), and stirred at ambient temperature for 18 hours. The reaction was treated with additional pre-stirred mixture of $K_3PO_4$ (1027 mg), 4-acetamidobenzenesulfonyl azide (595.7 mg), and dimethyl (2-oxopropyl)phosphonate (350 uL) in N,N-Dimethylacetamide (DMA) (5 mL). After stirring for 4 days, the reaction was partially concentrated, diluted with water, and stirred for 2 hours. The mixture was filtered; the solid was dissolved in EtOAc, dried over $Na_2SO_4$, filtered, and concentrated. The residue was purified by silica gel chromatography to afford the title compound (315.6 mg, 0.659 mmol, 26.5% yield) as off-white solid. $^1$H NMR (400 MHz, CHLOROFORM-d) δ ppm 6.73 (d, J=11.3 Hz, 1H), 6.21 (s, 1H), 5.14 (s, 1H), 4.31 (t, J=5.1 Hz, 2H), 3.89 (s, 3H), 3.60 (s, 3H), 3.45 (s, 1H), 2.82 (s, 3H), 2.76-2.69 (m, 2H), 2.26-2.09 (m, 2H), 1.80 (s, 3H), 1.12 (s, 9H); LCMS (m/z) ES$^+$=479 (M+1).

Step B, C, D (2S)(M)-2-(-2-(2-(benzylamino)-2-oxoacetyl)-4-(8-fluoro-5-methylchroman-6-yl)-1,6-dimethyl-1H-pyrrolo[2,3-b]pyridin-5-yl)-2-(tert-butoxy)acetic acid

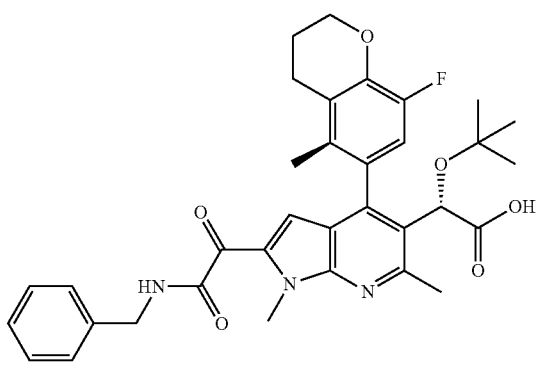

A mixture of (2S)(M)-methyl 2-(tert-butoxy)-2-(-2-ethynyl-4-(8-fluoro-5-methylchroman-6-yl)-1,6-dimethyl-1H-pyrrolo[2,3-b]pyridin-5-yl)acetate (225 mg, 0.470 mmol), TBAI (60.8 mg, 0.1646 mmol), and $KMnO_4$ (260 mg, 1.645 mmol) (premixed with celite-250 mg) in Dichloromethane (DCM) (3 mL) and Water (2 mL) was stirred at ambient temperature for 2.5 hours. The dark purple suspension was filtered through a pad of celite, washed with EtOAc, and concentrated to afford 264.8 mg yellow solid (K salt, mixture of desired oxalic acid. LCMS (m/z) ES$^+$=527 (M+1).

The residue (88 mg, 0.17 mmol) was dissolved in EtOAc (1.5 mL), treated with phenylmethanamine (0.026 mL, 0.24 mmol), DIEA (0.070 mL, 0.4 mmol), and T3P (0.190 mL, 0.32 mmol), and stirred at ambient temperature for 72 h. The reaction mixture was diluted with aq. sat. $NH_4Cl$, extracted with EtOAc, washed with Brine, dried over $Na_2SO_4$, filtered, and concentrated in vacuo. Purification with by silica gel chromatography (0-50% EtOAc/Hexane) afforded (2S)(M)-methyl 2-(-2-(2-(benzylamino)-2-oxoacetyl)-4-(8-fluoro-5-methylchroman-6-yl)-1,6-dimethyl-1H-pyrrolo[2,3-b]pyridin-5-yl)-2-(tert-butoxy)acetate (22.4 mg, 0.036 mmol, 21.40% yield) as yellow oil. LCMS (m/z) ES$^+$=616 (M+1).

A solution of (2S)(M)-methyl 2-(-2-(2-(benzylamino)-2-oxoacetyl)-4-(8-fluoro-5-methylchroman-6-yl)-1,6-dimethyl-1H-pyrrolo[2,3-b]pyridin-5-yl)-2-(tert-butoxy)acetate (22.4 mg, 0.036 mmol) in Methanol (0.5 mL) and Tetrahydrofuran (THF) (0.5 mL) was treated with 4M LiOH (0.090 mL, 0.36 mmol) and stirred at 60° C. for 18 hours. The reaction was diluted with 1N HCl, concentrated and purified by reverse phase HPLC to afford the title compound (2.6 mg, 3.89 μmol, 10.80% yield) as yellow solid. $^1$H NMR (400 MHz, CHLOROFORM-d) δ ppm 7.82 (s, 1H), 7.60 (br. s., 1H), 7.39-7.29 (m, 5H), 6.78 (d, J=11.0 Hz, 1H), 5.22 (s, 1H), 4.53 (d, J=5.8 Hz, 2H), 4.32 (t, J=5.1 Hz, 2H), 4.18 (s, 3H), 2.79 (s, 3H), 2.73 (t, J=6.4 Hz, 2H), 2.20-2.12 (m, 2H), 1.91 (s, 3H), 1.13 (s, 9H); LCMS (m/z) ES$^+$=602 (M+1).

Compounds in Table 16 (examples 421-442) were synthesized using the above procedures with the appropriate boronic acid coupling partner or alkylating reagent.

TABLE 16

| Example | Structure | MW | Observed Mass | $^1$H NMR (400 MHz, Chloroform-d) δ |
|---|---|---|---|---|
| 421 | [structure] | 573.68 | 574 | 8.80 (d, J = 5.3 Hz, 2H), 8.36 (s, 2H), 8.02-8.14 (m, 4H), 7.89 (s, 2H), 7.60-7.74 (m, 7H), 7.36-7.59 (m, 6H), 6.53 (s, 2H), 5.54 (s, 2H), 4.11 (s, 7H), 4.01 (s, 7H), 2.76 (s, 7H), 2.45 (s, 3H), 0.95 (s, 9H); |

TABLE 16-continued

| Example | Structure | MW | Observed Mass | ¹H NMR (400 MHz, Chloroform-d) δ |
|---|---|---|---|---|
| 422 | 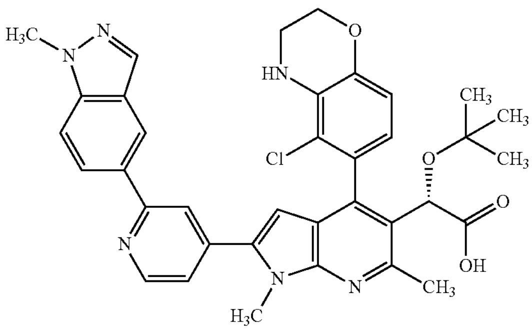 [SMILES: Cc1nc2c(cc(-c3ccnc(-c4ccc5c(cnn5C)c4)c3)n2C)c(-c2ccc3c(c2Cl)NCCO3)c1[C@H](OC(C)(C)C)C(=O)O] | 650.24 | 651 | 8.94 (d, J = 5.5 Hz, 1H), 8.36 (s, 1H), 8.15 (s, 1H), 8.04 (d, J = 1.0 Hz, 1H), 7.97 (d, 1H), 7.70 (d, J = 5.1 Hz, 1H), 7.60 (d, J = 8.8 Hz, 1H), 6.83 (d, J = 8.2 Hz, 1H), 6.60 (s, 1H), 6.46 (d, J = 8.2 Hz, 1H), 5.34 (s, 1H), 4.33 (t, J = 3.9 Hz, 2H), 4.13 (s, 3H), 4.09 (s, 3H), 3.52-3.63 (m, 2H), 2.94 (s, 3H), 1.14 (s, 9H) |
| 423 | 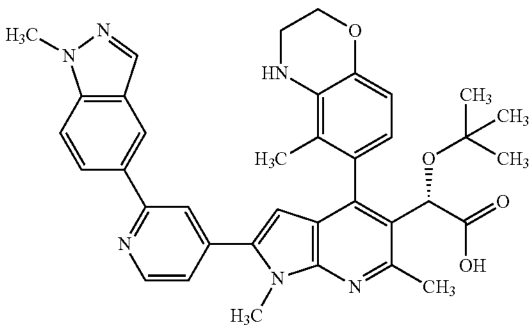 [SMILES: Cc1nc2c(cc(-c3ccnc(-c4ccc5c(cnn5C)c4)c3)n2C)c(-c2ccc3c(c2C)NCCO3)c1[C@H](OC(C)(C)C)C(=O)O] | 630.74 | 631 | 8.91 (s, 1 H), 8.35 (s, 1 H), 8.08 (s, 2 H), 7.95 (d, J = 7.8 Hz, 1 H), 7.74 (s, 1 H), 7.60 (d, J = 8.2 Hz, 1 H), 6.85 (d, J = 7.8 Hz, 1 H), 6.65 (d, J = 8.0 Hz, 1 H), 6.63-6.56 (m, 1 H), 5.27 (s, 1 H), 4.36 (s, 2 H), 4.20-4.08 (m, 6 H), 3.62 (s, 2 H), 2.90 (s, 3 H), 1.87 (s, 3 H), 1.12 (s, 9 H); |
| 424 | 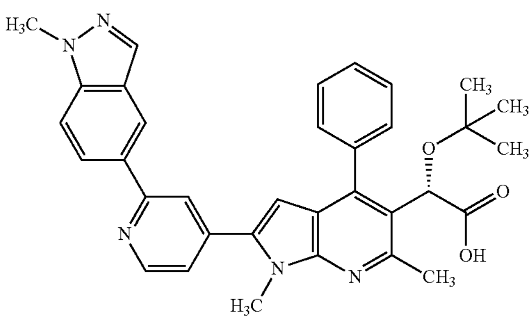 [SMILES: Cc1nc2c(cc(-c3ccnc(-c4ccc5c(cnn5C)c4)c3)n2C)c(-c2ccccc2)c1[C@H](OC(C)(C)C)C(=O)O] | 559.66 | 560 | 8.95 (s, 1 H), 8.34 (s, 1 H), 8.15 (s, 1 H), 8.04 (s, 1 H), 7.94 (d, J = 7.6 Hz, 1 H), 7.74 (d, 2 H), 7.63-7.42 (m, 5 H), 6.74 (s, 1 H), 5.48 (s, 1 H), 4.13 (s, 3 H), 4.10 (s, 3 H), 2.81 (s, 3 H), 0.94 (s, 9 H) |
| 425 | 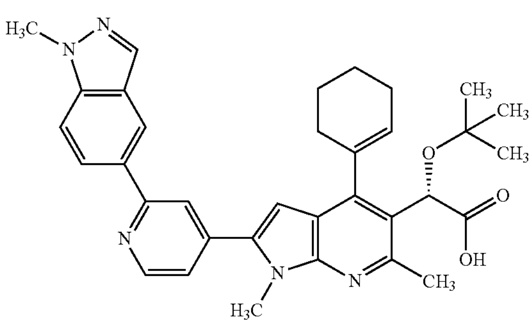 [SMILES: Cc1nc2c(cc(-c3ccnc(-c4ccc5c(cnn5C)c4)c3)n2C)c(C2=CCCCC2)c1[C@H](OC(C)(C)C)C(=O)O] | 563.69 | 564 | 8.99 (d, J = 1.6 Hz, 1 H), 8.39 (s, 1 H), 8.18 (s, 1 H), 8.08 (s, 1 H), 8.00 (d, J = 8.2 Hz, 1 H), 7.74 (s, 1 H), 7.63 (d, J = 8.2 Hz, 1 H), 6.91 (d, J = 17.8 Hz, 1 H), 6.25 (s, 0.5 H), 6.03-5.86 (s, 0.5 H), 5.81 (s, 0.5 H), 5.50 (s, 0.5 H), 4.16 (s, 3 H), 4.12-3.95 (m, 3 H), 2.84 (s, 3 H), 2.82-2.01 (m, 4 H), 2.13-1.64 (m, 4 H), 1.24 (s, 9 H); |

TABLE 16-continued

| Example | Structure | MW | Observed Mass | ¹H NMR (400 MHz, Chloroform-d) δ |
|---|---|---|---|---|
| 426 | 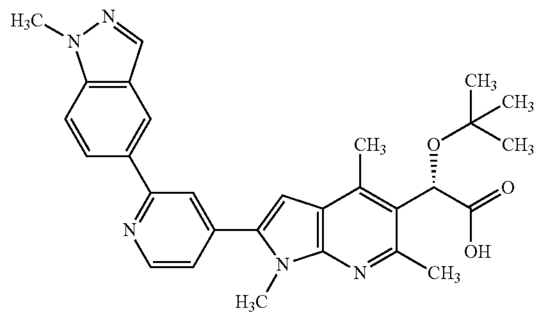 [SMILES: Cc1nc2c(cc(-c3ccnc(-c4ccc5c(cnn5C)c4)c3)n2C)c(C)c1[C@H](OC(C)(C)C)C(=O)O] | 497.59 | 498 | 8.99 (d, J = 5.7 Hz, 1 H), 8.40 (s, 1 H), 8.17 (s, 1 H), 8.08 (s, 1 H), 8.05-7.98 (m, 1 H), 7.69 (d, J = 5.7 Hz, 1 H), 7.62 (d, J = 8.8 Hz, 1 H), 7.04 (s, 1 H), 5.57 (s, 1 H), 4.16 (s, 3 H), 4.08 (s, 3 H), 2.87 (s, 3 H), 2.78 (s, 3 H), 1.26 (s, 9H) |
| 427 | 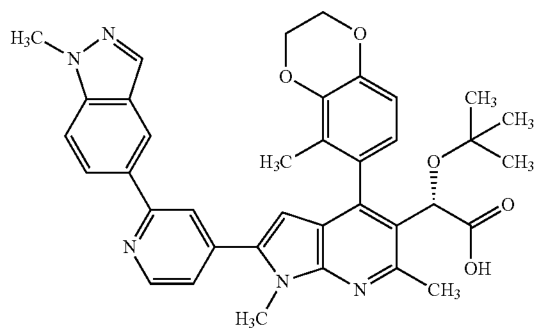 [SMILES: Cc1nc2c(cc(-c3ccnc(-c4ccc5c(cnn5C)c4)c3)n2C)c(-c2ccc3c(c2C)OCCO3)c1[C@H](OC(C)(C)C)C(=O)O] | 631.72 | 632 | 8.74 (d, J = 5.1 Hz, 1 H), 8.38 (s, 1 H), 8.12 (dd, J = 1.4, 8.8 Hz, 1 H), 8.07 (s, 1 H), 7.87 (s, 1 H), 7.50 (d, J = 8.8 Hz, 1 H), 7.34 (dd, J = 1.1, 5.0 Hz, 1 H), 6.87-6.77 (m, 1 H), 6.71 (d, J = 8.0 Hz, 1 H), 6.24 (s, 1 H), 5.32 (s, 1 H), 4.39-4.30 (m, 4 H), 4.12 (s, 3 H), 4.00 (s, 3 H), 2.88-2.75 (m, 3 H), 2.01 (s, 3 H), 1.14 (s, 9 H) |
| 428 | 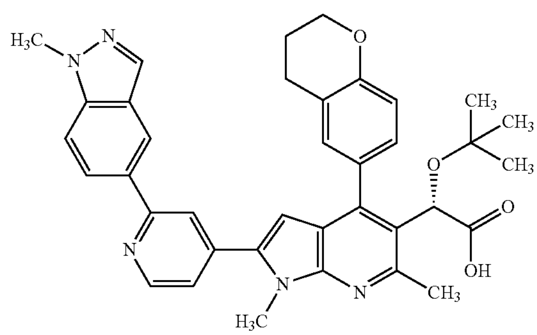 [SMILES: Cc1nc2c(cc(-c3ccnc(-c4ccc5c(cnn5C)c4)c3)n2C)c(-c2ccc3c(c2)CCCO3)c1[C@H](OC(C)(C)C)C(=O)O] | 615.72 | 616 | 8.97 (s, 1 H), 8.36 (d, J = 3.9 Hz, 1 H), 8.17 (s, 1 H), 8.06 (s, 1 H), 7.96 (d, J = 8.6 Hz, 1 H), 7.74 (s, 1 H), 7.62 (d, J = 8.8 Hz, 1 H), 7.53-7.43 (m, 1 H), 7.24-7.13 (m, 1 H), 6.98 (d, J = 8.4 Hz, 1 H), 6.82 (d, J = 3.3 Hz, 1 H), 5.57 (d, J = 1.8 Hz, 1 H), 4.30 (t, J = 5.0 Hz, 2 H), 4.15 (s, 3 H), 4.12 (s, 3 H), 2.96-2.85 (m, 2 H), 2.84 (s, 3 H), 2.20-2.03 (m, 2 H), 0.98 (d, J = 1.8 Hz, 9 H), 1.00-0.95 (m, 9 H) |
| 429 | 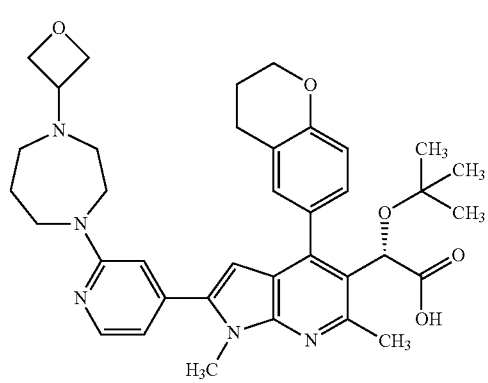 [SMILES: Cc1nc2c(cc(-c3ccnc(N4CCCN(C5COC5)CC4)c3)n2C)c(-c2ccc3c(c2)CCCO3)c1[C@H](OC(C)(C)C)C(=O)O] | 639.78 | 640 | 8.09 (d, J = 6.1 Hz, 1 H), 7.41-7.34 (m, 1 H), 7.24-7.15 (m, 1 H), 7.14-7.07 (m, 2 H), 6.90 (d, J = 8.2 Hz, 1 H), 6.60 (d, J = 6.1 Hz, 1 H), 5.47 (d, J = 7.0 Hz, 1 H), 4.79 (t, J = 6.2 Hz, 4 H), 4.46-4.36 (m, 1 H), 4.23 (t, J = 5.0 Hz, 2 H), 4.14-4.07 (m, 2 H), 3.95 (s, 3 H), 3.79 (t, J = 5.8 Hz, 2 H), 3.44-3.34 (m, 2 H), 3.27-3.21 (m, 2 H), 2.88-2.78 (m, 2 H), 2.75 (s, 3 H), 2.38-2.26 (m, 2 H), 2.12-1.94 (m, 2 H), 0.90 (s, 9 H) |

TABLE 16-continued

| Example | Structure | MW | Observed Mass | ¹H NMR (400 MHz, Chloroform-d) δ |
|---|---|---|---|---|
| 430 | 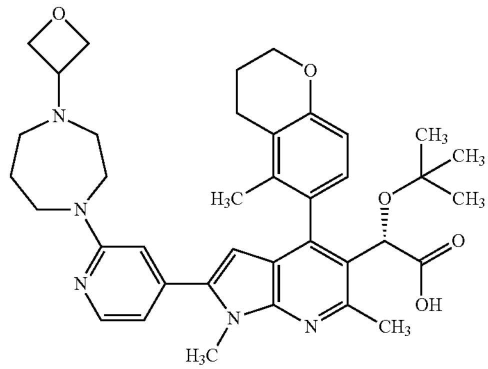 [SMILES: Cc1nc2c(cc(-c3ccnc(N4CCCN(C5COC5)CC4)c3)n2C)c(-c2ccc3c(c2C)CCCO3)c1[C@H](OC(C)(C)C)C(=O)O] | 653.81 | 654 | 8.15 (d, J = 6.1 Hz, 1 H), 6.95 (d, J = 5.7 Hz, 1 H), 6.90 (d, J = 8.4 Hz, 1 H), 6.83-6.77 (m, 2 H), 6.33 (s, 1 H), 5.28 (s, 1 H), 4.99 (t, J = 6.1 Hz, 3 H), 4.75 (t, J = 7.4 Hz, 3 H), 4.23 (d, J = 4.7 Hz, 4 H), 4.02 (s, 3 H), 3.77-3.74 (m, 3 H), 3.43-3.29 (m, 2 H), 3.28-3.16 (m, 2 H), 2.90 (s, 3 H), 2.79-2.64 (m, 2 H), 2.60-2.46 (m, 2 H), 2.19-2.05 (m, 2 H), 1.94 (s, 3 H), 1.12 (s, 9 H) |
| 431 | 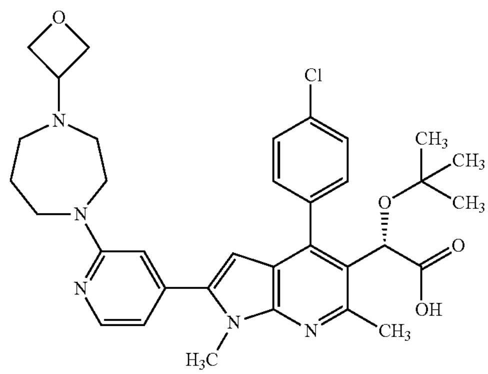 [SMILES: Cc1nc2c(cc(-c3ccnc(N4CCCN(C5COC5)CC4)c3)n2C)c(-c2ccc(Cl)cc2)c1[C@H](OC(C)(C)C)C(=O)O] | 617.17 | 618 | 8.06 (d, J = 6.6 Hz, 1 H), 7.76-7.66 (m, 1 H), 7.60 (d, J = 8.8 Hz, 2 H), 7.56-7.48 (m, 1 H), 7.32 (s, 1 H), 7.25 (dd, 1 H), 6.69 (s, 1 H), 5.34 (s, 1 H), 4.88-4.76 (m, 4 H), 4.50 (quin, J = 6.6 Hz, 1 H), 4.22-4.13 (m, 2 H), 4.00 (s, 3 H), 3.85 (t, J = 5.9 Hz, 2 H), 3.56-3.46 (m, 2 H), 3.43-3.33 (m, 2 H), 2.79 (s, 3 H), 2.48-2.36 (m, 2 H), 0.92 (s, 9 H) |
| 432 | 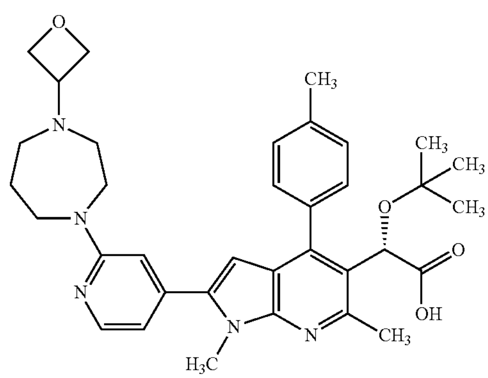 [SMILES: Cc1ccc(-c2c([C@H](OC(C)(C)C)C(=O)O)c(C)nc3c2cc(-c2ccnc(N4CCCN(C5COC5)CC4)c2)n3C)cc1] | 597.75 | 598 | 8.06 (d, J = 6.6 Hz, 1 H), 7.59 (d, J = 8.2 Hz, 1 H), 7.46-7.36 (m, 3 H), 7.32 (s, 1 H), 7.22 (d, J = 6.4 Hz, 1 H), 6.74 (s, 1 H), 5.44 (s, 1 H), 4.90-4.83 (m, 2 H), 4.83-4.76 (m, 2 H), 4.50 (quin, J = 6.6 Hz, 1 H), 4.22-4.12 (m, 2 H), 4.00 (s, 3 H), 3.84 (t, J = 5.7 Hz, 2 H), 3.55-3.46 (m, 2 H), 3.43-3.33 (m, 2 H), 2.81 (s, 3 H), 2.44 (s, 3 H), 2.43-2.36 (m, 2 H), 0.88 (s, 9 H) |
| 433 | 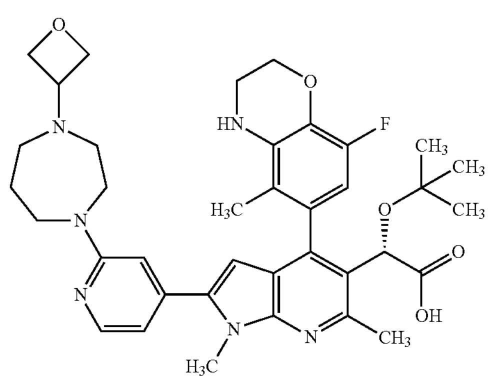 [SMILES: Cc1nc2c(cc(-c3ccnc(N4CCCN(C5COC5)CC4)c3)n2C)c(-c2cc(F)c3c(c2C)NCCO3)c1[C@H](OC(C)(C)C)C(=O)O] | 672.79 | 673 | 8.06 (d, J = 6.6 Hz, 1 H), 7.30 (s, 1 H), 7.21 (d, J = 6.6 Hz, 1 H), 6.55 (s, 1 H), 6.26 (d, J = 10.7 Hz, 1 H), 5.22 (s, 1 H), 4.93-4.83 (m, 2 H), 4.83-4.73 (m, 2 H), 4.50 (quin, J = 6.6 Hz, 1 H), 4.30-4.21 (m, 2 H), 4.22-4.13 (m, 2 H), 4.00 (s, 3 H), 3.84 (t, J = 5.7 Hz, 2 H), 3.58 (q, J = 7.0 Hz, 1 H), 3.54-3.42 (m, 4 H), 3.41-3.33 (m, 2 H), 2.89 (s, 3 H), 2.47-2.35 (m, 2 H), 1.72 (s, 3 H), 1.10 (s, 9 H) |

TABLE 16-continued

| Example | Structure | MW | Observed Mass | $^1$H NMR (400 MHz, Chloroform-d) δ |
|---|---|---|---|---|
| 434 | 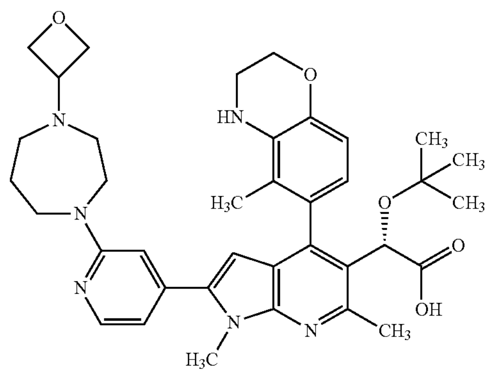 [SMILES: Cc1nc2c(cc(-c3ccnc(N4CCCN(C5COC5)CC4)c3)n2C)c(-c2ccc3c(c2C)NCCO3)c1[C@H](OC(C)(C)C)C(=O)O] | 654.8 | 655 | 8.08 (d, J = 6.2 Hz, 1 H), 7.13 (s, 1 H), 7.10 (d, J = 6.2 Hz, 1 H), 6.71 (d, J = 8.2 Hz, 1 H), 6.48 (d, J = 8.2 Hz, 1 H), 6.41 (s, 1 H), 5.22 (s, 1 H), 4.83-4.77 (m, 4 H), 4.43 (quin, J = 6.5 Hz, 1 H), 4.27-4.21 (m, 2 H), 4.11 (d, J = 4.1 Hz, 2 H), 3.97 (s, 3H), 3.79 (t, J = 6.0 Hz, 2 H), 3.58 (q, J = 7.0 Hz, 1 H), 3.53-3.44 (m, 2 H), 3.44-3.38 (m, 2 H), 3.31-3.29 (m, 2 H), 2.86 (s, 3 H), 2.39-2.30 (m, 2 H), 1.78 (s, 3 H), 1.08 (s, 9 H) |
| 435 | 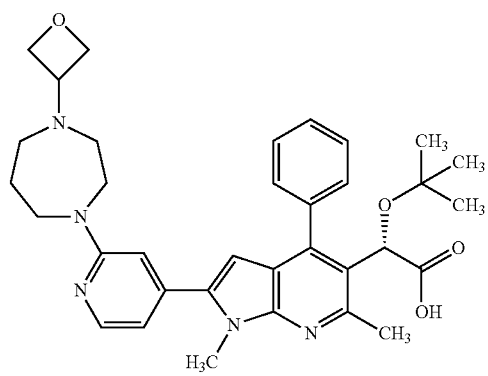 [SMILES: Cc1nc2c(cc(-c3ccnc(N4CCCN(C5COC5)CC4)c3)n2C)c(-c2ccccc2)c1[C@H](OC(C)(C)C)C(=O)O] | 583.72 | 584 | 8.11 (d, J = 6.2 Hz, 1 H), 7.69 (d, J = 8.0 Hz, 1 H), 7.58-7.47 (m, 4 H), 6.96 (br. s., 2 H), 6.42 (s, 1 H), 5.39 (s, 1 H), 4.92 (d, J = 2.5 Hz, 1 H), 4.79 (t, J = 7.2 Hz, 2 H), 4.74-4.68 (m, 2 H), 4.16-3.98 (m, 2 H), 3.92 (s, 3 H), 3.75 (t, J = 6.1 Hz, 2 H), 3.26-3.22 (m, 2 H), 3.20-3.07 (m, 2 H), 2.72 (s, 3 H), 2.30-2.20 (m, 2 H), 0.87 (s, 9 H) |
| 436 | 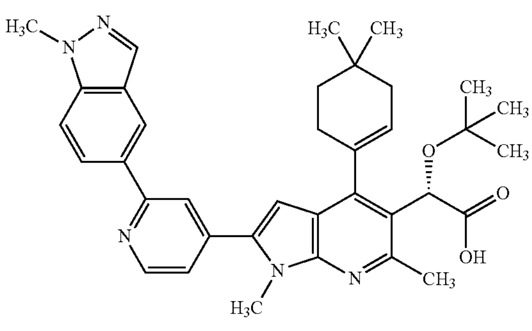 [SMILES: Cc1nc2c(cc(-c3ccnc(-c4ccc5c(cnn5C)c4)c3)n2C)c(C2=CCC(C)(C)CC2)c1[C@H](OC(C)(C)C)C(=O)O] | 591.74 | 592 | 8.97 (d, J = 5.5 Hz, 1 H), 8.37 (s, 1 H), 8.15 (s, 1 H), 8.04 (s, 1 H), 7.99 (d, J = 8.8 Hz, 1 H), 7.69 (d, J = 5.3 Hz, 1 H), 7.60 (d, J = 9.0 Hz, 1 H), 6.87-6.77 (m, 1 H), 5.73 (s, 1 H), 5.48 (s, 1 H), 4.13 (s, 3 H), 4.06 (s, 3 H), 2.84 (s, 3 H), 2.77-2.51 (m, 1 H), 2.39-2.20 (m, 1 H), 2.09 (q, J = 17.4 Hz, 2 H), 1.75-1.49 (m, 2 H), 1.22 (s, 9 H), 1.09 (s, 6 H) |
| 437 | 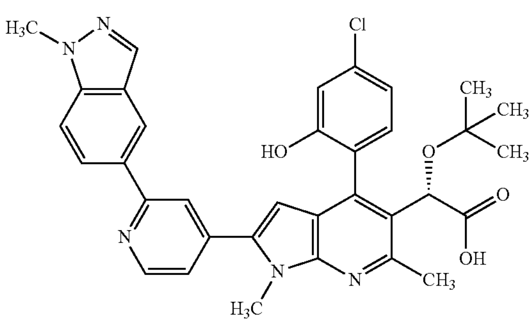 [SMILES: Cc1nc2c(cc(-c3ccnc(-c4ccc5c(cnn5C)c4)c3)n2C)c(-c2ccc(Cl)cc2O)c1[C@H](OC(C)(C)C)C(=O)O] | 609.21 | 610 | 1H NMR (400 MHz, Methanol-d4) = 8.72-8.66 (m, 1 H), 8.43 (d, J = 6.2 Hz, 2 H), 8.19 (s, 1 H), 8.05-7.94 (m, 2 H), 7.79 (d, J = 8.8 Hz, 1 H), 7.42 (d, J = 7.8 Hz, 0.15 H), 7.20 (d, J = 8.6 Hz, 0.85 H), 7.08-6.97 (m, 2 H), 6.89 (s, 0.15 H), 6.86 (s, 0.85 H), 5.34 (s, 0.15 H), 5.23 (s, 0.85 H), 4.11 (s, 3 H), 4.10 (s, 2.5 H), 4.09 (s, 0.5 H), 2.85 (s, 2.5 H), 2.78 (s, 0.5 H), 0.99 (s, 9 H) |

TABLE 16-continued

| Example | Structure | MW | Observed Mass | $^1$H NMR (400 MHz, Chloroform-d) δ |
|---|---|---|---|---|
| 438 | 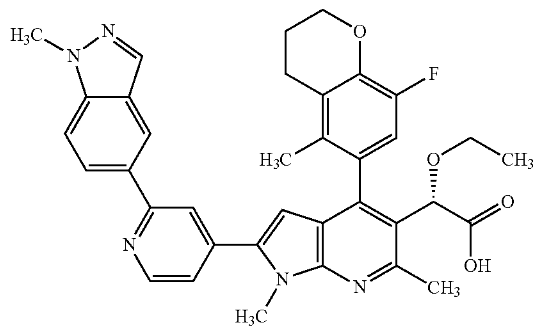 [SMILES: CCO[C@H](C(=O)O)c1c(C)nc2c(cc(-c3ccnc(-c4ccc5c(cnn5C)c4)c3)n2C)c1-c1cc(F)c2c(c1C)CCCO2] | 619.68 | 620 | 1H NMR (400 MHz, Methanol-d4) δ ppm = 8.97 (d, J = 6.1 Hz, 1 H), 8.36 (s, 1 H), 8.15 (s, 1 H), 8.03-7.95 (m, 3 H), 7.71-7.64 (m, 2 H), 7.60 (d, J = 8.8 Hz, 2 H), 6.75 (d, J = 10.9 Hz, 2 H), 6.49 (s, 2 H), 5.02 (s, 1 H), 4.30 (t, J = 5.0 Hz, 2 H), 4.14 (s, 3 H), 4.10 (s, 3 H), 3.52-3.39 (m, 2 H), 2.76 (s, 3 H), 2.73 (d, J = 7.6 Hz, 2 H), 2.20-2.09 (m, 2 H), ), 1.90 (s, 0 H), 1.19 (t, J = 6.9 Hz, 3 H) |
| 439 | 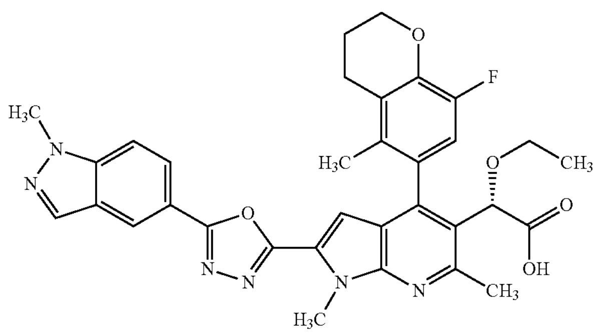 [SMILES: CCO[C@H](C(=O)O)c1c(C)nc2c(cc(-c3nnc(-c4ccc5c(cnn5C)c4)o3)n2C)c1-c1cc(F)c2c(c1C)CCCO2] | 610.63 | 611 | 8.52 (s, 1 H), 8.20 (dd, J = 1.4, 8.8 Hz, 1 H), 8.13 (s, 1 H), 7.54 (d, J = 9.0 Hz, 1 H), 7.06-6.73 (m, 2H), 5.11 (d, 1 H), 4.41-4.36 (m, 3 H), 4.36-4.29 (m, 2 H), 4.15 (s, 3 H), 3.53-3.29 (m, 2 H), 2.80-2.71 (m, 5 H), 2.28-2.11 (m, 2 H), 1.97-1.86 (m, 3 H), 1.22-1.14 (m, 3 H) |
| 440 | 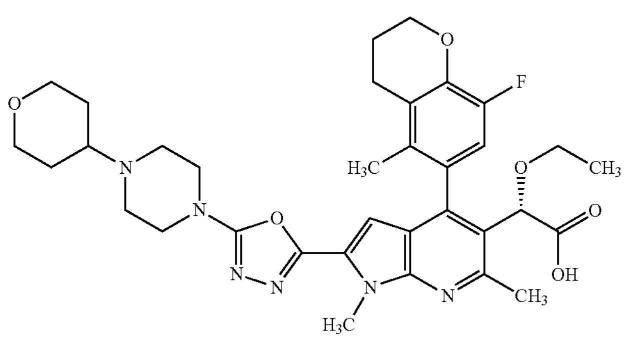 [SMILES: CCO[C@H](C(=O)O)c1c(C)nc2c(cc(-c3nnc(N4CCN(C5CCOCC5)CC4)o3)n2C)c1-c1cc(F)c2c(c1C)CCCO2] | 648.72 | 649 | 1H NMR (400 MHz, DMSO-d6) δ ppm = 9.85 (br. s., 1 H), 6.82 (d, J = 11.3 Hz, 1 H), 6.57-6.47 (m, 1 H), 4.86-4.62 (m, 1 H), 4.23 (t, J = 4.4 Hz, 2 H), 4.19-4.13 (m, 2 H), 4.12 (s, 3 H), 4.13-4.08 (m, 3 H), 3.99 (dd, J = 3.4, 11.2 Hz, 2 H), 3.66-3.39 (m, 6 H), 3.38-3.13 (m, 4 H), 2.72 (d, J = 7.0 Hz, 2 H), 2.67-2.57 (m, 3 H), 2.15-2.01 (m, 2 H), 1.96 (m, 2 H), 1.80 (s, 3 H), 1.73-1.54 (m, 2 H), 1.03 (q, J = 6.8 Hz, 3 H); |
| 441 | 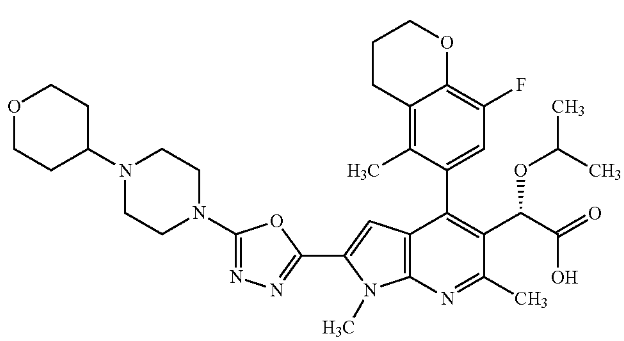 [SMILES: Cc1nc2c(cc(-c3nnc(N4CCN(C5CCOCC5)CC4)o3)n2C)c(-c2cc(F)c3c(c2C)CCCO3)c1[C@H](OC(C)C)C(=O)O] | 662.75 | 663 | 1H NMR (400 MHz, DMSO-d6) δ ppm = 6.80 (d, J = 11.3 Hz, 1 H), 6.48 (s, 1 H), 4.79 (s, 1 H), 4.21 (br. s., 2 H), 4.10 (s, 5 H), 3.97 (d, J = 17.0 Hz, 4 H), 3.67-3.37 (m, 6 H), 3.35-3.24 (m, 2 H), 3.24-3.14 (m, 2 H), 2.79-2.67 (m, 2 H), 2.63 (s, 3 H), 2.14-2.00 (m, 2 H), 1.94 (m, 2 H), 1.79 (s, 3 H), 1.63 (m, 2 H), 0.98 (d, J = 6.3 Hz, 3 H), 0.86 (d, J = 5.9 Hz, 3 H) |

TABLE 16-continued

| Example | Structure | MW | Observed Mass | $^1$H NMR (400 MHz, Chloroform-d) δ |
|---|---|---|---|---|
| 442 | 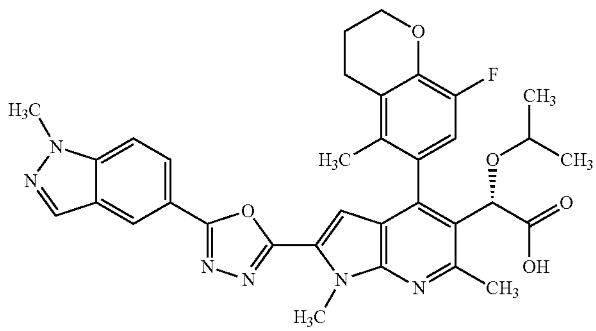 [SMILES: Cc1nc2c(cc(-c3nnc(-c4ccc5c(cnn5C)c4)o3)n2C)c(-c2cc(F)c3c(c2C)CCCO3)c1[C@H](OC(C)C)C(=O)O] | 624.66 | 625 | 8.51 (s, 1 H), 8.19 (dd, J = 1.3, 8.9 Hz, 1 H), 8.13 (s, 1 H), 7.53 (d, J = 8.8 Hz, 1 H), 6.79 (s, 1 H), 6.76 (d, J = 10.7 Hz, 1 H), 5.09 (s, 1 H), 4.40 (s, 3 H), 4.33 (t, J = 5.0 Hz, 2 H), 4.13 (s, 3 H), 3.65 (quin, J = 6.1 Hz, 1 H), 2.78 (s, 3 H), 2.77-2.70 (m, 2 H), 2.25-2.12 (m, 2 H), 1.91 (s, 3 H), 1.05 (dd, 6 H) |

Administration and Formulation

In another embodiment, there is provided a pharmaceutical composition comprising a pharmaceutically acceptable diluent and a therapeutically effective amount of a compound of Formulas I, II, or Ill, or a pharmaceutically acceptable salt thereof.

The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formulas I, II, or III may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, $Na_2CO_3$, $K_2CO_3$, NaH, and potassium-t-butoxide.

Salts derived from pharmaceutically acceptable organic non-toxic bases include salts of primary, secondary, and tertiary amines, including in part, trimethylamine, diethylamine, N,N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences*, 17th ed., Mack Publishing Company, Easton, Pa., 1985, p. 1418, the disclosure of which is hereby incorporated by reference only with regards to the lists of suitable salts.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formulas I, II, or III, containing one or more asymmetric carbon atoms can exist as two or more stereoisomers. Where a compound of Formulas I, II, or III, contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of Formulas I, II, or III, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formulas I, II, or III, contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formulas I, II, or III, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formulas I, II, or III, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Isotopically-labelled compounds of Formulas I, II, or III, can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be administered as prodrugs. Thus, certain derivatives of compounds of Formulas I, II, or III, which may have little or no pharmacological activity themselves can, when administered into or onto the body, be converted into compounds of Formulas I, II, or III, having the desired activity, for example, by hydrolytic cleavage. Such derivatives are referred to as 'prodrugs'.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered, in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used, the route and form of administration, and other factors. The drug can be administered more than once a day, such as once or twice a day.

Therapeutically effective amounts of the chemical entities described herein may range from approximately 0.01 to 200 mg per kilogram body weight of the recipient per day; such as about 0.01-100 mg/kg/day, for example, from about 0.1 to 50 mg/kg/day. Thus, for administration to a 70 kg person, the dosage range may be about 7-3500 mg per day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %. Representative pharmaceutical compositions containing at least one chemical entity described herein are described below.

The following examples serve to more fully describe the manner of making and using the above-described invention. It is understood that these examples in no way serve to limit the true scope of the invention, but rather are presented for illustrative purposes.

BIOLOGICAL EXAMPLES

Example 443

Anti-HIV Activity

MT4 Assay

Antiviral HIV activity and cytotoxicity values for compounds of the invention from Table 1 were measured in parallel in the HTLV-1 transformed cell line MT-4 based on the method previously described (Hazen et al., 2007, In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV (Hazen et al., "In vitro antiviral activity of the novel, tyrosyl-based human immunodeficiency virus (HIV) type 1 protease inhibitor brecanavir (GW640385) in combination with other antiretrovirals and against a panel of protease inhibitor-resistant HIV", *Antimicrob. Agents Chemother.* 2007, 51: 3147-3154; and Pauwels et al., "Sensitive and rapid assay on MT-4 cells for the detection of antiviral compounds against the AIDS virus", *J. of Virological Methods* 1987, 16: 171-185).

Luciferase activity was measured 96 hours later by adding a cell titer glo (Promega, Madison, Wis.). Percent inhibition of cell protection data was plotted relative to no compound control. Under the same condition, cytotoxicity of the compounds was determined using cell titer Glo™ (Promega, Madison, Wis.). IC$_{50}$s were determined from a 10 point dose response curve using 3-4-fold serial dilution for each compound, which spans a concentration range >1000 fold.

These values are plotted against the molar compound concentrations using the standard four parameter logistic equation:

$$y=((V\max * x\widehat{\,}n)/(K\widehat{\,}n + x\widehat{\,}n))+Y2$$

where:
Y2=minimum y  n=slope factor
Vmax=maximum y  x=compound concentration [M]
K=EC$_{50}$ When tested in the MT4 assay, certain compounds of Tables 1-16 were found to have IC$_{50}$ values listed in Table 17.

TABLE 17

| Example | HIV MT4 Assay IC$_{50}$(uM) |
|---|---|
| 1 | 0.0017 |
| 2 | 0.0156 |
| 3 | 0.0019 |
| 4 | 0.0016 |
| 5 | 0.0072 |
| 6 | 0.0148 |
| 7 | |
| 8 | 0.0056 |
| 9 | 0.0162 |
| 10 | 0.0303 |
| 11 | 0.0148 |
| 12 | |
| 13 | |
| 14 | |
| 15 | 0.0137 |

TABLE 17-continued

| Example | HIV MT4 Assay IC$_{50}$(uM) |
|---|---|
| 16 | |
| 17 | |
| 18 | 0.0263 |
| 19 | |
| 20 | |
| 21 | |
| 22 | |
| 23 | |
| 24 | |
| 25 | 0.0106 |
| 26 | 0.0029 |
| 27 | 0.0046 |
| 28 | 0.0018 |
| 29 | 0.0138 |
| 30 | 0.0041 |
| 31 | 0.011 |
| 32 | 0.0345 |
| 33 | 0.0072 |
| 34 | 0.0042 |
| 35 | 0.0109 |
| 36 | 8.4146 |
| 37 | 0.0474 |
| 38 | 0.0179 |
| 39 | 0.0173 |
| 40 | 0.0022 |
| 41 | 0.0046 |
| 42 | 0.0032 |
| 43 | 0.0729 |
| 44 | 0.014 |
| 45 | 0.0048 |
| 46 | 0.0078 |
| 47 | 0.0056 |
| 48 | 0.0044 |
| 49 | 0.1138 |
| 50 | 0.0087 |
| 51 | 0.004 |
| 52 | 0.0139 |
| 53 | 0.0021 |
| 54 | 0.0046 |
| 55 | 0.4105 |
| 56 | 0.015 |
| 57 | 0.0014 |
| 58 | 0.0054 |
| 59 | 0.016 |
| 60 | 0.0037 |
| 61 | 0.0026 |
| 62 | 0.0029 |
| 63 | 0.0154 |
| 64 | 0.0028 |
| 65 | 0.0024 |
| 66 | 0.0086 |
| 67 | 0.045 |
| 68 | 0.0064 |
| 69 | 0.0048 |
| 70 | 0.0031 |
| 71 | 0.0234 |
| 72 | 0.0046 |
| 73 | 0.0038 |
| 74 | 0.0565 |
| 75 | 0.1 |
| 76 | 0.1125 |
| 77 | 0.041 |
| 78 | 0.0058 |
| 79 | 0.6452 |
| 80 | 0.0213 |
| 81 | 2.2756 |
| 82 | 0.0477 |
| 83 | 0.0525 |
| 84 | 0.0147 |
| 85 | 0.0127 |
| 86 | 0.0132 |
| 87 | 0.0428 |
| 88 | 0.0134 |
| 89 | 0.025 |
| 90 | 0.0133 |
| 91 | 0.0122 |

TABLE 17-continued

| Example | HIV MT4 Assay IC$_{50}$(uM) |
|---|---|
| 92 | 0.0196 |
| 93 | 0.0239 |
| 94 | 0.0508 |
| 95 | 0.0524 |
| 96 | 0.35 |
| 97 | 0.0165 |
| 98 | 0.0162 |
| 99 | 0.0148 |
| 100 | 0.0142 |
| 101 | 0.0674 |
| 102 | 0.045 |
| 103 | 0.045 |
| 104 | 0.0375 |
| 105 | 0.0546 |
| 106 | 0.045 |
| 107 | 0.0445 |
| 108 | 0.131 |
| 109 | 0.1209 |
| 110 | 0.045 |
| 111 | 0.0275 |
| 112 | 1.3277 |
| 113 | 0.02 |
| 114 | 0.025 |
| 115 | 0.0156 |
| 116 | 0.04 |
| 117 | 0.0391 |
| 118 | 0.015 |
| 119 | 0.02 |
| 120 | 0.045 |
| 121 | 0.015 |
| 122 | 0.0116 |
| 123 | 0.1644 |
| 124 | 0.0325 |
| 125 | 0.0415 |
| 126 | 0.0225 |
| 127 | 0.0036 |
| 128 | 0.0103 |
| 129 | 0.0452 |
| 130 | 0.2906 |
| 131 | 0.0895 |
| 132 | 0.0329 |
| 133 | 0.104 |
| 134 | 0.0392 |
| 135 | 0.126 |
| 136 | 0.0425 |
| 137 | 0.0438 |
| 138 | 0.0015 |
| 139 | 0.002 |
| 140 | 0.0141 |
| 141 | 0.1492 |
| 142 | 0.0018 |
| 143 | 0.0125 |
| 144 | 0.1102 |
| 145 | 0.0453 |
| 146 | 0.4869 |
| 147 | 0.0453 |
| 148 | 0.0401 |
| 149 | 0.2189 |
| 150 | 9.3625 |
| 151 | 0.0436 |
| 152 | 0.0724 |
| 153 | 0.044 |
| 154 | 0.011 |
| 155 | 0.0819 |
| 156 | 0.0398 |
| 157 | 0.03 |
| 158 | 0.045 |
| 159 | 0.0279 |
| 160 | 0.15 |
| 161 | 0.0379 |
| 162 | 3.6498 |
| 163 | 0.043 |
| 164 | 0.0422 |
| 165 | 50 |
| 166 | 50 |
| 167 | 0.3566 |
| 168 | 12.6065 |
| 169 | 1.242 |
| 170 | 0.0042 |
| 171 | 0.0326 |
| 172 | 0.0059 |
| 173 | 0.3538 |
| 174 | 0.0036 |
| 175 | 0.0048 |
| 176 | 0.0256 |
| 177 | 0.0047 |
| 178 | 0.1755 |
| 179 | 0.847 |
| 180 | 1.9249 |
| 181 | 0.042 |
| 182 | 0.1307 |
| 183 | 0.0339 |
| 184 | 0.042 |
| 185 | 0.0322 |
| 186 | 0.0411 |
| 187 | 0.0265 |
| 188 | 0.0867 |
| 189 | 1.1894 |
| 190 | 0.0141 |
| 191 | 0.0049 |
| 192 | 0.0166 |
| 193 | 0.0123 |
| 194 | 0.0015 |
| 195 | 0.026 |
| 196 | 0.0123 |
| 197 | 6.8085 |
| 198 | 0.0263 |
| 199 | 0.0276 |
| 200 | 8.0462 |
| 201 | 0.0657 |
| 202 | 0.0928 |
| 203 | 6.0359 |
| 204 | 11.4292 |
| 205 | 0.3734 |
| 206 | 0.1258 |
| 207 | 0.311 |
| 208 | 0.0396 |
| 209 | 0.0094 |
| 210 | 0.005 |
| 211 | 0.1214 |
| 212 | 0.0288 |
| 213 | 0.0039 |
| 214 | 0.0446 |
| 215 | 0.03 |
| 216 | 0.0413 |
| 217 | 3.3808 |
| 218 | 0.0473 |
| 219 | 0.8074 |
| 220 | 1.7702 |
| 221 | 17.6048 |
| 222 | 0.3764 |
| 223 | 0.121 |
| 224 | 0.0414 |
| 225 | 0.4356 |
| 226 | 0.0459 |
| 227 | 0.0028 |
| 228 | 0.136 |
| 229 | 0.0122 |
| 230 | 0.0047 |
| 231 | 0.0487 |
| 232 | 0.002 |
| 233 | 0.0036 |
| 234 | 0.0447 |
| 235 | 0.0324 |
| 236 | 4.1364 |
| 237 | 0.0043 |
| 238 | 3.86 |
| 239 | 0.0065 |
| 240 | 0.3696 |
| 241 | 0.0212 |
| 242 | 0.0793 |
| 243 | 0.03 |

TABLE 17-continued

| Example | HIV MT4 Assay IC$_{50}$(uM) |
|---|---|
| 244 | 0.0253 |
| 245 | 0.0225 |
| 246 | 0.0151 |
| 247 | 18.1025 |
| 248 | 3.0472 |
| 249 | 0.0121 |
| 250 | 0.0401 |
| 251 | 0.0283 |
| 252 | 0.0652 |
| 253 | 0.0019 |
| 254 | 0.0038 |
| 255 | 0.0038 |
| 256 | 0.0345 |
| 257 | 0.002 |
| 258 | 0.0314 |
| 259 | 0.0019 |
| 260 | 0.0019 |
| 261 | 0.0468 |
| 262 | 0.1034 |
| 263 | 0.0031 |
| 264 | 0.4543 |
| 265 | 0.0048 |
| 266 | 0.1455 |
| 267 | 0.0261 |
| 268 | 0.0034 |
| 269 | 0.0805 |
| 270 | 0.1115 |
| 271 | 0.0016 |
| 272 | 0.294 |
| 273 | 0.9386 |
| 274 | 0.2082 |
| 275 | 1.0035 |
| 276 | 0.01 |
| 277 | 0.1 |
| 278 | 0.11 |
| 279 | 0.01 |
| 280 | |
| 281 | 0.0383 |
| 282 | 0.0568 |
| 283 | 0.4 |
| 284 | 0.0157 |
| 285 | 0.0466 |
| 286 | 0.015 |
| 287 | 0.4 |
| 288 | 0.2501 |
| 289 | 0.1708 |
| 290 | 0.0481 |
| 291 | 0.0444 |
| 292 | 0.0413 |
| 293 | 0.0443 |
| 294 | 0.0386 |
| 295 | 0.0512 |
| 296 | 0.0285 |
| 297 | 0.1302 |
| 298 | 0.2579 |
| 299 | 0.0393 |
| 300 | 0.0104 |
| 301 | 0.0039 |
| 302 | 0.0442 |
| 303 | 0.0039 |
| 304 | 0.0409 |
| 305 | 0.0449 |
| 306 | 0.0518 |
| 307 | 0.0123 |
| 308 | 0.014 |
| 309 | 0.046 |
| 310 | 0.0154 |
| 311 | 0.0045 |
| 312 | 0.0199 |
| 313 | 0.0084 |
| 314 | 0.0076 |
| 315 | 0.0406 |
| 316 | 0.5656 |
| 317 | 0.1175 |
| 318 | 0.0142 |
| 319 | 0.0049 |
| 320 | 0.38 |
| 321 | 0.0135 |
| 322 | 0.0046 |
| 323 | 0.0052 |
| 324 | 0.004 |
| 325 | 0.0136 |
| 326 | 0.0038 |
| 327 | 0.0094 |
| 328 | 0.0042 |
| 329 | 0.0134 |
| 330 | 0.0128 |
| 331 | 0.0043 |
| 332 | 0.0238 |
| 333 | 0.0165 |
| 334 | 0.0104 |
| 335 | 0.0101 |
| 336 | 0.0045 |
| 337 | 0.0046 |
| 338 | 0.0016 |
| 339 | 0.0288 |
| 340 | 0.0432 |
| 341 | 1.2481 |
| 342 | 0.0054 |
| 343 | 0.0106 |
| 344 | 0.13 |
| 345 | 0.0027 |
| 346 | 0.0027 |
| 347 | 0.0063 |
| 348 | 0.0031 |
| 349 | 0.003 |
| 350 | 0.0119 |
| 351 | 0.002 |
| 352 | 0.0055 |
| 353 | 0.007 |
| 354 | 0.005 |
| 355 | 0.0047 |
| 356 | 0.0098 |
| 357 | 0.004 |
| 358 | 0.0176 |
| 359 | 0.0041 |
| 360 | 0.0308 |
| 361 | 0.0147 |
| 362 | 0.0058 |
| 363 | 0.0099 |
| 364 | 0.0109 |
| 365 | 0.0867 |
| 366 | 0.0152 |
| 367 | 0.0175 |
| 368 | 0.0395 |
| 369 | 0.0113 |
| 370 | 0.0095 |
| 371 | 0.0084 |
| 372 | 0.0362 |
| 373 | 0.0052 |
| 374 | 0.0108 |
| 375 | 0.0015 |
| 376 | 0.0144 |
| 377 | 0.0059 |
| 378 | 0.0041 |
| 379 | 0.2085 |
| 380 | 0.0016 |
| 381 | 0.0027 |
| 382 | 0.0085 |
| 383 | 0.0041 |
| 384 | 0.0051 |
| 385 | 0.01 |
| 386 | 0.0059 |
| 387 | 0.0069 |
| 388 | 0.0093 |
| 389 | 0.0056 |
| 390 | 0.0054 |
| 391 | 0.0142 |
| 392 | 0.0049 |
| 393 | 0.0042 |
| 394 | 0.0164 |
| 395 | 0.0131 |

TABLE 17-continued

| Example | HIV MT4 Assay IC$_{50}$(uM) |
|---|---|
| 396 | 0.0155 |
| 397 | 0.0131 |
| 398 | 0.0136 |
| 399 | 0.0287 |
| 400 | 0.0063 |
| 401 | 0.0128 |
| 402 | 0.015 |
| 403 | 0.0129 |
| 404 | 0.0128 |
| 405 | 0.0027 |
| 406 | 0.0392 |
| 407 | 0.0254 |
| 408 | 0.0027 |
| 409 | 0.0134 |
| 410 | 0.0031 |
| 411 | 0.0076 |
| 412 | 0.0431 |
| 413 | 0.1477 |
| 414 | 0.017 |
| 415 | 0.0401 |
| 416 | 0.0267 |
| 417 | 0.0337 |
| 418 | 3.4357 |
| 419 | 3.236 |
| 420 | 0.0946 |
| 421 | 0.0076 |
| 422 | 0.0015 |
| 423 | 0.0018 |
| 424 | 0.0464 |
| 425 | 0.0345 |
| 426 | 45 |
| 427 | 0.0027 |
| 428 | 0.0046 |
| 429 | 0.075 |
| 430 | 0.0163 |
| 431 | 0.143 |
| 432 | 0.2 |
| 433 | 0.1274 |
| 434 | 0.0516 |
| 435 | 3.0057 |
| 436 | 0.0059 |
| 437 | 0.038 |
| 438 | 0.0049 |
| 439 | 0.003 |
| 440 | 0.3482 |
| 441 | 0.1601 |
| 442 | 0.0051 |

FORMULATION EXAMPLES

The following are representative pharmaceutical formulations containing a compound of Formula (I) or a pharmaceutically acceptable salt thereof.

Example 444

Tablet formulation

The following ingredients are mixed intimately and pressed into single scored tablets.

| Ingredient | Quantity per tablet (mg) |
|---|---|
| compound | 400 |
| cornstarch | 50 |
| croscarmellose sodium | 25 |
| lactose | 120 |
| magnesium stearate | 5 |

Example 445

Capsule Formulation

The following ingredients are mixed intimately and loaded into a hard-shell gelatin capsule.

| Ingredient | Quantity per capsule (mg) |
|---|---|
| compound | 200 |
| Lactose, spray-dried | 148 |
| magnesium stearate | 2 |

Example 446

Suspension Formulation

The following ingredients are mixed to form a suspension for oral administration.

| Ingredient | Amount |
|---|---|
| compound | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| Distilled water | q.s. (quantity sufficient) to 100 mL |

Example 447

Injectable formulation

The following ingredients are mixed to form an injectable formulation.

| Ingredient | Amount |
|---|---|
| compound | 0.2 mg-20 mg |
| sodium acetate buffer solution, | 0.4M 2.0 mL |
| HCl (1N) or NaOH (1N) | q.s. to suitable pH |
| water (distilled, sterile) | q.s. to 20 mL |

Example 448

Suppository Formulation

A suppository of total weight 2.5 g is prepared by mixing the compound with Witepsol® H-15 (triglycerides of saturated vegetable fatty acid; Riches-Nelson, Inc., New York), and has the following composition:

| Ingredient | Amount |
|---|---|
| compound | 500 mg |
| Witepsol ® H-15 | balance |

Although the invention has been shown and described above with reference to some embodiments, those skilled in the art will readily appreciate that the specific experiments detailed are only illustrative of the invention. It should be understood that various modifications can be made without departing from the spirit of the invention.

For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims. Accordingly, the invention is limited only by the following claims. All publications, issued patents, patent applications, books and journal articles, cited in this application are each herein incorporated by reference in their entirety.

What is claimed is:

1. A compound of Formula (II):

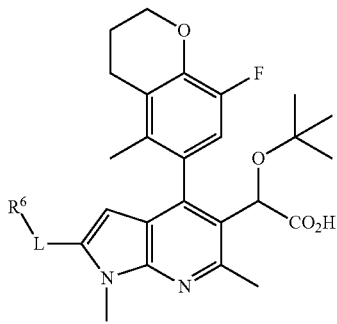

(II)

or a pharmaceutically acceptable salt thereof, wherein:
L is a 5- or 6-membered carbocyclic, heterocyclic, aromatic, or heteroaromatic ring, or $R^6$-L- is $R^6$—C($R^9$)NHC(O)—;
$R^6$ is selected from —H, ($C_1$-$C_6$)alkyl, ($C_1$-$C_6$)alkoxy, halo, nitrile, —$OR^{10}$($C_5$-$C_{14}$)aryl, —$OR^{10}$($C_5$-$C_{14}$)aryl($R^{11}$)$_m$, —$R^{10}$(Y)($R^{12}$)$_n$, —$OR^{10}R^{17}$, —$R^{10}R^{17}$, —$R^{17}R^{15}$, —$R^{10}(R^{14})_q$, —$OR^{10}(R^{14})_q$, —$OR^{10}$(Y), —$OR^{10}R^{18}$, —$OSO_2R^{15}$, —$R^{15}$, —($C_5$-$C_{14}$)aryl, —C(O)(Y), —C(O)$R^{15}$, —$R^{10}$($C_5$-$C_{14}$)aryl, —$R^{10}R^{15}$, —($C_5$-$C_{14}$)aryl$R^{15}$—(X), —(Y), —(Z), —(X)—(X), —(X)—(Y), —(X)—(Z), —(Y)—(X), —(Y)—(Y), —(Y)—(Z), —(Z)—(X), —(Z)—(Y), and —(Z)—(Z), and wherein each $R^6$ group is optionally substituted by one to four substituents selected from $R^{13}$;
$R^9$ is independently selected from —H and ($C_1$-$C_6$) alkyl;
$R^{10}$ is ($C_1$-$C_6$)alkyl;
$R^{11}$, $R^{12}$, and, $R^{13}$ are independently selected from the group consisting of ($C_1$-$C_6$)alkyl, ($C_1$-$C_6$)alkoxy, butoxycarbonyl, oxo, —$R^{10}OR^{10}$, halo, —$R^{15}$, —$R^{10}$($R^{14})_q$, —$OR^{10}(R^{14})_q$, —$SO_2R^{10}$; —C(O)$R^{10}$, —C(O)$R^{15}$, and —$R^{10}R^{17}$;
$R^{14}$ is halo;
$R^{15}$ is —N($R^{16}$)$_2$;
$R^{16}$ is independently selected from the group consisting of —H, ($C_1$-$C_6$)alkyl, hydroxyl, —$SO_2R^{10}$, —$SO_2N(R^{10})_2$, —C(O)NH$R^{10}$, —C(O)$R^{18}$, and —($C_5$-$C_{14}$)aryl($R^{11}$);
$R^{17}$ is —$OR^9$;
$R^{18}$ is —$CO_2R^9$;

X is a monocyclic or bicyclic ($C_5$-$C_{14}$)aryl or —C(O)($C_5$-$C_{14}$)aryl, wherein each aryl of X is optionally substituted by one to four substituents independently selected from $R^{11}$;
Y is independently selected from a monocyclic or bicyclic ($C_2$-$C_9$)heterocycle or —C(O)($C_2$-$C_9$)heterocycle; or monocyclic or bicyclic ($C_2$-$C_9$)heteroaryl or —C(O)($C_2$-$C_9$)heteroaryl, each heterocycle or heteroaryl having one to four heteroatoms selected from S, N or O, and wherein each heterocycle or heteroaryl of Y is optionally substituted by one to four substituents independently selected from $R^{12}$;
Z is a monocyclic or bicyclic ($C_3$-$C_{14}$)cycloalkyl or —C(O)($C_3$-$C_{14}$)cycloalkyl, wherein each cycloalkyl of Z is optionally substituted by one to four substituents independently selected from $R^{13}$;
m is zero or an integer selected from 1, 2, 3, or 4;
n is zero or an integer selected from 1, 2, or 3;
q is an integer selected from 1, 2, or 3.

2. The compound or salt according to claim 1, wherein L is selected from the group consisting of oxadiazolyl, thiadiazolyl, pyridinyl, pyrimidinyl, phenyl, dihydrobenzopyranyl, naphthalenyl, acetidinyl, pyrrolyl, pyrrolidinyl, pyrrolinyl, piperidinyl, morpholinyl, oxetanyl, pyranyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, pyrazolopyridine, benzoimidazole, pyridinone, benzotriazole, imidazopyridine, thienyl, isothiazolyl, triazolyl, imidazolyl, imidazolinyl, isoxazolyl, pyrrolyl, pyrazolyl, pyridazinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, phthalimidyl, and tetrahydropyridoquinolinyl.

3. The compound or salt according to claim 2, wherein $R^6$ is independently selected from the group consisting of —H, methyl, ethyl, propyl, butyl, hydroxyl, fluoro, chloro, bromo, methoxy, ethoxy, propoxy, methoxyethoxy, cyclopropyl, cyclohexyl, fluorophenylmethoxy, difluorophenylmethoxy, pyridinylmethoxy, trifluorophenylmethoxy, fluoropyridinylmethoxy, methylpyridinylmethoxy, phenyl, dimethyloxazolylmethoxy, thiophenylmethoxy, fluoroethoxy, chlorothiophenylmethoxy, methylthiophenylmethoxy, hydroxyethoxy, dimethylaminoethoxy, difluoromethoxy, pyrrolidinylethoxy, morpholinylethoxy, carboxylmethoxy, dimethylsulfamoyloxy, trifluoromethyl, methylsulfonylphenylmethoxy, chlorophenylmethoxy, pyrimidinylmethoxy, trifluoromethoxyphenylmethoxy, chlorobromophenylamino, piperidinyl, piperidinylmethyl, dioxothiomorpholinyl, morpholinyl, morpholinylcarbonyl, ethylamide, fluorophenyl, methoxyphenylmethyl, methylpyridinyl, phenylmethyl, phenylethyl, nitrile, aminocarbonyl, aminomethyl, morpholinylmethyl, bis(pyridinylmethyl)aminomethyl, pentylpyrazolyl, pyridinylmethylaminomethyl, acetamidomethyl, ethylureidomethyl, pyridinyl, carboxyformamidomethyl, methylsulfonamidomethyl, dimethylaminophenyl, dimethylaminosulfonylaminomethyl, methylpyrrolyl, methylpyrazolyl, methylfuranyl, furanyl, di methylpyrazolyl, pyrazolyl, methoxypyridinyl, pyrazolopyridine, benzoimidazole, pyridinone, benzotriazole, imidazopyridine, thienyl, isothiazolyl, triazolyl, imidazolyl, imidazolinyl, isoxazolyl, pyrrolyl, pyrazolyl, pyridazinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl, and dimethylisoxazolyl.

4. The compound or salt according to claim 3, wherein $R^6$ is substituted by zero to four substituents selected from the group consisting of halo, $(C_1-C_6)$alkyl, $(C_1-C_6)$alkoxy, trifluoroalkyl, trifluoroalkoxy, triazolyl, and butoxycarbonyl.

5. The compound or salt according to claim 4, wherein $R^6$ is substituted by zero to four substituents selected from the group consisting of chloro, fluoro, methyl, methoxy, trifluoromethyl, and trifluoromethoxy.

6. The compound or salt according to claim 5, wherein $R^9$ is independently selected from the group consisting of —H, methyl, ethyl, propyl, isopropyl, butyl, isobutyl, tert-butyl, pentyl, and septyl.

7. The compound or salt according to claim 5, wherein $R^{19}$ is independently selected from the group consisting of methyl, ethyl, propyl, isopropyl, butyl, isobutyl, tert-butyl, penty and septyl.

8. The compound or salt according to claim 1, wherein $R^{11}$, $R^{12}$, and $R^{13}$ are independently selected from the group consisting of —H, methyl, ethyl, methoxy, ethoxy, oxo, chloro, fluoro, bromo, trifluoromethyl, trifluoromethoxy, methylsulfonyl, —C(O)methyl, —C(O)$R^{15}$, and methylmethoxy.

9. The compound or salt according to claim 1, wherein $R^{16}$ is independently selected from the group consisting of —H, methyl, ethyl, hydroxyl, methylsulfonyl, —SO$_2$N(methyl)$_2$, —C(O)NHmethyl, and —C(O)$R^{18}$.

10. The compound or salt according to claim 1, wherein X is phenyl, wherein phenyl is optionally substituted by one to four substituents independently selected from $R^{11}$.

11. The compound or salt according to claim 1, wherein Y is selected from the group consisting of benzoxazinyl, pyridinyl, pyrimidinyl, oxanyl, indolyl, indazolyl, piperazinyl, dihydroindolyl, tetrahydropyridinyl, thiazolyl, tetrahydroquinolinyl, dihydrobenzopyranyl, naphthalenyl, acetidinyl, pyrrolyl, pyrrolidinyl, pyrrolinyl, piperidinyl, morpholinyl, oxetanyl, pyranyl, benzodioxolyl, benzodioxinyl, dihydrobenzodioxepinyl, quinolinyl, dihydrobenzofuranyl, tetrahydroisoquinolinyl, dihydrobenzoxazinyl, dihydroindenyl, benzothiazolyl, furanyl, pyrazolyl, and tetrahydropyridoquinolinyl, pyrazolopyridine, benzoimidazole, pyridinone, benzotriazole, imidazopyridine, thienyl, isothiazolyl, triazolyl, imidazolyl, imidazolinyl, isoxazolyl, pyrrolyl, pyrazolyl, pyridazinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, phthalimidyl, wherein Y is optionally substituted by one to four substituents independently selected from $R^{12}$.

12. The compound or salt according to claim 1, wherein Z is selected from the group consisting of cyclopropyl, cyclobutyl, cyclohexyl, and cycloheptyl, wherein Z is optionally substituted by one to four substituents independently selected from $R^{13}$.

13. The compound or salt according to claim 1, wherein $R^6$-L- is selected from the group consisting of

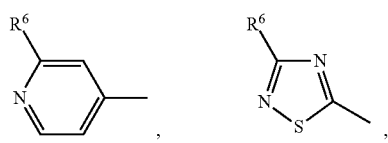

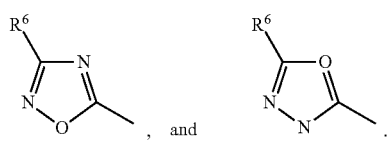

14. The compound according to claim 13, wherein $R^6$- is selected from the group consisting of

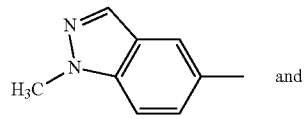

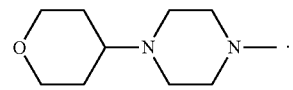

15. A pharmaceutical composition comprising a compound or salt according to claim 1.

16. The compound

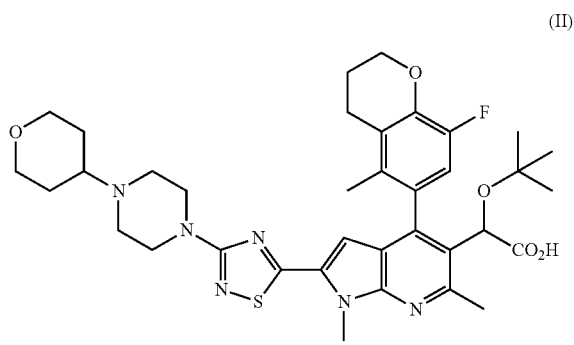 [SMILES: Cc1nc2c(cc(-c3nc(N4CCN(C5CCOCC5)CC4)ns3)n2C)c(-c2cc(F)c3c(c2C)CCCO3)c1C(OC(C)(C)C)C(=O)O]

(II)

or a pharmaceutically acceptable salt thereof.

17. A compound according to claim 16 having the stereochemistry shown below
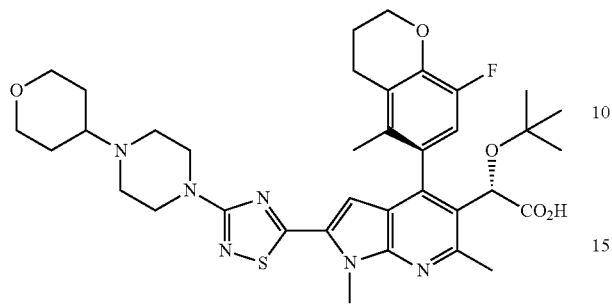
(II)
or a pharmaceutically acceptable salt thereof.